US012534509B2

(12) United States Patent
Kamb

(10) Patent No.: US 12,534,509 B2
(45) **Date of Patent: *Jan. 27, 2026**

(54) ENGINEERED IMMUNE CELLS WITH RECEPTOR CROSS-TALK

(71) Applicant: A2 BIOTHERAPEUTICS, INC., Agoura Hills, CA (US)

(72) Inventor: Alexander Kamb, Agoura Hills, CA (US)

(73) Assignee: A2 BIOTHERAPEUTICS, INC., Agoura Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/629,423

(22) Filed: Apr. 8, 2024

(65) Prior Publication Data

US 2024/0247232 A1 Jul. 25, 2024

Related U.S. Application Data

(63) Continuation of application No. 17/480,466, filed on Sep. 21, 2021, now Pat. No. 11,976,297.

(60) Provisional application No. 63/081,250, filed on Sep. 21, 2020, provisional application No. 63/081,237, filed on Sep. 21, 2020, provisional application No. 63/081,256, filed on Sep. 21, 2020, provisional application No. 63/081,231, filed on Sep. 21, 2020, provisional application No. 63/081,229, filed on Sep. 21, 2020, provisional application No. 63/081,242, filed on Sep. 21, 2020, provisional application No. 63/081,248, filed on Sep. 21, 2020, provisional application No. 63/081,258, filed on Sep. 21, 2020.

(51) Int. Cl.

| | |
|---|---|
| ***C07K 14/725*** | (2006.01) |
| ***A61K 35/17*** | (2025.01) |
| ***A61K 40/11*** | (2025.01) |
| ***A61K 40/31*** | (2025.01) |
| ***A61K 40/32*** | (2025.01) |
| ***A61K 40/42*** | (2025.01) |
| ***C07K 14/47*** | (2006.01) |
| ***C12N 5/0783*** | (2010.01) |
| ***C12N 15/85*** | (2006.01) |

(52) U.S. Cl.

CPC .......... *C07K 14/7051* (2013.01); *A61K 35/17* (2013.01); *A61K 40/11* (2025.01); *A61K 40/31* (2025.01); *A61K 40/32* (2025.01); *A61K 40/4204* (2025.01); *A61K 40/4268* (2025.01); *A61K 40/4269* (2025.01); *C07K 14/4702* (2013.01); *C12N 5/0637* (2013.01); *C12N 15/85* (2013.01); *C07K 2317/53* (2013.01); *C07K 2317/622* (2013.01); *C07K 2319/03* (2013.01); *C07K 2319/715* (2013.01); *C12N 2510/00* (2013.01)

(58) Field of Classification Search

CPC ..... C12N 5/0636; C12N 5/0637; A61K 35/17
See application file for complete search history.

(56) References Cited

U.S. PATENT DOCUMENTS

| | | | |
|---|---|---|---|
| 5,858,358 | A | 1/1999 | June et al. |
| 5,883,223 | A | 3/1999 | Gray |
| 6,352,694 | B1 | 3/2002 | June et al. |
| 6,534,055 | B1 | 3/2003 | June et al. |
| 6,692,964 | B1 | 2/2004 | June et al. |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |
| 10,040,846 | B2 | 8/2018 | Frigault et al. |
| 11,254,726 | B2 | 2/2022 | Kamb et al. |
| 2004/0043401 | A1 | 3/2004 | Sadelain et al. |
| 2004/0101519 | A1 | 5/2004 | June et al. |
| 2006/0034810 | A1 | 2/2006 | Riley et al. |
| 2006/0121005 | A1 | 6/2006 | Berenson et al. |
| 2015/0376296 | A1 | 12/2015 | Fedorov et al. |
| 2016/0289294 | A1 | 10/2016 | Pulé et al. |
| 2018/0111993 | A1 | 4/2018 | Pulé et al. |
| 2018/0251558 | A1 | 9/2018 | Maute et al. |
| 2019/0169289 | A1 | 6/2019 | Young et al. |
| 2021/0230247 | A1 | 7/2021 | Kamb et al. |
| 2022/0089674 | A1 | 3/2022 | Kamb |
| 2022/0089675 | A1 | 3/2022 | Kamb |
| 2022/0089676 | A1 | 3/2022 | Kamb |

(Continued)

FOREIGN PATENT DOCUMENTS

| | | | |
|---|---|---|---|
| WO | 2012/138475 | A1 | 10/2012 |
| WO | 2015/075468 | A1 | 5/2015 |

(Continued)

OTHER PUBLICATIONS

Alcover, 2018, Cell Biology of T Cell Receptor Expression and Regulation, Annu. Rev. Immunol., 36:103-25.

(Continued)

*Primary Examiner* — Christopher M Babic
*Assistant Examiner* — Jennifer S Spence
(74) *Attorney, Agent, or Firm* — Brown Rudnick LLP; Adam M. Schoen

(57) ABSTRACT

The present disclosure provides engineered immune cells and methods for their creation and use. The immune cells comprise activating and blocking receptors, that exhibit cross-talk between the receptors.

20 Claims, 35 Drawing Sheets

Specification includes a Sequence Listing.

(56) References Cited

U.S. PATENT DOCUMENTS

| | | | |
|---|---|---|---|
| 2022/0090013 | A1 | 3/2022 | Kamb |
| 2022/0090014 | A1 | 3/2022 | Kamb |
| 2022/0090015 | A1 | 3/2022 | Kamb |
| 2022/0090016 | A1 | 3/2022 | Kamb |
| 2022/0090017 | A1 | 3/2022 | Kamb |

FOREIGN PATENT DOCUMENTS

| | | | |
|---|---|---|---|
| WO | 2016/174407 | A1 | 11/2016 |
| WO | 2019068007 | A1 | 4/2019 |
| WO | 2021035093 | A1 | 2/2021 |

OTHER PUBLICATIONS

Arseneault, 2017, Loss of chromosome Y leads to down regulation of KDM5D and KDM6C epigenetic modifiers in clear cell renal cell carcinoma, Sci Rep, 7:44876.

Badran, 2002, Identification of three NFAT binding motifs in the 5'-upstream region of the human CD3gamma gene that differentially bind NFATc1, NFATc2, and NF-kappa B p50, J. Biological Chemistry, 277:47136-47148.

Berge, 1998, Selective expansion of a peripheral blood CD8+ memory T cell subset expressing both granzyme B and L-selectin during primary viral infection in renal allograft recipients, Trans Proc 30(8):3975-3977.

Brown, 2004, The LILR family: modulators of innate and adaptive immune pathways in health and disease, Tissue Antigens, 64:215-225.

Chen, 2013, Fusion Protein Linkers: Property, Design and Functionality, Adv Drug Deliv Rev, 65(10):1357-1369.

Cheng, 2017, Pan-cancer analysis of homozygous deletions in primary tumours uncovers rare tumour suppressors, Nature Comm, 8:1221, 14 pages.

El-Naggar, 1996, Genotypic analysis of primary head and neck squamous carcinoma by combined flurescence in situ hybridization and DNA flow cytometry, Am J Clin Pathol, 105(1):102-8.

Engel, 2015, CD Nomenclature 2015: Human Leukocyte Differentiation Antigen Workshops as a Driving Force in Immunology, J Immunol, 195:4555-4563.

Fedorov, 2013, PD-1- and CTLA-4-Based Inhibitory Chimeric Antigen Receptors (iCARs) Divert Off-Target Immunotherapy Responses, Sci Transl Med., 5(215):215ra172, 25 pages.

Guedan, 2019, Engineering and design of chimeric antigen receptors, Molecular Therapy: Methods & Clinical Development, 12:145-156.

Haanen, 1999, Selective expansion of cross-reactive CD8+ memory T cells by viral variants, J. Exp. Med, 190(9):1319-1328.

Hamburger, 2020, Engineered T cells directed at tumors with defined allelic loss, Molecular Immunology, Pergamon, GB, 128:298-310.

Jury, 2007, Lipid rafts in T cell signalling and disease, Seminars in Cell & Developmental Biology, 18:608-615.

Kagoya, 2018, A novel chimeric antigen receptor containing a JAK-STAT signaling domain mediates superior antitumor effects, Nature Medicine, 24(3):352-359.

Krogh, 2001, Predicting transmembrane protein topology with a hidden Markov model: application to complete genomes, J Mol Bio, 305(3):567-580.

Kumar, 2018, Natural killer cell pytotoxicity and its regulation by inhibitory receptors, Immunology, 154(3):383-393.

Lajoie, 2020, Designed protein logic to target cells with precise combinations of surface antigens, Science, 369(6511):1637-1643.

Lloyd, 2009, Modelling the human immune response: performance of a 1011 human antibody repertoire against a broad panel of therapeutically relevant antigens, Protein Engineering, Design & Selection, 22(3)159-168.

Passerini, 2008, STAT5-signaling cytokines regulate the expression of FOXP3 in CD4+CD25+ regulatory T cells and CD4+CD25- effector T cells, International Immunology, 20(3):421-431.

Paul, 2017, The Molecular Mechanism of Natural Killer Cells Function and its Importance in Cancer Immunotherapy, Front Immunol, 8:1124. doi: 10.3389/fimmu.2017.01124. PMID: 28955340; PMCID: PMC5601256.

Pegram, 2011, Activating and inhibitory receptors of natural killer cells, Immunol Cell Biol, 89(2):216-224.

San Jose, 2000, Triggering the TCR complex causes the downregulation of nonengaged receptors by a signal transduction-dependent mechanism, Immunity, 12(2):161-170.

Simons, 1997, Functional raft in cell membranes, Nature, 387:569-572.

Tao, 2020, CD19-CAR-T Cells Bearing a KIR/PD-1 Based Inhibitory CAR Eradicate CD19 + HLA-C1-Malignant B Cells While Sparing CD19 + HLA-C1 + Healthy B Cells, Cancers, 12(9):2612, 17 pages.

Ui-Tei, 2000, Sensitive assay of RNA interference in *Drosophila* and Chinese hamster cultured cells using firefly luciferase gene as target, FEBS Letters 479:79-82.

Wong, 2015, TMSB4Y is a candidate tumor suppressor on the Y chromosome and is deleted in male breast cancer, Oncotarget, 6(42):44927-40.

| Activator | Blocker | Blocker ESO peptide (uM) |
|---|---|---|
| MP1-CAR | - | 50 |
| MP1-CAR | - | 5 |
| MP1-CAR | - | 0.5 |
| MP1-CAR | - | 0 |
| MP1-CAR | ESO-Tmod | 50 |
| MP1-CAR | ESO-Tmod | 5 |
| MP1-CAR | ESO-Tmod | 0.5 |
| MP1-CAR | ESO-Tmod | 0 |

| Activator | Blocker | Activator MP1 peptide (uM) |
|---|---|---|
| MP1-CAR | - | 50 |
| MP1-CAR | - | 5 |
| MP1-CAR | - | 0.5 |
| MP1-CAR | ESO-Tmod | 50 |
| MP1-CAR | ESO-Tmod | 5 |
| MP1-CAR | ESO-Tmod | 0.5 |

Fold EC50 shift with blocker hinge variants

| Group | | C# | Hinge | Length (aa) | |
|---|---|---|---|---|---|
| Immune gene | | C1765 | 2B1 | 64 | |
| | | C3701 | 2B1 trunc | 32 | |
| | | C3746 | PD-1 | 26 | |
| | | C3747 | CTLA4 | 34 | |
| | | C3748 | BTLA | 24 | |
| Synthetic | Rigid | C3698 | A(EAAAK)3A | 17 | SEQ ID NO: 392 |
| | | C3699 | A(EAAAK)5A | 27 | SEQ ID NO: 393 |
| | Fflexible | C3749 | (G4Q)2 | 10 | SEQ ID NO: 394 |
| | | C3750 | (G4Q)5 | 25 | SEQ ID NO: 396 |
| | | C3751 | (G4Q)10 | 49 | SEQ ID NO: 397 |

| Construct | mAb | Notes |
|---|---|---|
| CT-479 | Zalutumumab | Ph III terminated due to skin rash & no benefit |
| CT-482 | 12D03 | No clinical data |
| CT-486 | Cetuximab (Erbitux) | Treatment for mCRC & HNC |
| CT-487 | Matuzumab | Ph II terminated due to no response |
| CT-488 | Panitumumab (Vectibix) | Treatment for mCRC |

$$\text{Killing \%} = \frac{UTD_{\text{Target cell area}} - CTL_{\text{Target cell area}}}{UTD_{\text{Target cell area}}} \%$$

| Construct | mAb | Notes |
|---|---|---|
| **CT-479** | Zalutumumab | Ph III terminated due to skin rash & no benefit |
| **CT-482** | 12D03 | No clinical data |
| **CT-486** | Cetuximab (Erbitux) | Treatment for mCRC & HNC |
| **CT-487** | Matuzumab | Ph II terminated due to no response |
| **CT-488** | Panitumumab (Vectibix) | Treatment for mCRC |

$$\text{Killing \%} = \frac{UTD_{\,Target\ cell\ area} - CTL_{\,Target\ cell\ area}}{UTD_{\,Target\ cell\ area}}\ \%$$

ENGINEERED IMMUNE CELLS WITH RECEPTOR CROSS-TALK

TECHNICAL FIELD

The present disclosure relates to engineered immune cells that have an enhanced safety profile and large therapeutic window.

SEQUENCE LISTING

The present application is being filed with a Sequence Listing in electronic format. The Sequence Listing is provided as a file entitled A2TH-003-02US-Sequence-Listing.xml, created on Apr. 8, 2024 and is 605 kilobytes in size. The information in electronic format of the Sequence Listing is incorporated by reference in its entirety.

BACKGROUND

Approximately 1.8 million people per year are diagnosed with a form of cancer in the United States. Similarly, it is estimated that 23.5 million Americans suffer from an autoimmune disease, almost all of which decrease life expectancy. Despite continual advances in treatment, education, and detection, there are over 600,000 deaths per year attributed to cancer in the U.S., while autoimmune diseases remain a leading cause of death among patients under the age 65.

Engineered immune cells have been touted as potentially effective treatments for a variety of severe conditions like cancer, viral infections, auto-immune ailments, and organ transplant rejection. These immune cells, whether chimeric antigen receptor (CAR)-engineered cells or T cell receptor (TCR)-engineered cells, often show efficacious results in vitro. However, in vivo, these results are rarely duplicated. Often, these treatments show a lack of efficacy in vivo and/or produce such severe side effects, that they cannot be used as therapeutics. Thus, despite decades of consistent research, only two CAR T cell therapies have received FDA approval—Kymriah™ for acute lymphoblastic leukemia and Yescarta™ for diffuse large B-cell lymphoma.

SUMMARY OF THE INVENTION

The present disclosure provides engineered immune cells that comprise two types of modular, engineered ligand binding receptors caused to be expressed on the surface of the cells. The first of these receptors is an activating receptor, which is designed to activate when bound to a cognate ligand on the surface of another cell, causing it to trigger an activating signal. The immune cells are engineered such that when the strength of the activating signal crosses a threshold, it causes a cytotoxic response by the immune cell, killing the cell expressing the cognate ligand. The second of these receptors is a blocking receptor, which when bound to a cognate blocking ligand on the surface of a non-target cell, is designed to activate and trigger a blocking signal. The blocking signal blocks the activating signal, which prevents the cytotoxic response against the non-target cell.

Generally, the activating receptors are designed to bind to cognate activating ligands that are expressed on both target cells, such as tumor cells, and non-target cells. The blocking ligands may be expressed only by non-target cells, or expressed at lower levels by target cells compared to non-target cells. In this way, when the engineered immune cells contact target cells, the activating receptors bind to the activating ligands, which leads to the cytotoxic response. In contrast, when the engineered immune cells contact non-target cells, the blocking receptors bind to the blocking ligands, blocking the cytotoxic response. This designed scheme provides the general means by which the engineered immune cells safely kill target cells, while limiting effects on non-target cells. However, the immune cells of the present disclosure have been engineered to provide several other advantageous features that expand their therapeutic window and efficacy, while limiting deleterious effects.

One of these advantageous features is that, when activated, the blocking receptors have been designed to reduce cell surface expression of the activating receptors. Thus, as the immune cells circulate to areas of a patient's body lacking target cells, the levels of activating receptors expressed on the surface of the cell are reduced. The receptors can be configured such that this reduction is reversible upon the activating receptors binding to their cognate ligands in the absence of the blocking ligands. This intentionally lowers the likelihood that a cytotoxic response will be triggered in the absence of an appropriate target, which enhances the safety profile of the immune cells.

Further, by engineering the immune cells to reduce the expression of activating receptors in the absence of an appropriate target cell, the immune cells are less likely to exhibit chronic activation and/or ligand-independent tonic signaling. As a result, the immune cells of the present disclosure are designed to limit immune cell exhaustion, differentiation, and activation-induced immune cell death, while concurrently exhibiting high generation and persistence.

A further advantage of the engineered immune cells of the present disclosure is that, when they contact target and/or non-target cells, the activating and blocking receptors are designed to diffuse into regions on the immune cell surface proximate to the target and/or non-target cells. The receptors form micro-clusters in these regions. In micro-clusters proximate to non-target cells, the blocking receptors bind to cognate ligands on the proximate non-target cells. The receptors can be configured such that cross-talk between the receptors causes a localized reduction in surface expression of the activating receptors, recruits more blocking receptors to the micro-cluster, and prevents breakup of the micro-cluster. This leads to a localized signal that blocks cytotoxic effects on the non-target cell.

In contrast, when the engineered immune cells contact target cells, activating receptors in micro-clusters proximate to the target cells are activated. This leads to a localized signal that, when it passes a threshold, triggers a cytotoxic response by the immune cell that kills the proximate target cells. The immune cells and receptors can be configured such that binding of the activating receptors to their cognate ligands may also locally reverse any reduced surface expression of the activating receptor. This ensures a sufficiently strong activating signal to trigger the cytotoxic response on the proximate target cell.

The immune cells of the present disclosure can form these aforementioned micro-clusters when simultaneously contacting both target and non-target cells. This ensures an appropriate, localized response that kills target cells, while minimizing deleterious effects on non-target cells.

The immune cells of the present disclosure also feature blocking receptors that are engineered to produce a ligand-dependent signal that dominates and blocks the activating signal from the activating receptors. This ensures that the immune cells can be configured to possess a strong safety profile with a wide therapeutic window.

Moreover, in some methods and systems of the disclosure, the engineered immune cells can be produced based on the levels of blocking and activating ligands expressed by non-target cells. Because the blocking receptors can be tuned to have a signal that dominates initial contact with a non-target cells, a sufficiently safe immune cell can be produced, without relying on a large surplus of blocking receptors expressed as compared to activating receptors. Further, the ability of the blocking receptors to reduce the surface expression of the activating receptors ensures that this level of safety increases in the presence of non-target cells.

Another advantage conferred by the immune cells of the present disclosure is that receptors can be produced using modular receptor components. Thus, the immune cells can be readily engineered to have receptor pairs that target desired ligands expressed on target and non-target cells. Moreover, the modular receptor components can be used and interchanged to tune or adjust the relative signal strengths of each receptor type. This ensures that an engineered immune cell's receptors provide a sufficiently strong activation signal, which can be adequately blocked to prevent non-target effects. A surprising discovery is that this modular nature extends to both chimeric antigen receptors (CAR) and T cell receptors (TCR). Not only are CARs and TCRs of the present disclosure able to interact with each other, but parts of CARs and TCRs can be interchanged to produce customized receptors and cells.

The relative signal strength and activity of each receptor type can also be modulated based on cross-talk between receptors. A surprising feature of the present disclosure is, not only that cross-talk can impact signal strength and activity, but that the impact of this cross-talk can change depending on the distance between pairs of blocking and activating receptors. As the distance between a blocking receptor and activating receptor decreases, the impact of this cross-talk increases. Thus, the present disclosure provides engineered immune cells configured to express receptors such that they are proximate to one another to ensure optimal interaction and strong cross-talk.

The receptors may be designed, for example, with physiochemical properties that ensure the receptors have a desired spacing. This spacing may ensure a maximum level of cross-talk between receptors and/or ensure that the receptors do not diffuse close enough to, for instance, invert the blocking receptor signal. The receptors can be engineered, for example, to have opposing charges or steric hindrances to prevent them from moving too close to one another. Alternatively, or in addition, the immune cells may be engineered to have receptors that are covalently linked to achieve a desired spacing. For example, a rigid covalent linker between the receptors can hold the receptors at a desired spacing from one another. The rigid linker concurrently keeps the receptors close enough to ensure cross-talk while maintain adequate spacing to prevent the blocking receptor from, for instance, inverting or becoming ligand-independent.

Another feature of the present disclosure is that the blocking receptor can be designed using interchangeable hinges that connect an extracellular ligand binding domain to a transmembrane domain and/or an intracellular domain. The hinges can be designed to have different lengths and flexibilities. The length and flexibility of a hinge can be used to tune the strength of the blocking signal. Longer and/or more flexible hinges can be used to increase the strength of the blocking receptor's signal or surface expression. In contrast, the blocking receptor can be engineered with shorter and/or more rigid hinges to decrease the strength of the blocking receptor's signal or surface expression. The blocking receptor can be configured to use a hinge selected from a group of hinges that have a known impact on the half maximal concentration ($EC_{50}$) of the activating ligand for the activating receptor to cause the immune cell to trigger a cytotoxic response. This allows pairs of blocking and activating receptors to be chosen or engineered to exhibit a desired level of activation/inhibition.

Thus, the present disclosure provides engineered immune cells, and methods for reliably producing them, with a large therapeutic window, i.e., cells with a large range between their minimum effective dose and maximum tolerated dose. The cells possess target-sensitive receptors that produce an activation signal sufficient to trigger cytotoxic effects when encountering target cells, while concurrently producing minimal non-target effects. The engineered immune cells of the present disclosure also exhibit low exhaustion, differentiation, tonic signaling, and activation-induced immune cell death, and other features consistent with effective in vitro and in vivo function.

In one aspect, the present disclosure provides an engineered immune cell that includes an activating receptor expressed on a surface of the engineered immune cell. Binding of the activating receptor to an activating ligand on a target cell promotes a cytotoxic response by the engineered immune cell. The immune cell also includes a blocking receptor expressed on the surface of the engineered immune cell. Binding of the blocking receptor to a blocking ligand on a target cell causes the engineered immune cell to exhibit reduced surface expression of the activating receptor. High exogenous IL-2 may overcome this level of regulation, though the activation/blockade is still enforced by other features of intracellular signaling of the activator and blocker receptors.

Binding of the blocking receptor to the blocking ligand on the target cell may also cause the blocking receptor to trigger an inhibitory signal that blocks the activating signal, thereby preventing the cytotoxic response by the immune cell. The engineered immune may have an inhibitory signal dominates and blocks the activating signal.

The reduced surface expression of the activating receptor of the cells of the present disclosure may be reversible. The reduced surface expression of the activating receptor may reverse upon the engineered immune cell binding to the activating ligand on a target cell in the absence of the blocking ligand. The reduced surface expression of the activating receptor may be localized to a region of the engineered immune cell surface proximal to the blocking receptor. When a plurality of the blocking receptor binds to a plurality of the blocking ligand, the reduced surface expression may be localized to regions of the engineered immune cell surface proximal to blocking receptors.

When the immune cell encounters a target cell having both the blocking and activating ligands, a plurality of activating and blocking receptors diffuse into a region on the of the immune cell surface proximal to the target cell and form a micro-cluster. In the micro-cluster, binding of blocking receptors to the blocking ligands causes the engineered immune cell to exhibit reduced surface expression of the activating receptor in the micro-cluster.

In certain immune cells of the disclosure, the blocking receptor cannot bind to the blocking ligand until the activating receptor binds to the activating ligand.

The present disclosure also provides method for treating a cancer using the immune cells of the disclosure. In certain methods of the disclosure, the method includes providing an engineered immune cell to a patient, wherein the engineered immune cell comprises an activating receptor and a blocking receptor, each expressed on a surface of the engineered immune cell. In certain methods, when the engineered immune cell encounters a tumor cell of the patient, the activating receptor binds to an activating ligand on the tumor cell while the blocking receptor remains unbound. This promotes a cytotoxic response by the engineered immune cell that results in a cytotoxic effect on the tumor cell. When the engineered immune cell encounters a normal cell of the patient, the blocking receptor binds to a blocking ligand on the normal cell and causes the engineered immune cell to exhibit reduced surface expression of the activating receptor. This causes a signal from the blocking receptor to dominate a signal from the activating receptor, which prevents the cytotoxic response by the engineered immune cell.

In certain methods, the reduced surface expression of the activating receptor is temporary. The reduced surface expression may be reversible. The reduced surface expression may be reversed upon the engineered immune cell binding to the first ligand on a tumor cell.

In certain methods of the disclosure, the reduced surface expression of the activating receptor may be localized to a region of the engineered immune cell surface proximal to the blocking receptor bound to the blocking ligand on the normal cell. A plurality of the blocking receptor may bind to a plurality of the blocking ligand on the normal cell, and the reduced surface expression may be localized to the region of the engineered immune cell surface proximal to the plurality of the blocking receptor.

A further aspect of the disclosure are methods of producing an engineered immune cell with activating and blocking receptors. The methods of the disclosure may include, producing an engineered immune cell that expresses activating receptors and blocking receptors based on a ratio of a quantity of an activating ligand to a quantity of a blocking ligand that are expressed in non-tumor cells of a patient.

In certain methods, a tumor cell of a patient expresses the activating ligand and does not express the blocking ligand.

In certain methods of the disclosure, binding of the activating receptors to the activating ligands triggers an activating signal that promotes a cytotoxic response by the engineered immune cell. Additionally, binding of the blocking receptors to blocking ligands on a non-tumor cell may cause the blocking receptors to trigger an inhibitory signal that blocks the activating signal.

In certain methods of the disclosure, the engineered immune cell expresses the blocking and activating receptors at a ratio based on the ratio of the quantity of the activating ligand to the quantity of the blocking ligand that are expressed in the non-tumor cells of the patient.

In some methods, the inhibitory signal of one of the blocking receptors dominates and blocks the activating signal of one of the activating receptors.

In certain methods, the ratio of the blocking receptors to the activating receptors is less than 1. The ratio of the blocking receptors to the activating receptors, needed to achieve a blocking signal to provide a certain level of blocking for the activating signal, may be inversely proportional to the quantity of the activating ligand expressed on non-tumor cells of the patient. In certain methods, when the immune cell contacts a non-tumor cell of the patient the blocking receptors bind to blocking ligands on the non-tumor cell and reversibly increase the ratio of blocking receptors to activating receptors expressed by the immune cell.

In certain methods of the disclosure, each blocking receptor comprises a ligand binding domain (LBD), a hinge, transmembrane domain, and intracellular domain (ICD), and the LBD, hinge, and ICD have a known effect on the strength of the inhibitory signal. Each activating receptor may comprise a ligand binding domain (LBD), a hinge, transmembrane domain, and the LBD has a known effect on the activation signal.

The present disclosure also provides a method of producing an engineered immune cell that includes obtaining a sample from a patient comprising target and non-target cells; performing an assay to determine a ratio of a quantity of an activating ligand to a quantity of a blocking ligand expressed on the non-target cells; and producing an engineered immune cell that expresses activating receptors and blocking receptors based on the determined ratio.

In certain methods, the target cells express the activating ligand and do not express the blocking ligand.

In some methods, binding of the activating receptors to the activating ligands triggers an activating signal that promotes a cytotoxic response by the engineered immune cell; and binding of the blocking receptors to blocking ligands on a non-target cell causes the blocking receptors to trigger an inhibitory signal that blocks the activating signal.

In some methods, the engineered immune cell expresses the blocking and activating receptors at a ratio based on the ratio of the quantity of the activating ligand to the quantity of the blocking ligand that are expressed in the non-target cells of the patient.

In certain methods, the inhibitory signal of one of the blocking receptors dominates and blocks the activating signal of one of the activating receptors. The ratio of the blocking receptors to the activating receptors is less than 1 in certain methods. The ratio of the blocking receptors to the activating receptors may be inversely proportional to the quantity of the activating ligand expressed on non-target cells of the patient. In some methods, when the immune cell contacts a non-target cell of the patient the blocking receptors bind to blocking ligands on the non-target cell and reversibly increases the ratio of blocking receptors to activating receptors expressed by the immune cell.

In certain methods of the disclosure, each blocking receptor comprises a ligand binding domain (LBD), a hinge, transmembrane domain, and intracellular domain (ICD), and the LBD, hinge, and ICD have a known effect on the strength of the inhibitory signal. Each activating receptor may comprise a ligand binding domain (LBD), a hinge, transmembrane domain, and the LBD has a known effect on the activation signal.

In a further aspect, the present disclosure provides engineered immune cells with activating and blocking receptors that exhibit cross-talk between receptors. Thus, the present disclosure provides an engineered immune cell with an activating receptor that triggers a cytotoxic signal that promotes a cytotoxic response of the engineered immune cell when the activating receptor binds a first ligand of a target cell; a blocking receptor that sends an interfering signal that inhibits the cytotoxic response of the engineered immune cell when the blocking receptor binds a second ligand of the target cell, wherein cross-talk between the activating receptor and the blocking receptor affects an activation threshold for the cytotoxic response.

In certain immune cells, in the absence of the first and second ligands, the effect of the cross-talk on the activation threshold is minimized and/or reduced. The effect of the cross-talk on the activation threshold may increase with proximity of the activating receptor to the blocking receptor.

In certain immune cells of the disclosure, the activating receptor and blocking receptor are covalently linked together, or have physicochemical properties favoring interaction with one another such that the receptors are proximal to one another.

In some immune cells of the disclosure, when the blocking receptor binds to the second ligand, the cross-talk between the blocking and activating receptors causes the immune cell to exhibit reduced surface expression of the activating receptor.

An immune cell of the disclosure may include a plurality of the activating and blocking receptors, and when the immune cell contacts a target cell the plurality of the activating and blocking receptors diffuses into a region on the surface of the immune cell proximal to the target cell and forms a micro-cluster in which the effect of the cross-talk on the activation threshold is localized.

In some immune cells of the disclosure, cross-talk between the activating receptor and the blocking receptor prevents the blocking receptor from binding to the second ligand until the activating receptor binds to the first ligand.

The present disclosure also provides methods for treating cancer using the immune cells of the present disclosure. Certain methods may include providing an engineered immune cell to a patient, wherein the engineered immune cell comprises an activating receptor and a blocking receptor, each expressed on a surface of the engineered immune cell. The activating receptor may trigger a cytotoxic signal that promotes a cytotoxic response of the engineered immune cell when the activating receptor binds a first ligand of a target cell; and the blocking receptor may send an interfering signal that inhibits the cytotoxic response of the engineered immune cell when the blocking receptor binds a second ligand of the target cell, wherein cross-talk between the activating receptor and the blocking receptor affects an activation threshold for the cytotoxic response.

In certain methods, the absence of the second ligand, the effect of the cross-talk on the activation threshold is minimized and/or reduced. The effect of the cross-talk on the activation threshold may increase with proximity of the activating receptor to the blocking receptor.

In certain methods, the activating receptor and blocking receptor are linked together or have physicochemical properties favoring interaction with one another, such that the receptors are proximal to one another.

In certain methods, when the blocking receptor binds to the second ligand, the cross-talk between the blocking and activating receptors causes the immune cell to exhibit reduced surface expression of the activating receptor. The immune cell may include a plurality of the activating and blocking receptors, and when the immune cell contacts a target cell the plurality of the activating and blocking receptors diffuses into a region on the surface of the immune cell proximal to the target cell and forms a micro-cluster in which the effect of the cross-talk on the activation threshold is localized.

In methods of the disclosure, the cross-talk between the activating receptor and the blocking receptor may prevent the blocking receptor from binding to the second ligand until the activating receptor binds to the first ligand.

The present disclosure also provides methods of producing engineered immune cells as disclosed herein. Certain methods include, determining an amount of cross-talk between an activating receptor and a blocking receptor for an engineered immune cell, wherein the amount of cross-talk between the activating receptor and the blocking receptor affects an activation threshold for the cytotoxic response; and producing an engineered immune cell that expresses different concentrations of activating receptors and blocking receptors based on the determined amount of cross-talk between the activating receptor and the blocking receptor.

In some methods for producing immune cells, in the absence of cognate ligands for the activating and blocking receptors, the amount of the cross-talk is minimized and/or reduced. The methods may include producing an engineered immune cell that expresses different concentrations of activating receptors and blocking receptors is further based on a ratio of a quantity of an activating ligand to a quantity of a blocking ligand that are expressed in non-tumor cells of a sample.

The cross-talk between the activating receptor and the blocking receptor may prevent the blocking receptor from binding to the blocking ligand until the activating receptor binds to the activating ligand. In certain methods, an amount of the cross-talk between the activating receptor and blocking receptor increases with proximity of the activating receptor to the blocking receptor.

Methods include producing immune cells where the activating receptor and blocking receptor may be covalently linked, or have physicochemical properties favoring interaction with one another such that the receptors are proximal to one another.

In a further aspect, the present disclosure provides engineered immune cells with activating and blocking receptors in which the blocking receptor provides an inhibitory signal that dominates the activation signal from the activating receptor.

Thus, the present disclosure includes an engineered immune cell with an activating receptor on the surface of the engineered immune cell, wherein binding of the activating receptor to a first ligand on a target cell causes the activating receptor to trigger an activating signal that promotes a cytotoxic response by the engineered immune cell; and a blocking receptor on the surface of the immune cell, wherein binding of the blocking receptor to a second ligand on a target cell causes the blocking receptor to trigger an inhibitory signal stronger than the activating signal such that the inhibitory signal dominates and blocks the activating signal from the activating receptor, thereby preventing a localized cytotoxic response by the engineered immune cell.

In certain immune cells of the disclosure, binding of the blocking receptor to the second ligand may cause the engineered immune cell to exhibit reduced surface expression of the activating receptor. The reduced surface expression may be reversible.

The immune cells may include a plurality of activating and blocking receptors and the ratio of the blocking receptors to the activating receptors expressed by the immune cells is less than or equal to 1.

In certain immune cells of the disclosure, the blocking receptor does not bind to the second ligand until the activating receptor binds to the activating ligand.

In certain cells, the inhibitory signal may be localized to a region of the engineered immune cell surface adjacent to the blocking receptor. Similarly, the activation signal may be localized to a region of the engineered immune cell surface adjacent to the activating receptor.

When the immune cells of the disclosure encounter a target cell having both the first and second ligands, a plurality of activating and blocking receptors may diffuse into a region on the of the immune cell surface proximal to the target cell and form a micro-cluster in which the blocking receptors prevent the localized cytotoxic response by the engineered immune cells. Binding of the blocking receptors in the micro-cluster to the second target antigen may prevent breakup of the micro-cluster. When the immune cells simultaneously contact a second target cell having the first ligand and lacking the second ligand, a second plurality of the activating receptors may diffuse into a second region on the surface of the immune cells proximal to the second target cell and form a second micro-cluster that promotes the localized cytotoxic response by the engineered immune cells that results in a cytotoxic effect on the second target cell.

The present disclosure also provides methods for treating cancer using the immune cells of the present disclosure. The methods include a method in which an engineered immune cell is provided to a patient, wherein the engineered immune cell comprises an activating receptor and a blocking receptor, each expressed on a surface of the engineered immune cell, wherein: when the engineered immune cell encounters a tumor cell, the activating receptor binds to a first ligand on the tumor cell and the activating receptor triggers an activating signal in the engineered immune cell that promotes a cytotoxic response by the engineered immune cell that results in a cytotoxic effect on the tumor cell; and when the engineered immune cell encounters a normal cell, the activating receptor binds to the first ligand on the normal cell and the blocking receptor binds to a second ligand on the normal cell, wherein the activating receptor triggers an activating signal in the engineered immune cell and the blocking receptor triggers an inhibitory signal in the engineered immune cell that is stronger than the activating signal such that the inhibitory signal dominates and blocks the activating signal from the activating receptor, thereby preventing a localized cytotoxic response by the engineered immune cell.

In some methods, binding of the blocking receptor to the second ligand causes the engineered immune cell to exhibit reduced surface expression of the activating receptor. The reduced surface expression may be reversible.

In methods of the disclosure, the immune cell may express different concentrations of the activating and blocking receptors based on a ratio of a quantity of the first ligand to a quantity of a second ligand expressed in a normal cell of the patient. The ratio of the concentration of blocking receptors expressed to activating receptors expressed may be less than or equal to 1.

In certain methods, when the immune cell encounters at least one tumor cell, a first plurality of the activating receptors diffuses into a first region on the surface of the immune cell proximal to the tumor cell and forms a first micro-cluster that promotes the localized cytotoxic response by the immune cell that results in a cytotoxic effect on the tumor cell. When the immune cell simultaneously encounters a normal cell, a plurality of the activating and blocking receptors may diffuse into a second region on the surface of the immune cell proximal to the normal cell and form a second micro-cluster causing the inhibitory signal from the blocking receptors to dominate the activating signal from the activating receptors in the second micro-cluster preventing the localized cytotoxic response by the engineered immune cell on the normal cell. Binding of the blocking receptors in the second micro-cluster to the second ligand may prevent breakup of the second micro-cluster.

In some methods of the disclosure, the blocking receptor does not bind to the second ligand until the activating receptor binds to the activating ligand.

Some methods include cross-talk between the activating receptor and the blocking receptor that affects an activation threshold for the localize cytotoxic response.

In a further aspect, the present disclosure provides engineered immune cells with activating and blocking receptors that have multiplex and localized activity. An immune cell of the disclosure may include activating and blocking receptors on a surface of the cell. When the engineered immune cell encounters a tumor cell and a healthy cell a first region of the activating and blocking receptors forms proximal to the healthy cell and blocking receptors in the first region inhibit cytotoxic effects on the healthy cell, while, simultaneously, a second region of the activating and blocking receptors forms proximal to the tumor cell and promotes a cytotoxic response by the engineered immune cell that exhibits cytotoxic effects on the tumor cell.

The activating and blocking receptors in the first region may bind to cognate activating and blocking ligands on the healthy cell, and the activating receptors in the second region may bind to cognate activating ligands on the tumor cell. The activating and blocking receptors may form a first micro-cluster in the first region, and the activating and blocking receptors may form a second micro-cluster in the second region.

Binding of the blocking receptors in the first micro-cluster to the cognate blocking ligands on the healthy cell may cause the engineered immune cell to exhibit reduced surface expression of the activating receptor in the first micro-cluster. Binding of the blocking receptors in the first micro-cluster to the cognate blocking ligands on the healthy cell may prevent breakup of the first micro-cluster.

The immune cell may express different concentrations of the activating and blocking receptors based on a ratio of a quantity of the activating ligand to a quantity of the blocking ligand expressed in a healthy cell. The ratio of the concentration of blocking receptors to activating receptors expressed by the immune cell may be less than or equal to 1.

In certain immune cells of the disclosure, the blocking receptors do not bind to the cognate blocking ligands until the activating receptors bind to cognate activating ligands.

In some immune cells of the disclosure, the cytotoxic response by the engineered immune cell that exhibits cytotoxic effects on the tumor cell is localized to the second region. The localized cytotoxic response does not exhibit cytotoxic effects on the healthy cell.

The present disclosure also provides methods for treating cancer using the immune cells of the disclosure. A method for treating cancer may include providing an engineered immune cell to a patient, the engineered immune cell comprising activating and blocking cell-surface receptors. When the engineered immune cell encounters a tumor cell and a healthy cell of the patient, a first set of the activating and blocking receptors collect into a first cell-surface region of the engineered immune cell proximal to the healthy cell in which the blocking receptors inhibit cytotoxic effects of the engineered immune cell on the healthy cell. Simultaneously, a second set of the activating and blocking receptors collect into a second cell-surface region of the engineered immune cell proximal to the tumor cell in which the activating receptors promote a cytotoxic response by the engineered immune cell that kills the tumor cell.

The activating and blocking receptors in the first cell-surface region may bind to cognate activating and blocking ligands on the healthy cell, and the activating receptors in the second cell-surface region may bind to cognate activating ligands on the tumor cell.

The activating and blocking receptors may form a first micro-cluster on the first cell-surface region, and the activating and blocking receptors may form a second micro-cluster on the second cell-surface region.

Binding of the blocking receptors in the first micro-cluster to the cognate blocking ligands on the healthy cell may cause the engineered immune cell to exhibit reduced surface expression of the activating receptor in the first micro-cluster. Binding of the blocking receptors in the first micro-cluster to the cognate blocking ligands on the healthy cell may prevent breakup of the first micro-cluster.

In some methods of the disclosure, the immune cell expresses different concentrations of the activating and blocking receptors based on a ratio of a quantity of the activating ligand to a quantity of a blocking ligand expressed in a healthy cell. The ratio of the concentration of blocking receptors to activating receptors expressed by the immune cell may be less than or equal to 1.

In certain methods, blocking receptors do not bind to the cognate blocking ligands until the activating receptors bind to the cognate activating ligands.

In certain methods of the disclosure, the cytotoxic response is localized to the second cell-surface region. The localized cytotoxic response does not exhibit cytotoxic effects on the healthy cell.

In a further aspect, the present disclosure provides immune cells that have activating and blocking receptors that form micro-clusters on the surface of the immune cells.

An engineered immune cell of the disclosure may include activating and blocking receptors on a surface of the engineered immune cell, wherein: when the engineered immune cell encounters a tumor cell, a first plurality of the activating receptors diffuse into a first region on the surface of the engineered immune cell and form a first micro-cluster proximal to the tumor cell that promotes a cytotoxic response by the engineered immune cell that results in cytotoxic effects on the tumor cell; and when the engineered immune cell encounters a normal cell, a second plurality of the activating and blocking receptors diffuse into a second region on the surface of the engineered immune cell and form a second micro-cluster proximal to the normal cell, wherein the blocking receptors in the second micro-cluster inhibit cytotoxic effects on the normal cell.

The activating receptors in the first micro-cluster may bind to cognate activating ligands on the tumor cell, and the activating and blocking receptors in the second micro-cluster may bind to cognate activating and blocking ligands on the normal cell. When the immune cell encounters a normal cell, the second micro-cluster may mediate formation of a complementary cluster of ligands on the normal cell. Binding of the blocking receptors in the second micro-cluster to the cognate blocking ligands on the normal cell may cause the engineered immune cell to exhibit reduced surface expression of the activating receptor in the second micro-cluster. Binding of the blocking receptors in the second micro-cluster to the cognate blocking ligands on the normal cell may prevent breakup of the second micro-cluster.

In some immune cells of the disclosure, when the immune cell simultaneously contacts a normal cell and a tumor cell, the first plurality of the activating receptors diffuse into the first region and form the first micro-cluster proximal to the tumor cell that promotes the cytotoxic response by the engineered immune cell that results in cytotoxic effects on the tumor cell; and the second plurality of the activating and blocking receptors diffuse into the second region and form the second micro-cluster proximal to the normal cell in which the blocking receptors inhibit cytotoxic effects on the normal cell. Expression of the activating receptor in the second micro-cluster may be reduced after the second micro-cluster forms.

The immune cell may express different concentrations of the activating and blocking receptors based on a ratio of a quantity of the activating ligand to a quantity of a blocking ligand expressed in a normal cell of a patient. The ratio of the concentration of blocking receptors expressed to activating receptors expressed is less than or equal to 1.

In some immune cells of the disclosure, the blocking receptors do not bind to the cognate blocking ligands until the activating receptors bind to the cognate activating ligands.

The present disclosure provides methods for treating cancer using the immune cells disclosed herein. A method for treating cancer may include providing an engineered immune cell to a patient, the engineered immune cell comprising activating and blocking cell-surface receptors.

When the engineered immune cell encounters a normal cell, a first plurality of the activating and blocking receptors collect into a micro-cluster within a region of the cell-surface of the engineered immune cell proximal to the normal cell, wherein binding of one of the blocking receptors in the micro-cluster to a blocking ligand on the normal cell inhibits breakup of the micro-cluster, and wherein the engineered immune cell kills tumor cells that exhibit an activating ligand bound by the activating receptor and do not exhibit the blocking ligand such that the blocking receptor remains unbound.

When the immune cell simultaneously contacts a normal cell and a tumor cell, a first plurality of the activating receptors may diffuse into the first region and form the first micro-cluster proximal to the tumor cell that promotes the cytotoxic response by the engineered immune cell that results in cytotoxic effects on the tumor cell, and a second plurality of the activating and blocking receptors may diffuse into the second region and form the second micro-cluster proximal to the normal cell, wherein binding of one of the blocking receptors in the second micro-cluster to a first ligand on the normal cell inhibits breakup of the micro-cluster.

Binding of the blocking receptors in the second micro-cluster to the first ligands on the normal cell inhibits the cytotoxic effects on the normal cell. The cytotoxic effects on the tumor cell may be localized proximal to the first micro-cluster.

Binding of the blocking receptor to the first ligand on the normal cell may cause a plurality of the first ligand on the normal cell to diffuse into a region proximal to the immune cell and form a complementary micro-cluster. Binding of the blocking receptors in the micro-cluster to the first ligand on the normal cell may cause the engineered immune cell to exhibit reduced surface expression of the activating receptor in the micro-cluster. The reduced surface expression may be reversible.

The immune cell may express different concentrations of the activating and blocking receptors based on a ratio of a quantity of the first ligand to a quantity of the second ligand expressed on a normal cell. The ratio of the concentration of blocking receptors to activating receptors expressed by the immune cell may be less than or equal to 1.

In certain methods of the disclosure, the blocking receptors in the micro-cluster do not bind to the first ligands until the activating receptors bind to the second ligands on the normal cell.

In a further aspect, the present disclosure provides engineered immune cells and methods of making and using them wherein the immune cells comprise a hinge that modulates an effect of the blocking signal and/or receptors.

Thus, the present disclosure provides a method of producing an engineered immune cell, the method including, causing an immune cell to express cell surface activating receptors and blocking receptors, wherein the blocking receptors comprise a selected hinge. Binding of the activating receptors to activating ligands on a target cell triggers an activating signal that promotes a cytotoxic response by the immune cell. Binding of the blocking receptors to blocking ligands on a non-target cell causes the blocking receptors to trigger a blocking signal that inhibits the activating signal. The selected hinge is selected to modulate an effect of the blocking signal on the activating signal.

In certain methods, the selected hinge comprises a peptide having a certain length, and the length of the peptide modulates the effect of the blocking signal on the activating signal. The effect of the blocking signal on the activating signal may be an increased inhibition of the activating signal. The increased inhibition of the activating signal may increase a half maximal effective concentration ($EC_{50}$) of the activating ligand for the activating receptors to promote the cytotoxic response.

In certain methods and immune cells of the disclosure, cross-talk and/or structure function interactions between the hinge of the blocking receptor and the activating receptor further impart different signal strengths for the blocking receptor.

The effect of the blocking signal on the activating signal may be a decreased inhibition of the activating signal, and the length of the peptide is less than about 24 amino acids.

In certain aspects of the disclosure, the engineered immune cell is caused to express the blocking and activating receptors at a ratio, and the ratio blocking receptors to activating receptors expressed is decreased as the length of the peptide of the selected hinge is increased. The peptide may further have a degree of flexibility, and the peptide's length and degree of flexibility modulate the effect of the blocking signal on the activating signal.

The selected hinge may be selected from hinges that each have a known effect on the $EC_{50}$ of the activating ligand for the activating receptors to promote the cytotoxic response. The length of the peptide of each hinge that may have a known effect on the $EC_{50}$ of the activating ligand is between 10 and 64 amino acids in length. The peptide of the selected hinge may be at least 24 amino acids in length. The peptide of the selected hinge may be at least 64 amino acids in length. In certain aspects, the hinge having a peptide of 64 amino acids in length causes at least a fifty-fold increase in the $EC_{50}$ relative to a hinge having a peptide of 10 amino acid in length. In certain aspects, the hinges that each have a known effect on the EC50 comprise hinges 2B1, 2B1 truncated, PD-1, CTLA4, BTLA, SEQ ID NO: 392, SEQ ID NO: 393, SEQ ID NO: 394, SEQ ID NO: 395, SEQ ID NO: 396 and SEQ ID NO: 397.

In certain aspects of the disclosure, the length of the peptide increases surface expression of the blocking receptor.

In certain aspects, the hinge peptide is derived from leukocyte immunoglobulin-like receptor subfamily B member 1 (LILRB1).

In certain aspects of the disclosure, the hinge comprises a peptide having a degree of flexibility, and the peptide's degree of flexibility modulates the effect of the blocking signal on the activating signal. The peptide may be a flexible peptide and the effect of the blocking signal on the activating signal is an increased inhibition of the activating signal. The flexible peptide may comprise glycine-glutamine repeats and/or glycine-serine repeats.

In certain aspects, the hinge comprises a rigid peptide, and the peptide and the effect of the blocking signal on the activating signal is reduced inhibition of the activating signal. The rigid peptide may include, for example, an alpha-helix, repeats of (XP) where X is any amino acid, and/or repeats consisting of alanine, glutamic acid, and lysine.

In certain aspects, the present disclosure provides engineered immune cells, and methods of making and using the same, wherein activating and blocking receptors are spaced apart by at least an average minimum distance on the immune cell surface.

Thus, in certain aspects, the disclosure provides a method of producing an engineered immune cell, the method including, causing an immune cell to express cell surface activating and blocking receptors. Binding of the activating receptor to an activating ligand on a target cell triggers an activating signal that promotes a cytotoxic response by the engineered immune cell. Binding of the blocking receptor to a blocking ligand on a non-target cell causes the blocking receptor to trigger a blocking signal that inhibits the activating signal. Wherein the receptors remain spaced apart by at least an average minimum distance on the immune cell surface.

The blocking signal of a blocking receptor may invert to an activating signal when a blocking receptor is spaced at a distance less than the average minimum distance from the activating receptor.

In certain aspects, the method also includes determining the distance less than the average minimum distance at which the blocking signal inverts.

In certain methods, the average minimum distance is about 100-1000 angstroms. In certain methods, the average minimum distance is about between about 100 to 200, 200 to 300, 300 to 400, 400 to 500, 500 to 600, 600 to 700, 700 to 800, 800 to 900, or 900 to 1000 angstroms. In certain methods, the average minimum distance is greater or equal to 200 angstroms. In certain methods, the average minimum distance is about 200 angstroms.

In certain methods, each receptor has a ligand binding domain (LBD), a hinge, a transmembrane domain, and an intracellular domain (ICD).

Certain methods further include covalently or non-covalently linking the receptors via a spacer such that the receptors are separated by a known spacing. The spacer may comprise a C- or N-terminal fusion. The receptors may be linked to the spacer via the LBD or ICD of each receptor. The receptors may be linked to the spacer at their respective hinge. The spacer may comprise one or more moieties that allow non-covalent binding of the receptors at their respective hinge. The spacer may comprise, for example, two moieties, that are independently fused to the LBD, ICD, or hinge of each receptor. The receptors may be linked via a spacer that comprises a non-covalent interacting motif that mediates protein-protein interaction, such as leucine zipper. The receptors may be covalently attached via the spacer, and the spacer may comprise a cleavable linker such as a disulfide linker.

In certain aspects, the receptors are linked via a spacer that comprises a rigid peptide linker. The rigid peptide may include, for example, an alpha-helix, repeats of XP where X is any amino acid, and/or repeats consisting of alanine, glutamic acid, and lysine.

In certain aspects, the receptors have physiochemical properties that prevent the receptors from being spaced at a distance less than the average minimum distance. The physiochemical properties may include, for example, opposite charges engineered by design on the receptor sequences, leading to attraction, compared to neutral or similar charges. The physiochemical properties may also or alternatively include, for example, steric effects, non-covalent interactions, and/or van der Waals interactions.

In certain aspects, the present disclosure includes an engineered immune cell comprising a cell surface activating receptor and a cell surface blocking receptor, wherein each of the cell surface activating receptor and the cell surface blocking receptor comprise physiochemical properties that prevent the cell surface activating receptor and the cell surface blocking receptor from being spaced at a distance less than an average minimum distance.

In certain aspects, the average minimum distance is about 100-1000 angstroms. In certain methods, the average minimum distance is about 1000, 900, 800, 700, 600, 500, 400, 300, 200, or 100 angstroms. In certain methods, the average minimum distance is greater or equal to 200 angstroms. In certain methods, the average minimum distance is about 200 angstroms.

In certain aspects, the receptors have physiochemical properties that prevent the receptors from being spaced at a distance less than the average minimum distance. The physiochemical properties may include, for example, opposite charges engineered by design on the receptor sequences, leading to attraction, compared to neutral or similar charges. The physiochemical properties may also or alternatively include, for example, steric effects, non-covalent interactions, and/or van der Waals interactions.

In a further aspect, the present disclosure provides an engineered immune cell comprising a cell surface activating receptor, a cell surface blocking receptor, and a spacer operably associated with the cell surface activating receptor and the cell surface blocking receptor, wherein the spacer is configured to maintain the cell surface activating receptor and the cell surface blocking receptor spaced apart by at least an average minimum distance on the immune cell surface.

In certain aspects, the average minimum distance is about 100-1000 angstroms. In certain methods, the average minimum distance is about 1000, 900, 800, 700, 600, 500, 400, 300, 200, or 100 angstroms. In certain methods, the average minimum distance is greater or equal to 200 angstroms. In certain methods, the average minimum distance is about 200 angstroms.

In certain aspects, each receptor of the engineered immune cell has a ligand binding domain (LBD), a hinge, a transmembrane domain, and an intracellular domain (ICD).

The spacer may covalently or non-covalently link the receptors such that the receptors are separated by a known spacing. The spacer may comprise a C- or N-terminal fusion. The receptors may be linked to the spacer via the LBD or ICD of each receptor. The receptors may be linked to the spacer at their respective hinge. The spacer may comprise one or more moieties that allow non-covalent binding of the receptors at their respective hinge. The spacer may comprise, for example, two moieties that are independently fused to the LBD, ICD, or hinge of each receptor. The receptors may be linked via a spacer that comprises a non-covalent interacting motif that mediates protein-protein interaction, such as leucine zipper. The receptors may be covalently attached via the spacer, and the spacer may comprise a cleavable linker such as a disulfide linker.

In certain aspects, the receptors are linked via a spacer that comprises a rigid peptide linker. The rigid peptide may include, for example, an alpha-helix, repeats of XP where X is any amino acid, and/or repeats consisting of alanine, glutamic acid, and lysine.

In a further aspect, the disclosure provides a method for treating cancer that includes providing an engineered immune cell to a patient, wherein the engineered immune cell comprises an activating receptor and a blocking receptor, each expressed on a surface of the engineered immune cell. The activating receptor triggers a cytotoxic signal that promotes a cytotoxic response of the engineered immune cell when the activating receptor binds a first ligand of a target cell. The blocking receptor sends an interfering signal that inhibits the cytotoxic response of the engineered immune cell when the blocking receptor binds a second ligand of the target cell. The receptors remain spaced apart by at least an average minimum distance on the immune cell surface.

In certain methods, the average minimum distance is about 100-1000 angstroms. In certain methods, the average minimum distance is about 1000, 900, 800, 700, 600, 500, 400, 300, 200, or 100 angstroms. In certain methods, the average minimum distance is greater or equal to 200 angstroms. In certain methods, the average minimum distance is about 200 angstroms.

In certain methods, the receptors possess physiochemical properties that prevent the cell surface activating receptor and the cell surface blocking receptor from being spaced at a distance less than an average minimum distance.

In certain aspects, the receptors have physiochemical properties that prevent the receptors from being spaced at a distance less than the average minimum distance. The physiochemical properties may include, for example, opposite charges engineered by design on the receptor sequences, leading to attraction, compared to neutral or similar charges. The physiochemical properties may also or alternatively include, for example, steric effects, non-covalent interactions, and/or van der Waals interactions.

In certain aspects, the immune cell includes a spacer operably associated with the cell surface activating receptor and the cell surface blocking receptor, wherein the spacer is configured to maintain the cell surface activating receptor and the cell surface blocking receptor spaced apart by at least an average minimum distance on the immune cell surface.

In certain methods, each receptor has a ligand binding domain (LBD), a hinge, a transmembrane domain, and an intracellular domain (ICD).

The spacer may covalently or non-covalently link the receptors such that the receptors are separated by a known spacing. The spacer may comprise a C- or N-terminal fusion. The receptors may be linked to the spacer via the LBD or ICD of each receptor. The receptors may be linked to the spacer at their respective hinge. The spacer may comprise one or more moieties that allow non-covalent binding of the receptors at their respective hinge. The spacer may comprise, for example, two moieties that are independently fused to the LBD, ICD, or hinge of each receptor. The receptors may be linked via a spacer that comprises a non-covalent interacting motif that mediates protein-protein interaction, such as leucine zipper. The receptors may be covalently attached via the spacer, and the spacer may comprise a cleavable linker such as a disulfide linker.

DETAILED DESCRIPTION

Figure 1:
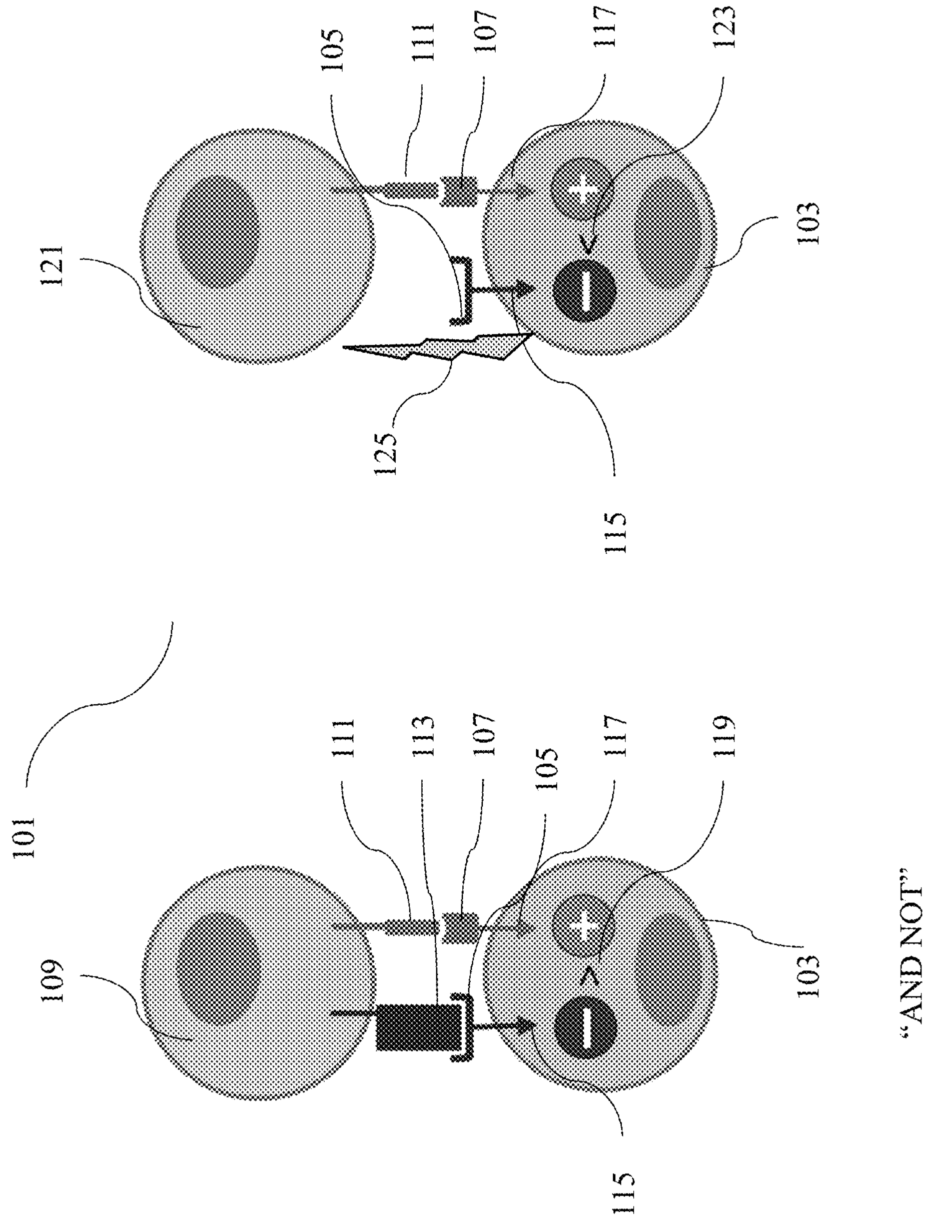
FIG. 1 shows a schematic of the immune cells expressing activating and blocking receptors.

The present disclosure provides engineered immune cells featuring "AND NOT" Boolean logic by expressing engineered activating and blocking receptors. The cells are designed such that when the activating receptors bind to cognate activating ligands on a target cell, they produce an activating signal. If the strength of the activating signal crosses a threshold, it causes a cytotoxic response by the immune cell, killing the cell expressing the cognate ligands. The second of these receptors is a blocking receptor, which is designed to bind to a cognate blocking ligand on the surface of another cell, thereby activating the receptor and causing it to trigger a blocking signal that blocks the activating signal, which prevents the cytotoxic response. The "AND NOT" Boolean logic engineered into the immune cells of the present disclosure makes them ideal for use as therapeutic agents.

Thus, in an exemplary method of the disclosure, a patient diagnosed with a medical condition, such as cancer, is treated with engineered immune cells that target and kill the patient's cancer cells while preserving their normal, healthy cells. One or more cellular samples may be taken from the patient, such as from a blood draw or tumor biopsy. Target cells, such as tumor cells, are identified in the sample. The identified target cells are assayed to determine the levels of expression of one or more cell-surface ligands. This may include, for example, assessing RNA expression profiles for various cell-surface receptors or using antibody probes that bind to certain cell surface receptors. Assaying target cells may determine, for example, that target cells do not express a certain cell surface ligand due to a loss of heterozygosity.

Then, immune cells, such as T cells, are harvested from the patient. These cells are caused to express engineered activating and blocking receptors. The blocking receptor is designed to bind to a blocking ligand expressed on healthy cells of the patient. This blocking ligand may be chosen because it is lost from cancer cells, e.g., due to loss of heterozygosity. The activating receptor is designed to bind to an activating ligand that is expressed on both healthy cells and cancer cells of the patient.

After the engineered immune cells are proliferated, the cells are administered to the patient. The immune cells are designed such that when an immune cell encounters a cancer cell in the patient's body, the activating receptors bind to activating ligands on the cancer cell. This triggers a cytotoxic immune response by the immune cell that kills the cancer cell. When the immune cell encounters a healthy cell the activating and blocking receptors bind to activating and blocking ligands on the healthy cell. Binding of the blocking receptors to blocking ligands inhibits and blocks the cytotoxic immune response triggered by the activating receptors binding to activating ligands. In this way, the engineered immune cells are designed to limit deleterious effects on non-target cells.

FIG. 1 shows a schematic of this "AND NOT" Boolean logic in the immune cells of the present disclosure. In FIG. 1, the immune cells 103 comprise a blocking receptor 105 and an activating receptor 107. A non-target cell 109 expresses an activating ligand 111 and blocking ligand 113. When the immune cell 103 contacts the non-target cell, the activating receptor 107 binds to the activating ligand 111 triggering an activating signal 117. Concurrently, the blocking receptor 105 binds to the blocking ligand 113, triggering a blocking signal 115. As shown schematically, when the immune cell 103 contacts a non-target cell, the strength of blocking signal is greater than the activating signal 119. Binding both blocking ligands and activating ligands causes the "AND NOT" state in the immune cell. The signal from the blocking receptors blocks the activating signal. As such, the activating signal cannot pass the threshold to trigger a cytotoxic response, which prevents a deleterious effect on the non-target cell expressing both ligands.

Conversely, a target cell 121, such as a tumor cell, expresses a blocking ligand 111, but does not express an activating ligand, or expresses an activating ligand at a lower level compared to the non-target cell 109. Thus, when the immune cell 103 contacts the target cell 121, the activating receptor 107 binds to the activating ligand 111, triggering an activating signal 117. As shown schematically, when the immune cell 103 contacts a non-target cell, the strength of the activating signal is greater than the blocking signal 123. When the strength of the activating signal crosses an activation threshold, the immune cell produces a cytotoxic response 125 that kills the target cell 121.

Generally, the cognate antigens chosen for the activating receptors are expressed on both target cells, such as tumor cells, and non-target cells. The selected blocking ligands are expressed only by non-target cells, or expressed at lower levels by target cells compared to non-target cells. In this way, when the engineered immune cells contact target cells, the activating receptors bind to the activating ligands, which leads to the cytotoxic response. In contrast, when the engineered immune cells contact non-target cells, the blocking and activating receptors bind to their cognate blocking and activating ligands. This completes the "AND NOT" Boolean logic, thereby blocking the cytotoxic response. This scheme provides the general means by which the engineered immune cells safely kill target cells while limiting effects on non-target cells.

Engineered immune cells have been used as cancer therapies, such as immunotherapies. Traditionally, engineered immune cells have been designed to target molecular targets such as neo-antigens. Neo-antigens are a class of somatic mutant proteins that are mutated during somatic growth of tumors. They provide ideal targets for immune cell therapies because they comprise variants not found on non-target, healthy cells of a patient. However, very few cancers express neo-antigens. Thus, different targets must be pursued to treat most types of cancer using engineered immune cells. However, in prior immune cell therapies that lacked the blocking receptors of the present disclosure, when the immune cells targeted antigens expressed by healthy and non-health cells, severe adverse effects arose due to non-target activity. In cancer immunology, this phenomenon is known as on-target, off-tumor recognition.

The engineered immune cells and receptors of the present disclosure provide greater flexibility in choice of molecular target. The efficacy of the blocking receptor ensures that non-target effects are limited. Thus, the immune cells of the present disclosure can be designed to target widely expressed, cell surface molecules as the activating ligand. Exemplary ligands include a cell adhesion molecule, a cell-cell signaling molecule, an extracellular domain, a molecule involved in chemotaxis, a glycoprotein, a G protein-coupled receptor, a transmembrane, a receptor for a neurotransmitter or a voltage gated ion channel.

Activating receptors of the present disclosure may be configured to target activating ligands that are encoded by genes with essential cellular functions. Advantageously, this can prevent antigen escape, increasing the long-term efficacy of the engineered immune cells as a therapeutic. By selecting activating ligands encoded by genes with essential cellular functions, loss or escape of the ligand, such as through aneuploidy in cancer cells, is less likely. Thus, the activating ligand may be encoded by a gene that is haploinsufficient, i.e., loss of copies of the gene encoding the ligand are not tolerated by the cell and lead to cell death, or a disadvantageous mutant phenotype. In fact, the engineered immune cells of the present disclosure may be designed to target activating ligands expressed on all cells of patient.

Advantageously, because the immune cells of the present disclosure can be engineered to use widely-expressed activating ligands, several problems can be avoided. For example, prior engineered immune cells often targeted minimally expressed antigens, such as certain neo-antigens. Thus, to ensure an adequate activating signal, prior immune cells were engineered with activating receptors that had very high expression or affinities for their activating ligands.

However, merely increasing the density or affinity of receptors is inadequate to ensure efficacy. High receptor affinity can lead to proportionally severe, toxic effects on non-target cells. It can also hinder an engineered immune cell from disassociating from a target cell, which limits the ability of the immune cell to subsequently bind to and kill other target cells. Further, high affinity can cause receptors to be continually activated. This chronic activation can lead to immune cell exhaustion, reduced generation and persistence, increasing differentiation to undesired phenotypes, and activation-induced immune cell death. Increasing density can lead to similar effects through ligand-independent, tonic signaling.

Use of widely expressed activating ligands, made safe through the use of a blocking receptor, allows the engineered immune cells of the present disclosure to avoid these potential issues.

The blocking receptor can be designed to bind to a cell surface molecule not expressed on the surface of the target cell, or expressed at sufficiently low levels on a target cell. Thus, where the engineered immune cells are used to treat cancer, the blocking ligand may be chosen based on the loss of heterozygosity (LOH) of the target cancer cells, i.e., the cancer cells no longer express the ligand due to a loss of genetic material from one of the homologous chromosomes. Exemplary genes whose expression is frequently lost in cancer cells, for example due to LOH, include, HLA class I alleles, minor histocompatibility antigens (MiHAs), and Y chromosome genes (in males where the homologous chromosome is the X chromosome).

As will be discussed, the immune cells of the present disclosure possess several features that leverage the general nature of the "AND NOT" Boolean logic, to provide effective, target-specific effects while minimizing deleterious non-target effects.

Reduced Activator Expression

Surprisingly, the engineered immune cells of the present disclosure, which express activating and blocking receptors, can be designed to exhibit reduced surface expression of activating receptors when they contact non-target cells.

Figure 2:
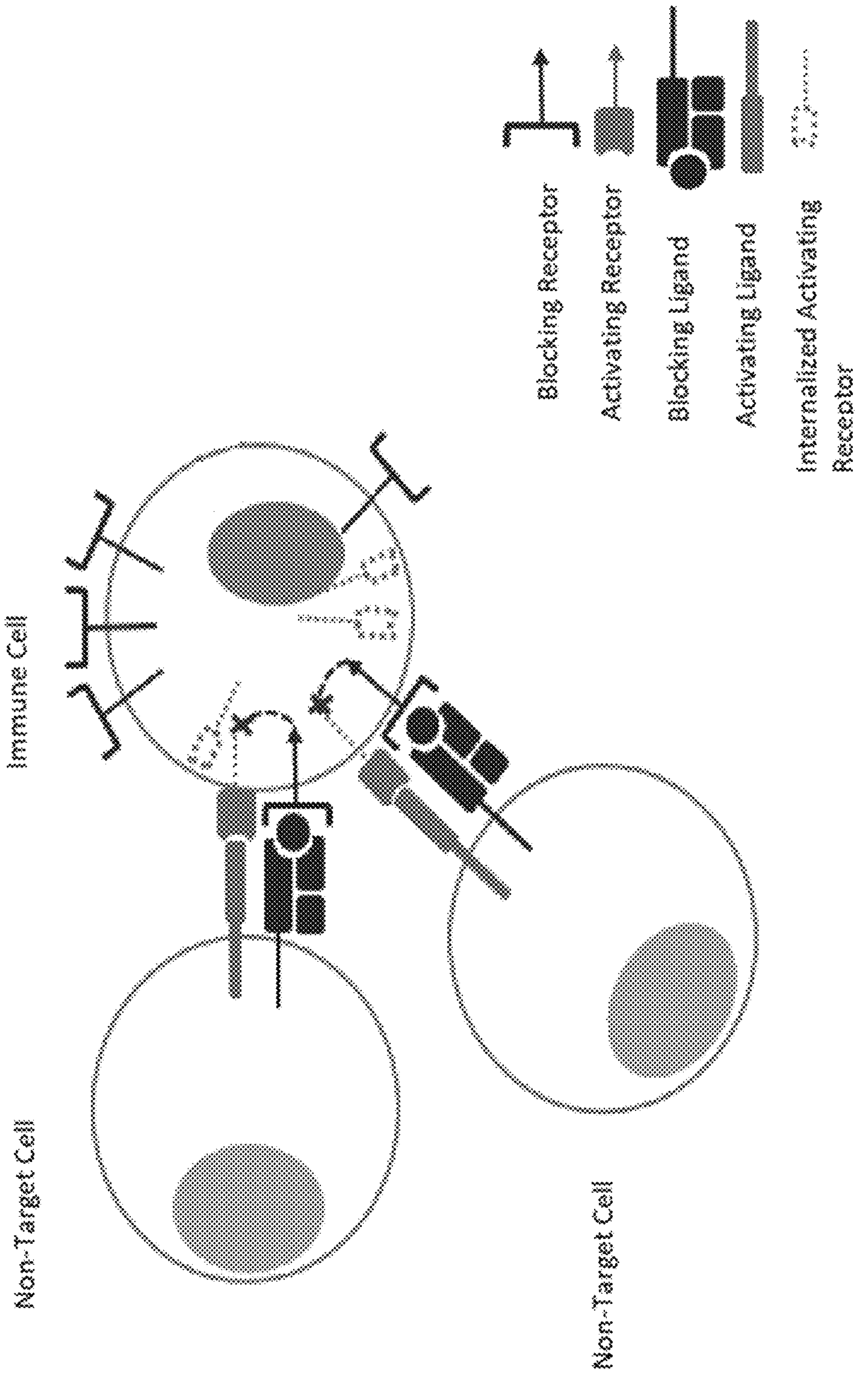
FIGS. 2-3 show reduced surface expression of activating receptors and reversibility of reduced surface expression of activating receptors.

This ability to reduce surface expression is shown schematically in FIG. 2. When an engineered immune cell contacts non-target cells, the blocking receptors and activating receptors bind to their cognate activating ligands and blocking ligands expressed on the non-target cell. As explained, this causes the blocking signal to inhibit the activating signal. Further, activation of the blocking receptors causes reduced surface expression of the activating receptors. The activating receptors may be internalized, such that they are no longer on the surface of the immune cell and able to interact with activating ligands. As a result, the threshold to trigger a cytotoxic response by the immune cell is raised. Thus, the immune cells may temporarily exhibit a reduced propensity to kill cells, which can increase the therapeutic window of the cells.

Figure 3:
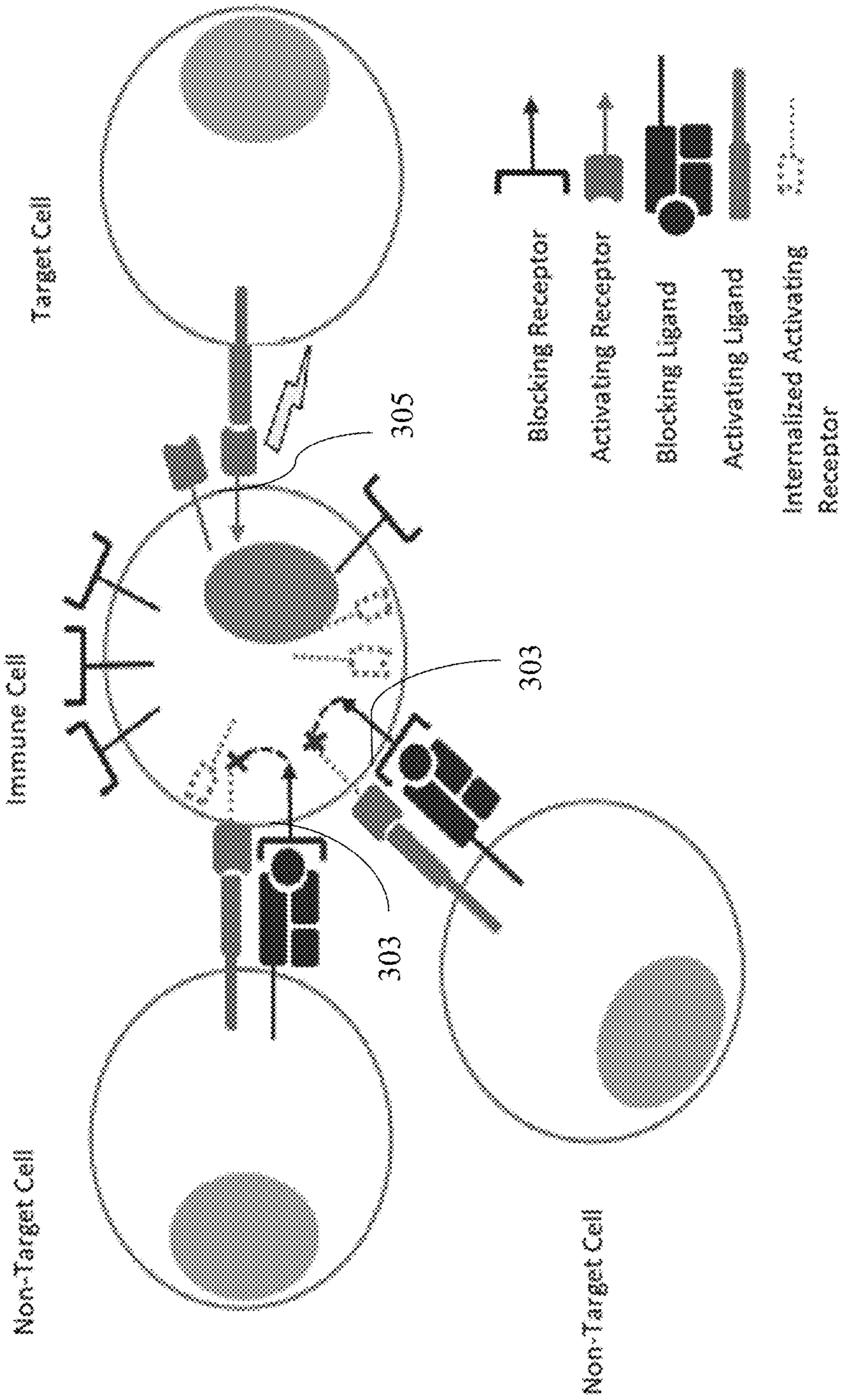

As shown in FIG. 3, when the immune cell contacts a target cell, this reduced surface expression of the activating receptor does not occur and/or is reversed. Thus, when the immune cell encounters a target cell, the activating receptors bind to activating ligands. This provides the activating signal, but also causes the immune cell to reverse the reduced surface expression of the activating receptors. When the activating receptors are expressed on the surface of the immune cell at higher numbers, the activation threshold to trigger the cytotoxic response is reduced. Thus, immune cells in contact with target cells may temporarily exhibit an increased propensity to kill cells.

In certain immune cells of the disclosure, the reduced and/or regained expression of the activating receptor can be localized to a region of the immune cell surface proximate to a target or non-target cell. Thus, returning to FIG. 3, when the immune cell contacts a non-target cells, reduction of the activating receptors occurs in regions 303 proximate to the non-target cells. This can desensitize the immune cell in the regions 303 proximate to each non-target cell, which raises the activation threshold to trigger the cytotoxic response. Similarly, the immune cell can contact a target cell, and reduced surface expression of the activating receptor is reversed and/or does not occur in a region(s) 305 proximate to the target cell(s). This allows the region 305 proximate to the target cell to experience a local activation signal sufficient to trigger a localized cytotoxic response.

Advantageously, these localized responses can occur as an immune cell simultaneously and/or sequentially contacts target and non-target cells. Thus, as shown in FIG. 3, the immune cells can provide an activating signal localized to a region 305 proximate to a target cell, while also modulating expression of the activating receptor to reduce the activation threshold in the same region. Simultaneously, the immune cell can provide localized blocking signals and localized, reduced expression of the blocking receptor.

Reducing surface expression of the activating receptors. when not in contact with target cells. confers several advantages to the immune cells of the present disclosure. For example, if an immune cell circulates away from target cells, such as in a tumor, the immune cell is presumably more likely to contact non-target cells. By reducing the surface expression of the activating receptor in response to a lack of target cells, the immune cell increases its activation threshold, which can temporarily reduce the propensity of the immune cell to trigger a cytotoxic response. This designed feature of the engineered immune cells acts as a "safe mode", which enhances the safety and protective effects provided by the "AND NOT" Boolean logic, and further limits deleterious effects caused by the immune cells.

Further, while in this "safe mode", fewer activating receptors are available to activate. Thus, the immune cells of the present disclosure are less likely to experience chronic activation or ligand-independent tonic signaling. As a result, the immune cells are less susceptible to exhaustion, differentiation, and activation-induced immune cell death, while concurrently exhibiting high generation and persistence.

An additional and important feature of this reduced expression is that it does not extend to the engineered blocking receptors. Only the engineered activating receptors experience appreciable amounts of reduced expression. This ensures the safety profile of the immune cells of the present disclosure is maintained.

Thus, the present disclosure provides an engineered immune cell with an activating receptor and blocking receptor expressed on a surface of the engineered immune cell, wherein binding of the activating receptor to an activating ligand on a target cell promotes a cytotoxic response by the engineered immune cell, and binding of the blocking receptor to a blocking ligand causes the engineered immune cell to exhibit reduced surface expression of the activating receptor.

The present disclosure also provides a method for treating a cancer that includes providing an engineered immune cell to a patient, wherein the engineered immune cell comprises an activating receptor and a blocking receptor, each expressed on a surface of the engineered immune cell. When the engineered immune cell encounters a tumor cell of the patient, the activating receptor binds to an activating ligand on the tumor cell while the blocking receptor remains unbound, thereby promoting a cytotoxic response by the engineered immune cell that results in a cytotoxic effect on the tumor cell. When the engineered immune cell encounters a normal cell of the patient the blocking receptor binds to a blocking ligand on the normal cell and causes the engineered immune cell to exhibit reduced surface expression of the activating receptor, thereby causing a signal from the blocking receptor to dominate a signal from the activating receptor and prevent the cytotoxic response by the engineered immune cell.

Micro-Clusters

A further advantageous feature of the engineered immune cells disclosed herein is that the cells and receptors can be designed such that the activating and blocking receptors form micro-clusters on the surface of the immune cell. This ability to form micro-clusters provides an engineered immune cell with the ability to sense its proximity to target/non-target cells and provide an appropriate, localized response.

Figure 20:
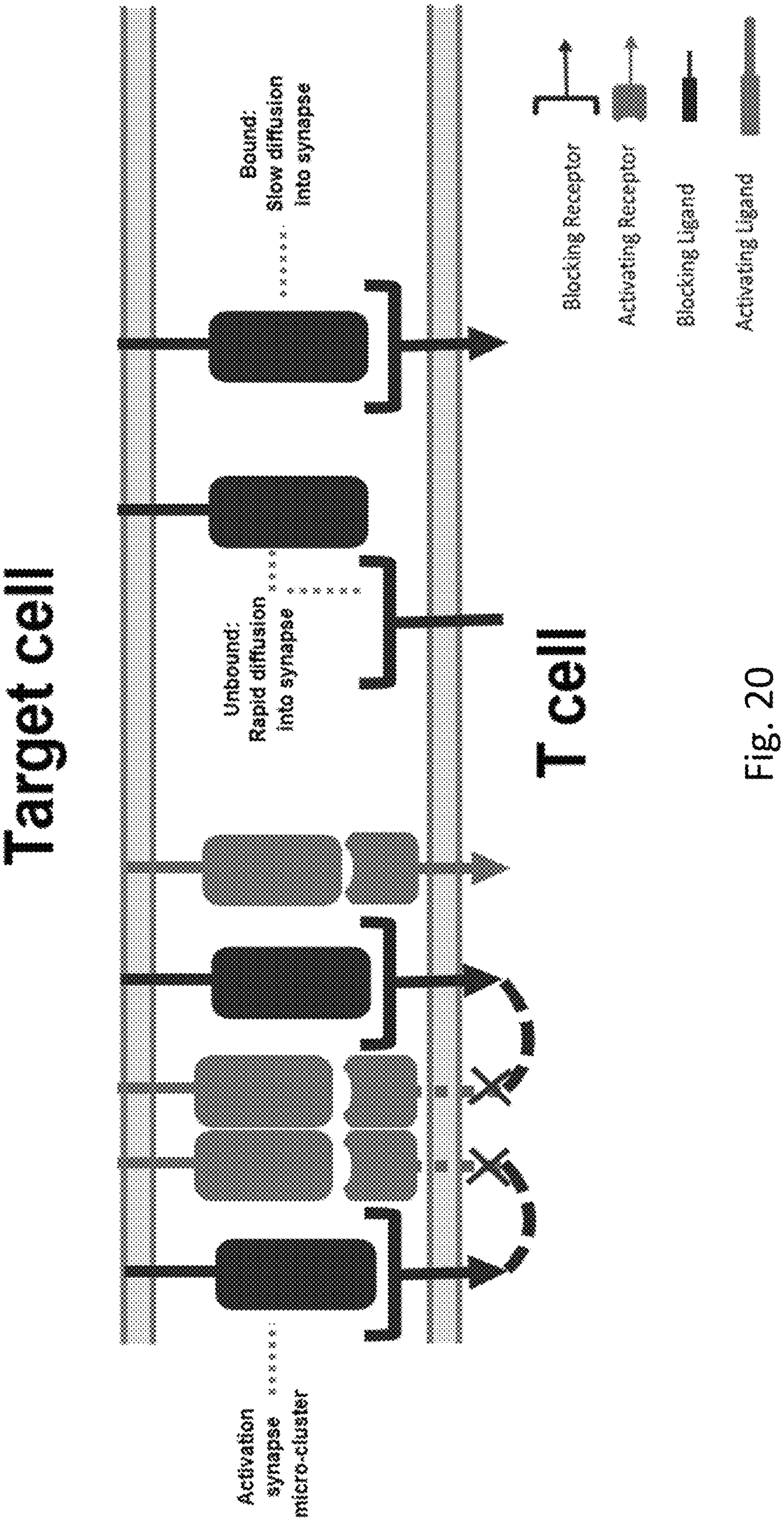
FIG. 20 shows a schematic of micro-clustering.

FIG. 20 shows a schematic of the micro-clustering behavior. When an immune cell encounters a target or non-target cell, its activating/blocking receptors bind to cognate ligands on the encountered cell(s). Cross-talk between these bound receptors and unbound receptors on the surface of the immune cell causes the unbound receptors to diffuse to a region on the immune cell surface proximate to the encountered cell(s). When the receptors diffuse into this region, they form a micro-cluster in which the ligand binding domains of the receptors locate in an activation synapse between the immune cell and the encountered cell(s).

Forming a micro-cluster with both activating and blocking receptors ensures that, when the blocking receptors are activated in the presence of an appropriate ligand on a non-target cell, the blocking signal is triggered proximate to the activation signal. This ensures that the blocking receptors can provide a localized inhibitory effect on the activation signal, thereby protecting the non-target cell. Thus, the micro-clusters enhance the "AND NOT" Boolean logic conferred by the activating and blocking receptors.

Advantageously, the engineered immune cells can be configured such that the activating and/or blocking ligands on target and/or non-target cells to experience a similar clustering effect on the surface of the encountered cell(s). Unbound activating and blocking ligands diffuse into an area on the target/non-target cell surface proximate to the immune cell, and become available for binding to a cognate receptor in the activation synapse.

Receptors are held in place on the surface of the immune cell by binding to cognate ligands in the activation synapse. This ensures that the receptors remain confined to a micro-cluster while the immune cell is in contact with a target/non-target cell. Maintaining the receptors within a micro-cluster helps assure that adequate numbers of activating and/or blocking receptors are within a region proximate to an encountered cell(s) to provide the requisite activating or blocking signal. It also increases the relative strength of both the activating and blocking receptors, which widens the therapeutic window of the immune cells of the disclosure.

The ability of the receptors to form micro-clusters also enhances the localized, reduced expression of the activating receptors when an immune cell encounters a non-target cell. By bringing activating and blocking receptors in close proximity, e.g., within the confines of a micro-cluster, the effect of cross-talk between the receptors is increased. This cross-talk leads to localized, reduced expression of the activating receptors in the micro-cluster.

Thus, the present disclosure provides an engineered immune cell comprising activating and blocking receptors on a surface of the engineered immune cell. When the engineered immune cell encounters a tumor cell, a first plurality of the activating receptors diffuse into a first region on the surface of the engineered immune cell and form a first micro-cluster proximal to the tumor cell that promotes a cytotoxic response by the engineered immune cell that results in cytotoxic effects on the tumor cell. When the engineered immune cell encounters a normal cell, a second plurality of the activating and blocking receptors diffuse into a second region on the surface of the engineered immune cell and form a second micro-cluster proximal to the normal cell, wherein the blocking receptors in the second micro-cluster inhibit cytotoxic effects on the normal cell.

The present disclosure also includes a method for treating cancer, the method comprising providing an engineered immune cell to a patient, the engineered immune cell comprising activating and blocking cell-surface receptors. When the engineered immune cell encounters a normal cell, a first plurality of the activating and blocking receptors collect into a micro-cluster within a region of the cell-surface of the engineered immune cell proximal to the normal cell. Binding of one of the blocking receptors in the micro-cluster to a blocking ligand on the normal cell inhibits breakup of the micro-cluster. The engineered immune cell kills tumor cells that exhibit an activating ligand bound by the activating receptor and do not exhibit the blocking ligand such that the blocking receptor remains unbound.

Multiplex and Localized Signaling

Figure 21:
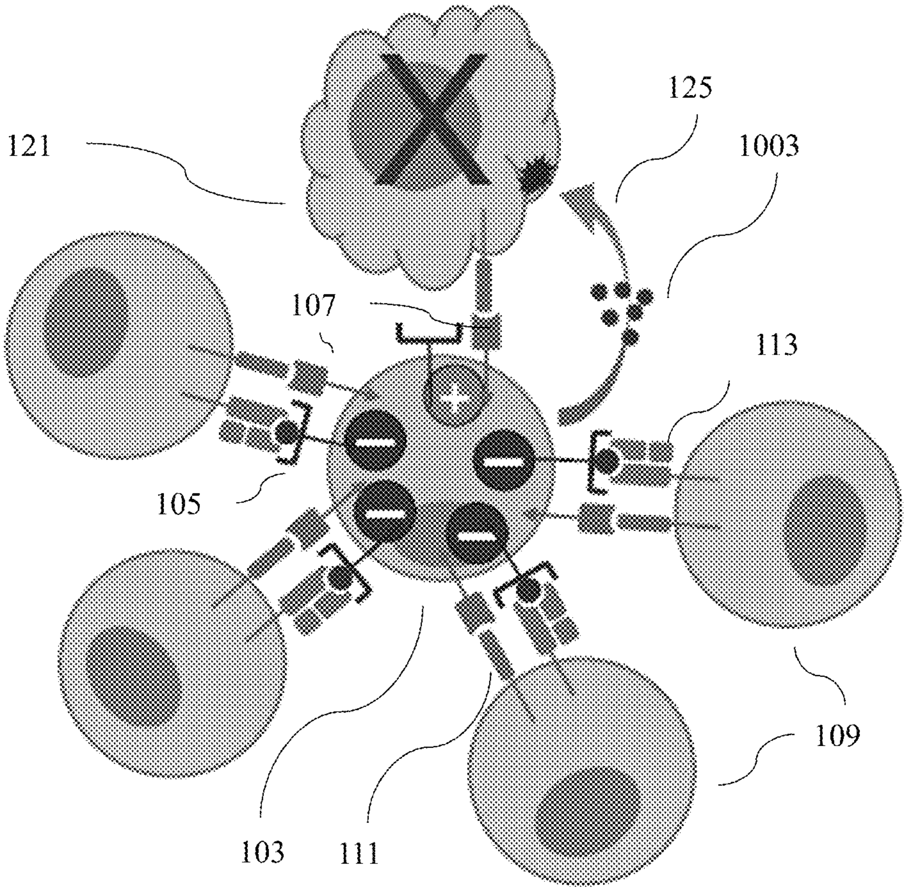
FIG. 21 shows a schematic of multiplex and localized signaling by the activating and blocking receptors.

The engineered immune cells of the present disclosure have been designed to exhibit multiplex and localized activity. A shown in FIG. 21 an engineered immune cell 103 can simultaneously contact both target cells 121 and non-target cells 109. On regions of the immune cell 103 surface proximate to a non-target cell, the activating receptors 107 and blocking receptors 105 bind to activating ligands 111 and blocking ligands 113 on the non-target cell. As a result, a localized blocking signal inhibits a cytotoxic response 125 by the immune cell on the proximate non-target cell. Simultaneously or sequentially, the immune cell 103 can contact a target cell 121. The activating receptor 107 binds to the activating ligand 111 on the target cell 121. This causes a localized cytotoxic response 125, which may release cytotoxic granules 2103. The cytotoxic response only targets the target cell 121. The localized inhibition of the cytotoxic response in areas proximate to the non-target cells 109 protects them from an undesired immune response.

Thus, the present disclosure provides an engineered immune cell that includes activating and blocking receptors on the surface of the cell. When the engineered immune cell encounters a tumor cell and a healthy cell, a first region of the activating and blocking receptors form proximal to the healthy cell and blocking receptors in the first region inhibit cytotoxic effects on the healthy cell. Simultaneously, a second region of the activating and blocking receptors form proximal to the tumor cell and promotes a cytotoxic response by the engineered immune cell that exhibits cytotoxic effects on the tumor cell.

The present disclosure also provides a method for treating cancer that includes providing an engineered immune cell to a patient. The engineered immune cell has activating and blocking cell-surface receptors. When the engineered immune cell encounters a tumor cell and a healthy cell of the patient, a first set of the activating and blocking receptors collect into a first cell-surface region of the engineered immune cell proximal to the healthy cell in which the blocking receptors inhibit cytotoxic effects of the engineered immune cell on the healthy. Simultaneously, a second set of the activating and blocking receptors collect into a second cell-surface region of the engineered immune cell proximal to the tumor cell in which the activating receptors promote a cytotoxic response by the engineered immune cell that kills the tumor cell.

Dominant Blocking Receptors

The engineered immune cells of the present disclosure can be configured to have blocking receptors that produce a blocking signal that can overwhelm and fully inhibit the activating signal from the activating receptors.

Figure 22:
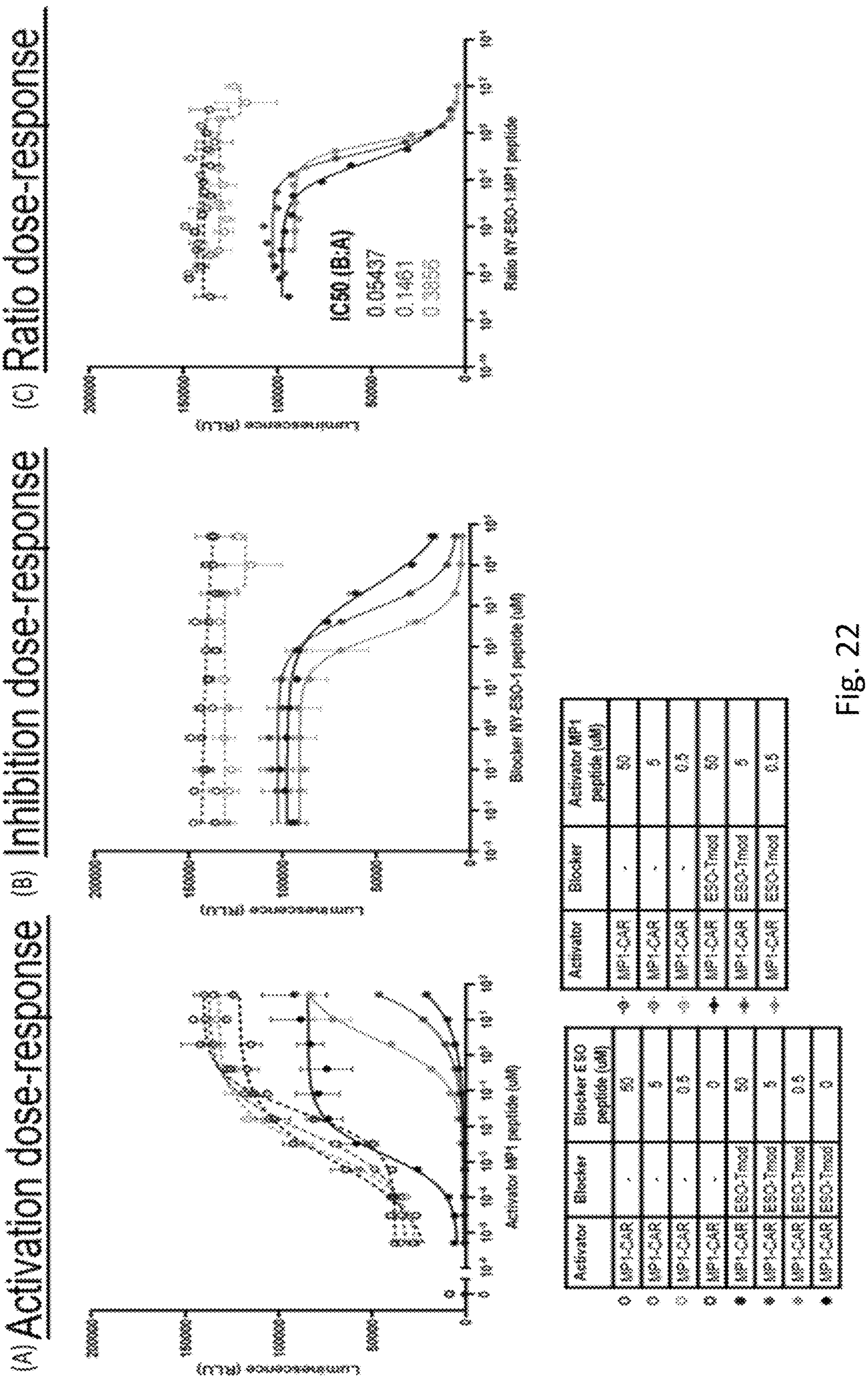
FIG. 22 provides experimental results showing that activity of the blocking receptors is ligand-dependent.

As shown in FIG. 22, which is explained in greater detail below, the cells can be designed to express activating and blocking receptors that, when expressed at equivalent concentrations, it takes less blocking antigen relative activating antigen to inhibit the activating signal. Thus, each blocking receptor can inhibit the activating signal of one or more activating receptors. This means that the blocking signal from a single blocking receptor can dominate and inhibit the activating signal from a single activating receptor. This helps solidify the safety profile of the "AND NOT" Boolean logic used by the immune cells of the present disclosure.

Figure 23:
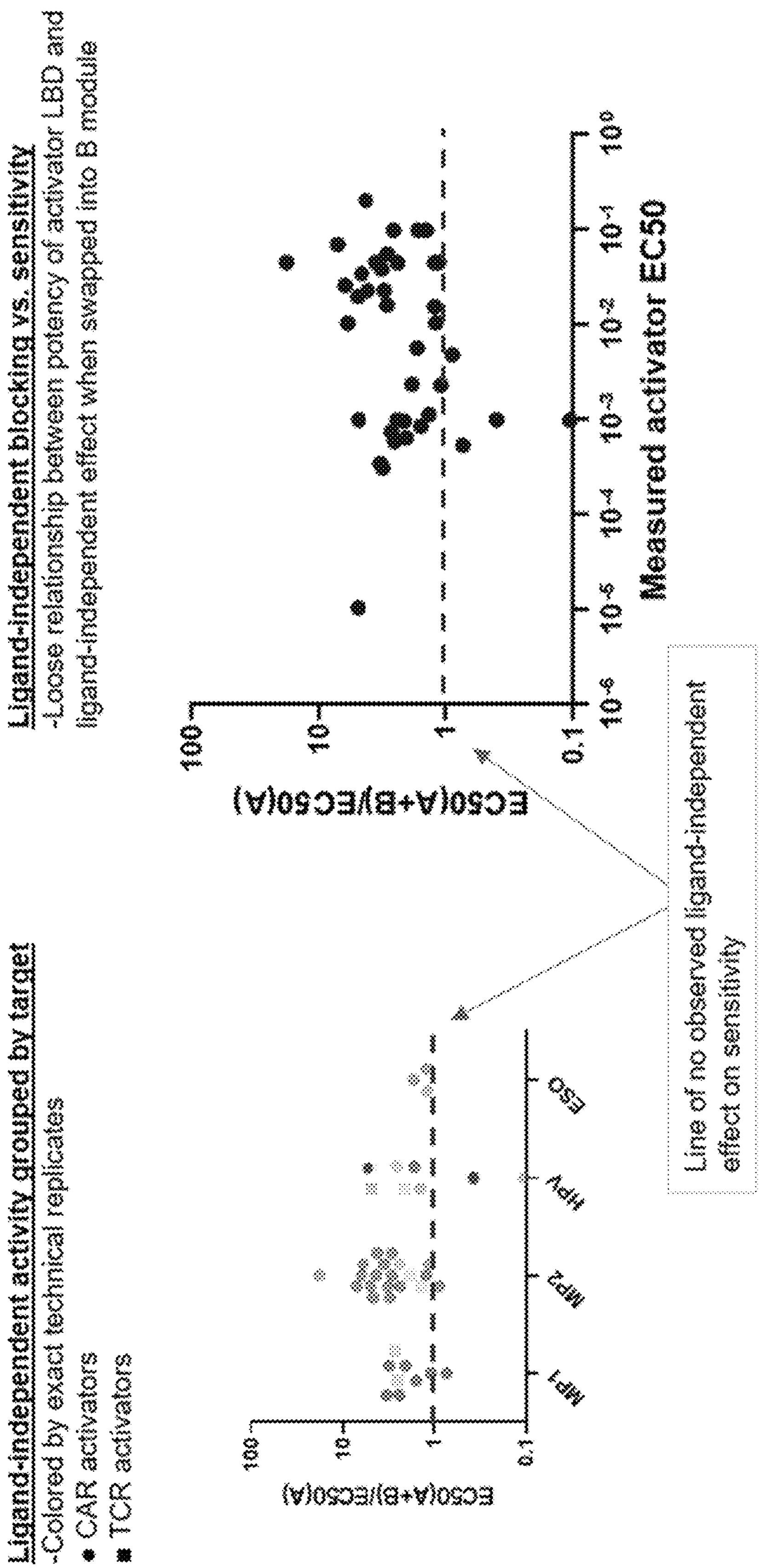
FIG. 23 provides experimental results showing that the blocking receptors cause minimum ligand-independent inhibition of the activating receptors.

As shown in FIG. 23, the blocking receptors can be engineered to provide minimal ligand-independent blocking activity on the activating receptors. As a corollary, the blocking receptors can provide overwhelmingly ligand-dependent activity.

Thus, the immune cells of the present disclosure may include blocking receptors that provide, for example, a less than 10× shift in the $EC_{50}$ of the activating receptors when the immune cells are contacted with the activating ligand in the absence of the blocking ligand. The immune cells of the present disclosure can provide a less than 3× shift in the $EC_{50}$ of the activating receptors when the immune cells are contacted with the activating ligand in the absence of the blocking ligand.

Since the blocking receptors of the present disclosure can provide an overwhelmingly ligand-dependent, dominate blocking signal, the levels of activating ligand and blocking ligand expressed on a non-target cell can be used to inform the appropriate levels of activating and blocking receptor expressed by the engineered immune cells of the present disclosure. The dominate blocking signal provides assurance that ligand quantity can be used as a proxy to inform the levels of activating and blocking receptors that should be expressed in order to assure sufficient inhibition. Moreover, the ligand-dependent nature of the blocking signal means that the expression of the blocking receptor will require little to no adjustment to prevent unintended increases to the $EC_{50}$ of the activating receptors in the absence of the blocking ligand.

Thus, the present disclosure provides methods for producing engineered immune cells that express activating and blocking receptors based on a ratio of a quantity of activating ligands to a quantity of blocking ligands that are expressed in a normal, non-tumor cell of a patient. The activating and blocking receptors may be expressed at a ratio based upon the ratio of the quantity of activating ligands to the quantity of blocking ligands expressed by the normal cell.

The present disclosure also provides an engineered immune cell with an activating receptor on a surface of the engineered immune cell. Binding of the activating receptor to an activating ligand on a target cell causes the activating receptor to trigger an activating signal that promotes a cytotoxic response by the engineered immune cell. The cell also has a blocking receptor. Binding of the blocking receptor to a blocking ligand on a target cell causes the blocking receptor to trigger an inhibitory signal stronger than the activating signal such that the inhibitory signal dominates and blocks the activating signal from the activating receptor, thereby preventing a localized cytotoxic response by the engineered immune cell.

The disclosure further includes a method for treating cancer, the method comprising providing an engineered immune cell to a patient. The engineered immune cell comprises an activating receptor and a blocking receptor, each expressed on a surface of the engineered immune cell. When the engineered immune cell encounters a tumor cell, the activating receptor binds to an activating ligand on the tumor cell and the activating receptor triggers an activating signal in the engineered immune cell that promotes a cytotoxic response by the engineered immune cell that results in a cytotoxic effect on the tumor cell. When the engineered immune cell encounters a normal cell, the activating receptor binds to the activating ligand on the normal cell and the blocking receptor binds to a blocking ligand on the normal cell. This leads to the activating receptor triggering an activating signal in the engineered immune cell and the blocking receptor triggering an inhibitory signal in the engineered immune cell that is stronger than the activating signal, such that the inhibitory signal dominates and blocks the activating signal from the activating receptor, thereby preventing a localized cytotoxic response by the engineered immune cell.

Modulating Activating and Blocking Signals of Receptors

The present disclosure also provides strategies for engineering receptors in a manner that modulates receptor signal strength to ensure strong activation signals and sufficient blocking signals.

Figure 24:
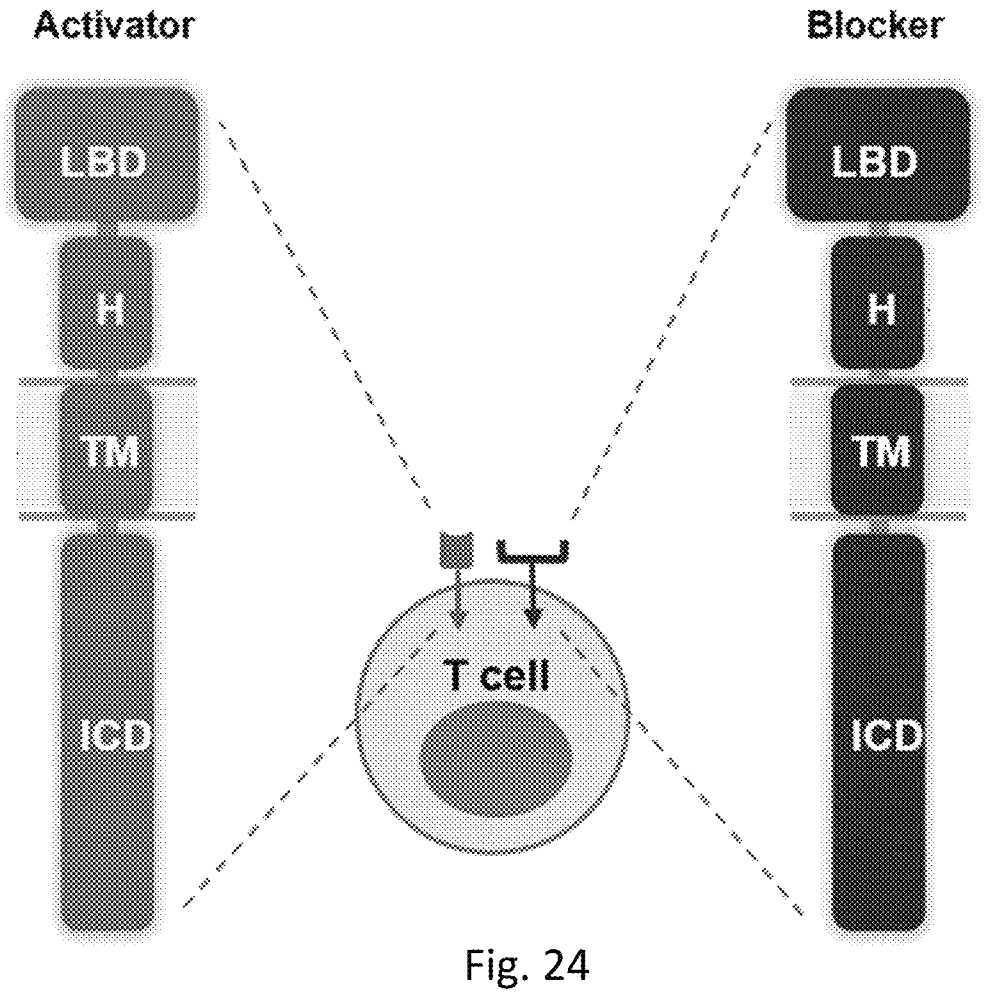
FIG. 24 provides a schematic of the activating and blocking receptors.

FIG. 24 shows a schematic of the blocking and activating receptors of the present disclosure. In general, each type of receptor can comprise four parts, the ligand binding domain ("LBD"), the hinge ("H"), the transmembrane domain ("TM"), and the intracellular domain ("ICD"). Each of these four parts can have an impact on the structure-activity relationship of each receptor. By altering these parts, the behavior of each receptor can be finely tuned to exhibit desired activity. For example, altering these parts can cause the receptors to exhibit varying specificity and affinity for cognate ligands, strengths of activating and/or blocking signals, levels of cross-talk between receptors, and/or receptor surface expression.

The hinge is an extracellular domain between a receptor's extracellular ligand binding domain and transmembrane domain and/or intracellular domain. Surprisingly, the Inventors of the present disclosure have found that, for the activating receptor, a wide variety of hinge lengths and sequences are tolerated. Thus, changes to the activating receptor hinge can provide relatively little change to the structure activity relationship of the activating receptor. For example, changes to the hinge were shown to cause only minimal contributions to the activating receptors' $EC_{50}$, baseline signaling, and maximum signaling.

In contrast, the Inventors of the present disclosure have found that modifications to the hinge can be used to modulate the activity of the blocking receptor, including increases in the surface expression of the blocking receptor and blocking signal strength. Thus, a feature of the present disclosure is that the blocking receptor can be designed using interchangeable hinges that connect an extracellular ligand binding domain to a transmembrane domain and/or an intracellular domain.

Figure 25:
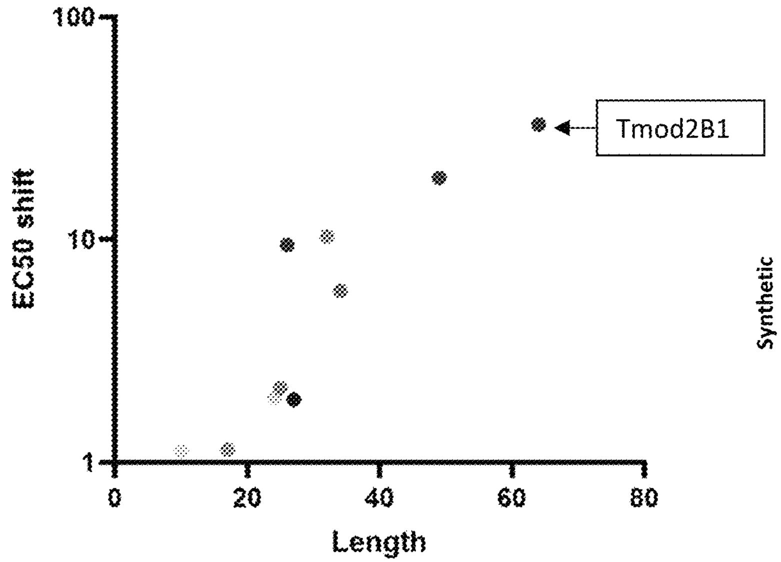
FIG. 25 provides experimental results for the effect the hinge of the blocking receptor has on blocking strength.

The hinges can be designed to have different lengths and flexibilities. As shown in FIG. 24, flexible hinges inure blocking receptors with a greater blocking strength compared to rigid hinges. However, a greater change to blocking strength can be provided by changing the length of the hinge. As shown in FIG. 25, lengthening a hinge from about 25 amino acids to about 35 amino acids confers a significant increase in blocker strength. This increase becomes more dramatic, as the hinge length approaches 65 amino acids in length. As also shown in FIG. 25, the relative flexibility/rigidity of a hinge also impacts the strength of a blocker. Although, this impact is reduced compared to that provided by the hinge length.

Thus, the blocking receptors can be designed with longer and/or more flexible hinges to increase the strength of the blocking receptor's signal or surface expression. In contrast, the blocking receptor can be engineered with shorter and/or more rigid hinges to decrease the strength of the blocking receptor's signal or surface expression. The blocking receptor can be configured to use a hinge selected from a group of hinges that have a known impact on the $EC_{50}$ of the activating ligand for the activating receptor to cause the immune cell to trigger a cytotoxic response. This allows pairs of blocking and activating receptors to be chosen or engineered to exhibit a desired level of activation/inhibition.

Advantageously, as the activating receptor can tolerate a wide variety of hinges, the activating receptors can be engineered with hinges that interact with a blocking receptor at the structural level. Different activator hinges may provide varying levels of interaction with a specific blocker. Thus, various activator hinges can be tested with a particular blocking receptor to determine the identity of activating receptor hinges that lead to increased blocking by a particular blocking receptor. Such testing may include, for example, changing the hinge of an activating receptor and measuring the blocking receptor strength, i.e., the $IC_{50}$, of a particular blocking receptor when a particular activating receptor hinge is used.

Figure 26:
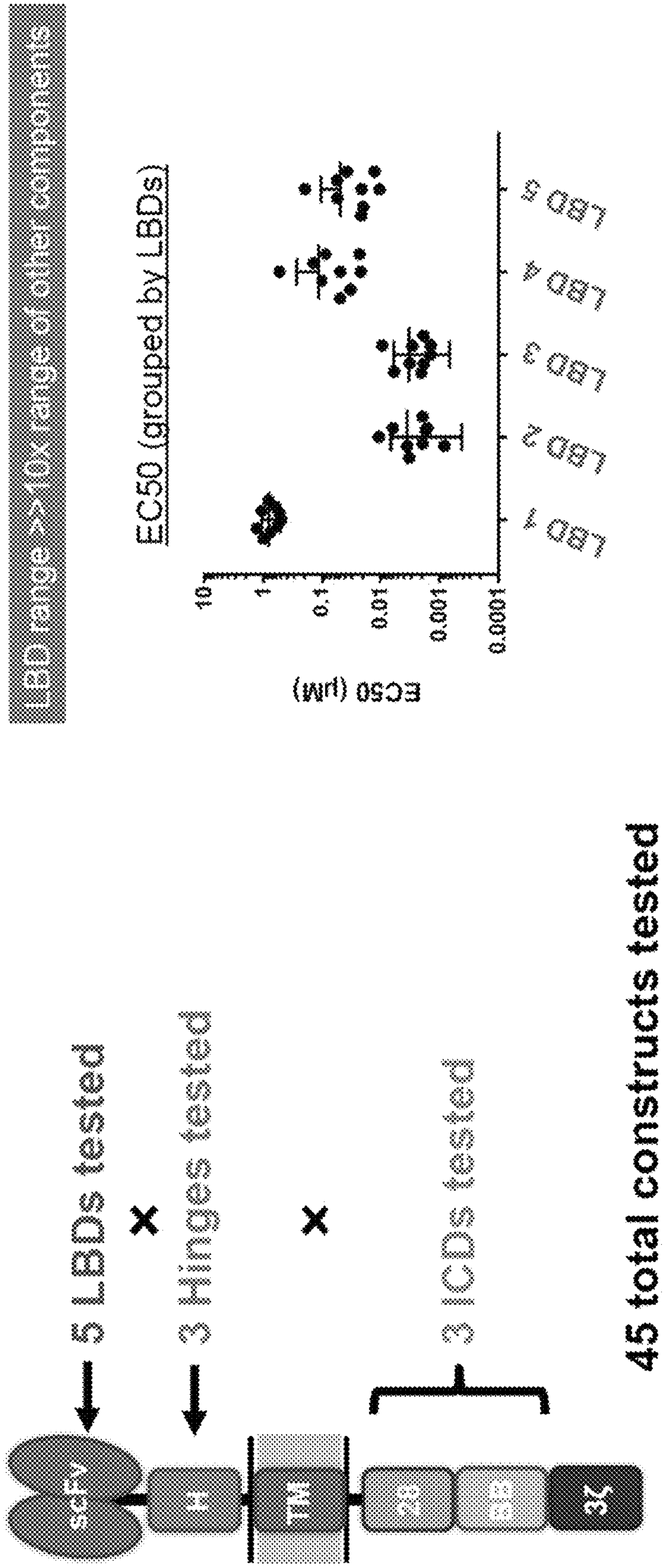
FIG. 26 provides experimental results showing that the identity of the ligand binding domain of the activating receptor drives the activity of the receptor.

The Inventors of the present disclosure found that the identity of the ligand binding domain of the engineered activating receptors has the greatest impact on the structure activity relationship of the receptors. As shown in FIG. 26, different ligand binding domains, which all bind to the same activating ligand, provide effects on the receptors' $EC_{50}$ that differ by orders of magnitude. In contrast, the identity of the hinge and/or intracellular domain provides a smaller impact on the receptors' $EC_{50}$.

Figure 27:
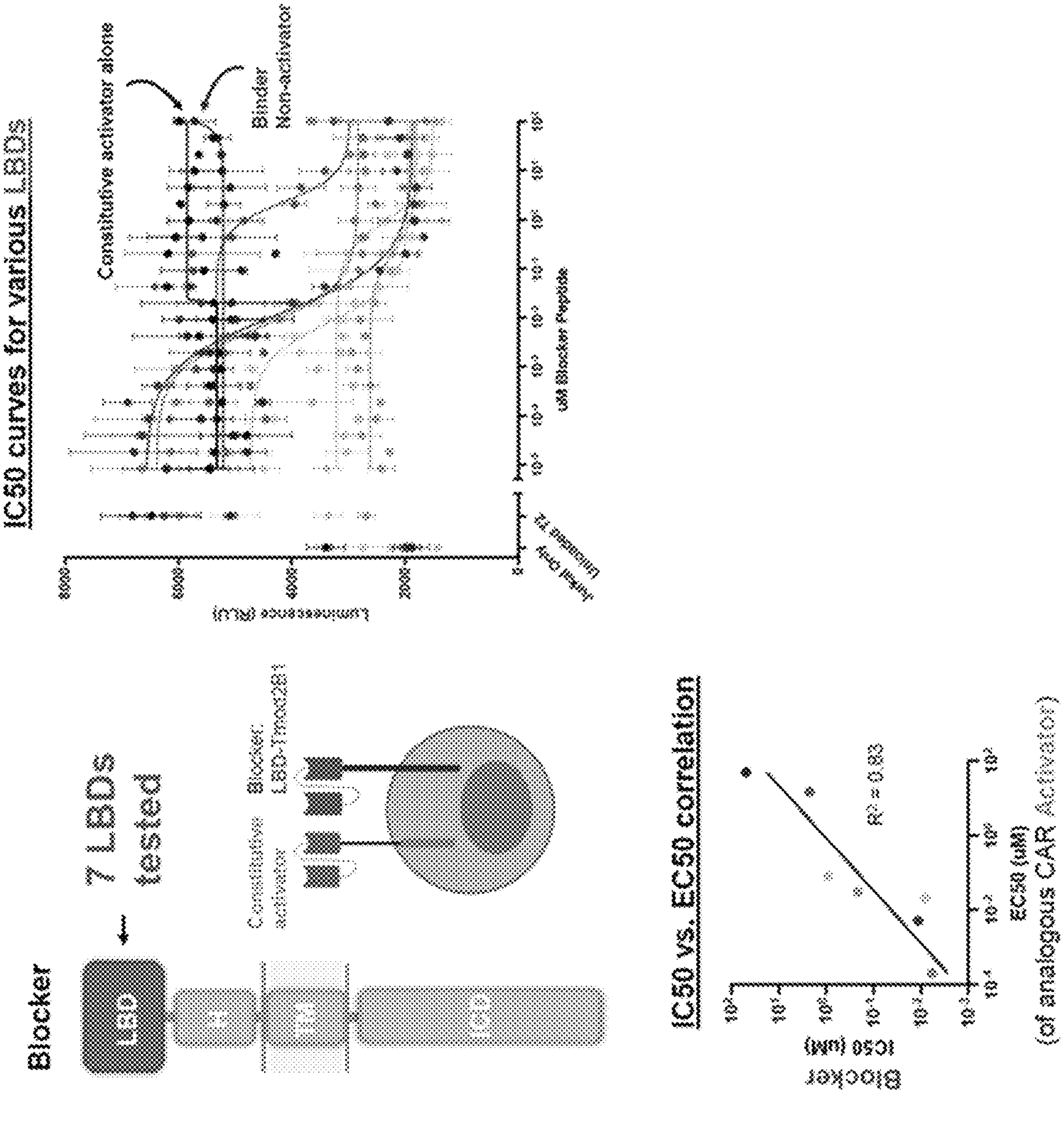
FIG. 27 provides experimental results showing the effect the ligand binding domain has on the blocking receptor.

As with the LBD of the activating receptor, the identity of the blocking receptor LBD can have large effects on the $IC_{50}$ of the engineered immune cells of the present disclosure. This is shown in FIG. 27, where several different ligand binding domains were tested for their effect on the $IC_{50}$ of engineered immune cells. Interestingly, the Inventors of the present disclosure found that when a ligand binding domain was switched between an activating receptor and blocking receptor, the LBD provided a correlative effect on the $IC_{50}$ and $EC_{50}$ of an immune cell.

Figure 32:
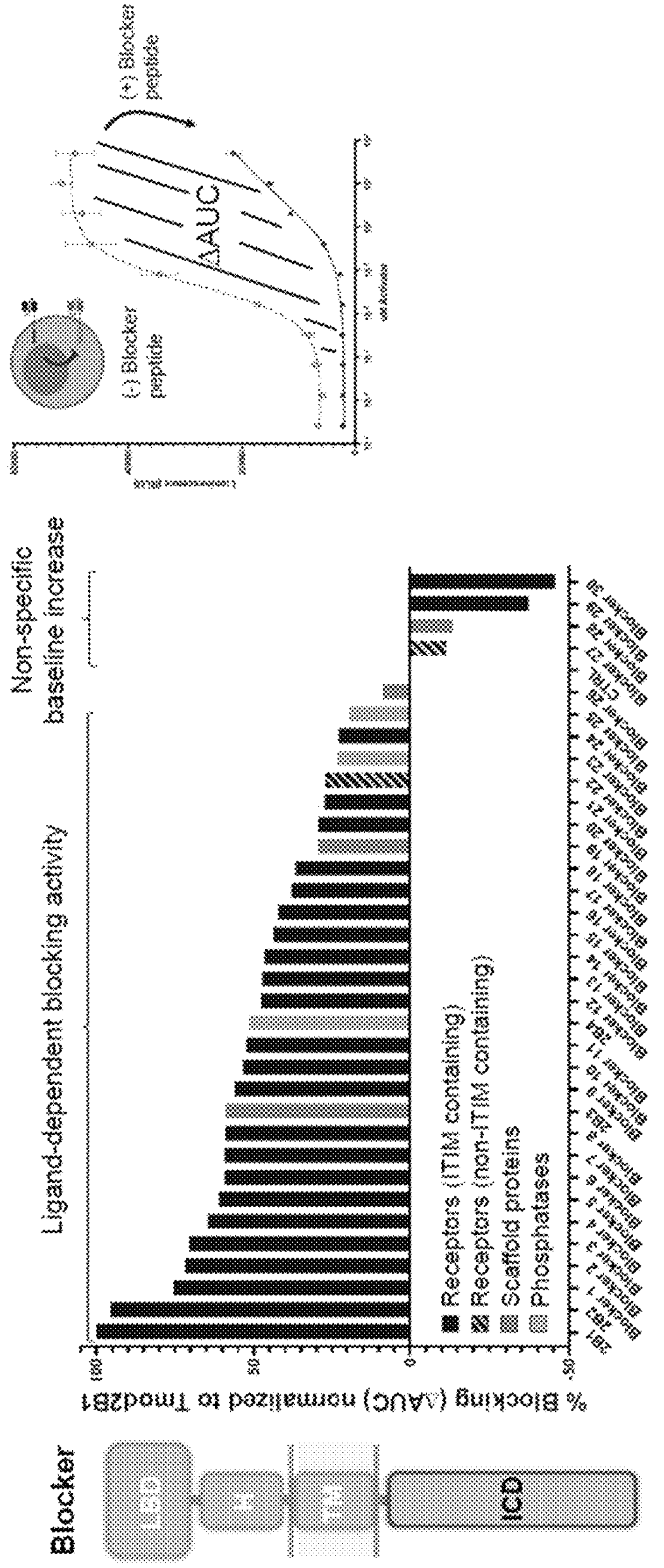
FIG. 32 provides experimental results showing the effect the intracellular domain has on the strength of the blocking receptor signal.

The Inventors of the present disclosure found that a wide variety of commonly used intracellular domains have relatively minimal impacts on the $EC_{50}$ of the activating receptor. Conversely, the Inventors discovered that the intracellular domain of the blocking receptor can have large effects on the strength of the blocking signal. Thus, the intracellular domain of the blocking receptor can be changed to modulate the strength of the blocking signal to ensure adequate inhibition. As shown in FIG. 32, changing the intracellular domain of the blocking receptor can have wide ranging effects on the strength of the blocking signal.

Receptor Cross-Talk

The present disclosure also provides engineered immune cells in which the activity of the activating and blocking receptors is modulated via cross-talk between the receptors.

Figure 33:
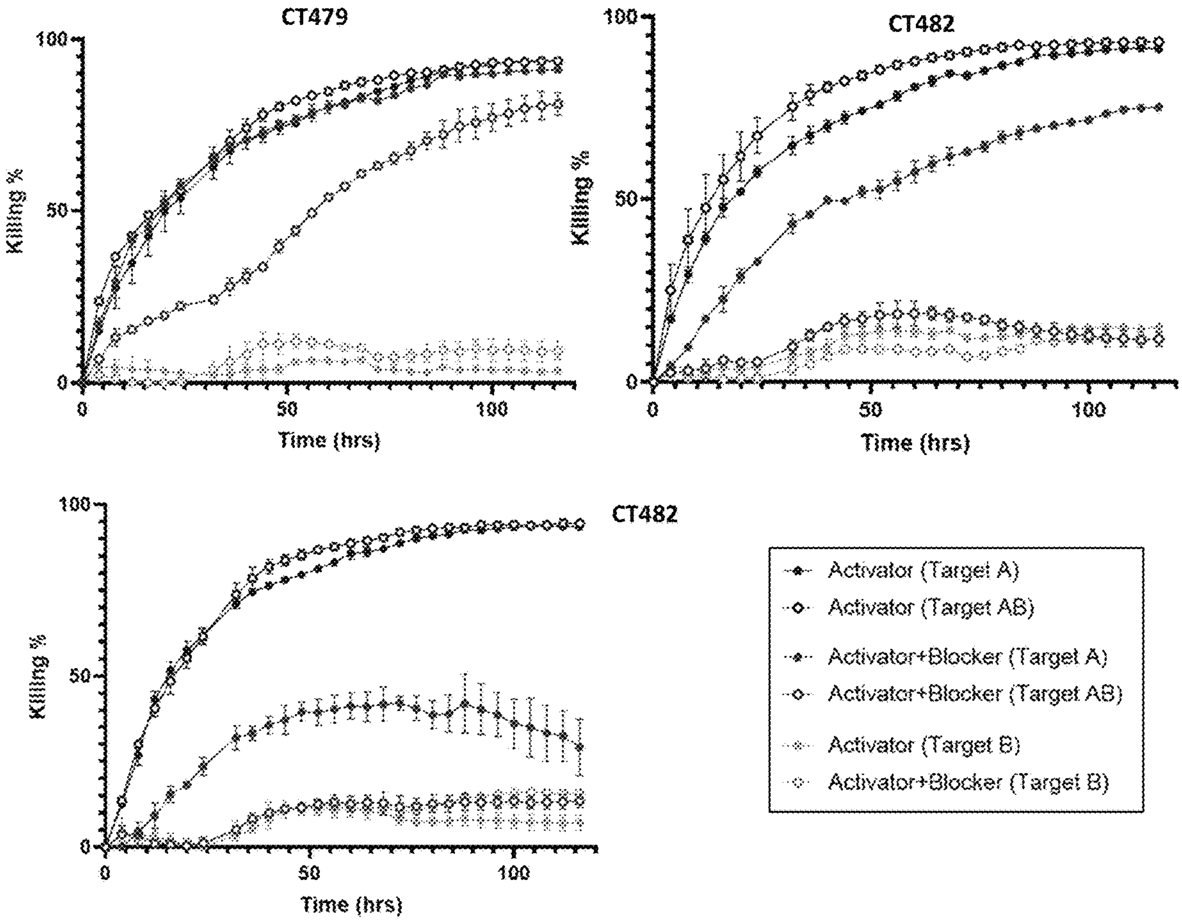
FIGS. 33-34 provide experimental results that indicate cross-talk between receptors.
Figure 34:
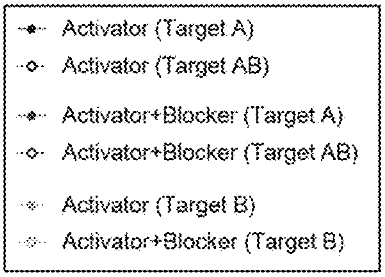
Figure 34:
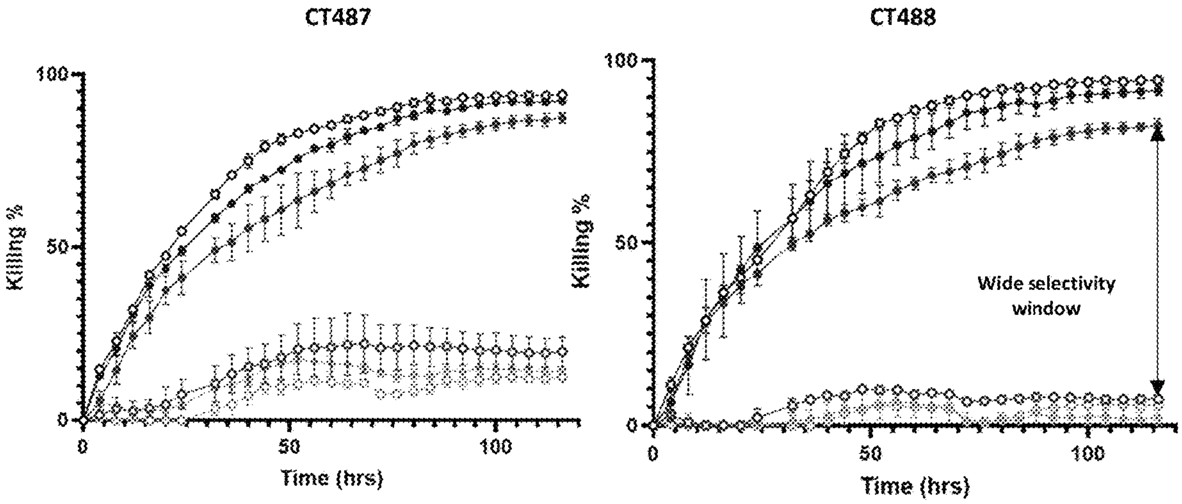

FIGS. 33-34 show the impact receptor cross-talk can have on the ability of the blocking receptor to inhibit the activation signal. Engineered immune cells were created with one of five different activating receptors. Though the activating receptors differed between the cell lines, each targeted the same activating ligand, epidermal growth factor receptor (EGFR), using a different antibody. As shown by the five graphs at the bottom in FIGS. 33-34, each of the different activating receptors provided the immune cells with equivalent abilities to kill target cells. Then, immune cells were created that had one of the five activating receptors and the same blocking receptor. Addition of the blocker caused some of the immune cells, like CT486, to exhibit a significant decrease in the cells' ability to kill target cells. The blocking receptors also provided varying effects in the ability of the immune cells to inhibit the activating signal in the presence of non-target cells.

This disparity in behavior between different activating receptors and a blocking receptor can be attributed to cross-talk between the receptors.

Thus, the present disclosure provides an engineered immune cell that includes an activating receptor that triggers a cytotoxic signal that promotes a cytotoxic response of the engineered immune cell when the activating receptor binds to an activating ligand of a target cell, a blocking receptor that sends an interfering signal that inhibits the cytotoxic response of the engineered immune cell when the blocking receptor binds a blocking ligand, and cross-talk between the activating receptor and the blocking receptor that affects an activation threshold for the cytotoxic response.

The disclosure also includes a method for treating cancer, the method includes providing an engineered immune cell to a patient. The engineered immune cell comprises an activating receptor and a blocking receptor, each expressed on a surface of the engineered immune cell. The activating receptor triggers a cytotoxic signal that promotes a cytotoxic response of the engineered immune cell when the activating receptor binds to an activating ligand of a target cell. The blocking receptor sends an interfering signal that inhibits the cytotoxic response of the engineered immune cell when the blocking receptor binds a blocking ligand. Cross-talk between the activating receptor and the blocking receptor affects an activation threshold for the cytotoxic response.

Modulating Receptor Proximity

The Inventors of the present disclosure made the surprising discovery that the strength of the blocking signal can increase as the distance between activating and blocking receptors decreases, and that when the receptors are separated by a particular average minimum distance, the blocking signal provides a maximum inhibitory effect on an activating receptor. Thus, the present disclosure provides engineered immune cells, and methods of making using engineered immune cells, with activating and blocking receptors spaced apart by at least a minimum average distance on the immune cell surface. The present Inventors also discovered that when activating and blocking receptors are within a certain, close proximity to one another, the activation of the blocking receptor may cause the blocking receptor to invert and provide an activating signal.

In certain engineered immune cells of the present disclosure, this average minimum distance is between about 100 to 200, 200 to 300, 300 to 400, 400 to 500, 500 to 600, 600 to 700, 700 to 800, 800 to 900, or 900 to 1000 angstroms.

Figure 35:
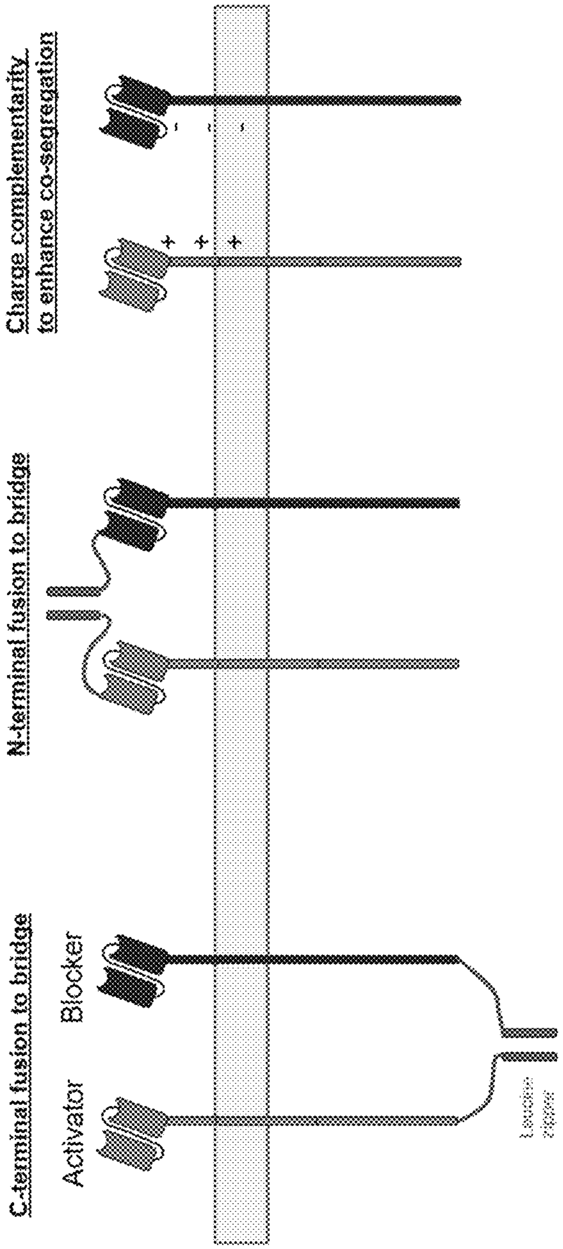
FIG. 35 shows various ways to control the distance between activating and blocking receptors.

As shown in FIG. 35, the Inventors devised several strategies to ensure that the activating and blocking receptors are spaced at a distance to ensure a high blocking signal strength. For example, the receptors can be attached via a C-terminal or N-terminal bridge. Alternatively or in addition, the receptors can be designed to have substituent groups or amino acids with opposing charges to enforce spacing between receptors. Bulky substituent groups or amino acids can also be used to cause steric effects that prevent the receptors from diffusing too close to one another.

Thus, the present disclosure provides engineered immune cells with activating and blocking receptors that possess physiochemical properties that maintain an average minimum distance between the receptors on the cell surface. Physiochemical properties may include, for example, opposing charges on each of the cell surface activating receptor and the cell surface blocking receptor, non-covalent interactions, van der Walls interactions, and/or steric effects.

The present disclosure also or alternatively provides engineered immune cells that have a spacer operably associated with an activating and blocking receptor on the cell surface that is configured to maintain an average minimum distance between the receptors on the cell surface. The spacer may covalently or non-covalently link the activating and blocking receptors. The spacer may include C- or N-terminal fusion that links the receptors. The spacer may alternatively or in addition include two moieties that allow non-covalent binding between the LBD, ICD, and/or hinge of each receptor. The spacer may also or alternatively include a non-covalent interacting motif that mediates protein-protein interaction, such as a leucine zipper.

The distance between the activating and blocking receptors may be controlled by using a spacer that includes a linker. Any linker may be used, and many fusion protein linker formats are known. For example, the linker may be flexible or rigid. Non-limiting examples of rigid and flexible linkers are provided in Chen et al. (Adv Drug Deliv Rev. 2013; 65(10):1357-1369).

Non-limiting exemplary rigid linkers include alpha helix-forming linkers with the sequence of $(EAAAK)_n$ and $(EAAAK)_nA$, wherein n=1-10. Another exemplary rigid linker is a proline rich linker having the sequence $(XP)_n$ where X is any amino acid and is preferably selected from A, G, and E and n=1-10, and glycine-serine linkers with a high ratio of serine to glycine.

The ligand binding domains described herein may be linked to each other in a random or specified order. The ligand binding domains described herein may be linked to each other in any orientation of N to C terminus.

Optionally, a short oligo- or polypeptide linker, for example, between 2 and 40 amino acids (e.g., 2, 3, 4, 5, 6, 7, 8, 9, or 10 amino acids) in length may form the linkage between the domains. The linker is a peptide of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 amino acid residues.

Non-limiting examples of amino acids found in linkers include Gly, Ser, Glu, Gin, Ala, Leu, Iso, Lys, Arg, Pro, and the like.

The linker may be [(Gly)n1Ser]n2, where n1 and n2 may be any number (e.g. n1 and n2 may independently be 1, 2, 4, 5, 6, 7, 8, 9, 10 or more than 10). The linker may be flexible polypeptide linker that is a Gly/Ser linker and comprises the amino acid sequence (Gly-Gly-Ser), (Gly-Gly-Gly-Ser), or (Gly-Gly-Gly-Gly-Ser) which can be repeated n times, where n is a positive integer equal to or greater than 1. For example, n=1, n=2, n=3, n=4, n=5, n=6, n=7, n=8, n=9 and n=10. The linker may include multiple repeats of (Gly Gly Ser), (Gly Ser) or (Gly Gly Gly Ser). Also included within the scope of the invention are linkers described in WO2012/138475 (incorporated herein by reference). In some embodiments, the flexible polypeptide linkers include, but are not limited to, GGS, GGGGS (SEQ ID NO: 226), GGGGS GGGGS (SEQ ID NO: 227), GGGGS GGGGS GGGGS (SEQ ID NO: 228), GGGGS GGGGS GGGGS GG (SEQ ID NO: 229) or GGGGS GGGGS GGGGS GGGGS (SEQ ID NO: 230). In some embodiments, the linkers include multiple repeats of (Gly Gly Ser), (Gly Ser) or (Gly Gly Gly Ser (SEQ ID NO: 231)).

The linker sequence may comprise a long linker (LL) sequence. The long linker sequence may comprise GGGGS, repeated four times. Such a linker may be used to link intracellular domains in a TCR alpha fusion protein of the disclosure. The long linker sequence may comprise GGGGS, repeated three times. The linker sequence may comprise a short linker (SL) sequence. The short linker sequence may comprise GGGGS. A glycine-serine doublet can be used as a suitable linker. Alternatively, domains are fused directly to each other via peptide bonds without use of a linker.

By reducing the G:S ratio in a Gly-Ser linker, the linker can be made more rigid.

The strength of the blocking signal may be the strongest when the activating and blocking receptors are separated by a distance of 0-1000 angstroms. The strength of the blocking signal may be the strongest when the activating and blocking receptors are separated by a distance of 0-50 angstroms, 50-100 angstroms, 100-200 angstroms, 200-300 angstroms, 300-400 angstroms, 400-500 angstroms, 500-600 angstroms, 600-700 angstroms, 700-800 angstroms, 800-900 angstroms, or 900-1000 angstroms. Preferably, the distance is about 200 angstroms.

Thus, the present disclosure provides an engineered immune cell with an activating receptor on the cell surface that triggers a cytotoxic signal that promotes a cytotoxic response of the engineered immune cell when the activating receptors binds to a first ligand on a target cell; and a blocking receptor on the cell surface that sends an interfering signal that inhibits the cytotoxic response of the engineered immune cell when the blocking receptor binds a second ligand of the target cell. Proximity of the blocking receptor to the activating receptor effects an activation threshold for the cytotoxic response, and the activating and blocking receptors physiochemical properties favoring interaction with one another, such that the receptors are spaced apart at an average distance on the immune cell surface.

The present disclosure also provides a method for treating cancer that includes providing an engineered immune cell to a patient, wherein the engineered immune cell comprises an activating receptor and a blocking receptor, each expressed on a surface of the engineered immune cell. The activating receptor triggers a cytotoxic signal that promotes a cytotoxic response of the engineered immune cell when the activating receptor binds a first ligand of a target cell, and the blocking receptor sends an interfering signal that inhibits the cytotoxic response of the engineered immune cell when the blocking receptor binds a second ligand of the target cell. Proximity of the blocking receptor to the activating receptor affects an activation threshold for the cytotoxic response, and the activating and blocking receptors physiochemical properties favoring interaction with one another, such that the receptors are spaced apart at an average distance on the immune cell surface.

The present disclosure also provides a method of producing an engineered immune cell that includes producing an engineered immune cell that expresses activating receptors and blocking receptors based on a determined distance between the receptors, wherein an activation threshold for a cytotoxic response by the immune cell is maximized when the receptors are separated on the cell surface by the determined average distance.

Receptor Types

The present disclosure provides immune cells comprising activating and blocking receptors, which may independently comprise a chimeric antigen receptor (CAR) a T cell receptor (TCR) or a combination of components from CARs or TCRs.

Figure 28:
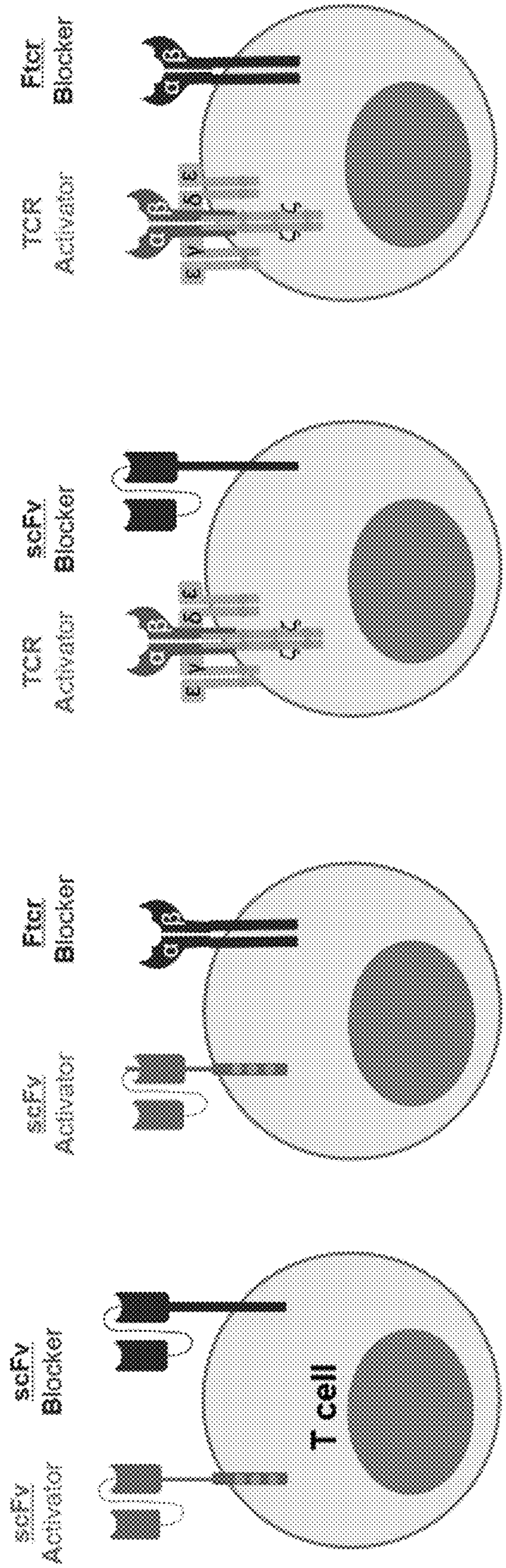
FIG. 28 shows combinations of various CAR- and TCR-based activating and blocking receptors.
Figure 29:
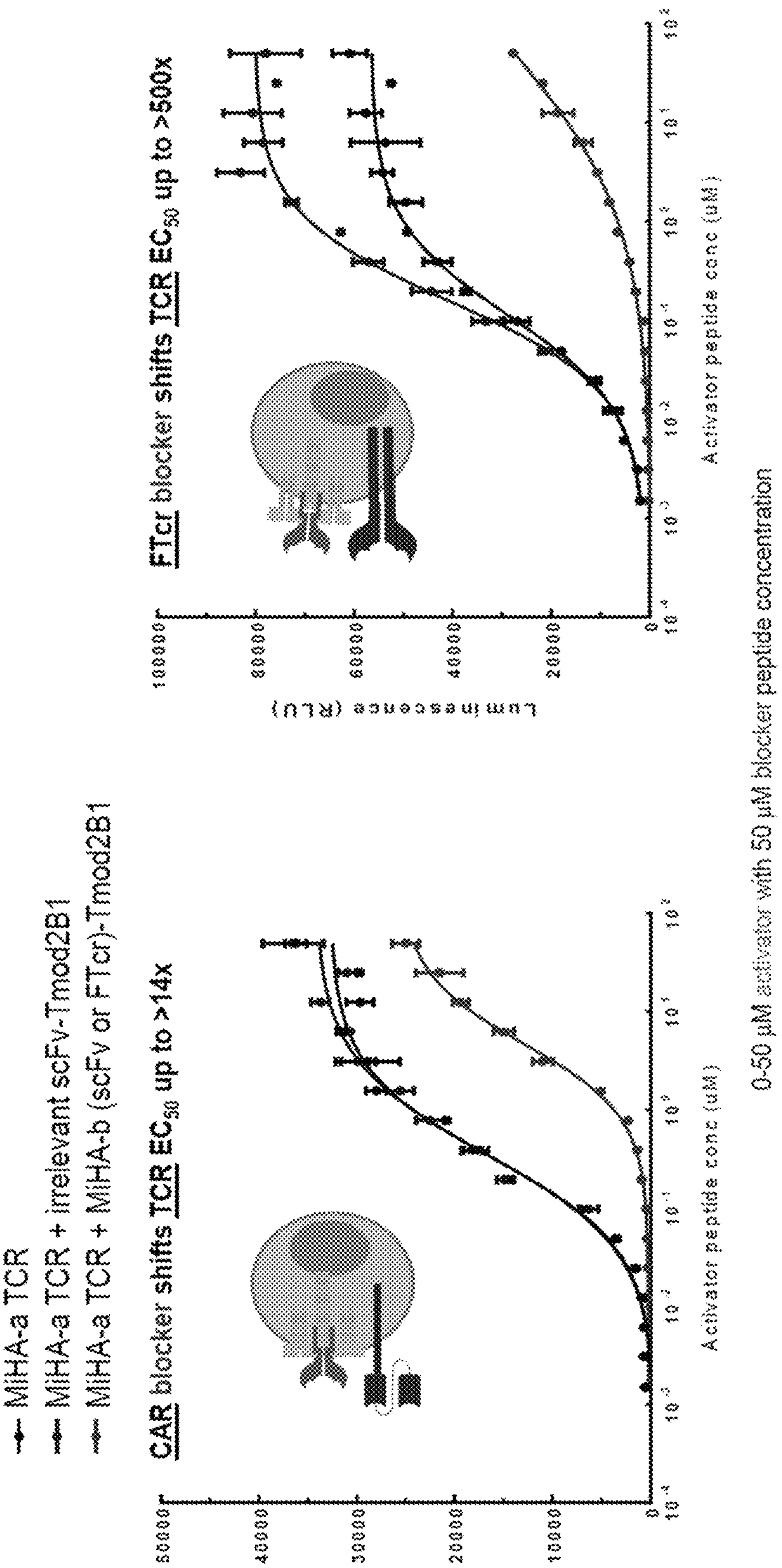
FIG. 29 provides experimental results showing that a CAR-based blocking receptor can inhibit a TCR-based activating receptor.

As shown in FIG. 28, the immune cells of the present disclosure can use receptors that comprise various combinations of TCRs and CARs. For example, as shown in FIG. 29, both a blocking CAR and blocking TCR can effectively inhibit the activation signal of a TCR-based activating receptor.

Moreover, the receptors of the present disclosure can effectively use components of both CARs and TCRs to achieve desired receptor activity.

Figure 30:
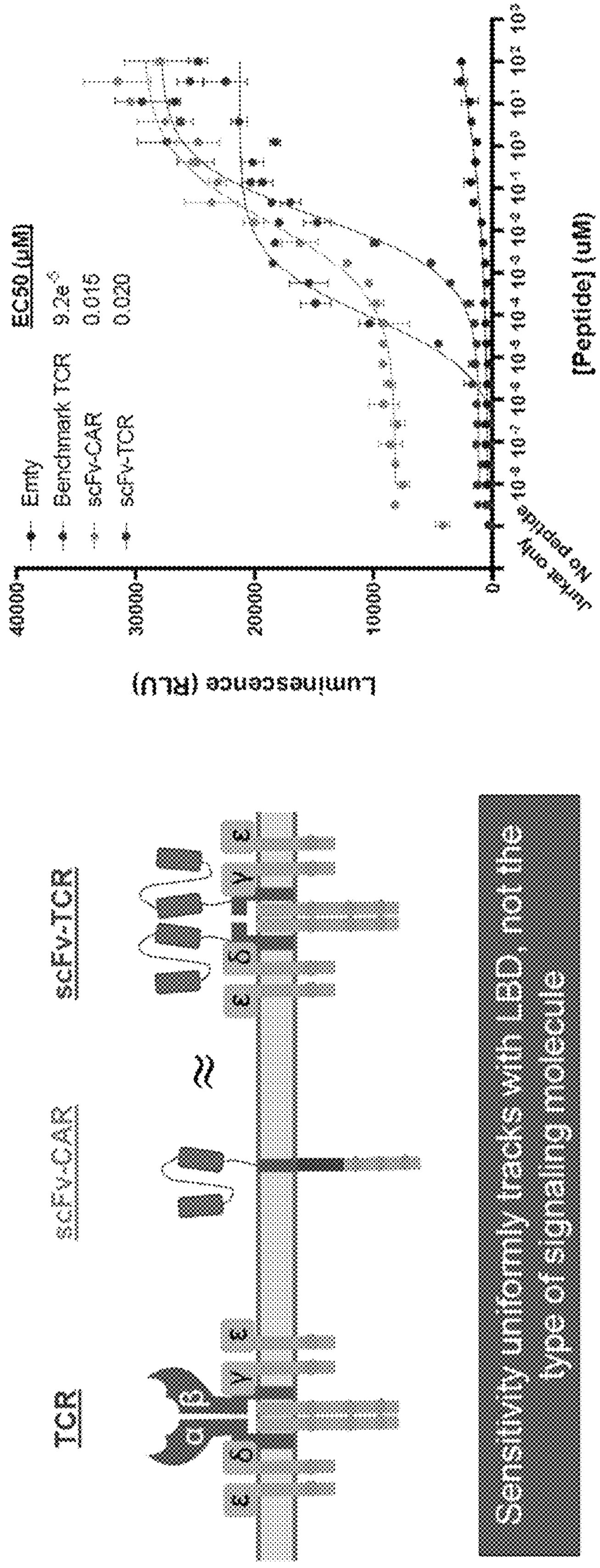
FIG. 30 provides experimental results showing that a CAR ligand binding domain can be used with a TCR activating receptor intracellular domain.

As shown in FIG. 30, the ligand binding domain of a CAR activating receptor can be used with the intracellular domain of a TCR activating receptor, and still provide a target-specific activation signal.

Figure 31:
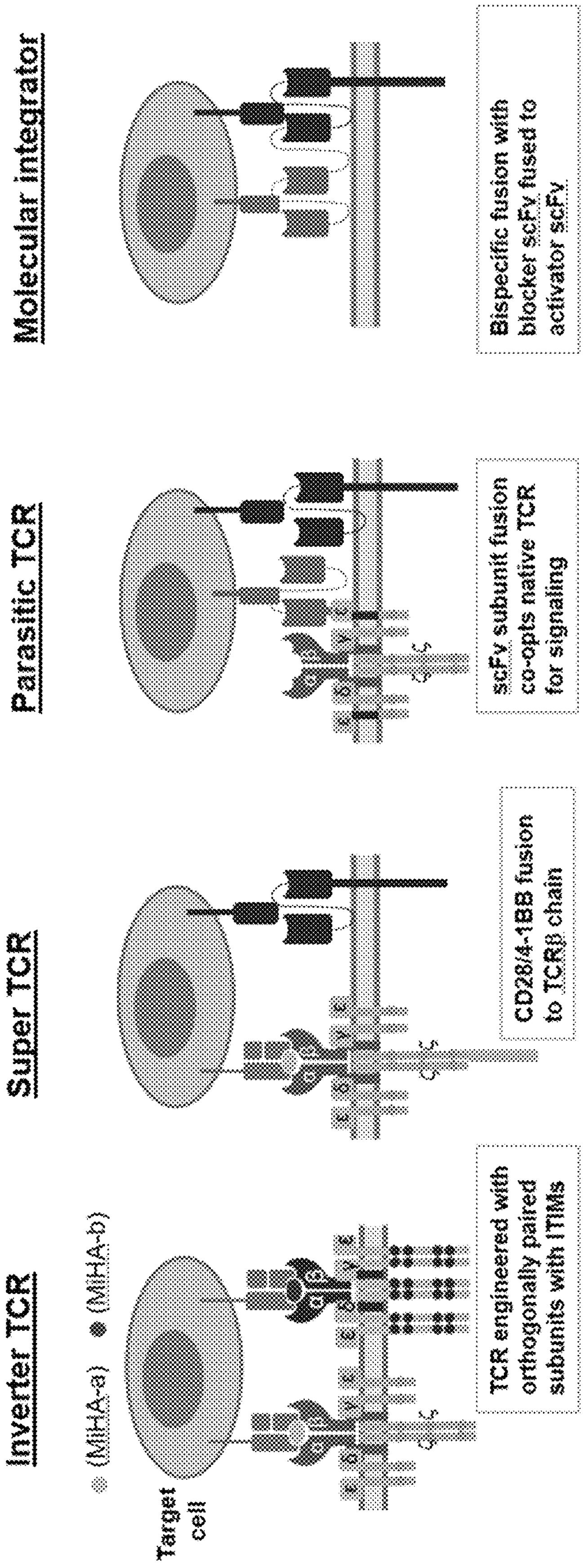
FIG. 31 shows different receptors that can be created in accordance with the present disclosure.

As shown in FIG. 31, the various components of TCRs and CARs can be interchanged to provide receptors with activities beyond blocking and activating receptors. For example, the components can be used to create Inverter TCRs, Super TCRs, Parasitic TCRs, and Molecular Integrators.

In some embodiments, one or more of the blocking receptor and activating receptor comprise a CAR. All CAR architectures are envisaged as within the scope of the instant disclosure.

The CARs of the present disclosure comprise an extracellular hinge region. Incorporation of a hinge region can affect cytokine production from CAR-T cells and improve expansion of CAR-T cells in vivo. Exemplary hinges can be isolated or derived from IgD and CD8 domains, for example IgG1, CD8α, or CD28, such as those disclosed by the Inventors of the present disclosure in PCT International Application No. PCT/US2020/045250 and PCT/US2021/030149, which are incorporated herein by reference in their entirety.

For example, exemplary hinges used in the receptors disclosed herein, which are isolated or derived from CDSa or CD28 include a CDSa hinge comprising an amino acid sequence having at least 80% identity, at least 90% identity, at least 95% identity, at least 99% identity or is identical to a sequence of SEQ ID NOS: 1 or 3 or encoded by SEQ ID NO: 4.

The CARs of the present disclosure can be designed to comprise a transmembrane domain that is fused to the hinge of the CAR. The transmembrane domain may be naturally associated with one of the domains of the CAR, such as the hinge or intracellular domain. For example, a CAR comprising a CD28 co-stimulatory domain might also use a CD28 transmembrane domain. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or synthetic source. When the source is natural, the domain may be derived from any membrane-bound or transmembrane protein. Transmembrane regions may be isolated or derived from (i.e., comprise at least the transmembrane region(s) of) the alpha, beta, or zeta chain of the T-cell receptor, CD28, CD3 epsilon, CD45, CD4, CD5, CD8, CD9, CD16, CD22, CD33, CD37, CD64, CD80, CD86, CD134, CD137, CD154, or from an immunoglobulin such as IgG4.

Alternatively, the transmembrane domain may be synthetic, in which case it can comprise predominantly hydrophobic residues such as leucine and valine. Certain transmembrane domains may comprise a triplet of phenylalanine, tryptophan and valine found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker. The CARs may comprise a CD28 transmembrane domain or an IL-2Rbeta transmembrane domain, such as those disclosed by the present Inventors in PCT International Application No. PCT/US2020/045250 and PCT/US2021/030149, incorporated herein by reference.

For example, the CD28 transmembrane domain may comprise an amino acid sequence having at least 80% identity, at least 90% identity, at least 95% identity, at least 99% identity or is identical to a sequence of SEQ ID NO: 5. The CD28 transmembrane domain may be encoded by a nucleotide sequence having at least 80% identity, at least 90% identity, at least 95% identity, at least 99% identity or is identical to SEQ ID NO: 6. An exemplary IL-2R beta transmembrane domain as disclosed here may comprise an amino acid sequence having at least 80% identity, at least 90% identity, at least 95% identity, at least 99% identity or is identical to SEQ ID NO: 7. In some aspects, an exemplary IL-2Rbeta transmembrane domain is encoded by a nucleotide sequence having at least 80% identity, at least 90% identity, at least 95% identity, at least 99% identity or is identical to a sequence of SEQ ID NO: 8.

The intracellular signaling domains of CARs used as parts of the activating or blocking receptors are responsible for activation of at least one of the normal effector functions of the immune cell in which the CAR has been placed. The term "effector function" refers to a specialized function of a cell. Effector functions of a regulatory T cell, for example, include the suppression or downregulation of induction or proliferation of effector T cells. Thus, the term "intracellular signaling domain" refers to the portion of a protein which transduces the effector function signal and directs the cell to perform a specialized function.

While usually an entire intracellular signaling domain can be employed, in many cases it is not necessary to use the entire domain. To the extent that a truncated portion of the intracellular signaling domain is used, such truncated portion may be used in place of the intact chain as long as it transduces the effector function signal. In some cases, multiple intracellular domains can be combined to achieve the desired functions of CAR-T cells of the instant disclosure. The term intracellular signaling domain is thus meant to include any truncated portion of one or more intracellular signaling domains sufficient to transduce the effector function signal.

Examples of intracellular signaling domains for use in the CARs of the instant disclosure include the cytoplasmic sequences of the T cell receptor (TCR) and co-receptors that act in concert to initiate signal transduction following antigen receptor engagement, as well as any derivative or variant of these sequences and any synthetic sequence that has the same functional capability. In certain receptors of the disclosure, the intracellular activation domain ensures that there is T cell receptor (TCR) signaling necessary to activate the effector functions of the CAR-T cell.

The CAR intracellular domains of the instant disclosure may comprise at least one cytoplasmic activation domain. The at least one cytoplasmic activation domain can be a CD247 molecule (CD3ζ) activation domain, a stimulatory killer immunoglobulin-like receptor (KIR) KIR2DS2 activation domain, or a DNAX-activating protein of 12 kDa (DAP12) activation domain, such as those disclosed by the present inventors in PCT International Application No. PCT/US2020/045250 and PCT/US2021/030149, which are incorporated by reference.

For example, the CD3z activation domain comprises an amino acid sequence having at least 80% identity, at least 90% identity, at least 95% identity, at least 99% identity or is identical to SEQ ID NO: 9 and/or encoded by a nucleotide sequence having at least 80% identity, at least 90% identity, at least 95% identity, at least 99% identity or is identical to a sequence of SEQ ID NO: 10.

It is known that signals generated through a TCR alone can be insufficient for full activation of a T cell, and that a secondary or co-stimulatory signal may be also required. Thus, T cell activation can be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory or inhibitory manner. Exemplary cytoplasmic signaling sequences are disclosed by the present Inventors in PCT International Application No. PCT/US2020/045250, which is incorporated by reference.

Primary cytoplasmic signaling sequences that act in a stimulatory manner may contain signaling motifs which are known as immunoreceptor tyrosine-based activation motifs or ITAMs. In certain receptors of the disclosure, the cytoplasmic signaling domain contains 1, 2, 3, 4, or 5 ITAMs.

In certain receptors of the disclosure, the cytoplasmic domain comprises a CD3ζ activation domain. The CD3ζ activation domain may comprise a single ITAM, two ITAMs, or three ITAMs.

Further examples of ITAM containing primary cytoplasmic signaling sequences that can be used in the CARs of the instant disclosure include those derived from TCRζ, FcRγ, FcRβ, CD37, CD36, CD3E, CD3ζ, CD5, CD22, CD79a, CD79b, and CD66d. It is particularly preferred that cytoplasmic signaling molecule in the CAR of the instant invention comprises a cytoplasmic signaling sequence derived from CD3ζ.

In certain receptors of the disclosure, the cytoplasmic domain of the CAR may comprise the CD3ζ signaling domain by itself or combined with any other desired cytoplasmic domain(s). For example, the cytoplasmic domain of the CAR can comprise a CD3ζ chain portion and a co-stimulatory domain.

For example, the CD3z activation domain may comprise a single ITAM and comprises an amino acid sequence having at least 80% identity, at least 90% identity, at least 95% identity, at least 99% identity or is identical to a sequence of SEQ ID NO: 11 and/or encoded by a nucleotide sequence having at least 80% identity, at least 90% identity, at least 95% identity, at least 99% identity or is identical to SEQ ID NO: 12.

The co-stimulatory domain refers to a portion of a CAR comprising the intracellular domain of a costimulatory molecule. A costimulatory molecule is a cell surface molecule, other than an antigen receptor or its ligands, that is required for an efficient response of lymphocytes to an antigen. In receptors of the disclosure, the costimulatory domain is selected from the group consisting of IL2Rβ, Fc Receptor gamma (FcRγ), Fc Receptor beta (FcRβ), CD3g molecule gamma (CD37), CD36, CD3F, CD5 molecule (CD5), CD22 molecule (CD22), CD79a molecule (CD79a), CD79b molecule (CD79b), carcinoembryonic antigen related cell adhesion molecule 3 (CD66d), CD27 molecule (CD27), CD28 molecule (CD28), TNF receptor superfamily member 9 (4-1BB), TNF receptor superfamily member 4 (OX40), TNF receptor superfamily member 8 (CD30), CD40 molecule (CD40), programmed cell death 1 (PD-1), inducible T cell costimulatory (ICOS), lymphocyte function-associated antigen-1 (LFA-1), CD2 molecule (CD2), CD7 molecule (CD7), TNF superfamily member 14 (LIGHT), killer cell lectin like receptor C2 (NKG2C) and CD276 molecule (B7-H3) c-stimulatory domains, or functional fragments thereof.

The cytoplasmic domains within the cytoplasmic signaling portion of the CARs of the instant disclosure may be linked to each other in a random or specified order. Optionally, a short oligo- or polypeptide linker, for example between 2 and 10 amino acids in length may form the linkage. A glycine-serine doublet provides an example of a suitable linker.

The intracellular domains of CARs of the instant disclosure may include at least one co-stimulatory domain. The co-stimulatory domain may be isolated or derived from CD28.

An exemplary CD28 co-stimulatory domain comprises an amino acid sequence having at least 80% identity, at least 90% identity, at least 95% identity, at least 99% identity or is identical to a sequence of SEQ ID NO: 13 and/or encoded by a nucleotide sequence having at least 80% identity, at least 90% identity, at least 95% identity, at least 99% identity or is identical to a sequence of SEQ ID NO: 14.

The intracellular domain of the CARs of the instant disclosure may include an interleukin-2 receptor beta-chain (IL-2Rbeta or IL-2R-beta) cytoplasmic domain. The IL-2Rbeta domain may be truncated. The IL-2Rbeta cytoplasmic domain may comprise one or more STAT5-recruitment motifs, which may be outside the IL-2Rbeta cytoplasmic domain.

An exemplary IL-2Rbeta intracellular domain may comprise an amino acid sequence having at least 80% identity, at least 90% identity, at least 95% identity, at least 99% identity or is identical to a sequence of SEQ ID NO: 15 and/or encoded by a nucleotide sequence having at least 80% identity, at least 90% identity, at least 95% identity, at least 99% identity or is identical to a sequence of SEQ ID NO: 16.

Exemplary STAT5-recruitment motifs are provided by Passerini et al., (2008) STAT5-signaling cytokines regulate the expression of FOXP3 in CD4+CD25+ regulatory T cells and CD4+CD25+ effector T cells, *International Immunology, Vol.* 20, No. 3, pp. 421-431, and by Kagoya et al., (2018) A novel chimeric antigen receptor containing a JAK-STAT signaling domain mediates superior antitumor effects. *Nature Medicine* doi:10.1038/nm.4478, which are each incorporated herein by reference.

An exemplary STAT-recruitment motif used herein may consist of SEQ ID NO: 17.

In certain blocking receptors of the disclosure, the inhibitory signal is transmitted through the intracellular domain of the receptor. Thus, the blocking receptor may comprise an inhibitory intracellular domain.

The inhibitory intracellular domain may comprise an immunoreceptor tyrosine-based inhibitory motif (ITIM). The inhibitory intracellular domain comprising an ITIM can be isolated or derived from an immune checkpoint inhibitor such as CTLA-4 and PD-1. CTLA-4 and PD-1 are immune inhibitory receptors expressed on the surface of T cells, and play a pivotal role in attenuating or terminating T cell responses.

"ITIM" refers to a conserved sequence of amino acids with a consensus sequence provided in SEQ ID NO: 274. Exemplary ITIMs include, those having sequences of SEQ ID NOS: 67, 68, 69, and 70. In some embodiments, the intracellular domain comprises a sequence at least 95% identical to SEQ ID NOS: 71, 72, 73, 74, 75, or 76.

Inhibitory domains can also be isolated from human tumor necrosis factor related apoptosis inducing ligand (TRAIL) receptor and CD200 receptor 1.

The inhibitory domain may comprise an intracellular domain, a transmembrane or a combination thereof. Alternatively, the inhibitory domain comprises an intracellular domain, a transmembrane domain, a hinge region or a combination thereof. The inhibitory domain may contain an immunoreceptor tyrosine-based inhibitory motif (ITIM). The inhibitory domain comprising an ITIM can be isolated or derived from an immune checkpoint inhibitor such as CTLA-4 and PD-1.

Inhibitory domains can be isolated from human tumor necrosis factor related apoptosis inducing ligand (TRAIL) receptor and CD200 receptor 1. The inhibitory domain may be isolated or derived from a human protein, for example a human TRAIL receptor, CTLA-4, or PD-1 protein. In some embodiments, the TRAIL receptor comprises TR10A, TR10B or TR10D.

Endogenous TRAIL is expressed as a 281-amino acid type II trans-membrane protein, which is anchored to the plasma membrane and presented on the cell surface. TRAIL is expressed by natural killer cells, which, following the establishment of cell-cell contacts, can induce TRAIL-dependent apoptosis in target cells. Physiologically, the TRAIL-signaling system was shown to be essential for immune surveillance, for shaping the immune system through regulating T-helper cell 1 versus T-helper cell 2 as well as "helpless" CD8+ T-cell numbers, and for the suppression of spontaneous tumor formation.

The inhibitory domain may comprise an intracellular domain isolated or derived from a CD200 receptor. The cell surface glycoprotein CD200 receptor 1 (Uniprot ref: Q8TD46) represents another example of an inhibitory intracellular domain of the present invention. This inhibitory receptor for the CD200/OX2 cell surface glycoprotein limits inflammation by inhibiting the expression of proinflammatory molecules including TNF-alpha, interferons, and inducible nitric oxide synthase (iNOS) in response to selected stimuli.

The inhibitory domain may be isolated or derived from killer cell immunoglobulin like receptor, three Ig domains and long cytoplasmic tail 2 (KIR3DL2), killer cell immunoglobulin like receptor, three Ig domains and long cytoplasmic tail 3 (KIR3DL3), leukocyte immunoglobulin like receptor B1 (LIR1), programmed cell death 1 (PD1), Fc gamma receptor IIB (FcgRIIB), killer cell lectin like receptor K1 (NKG2D), CTLA-4, a domain containing a synthetic consensus ITIM, a ZAP70 SH2 domain (e.g., one or both of the N and C terminal SH2 domains), or ZAP70 KI_K369A (kinase inactive ZAP70).

The inhibitory domain may be isolated or derived from a human protein. The blocking receptor may comprise a cytoplasmic domain and transmembrane domain isolated or derived from the same protein. For example, an ITIM containing protein. The blocking receptor may comprise a cytoplasmic domain, a transmembrane domain, and an extracellular domain or a portion thereof isolated or derived isolated or derived from the same protein. The blocking receptor may comprise a hinge region isolated or derived from isolated or derived from the same protein as the intracellular domain and/or transmembrane domain.

In certain immune cells of the disclosure, one or more of the activating and blocking receptors comprise a T Cell Receptor (TCR).

A "TCR", sometimes also called a "TCR complex" or "TCR/CD3 complex" refers to a protein complex comprising a TCR alpha chain, a TCR beta chain, and one or more of the invariant CD3 chains (zeta, gamma, delta and epsilon), sometimes referred to as subunits.

The TCR alpha and beta chains can be disulfide-linked to function as a heterodimer to bind to peptide-MHC complexes. Once the TCR alpha/beta heterodimer engages peptide-MHC, conformational changes in the TCR complex in the associated invariant CD3 subunits are induced, which leads to their phosphorylation and association with downstream proteins, thereby transducing a primary stimulatory signal. In an exemplary TCR complex, the TCR alpha and TCR beta polypeptides form a heterodimer, CD3 epsilon and CD3 delta form a heterodimer, CD3 epsilon and CD3 gamma for a heterodimer, and two CD3 zeta form a homodimer.

The LBD of the activating or blocking receptors may be fused to an extracellular domain of a TCR subunit. The TCR subunit can be TCR alpha, TCR beta, CD3 delta, CD3 epsilon or CD3 gamma. Both the first and second ligand binding domains may be fused to the same TCR subunit in different TCR receptors. Alternatively, the first and second ligand binding domains are fused to different TCR subunits in different TCR receptors.

The LBD of the activating receptor and blocking receptor may each independently comprise an scFv domain or a Vβ-only domain.

TCR subunits include TCR alpha, TCR beta, CD3 zeta, CD3 delta, CD3 gamma and CD3 epsilon. Any one or more of TCR alpha, TCR beta chain, CD3 gamma, CD3 delta or CD3 epsilon, or fragments or derivatives thereof, can be fused to one or more domains capable of providing a stimulatory signal of the disclosure, thereby enhancing TCR function and activity. Any one or more of TCR alpha, TCR beta chain, CD3 gamma, CD3 delta or CD3 epsilon, or fragments or derivative thereof, can be fused to an inhibitory intracellular domain of the disclosure.

The receptors of the present disclosure may comprise TCRs comprising a TCR variable domain. The TCR variable domain specifically binds to an antigen in the absence of a second TCR variable domain (a Vβ-only domain).

The TCRs may comprise additional elements besides the TCR variable domain, including additional amino acid sequences, additional protein domains (covalently associated, non-covalently associated or covalently and non-covalently associated with the TCR variable domain), fusion or non-covalent association of the TCR variable domain with other types of macromolecules (for example polynucleotides, polysaccharides, lipids, or a combination thereof), fusion or non-covalent association of the TCR variable domain with one or more small molecules, compounds, or ligands, or a combination thereof. Any additional element, as described, may be combined provided that the TCR variable domain is configured to specifically bind the epitope in the absence of a second TCR variable domain.

TCRs comprising a Vβ-only domain as described herein may comprise a single TCR chain (e.g. α, β, γ, or δ chain), or may comprise a single TCR variable domain (e.g. of α, β, γ, or δ chain). If a TCR is a single TCR chain, then the TCR chain comprises a transmembrane domain, a constant (or C domain) and a variable (or V domain), but does not comprise a second TCR variable domain. The TCRs may comprise or consist of a TCR α chain, a TCR β chain, a TCR γ chain or a TCR δ chain. The TCRs may be a membrane bound proteins. The TCRs may alternatively be membrane associated proteins.

The TCRs may use a surrogate a chain that lacks a Vα segment, which forms activation competent TCRs complexed with the six CD3 subunits. The TCRs may function independently of a surrogate a chain that lacks a Vα segment. For example, one or more TCRs may be fused to transmembrane (e.g., CD3ζ and CD28) and intracellular domain proteins (e.g., CD3ζ, CD28, and/or 4-1BB) that are capable of activating T cells in response to antigen.

TCRs may comprise one or more single TCR chains fused to the Vβ-only domain described herein. For example, the TCRs may comprise, or consist essentially of single α TCR chain, a single β TCR chain, a single γ TCR chain, or a single δ TCR chain fused to one or more Vβ-only domains.

The TCRs may engage antigens using complementarity determining regions (CDRs). Each TCR may contain three complement determining regions (CDR1, CDR2, and CDR3).

The first and/or second ligand binding Vβ-only domain may be a human TCR variable domain. Alternatively, the first and/or second Vβ-only domain may be a non-human TCR variable domain. The first and/or second Vβ-only domain may be a mammalian TCR variable domain. The first and/or second Vβ-only domain may be a vertebrate TCR variable domain.

Where Vβ-only domain is incorporated into a fusion protein, for example a fusion protein comprising a TCR subunit, and optionally, an additional stimulatory intracellular domain, the fusion protein may comprise a Vβ-only domain and any other protein domain or domains.

TCR receptors comprising transmembrane domains isolated or derived from any source are envisaged as within the scope of the fusion proteins of the disclosure.

The TCR transmembrane domain may be one that is associated with one of the other domains of the fusion protein, or isolated or derived from the same protein as one of the other domains of the fusion protein. The transmembrane domain and the second intracellular domain may be from the same protein, for example a TCR complex subunit such as TCR alpha, TCR beta, CD3 delta, CD3 epsilon or CD3 gamma. The extracellular domain (svd-TCR), the transmembrane domain and the second intracellular domain may be from the same protein, for example a TCR complex subunit such as TCR alpha, TCR beta, CD3 delta, CD3 epsilon or CD3 gamma.

The TCR extracellular domain (comprising one or more ligand binding domains, such as Vβ-only domain and scFv domains), the transmembrane domain and the intracellular domain(s) may be from different proteins. For example, the engineered svd-TCR may comprise a CD28 transmembrane domain with a CD28, 4-1BB and CD3ζ intracellular domain.

The TCR transmembrane domain may be derived from a natural or recombinant source. When the source is natural, the domain may be derived from any membrane-bound or transmembrane protein.

The transmembrane domain may be capable of signaling to the intracellular domain(s) whenever the TCR complex is bound to a target. A transmembrane domain of particular use in this receptors of the disclosure may include at least the transmembrane region(s) of the alpha, beta, or zeta chain of the TCR, CD3 delta, CD3 epsilon or CD3 gamma, CD28, CD3 epsilon, CD45, CD4, CD5, CD8, CD9, CD16, CD22, CD33, CD37, CD64, CD80, CD86, CD134, CD137, CD154.

The transmembrane domain can be attached to the extracellular region of the fusion protein, e.g., the antigen binding domain of the TCR alpha or beta chain, via a hinge, e.g., a hinge from a human protein. For example, in one embodiment, the hinge can be a human immunoglobulin (Ig) hinge, e.g., an IgG4 hinge, or a CD8a hinge. The hinge may be isolated or derived from CD8a or CD28.

For example, an exemplary hinge isolated or derived from CD8a hinge comprises an amino acid sequence having at least 80% identity, at least 90% identity, at least 95% identity, at least 99% identity or is identical to a sequence of SEQ ID NO: 1 and/or encoded by a nucleotide sequence having at least 80% identity, at least 90% identity, at least 95% identity, at least 99% identity or is identical to a sequence of SEQ ID NO: 2.

An exemplary CD28 hinge may comprise an amino acid sequence having at least 80% identity, at least 90% identity, at least 95% identity, at least 99% identity or is identical to SEQ ID NO: 3 and/or is encoded by a nucleotide sequence having at least 80% identity, at least 90% identity, at least 95% identity, at least 99% identity or is identical to a sequence of SEQ ID NO: 4.

The transmembrane domain may comprise a TCR alpha transmembrane domain, a TCR beta transmembrane domain, or a CD3 zeta transmembrane domain, such as those disclosed by the present Inventors in PCT International Application No. PCT/US2020/045250, which is incorporated by reference.

A transmembrane domain can include one or more additional amino acids adjacent to the transmembrane region, e.g., one or more amino acids associated with the extracellular region of the protein from which the transmembrane was derived (e.g., 1, 2, 3, 4, 5, 6, 7, 8, 9, 10 or up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 or up to 15 amino acids of the intracellular region).

The transmembrane domain can be selected or modified by amino acid substitution to avoid binding of such domains to the transmembrane domains of the same or different surface membrane proteins, e.g., to minimize interactions with other members of the receptor complex or to minimize interactions with other receptors. This can help, for example, to ensure that the receptors remain at a sufficient distance apart on the surface of the immune cell to prevent blocking receptor inversion.

When present, the transmembrane domain may be a natural TCR transmembrane domain, a natural transmembrane domain from a heterologous membrane protein, or an artificial transmembrane domain. The transmembrane domain may be a membrane anchor domain.

Without limitation, a natural or artificial transmembrane domain may comprise a hydrophobic a helix of about 20 amino acids, often with positive charges flanking the transmembrane segment.

The transmembrane domain may have one transmembrane segment or more than one transmembrane segment. Prediction of transmembrane domains/segments may be made using publicly available prediction tools, e.g., TMHMM (Krogh et al., *Journal of Molecular Biology* 2001, 305(3):567-580) and TMpred (Hoppe-Seyler, *Hofmann & Stoffel Biol. Chem.* 1993; 347: 166), which are incorporated by reference. Non-limiting examples of membrane anchor systems include platelet derived growth factor receptor (PDGFR) transmembrane domain, glycosylphosphatidylinositol (GPI) anchor (added post-translationally to a signal sequence) and the like.

In certain aspects, transmembrane domain comprises a TCR alpha transmembrane domain. In some embodiments, the TCR alpha transmembrane domain comprises an amino acid sequence having at least 85% identity, at least 90% identity, at least 95% identity, at least 96% identity, at least 97% identity, at least 98% identity, at least 99% identity or is identical to a sequence of SEQ ID NO: 26 and/or is encoded by a nucleotide sequence having at least 80% identity, at least 90% identity, at least 95% identity, at least 99% identity or is identical to a sequence of SEQ ID NO: 27.

In some embodiments, the transmembrane domain comprises a TCR beta transmembrane domain. In some embodiments, the TCR beta transmembrane domain comprises an amino acid sequence having at least 85% identity, at least 90% identity, at least 95% identity, at least 96% identity, at least 97% identity, at least 98% identity, at least 99% identity or is identical to a sequence of SEQ ID NO: 28 or 35 and/or is encoded by a nucleotide sequence having at least 80% identity, at least 90% identity, at least 95% identity, at least 99% identity or is identical to a sequence of SEQ ID NO: 20 or 36.

In some embodiments, the transmembrane comprises a CD3 zeta transmembrane domain. In some embodiments, the CD3 zeta transmembrane domain comprises an amino acid sequence having at least 85% identity, at least 90% identity, at least 95% identity, at least 96% identity, at least 97% identity, at least 98% identity, at least 99% identity or is identical to a sequence of SEQ ID NO: 29.

In some embodiments, the CD3 zeta transmembrane domain comprises, or consists essentially of, SEQ ID NO: 29. The disclosure provides fusion proteins comprising an intracellular domain. An "intracellular domain," refers to an intracellular portion of a protein. The TCR intracellular domain may comprise one or more domains capable of providing a stimulatory signal to a transmembrane domain. The intracellular domain may comprise a first intracellular domain capable of providing a stimulatory signal and a second intracellular domain capable of providing a stimulatory signal. The intracellular domain may comprise a first, second and third intracellular domain capable of providing a stimulatory signal.

The intracellular domains capable of providing a stimulatory signal may be selected from the group consisting of a CD28 molecule (CD28) domain, a LCK proto-oncogene, Src family tyrosine kinase (Lck) domain, a TNF receptor superfamily member 9 (4-1BB) domain, a TNF receptor superfamily member 18 (GITR) domain, a CD4 molecule (CD4) domain, a CD8a molecule (CD8α) domain, a FYN proto-oncogene, Src family tyrosine kinase (Fyn) domain, a zeta chain of T cell receptor associated protein kinase 70 (ZAP70) domain, a linker for activation of T cells (LAT) domain, lymphocyte cytosolic protein 2 (SLP76) domain, (TCR) alpha, TCR beta, CD3 delta, CD3 gamma and CD3 epsilon intracellular domains.

The TCR intracellular domain may comprise at least one intracellular signaling domain. An intracellular signaling domain generates a signal that promotes a function a cell, for example an immune effector function of a TCR containing cell, e.g., a TCR-expressing T cell. In certain methods and cells of the disclosure, the intracellular domain of the fusion proteins includes at least one intracellular signaling domain. For example, the intracellular domains of CD3 gamma, delta or epsilon comprise signaling domains.

The extracellular domain, transmembrane domain and intracellular domain may be isolated or derived from the same protein, for example T cell receptor (TCR) alpha, TCR beta, CD3 delta, CD3 gamma or CD3 epsilon.

Examples of intracellular domains for use in fusion proteins of the disclosure include the cytoplasmic sequences of the TCR alpha, TCR beta, CD3 zeta, and 4-1BB, and the intracellular signaling co-receptors that act in concert to initiate signal transduction following antigen receptor engagement, as well as any derivative or variant of these sequences and any recombinant sequence that has the same functional capability.

The intracellular signaling domain may comprise a primary intracellular signaling domain. Exemplary primary intracellular signaling domains include those derived from the proteins responsible for primary stimulation, or antigen dependent stimulation.

In some embodiments, the stimulatory domain comprises a CD28 intracellular domain. In some embodiments, the CD28 intracellular domain comprises an amino acid sequence having at least 85% identity, at least 90% identity, at least 95% identity, at least 96% identity, at least 97% identity, at least 98% identity, at least 99% identity or is identical to a sequence of SEQ ID NO: 37 and/or is encoded by a nucleotide sequence having at least 80% identity, at least 90% identity, at least 95% identity, at least 99% identity or is identical to a sequence of SEQ ID NO: 30.

In some embodiments, the stimulatory domain comprises a 4-IBB intracellular domain. In some embodiments, the 4-IBB intracellular domain comprises an amino acid sequence having at least 85% identity, at least 90% identity, at least 95% identity, at least 96% identity, at least 97% identity, at least 98% identity, at least 99% identity or is identical to a sequence of SEQ ID NO: 39 and/or is encoded by a nucleotide sequence having at least 80% identity, at least 90% identity, at least 95% identity, at least 99% identity or is identical to a sequence of SEQ ID NO: 40.

An intracellular signaling domain is generally responsible for activation of at least one of the normal effector functions of the immune cell in which the fusion protein has been introduced. The term "effector function" refers to a specialized function of a cell. Effector function of a T cell, for example, may be cytolytic activity or helper activity including the secretion of cytokines.

Thus, "intracellular signaling domain" refers to the portion of a protein which transduces the effector function signal and directs the cell to perform a specialized function. While in some cases the entire intracellular signaling domain can be employed, in many cases it is not necessary to use the entire intracellular signaling domain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

The intracellular domain may comprise the entirety or a portion of a CD3 delta intracellular domain, a CD3 epsilon intracellular domain, a CD3 gamma intracellular domain, or a CD3 zeta intracellular domain, such as those disclosed by the present inventors in PCT International Application No. PCT/US2020/045250, which is incorporated by reference.

The intracellular domain may comprise a TCR alpha intracellular domain or a TCR beta intracellular domain, such as those disclosed by the present inventors in PCT International Application No. PCT/US2020/045250, incorporated by reference.

The intracellular signaling domain may comprise at least one stimulatory intracellular domain. The intracellular signaling domain may comprise a primary intracellular signaling domain, such as a CD3 delta, CD3 gamma and CD3 epsilon intracellular domain, and one additional stimulatory intracellular domain, for example a co-stimulatory domain. The intracellular signaling domain may comprise a primary intracellular signaling domain, such as a CD3 delta, CD3 gamma and CD3 epsilon intracellular domain, and two additional stimulatory intracellular domains.

An exemplary CD3 delta intracellular domain may comprise, for example, an amino acid sequence having at least 85% identity, at least 90% identity, at least 95% identity, at least 96% identity, at least 97% identity, at least 98% identity, at least 99% identity or is identical to a sequence of SEQ ID NO: 30 and/or is encoded by a nucleotide sequence having at least 80% identity, at least 90% identity, at least 95% identity, at least 99% identity or is identical to a sequence of SEQ ID NO: 31.

An exemplary CD3 epsilon intracellular domain may comprise, for example, an amino acid sequence having at least 85% identity, at least 90% identity, at least 95% identity, at least 96% identity, at least 97% identity, at least 98% identity, at least 99% identity or is identical to a sequence of SEQ ID NO: 32 and/or is encoded by a nucleotide sequence having at least 80% identity, at least 90% identity, at least 95% identity, at least 99% identity or is identical to a sequence of SEQ ID NO: 19.

An exemplary CD3 gamma intracellular domain may comprise, for example, an amino acid sequence having at least 85% identity, at least 90% identity, at least 95% identity, at least 96% identity, at least 97% identity, at least 98% identity, at least 99% identity or is identical to a sequence of SEQ ID NO: 22 and/or is encoded by a nucleotide sequence having at least 80% identity, at least 90% identity, at least 95% identity, at least 99% identity or is identical to a sequence of SEQ ID NO: 9.

Exemplary co-stimulatory intracellular signaling domains include those derived from proteins responsible for co-stimulatory signals, or antigen independent stimulation.

The term "co-stimulatory molecule" refers to the cognate binding partner on a T-cell that specifically binds with a co-stimulatory ligand, thereby mediating a co-stimulatory response by the T-cell, such as, but not limited to, proliferation. Co-stimulatory molecules are cell surface molecules other than antigen receptors. Co-stimulatory molecules and their ligands are required for an efficient immune response. Co-stimulatory molecules include, but are not limited to an MHC class I molecule, BTLA, a Toll ligand receptor, as well as DAP10, DAP12, CD30, LIGHT, OX40, CD2, CD27, CDS, ICAM-1, LFA-1 (CD11a/CD18) 4-1BB (CD137, TNF receptor superfamily member 9), and CD28 molecule (CD28).

A "co-stimulatory domain", sometimes referred to as "a co-stimulatory intracellular signaling domain" can be the intracellular portion of a co-stimulatory protein. A co-stimulatory domain can be a domain of a co-stimulatory protein that transduces the co-stimulatory signal. A co-stimulatory protein can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, a ligand that specifically binds with CD83, CD4, and the like. The co-stimulatory domain can comprise the entire intracellular portion, or the entire native intracellular signaling domain, of the molecule from which it is derived, or a functional fragment thereof.

The stimulatory domain may comprise a co-stimulatory domain. The co-stimulatory domain may comprise a CD28 or 4-1BB co-stimulatory domain. CD28 and 4-1BB are well characterized co-stimulatory molecules required for full T cell activation and known to enhance T cell effector function. For example, CD28 and 4-1BB have been utilized in chimeric antigen receptors (CARs) to boost cytokine release, cytolytic function, and persistence over the first-generation CAR containing only the CD3 zeta signaling domain. Likewise, inclusion of co-stimulatory domains, for example CD28 and 4-1BB domains, in engineered TCR can increase T cell effector function and specifically allow co-stimulation in the absence of co-stimulatory ligand, which is typically down-regulated on the surface of tumor cells.

The stimulatory domain may comprise or be derived from a CD28 intracellular domain or a 4-1BB intracellular domain, such as those disclosed by the present inventors in PCT International Application No. PCT/US2020/045250, which is incorporated herein by reference.

The disclosure provides inhibitory intracellular domains which can be fused to the transmembrane or intracellular domain of any of the TCR subunits to generate a blocking TCR.

The inhibitory intracellular domain may comprise an immunoreceptor tyrosine-based inhibitory motif (ITIM). The inhibitory intracellular domain comprising an ITIM can be isolated or derived from an immune checkpoint inhibitor such as CTLA-4 and PD-1.

Inhibitory domains can be isolated from human tumor necrosis factor related apoptosis inducing ligand (TRAIL) receptor and CD200 receptor 1.

The inhibitory domain may comprise an intracellular domain, a transmembrane domain or a combination thereof. The inhibitory domain may comprise an intracellular domain, a transmembrane domain, a hinge region or a combination thereof. The inhibitory domain may comprise an immunoreceptor tyrosine-based inhibitory motif (ITIM). The inhibitory domain comprising an ITIM can be isolated or derived from an immune checkpoint inhibitor such as CTLA-4 and PD-1.

Inhibitory domains can be isolated from human tumor necrosis factor related apoptosis inducing ligand (TRAIL) receptor and CD200 receptor 1. The inhibitory domain can be isolated or derived from a human protein, for example a human TRAIL receptor, CTLA-4, or PD-1 protein. In some embodiments, the TRAIL receptor comprises TR10A, TR10B or TR10D.

Endogenous TRAIL is expressed as a 281-amino acid type II trans-membrane protein, which is anchored to the plasma membrane and presented on the cell surface. TRAIL is expressed by natural killer cells, which, following the establishment of cell-cell contacts, can induce TRAIL-dependent apoptosis in target cells. Physiologically, the TRAIL-signaling system was shown to be essential for immune surveillance, for shaping the immune system through regulating T-helper cell 1 versus T-helper cell 2 as well as "helpless" CD8+ T-cell numbers, and for the suppression of spontaneous tumor formation.

The inhibitory domain may comprise an intracellular domain isolated or derived from a CD200 receptor. The cell surface glycoprotein CD200 receptor 1 (Uniprot ref: Q8TD46) represents another example of an inhibitory intracellular domain of the present invention. This inhibitory receptor for the CD200/OX2 cell surface glycoprotein limits inflammation by inhibiting the expression of proinflammatory molecules including TNF-alpha, interferons, and inducible nitric oxide synthase (iNOS) in response to selected stimuli.

The inhibitory domain may be isolated or derived from killer cell immunoglobulin like receptor, three Ig domains and long cytoplasmic tail 2 (KIR3DL2), killer cell immunoglobulin like receptor, three Ig domains and long cytoplasmic tail 3 (KIR3DL3), leukocyte immunoglobulin like receptor B1 (LIR1), programmed cell death 1 (PD1), Fc gamma receptor IIB (FcgRIIB), killer cell lectin like receptor K1 (NKG2D), CTLA-4, a domain containing a synthetic consensus ITIM, a ZAP70 SH2 domain (e.g., one or both of the N and C terminal SH2 domains), or ZAP70 KI_K369A (kinase inactive ZAP70).

The inhibitory domain can be isolated or derived from a human protein.

The blocking receptor may comprise a cytoplasmic domain and transmembrane domain isolated or derived from the same protein, for example an ITIM containing protein. The blocking receptor may comprise a cytoplasmic domain, a transmembrane domain, and an extracellular domain or a portion thereof isolated or derived isolated or derived from the same protein, for example an ITIM containing protein. The blocking receptor may comprise a hinge region isolated or derived from isolated or derived from the same protein as the intracellular domain and/or transmembrane domain, for example an ITIM containing protein.

The blocking receptor may be a TCR comprising an inhibitory domain (an inhibitory TCR). The inhibitory TCR may comprise an inhibitory intracellular domain and/or an inhibitory transmembrane domain. The inhibitory intracellular domain can be fused to the intracellular domain of any one or more subunits of the TCR complex, including TCR alpha, TCR beta, CD3 delta, CD3 gamma or CD3 epsilon, or a portion of any thereof. The inhibitory intracellular domain can be fused to the transmembrane domain of TCR alpha, TCR beta, CD3 delta, CD3 gamma or CD3 epsilon.

The blocking receptor may comprise a hinge, transmembrane domain, and/or an intracellular domain derived from leukocyte immunoglobulin like receptor B1 (LILRBI). The blocking receptor may comprise the intracellular domain of the protein phosphoprotein membrane anchor with glycosphingolipid microdomains 1 (PAG1) or a functional variant thereof, and optionally hinge, a transmembrane domain, and/or one or more further intracellular domains. The transmembrane domain may be the transmembrane domain of PAG1. The hinge, transmembrane domain, and/or a further intracellular domain may be from leukocyte immunoglobulin like receptor B1 (LILRB1), PAG1 or a combination thereof. Examples of such blocking receptors have been disclosed by the Inventors of the present disclosure in U.S. Provisional Application Nos. 63/018,881 and 62/946,888 and PCT/US2021/030149, which are herein incorporated by reference in its entirety.

In some embodiments of the receptors having one or more domains isolated or derived from LILRB1, the one or more domains of LILRB1 comprise an amino acid sequence that is at least 80%, at least 90%, at least 95%, at least 96%, at least 97%, at least 98%, at least 99% or is identical to a sequence or subsequence of SEQ ID NO: 65, 77, 78, 79, 80, 81, 82, 83, 84, or 85 and/or is encoded by a polynucleotide sequence that is at least 80%, at least 90%, at least 95%, at least 96%, at least 97%, at least 98%, at least 99% or is identical to a sequence or subsequence of SEQ ID NO: 66.

In various embodiments, an blocking receptor is provided, comprising a polypeptide, wherein the polypeptide comprises one or more of: an LILRB1 hinge domain or functional fragment or variant thereof; an LILRB1 transmembrane domain or a functional variant thereof; and an LILRB1 intracellular domain or an intracellular domain comprising at least one, or at least two immunoreceptor tyrosine-based inhibitory motifs (ITIMs), wherein each ITIM is independently selected from and/or includes a sequence of SEQ ID NOS: 67, 68, 69, 70, 71, 72, 73, 74, 75, or 76.

Assays

Provided herein are assays that can be used to measure the activity of the engineered receptors and immune cells disclosed herein.

Receptor activity may be assayed using a cell line engineered to express a reporter of receptor activity such as a luciferase reporter. Exemplary cell lines include Jurkat T cells, although any suitable cell line known in the art may be used. For example, Jurkat cells expressing a luciferase reporter under the control of an NFAT promoter can be used as effector cells. Expression of luciferase by this cell line reflects TCR-mediated signaling.

Nuclear factor of activated T cells (NFAT) is a family of transcription factors shown to be important in immune response. The NFAT transcription factor family consists of five members NFATc1, NFATc2, NFATc3, NFATc4, and NFAT5. NFAT plays a role in regulating inflammation. As used herein, an NFAT promoter is a promoter that is regulated (i.e., activated or repressed) when NFAT is expressed in a cell. NFAT target promoters are described in Badran, B. M. et al., (2002) *J. Biological Chemistry*, Vol. 277: 47136-47148, incorporated herein by reference, and contain NFAT consensus sequences such as GGAAA.

The reporter cells can be transfected with each of the various fusion protein constructs, combinations of fusion protein constructs or controls described herein. Expression of the fusion proteins in reporter cells can be confirmed by using fluorescently labeled MHC tetramers, for example Alexa Fluor 647-labeled NY-ESO-1-MHC tetramer, to detect expression of the fusion protein.

To assay the activity of engineered receptors, target cells can be loaded with activating or blocking ligands prior to exposure to the cells comprising the reporter and the engineered receptor(s). For example, target cells can be loaded with ligands at least 12, 14, 16, 18, 20, 22 or 24 hours prior to exposure to immune cells. Exemplary target cells include A375 cells, although any suitable cells known in the art may be used. In some cases, target cells can be loaded with serially diluted concentrations of a ligand, such as NY-ESO-1 peptide. The immune cells can then be cocultured with target cells for a suitable period of time, for example 6 hours. Luciferase is then measured by luminescence reading after co-culture. Luciferase luminescence can be normalized to maximum and minimum intensity to allow comparison of activating peptide concentrations for each engineered receptor construct.

Provided herein are methods of determining the relative $EC_{50}$ of engineered receptors of the disclosure. As used herein, "$EC_{50}$" refers to the concentration of an inhibitor or agent to cause half the maximal response (or binding). Binding of the ligand, or probe to the engineered receptor can be measured by staining with labeled peptide or labeled peptide-MHC complex, for example MHC:NY-ESO-1 pMHC complex conjugated with fluorophore. $EC_{50}$ can be obtained by nonlinear regression curve fitting of reporter signal with peptide titration. Probe binding and $EC_{50}$ can be normalized to the levels of benchmark TCR without a fusion protein, e.g. NY-ESO-1 (clone 1G4).

Methods of assessing the effects of receptor activation on gene expression are known in the art, and include the use of reporter genes, whose expression can be quantified. Reporter genes can be used for identifying potentially transfected or transduced cells and for evaluating the functionality of regulatory sequences.

In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene. See, e.g., Ui-Tei et al., 2000 *FEBS Letters* 479: 79-82, which is incorporated herein by reference.

Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription. In exemplary embodiments, an NFAT promoter operably linked to a reporter gene is used to evaluate the expression of the receptors of the disclosure on NFAT signaling.

Exemplary assays have been disclosed by the present Inventors in PCT International Application Nos. PCT/US2019/037038, PCT/US2020/045250, PCT/US2020/045228, PCT/US2020/045373, and PCT/CA2016/051421, and U.S. Provisional Application Nos. 62/946,888, 62/934,419, 63/076,123, 63/068,244, 63/068,249, 63/068,245, 63/068,246, 63/065,324, and 63/037,975, which are each incorporated herein by reference.

Immune Cells

An immune cell can be a cell involved in the innate or adaptive (acquired) immune systems. Exemplary innate immune cells include phagocytic cells such as neutrophils, monocytes and macrophages, Natural Killer (NK) cells, polymophonuclear leukocytes such as neutrophils eosinophils and basophils and mononuclear cells such as monocytes, macrophages and mast cells. Immune cells with roles in acquired immunity include lymphocytes such as T-cells and B-cells. An engineered immune cell of the present disclosure can be derived from an innate immune cell and/or can be a modified innate immune cell.

A T cell is a type of lymphocyte that originates from a bone marrow precursor that develops in the thymus gland. There are several distinct types of T-cells which develop upon migration to the thymus, which include, helper CD4+ T-cells, cytotoxic CD8+ T cells, memory T cells, regulatory CD4+ T-cells and stem memory T-cells. Different types of T cells can be distinguished by the ordinarily skilled artisan based on their expression of markers. Methods of distinguishing between T cell types will be readily apparent to the ordinarily skilled artisan.

The present disclosure also comprises methods of producing and modifying the engineered immune cells disclosed herein. The engineered immune cells of the present disclosure can be derived from any naturally occurring immune cell.

Methods of producing the disclosed immune cells may comprise introducing polynucleotide encoding the activating and blocking receptors into cells, optionally using vectors. The resulting cells express the polynucleotide encoding the receptors.

Methods transforming populations of immune cells, such as T cells, with vectors will be readily apparent to the person of ordinary skill in the art. For example, CD3+ T cells can be isolated from PBMCs using a CD3+ T cell negative isolation kit (Miltenyi), according to manufacturer's instructions. T cells can be cultured at a density of 1×10^6 cells/mL in X-Vivo 15 media supplemented with 5% human A/B serum and 1% Pen/strep in the presence of CD3/28 Dynabeads (1:1 cell to bead ratio) and 300 Units/mL of IL-2 (Miltenyi). After 2 days, T cells can be transduced with viral vectors, such as lentiviral vectors using methods known in the art. In some embodiments, the viral vector is transduced at a multiplicity of infection (MOI) of 5. Cells can then be cultured in IL-2 or other cytokines such as combinations of IL-7/15/21 for an additional 5 days prior to enrichment.

Methods of isolating and culturing other populations of immune cells, such as B cells, or other populations of T cells, will be readily apparent to the person of ordinary skill in the art. Although this method outlines a potential approach it should be noted that these methodologies are rapidly evolving. For example, high levels of viral transduction of peripheral blood mononuclear cells can be achieved after 5 days of growth to generate a >99% CD3+ highly transduced cell population.

In some embodiments, the first and second receptors are encoded by a single vector. Methods of encoding multiple polypeptides using a single vector will be known to persons of ordinary skill in the art, and include, inter alia, encoding multiple polypeptides under control of different promoters, or, if a single promoter is used to control transcription of multiple polypeptides, use of sequences encoding internal ribosome entry sites (IRES) and/or self-cleaving peptides. Exemplary self-cleaving peptides include T2A, P2A, E2A and F2A self-cleaving peptides. In some embodiments, the T2A self-cleaving peptide comprises a sequence of EGRGSLLTCGDVEENPGP (SEQ ID NO: 271). In some embodiments, the P2A self-cleaving peptide comprises a sequence of ATNFSLLKQAGDVEENPGP (SEQ ID NO: 192). In some embodiments, the E2A self-cleaving peptide comprises a sequence of QCTNYALLKLAGDVESNPGP (SEQ ID NO: 272). In some embodiments, the F2A selfcleaving peptide comprises a sequence of VKQTLNFDLLKLAGDVESNPGP (SEQ ID NO: 273).

Methods of activating and culturing populations immune cells comprising the receptors, polynucleotides, or vectors of the disclosure will be readily apparent to the person of ordinary skill in the art.

Whether prior to or after genetic modification, the immune cells of the present disclosure can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041, 10040846; and U.S. Pat. Appl. Pub. No. 2006/0121005, each of which are incorporated herein by reference.

Immune cells of the instant disclosure can be expanded and activated in vitro. Generally, the immune cells of the instant disclosure are expanded in vitro by contact with a surface having an attached agent that stimulates a CD3/TCR complex associated signal and a ligand that stimulates a co-stimulatory molecule on the surface of the immune cells. Immune cell populations may be stimulated as described herein, such as by contact with an anti-CD3 antibody. For co-stimulation of an accessory molecule on the surface of the immune cells, a ligand that binds the accessory molecule can be used. For example, a population of T cells can be contacted with an anti-CD3 antibody and an anti-CD28 antibody, under conditions appropriate to stimulate proliferation of the T cells. In order to stimulate proliferation of either CD4+ T cells or CD8+ T cells, an anti-CD3 antibody and an anti-CD28 antibody can be used. Examples of an anti-CD28 antibody include 9.3, B-T3, XR-CD28 (Diaclone, Besangon, France) can be used as can other methods commonly known in the art, such as in Berg et al., *Transplant Proc.* 30(8):3975-3977, 1998; Haanen et al., *J. Exp. Med.* 190(9):13191328, 1999; and Garland et al., *J. Immunol Meth.* 227(1-2):53-63, 1999, each of which is incorporated herein by reference.

The primary stimulatory signal and the co-stimulatory signal for an immune cell of the disclosure may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. The agent providing the co-stimulatory signal may be bound to a cell surface and the agent providing the primary activation signal is in solution or coupled to a surface. Both agents can be in solution. The agents may be in soluble form, and then cross-linked to a surface, such as a cell expressing Fc receptors or an antibody or other binding agent which will bind to the agents. U.S. Patent Application Publication Nos. 2004/0101519 and 2006/0034810, which are incorporated herein by reference, disclose artificial antigen presenting cells (aAPCs) that are contemplated for use in activating and expanding immune cells of the present invention.

The two agents may be immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts.

In certain methods of the disclosure, a 1:1 ratio of each antibody bound to the beads for CD4+ immune cell expansion and growth is used. The ratio of CD3:CD28 antibody bound to the beads may range from 100:1 to 1:100, and all integer values there between. In one aspect of the present disclosure, more anti-CD28 antibody is bound to the particles than anti-CD3 antibody, i.e., the ratio of CD3:CD28 is less than one. In certain methods of the disclosure, the ratio of anti CD28 antibody to anti CD3 antibody bound to the beads is greater than 2:1.

Ratios of particles to cells from 1:500 to 500:1, and any integer values in between, may be used to stimulate immune cells, such as T cells, or other target cells. As those of ordinary skill in the art can readily appreciate, the ratio of particles to cells may depend on particle size relative to the target cell. For example, small sized beads may only bind a few cells, while larger beads can bind many.

In certain methods of the disclosure, the ratio of cells to particles ranges from 1:100 to 100:1, and any integer values in-between, can be used to stimulate the immune cells. In certain methods of the disclosure, the ratio comprises 1:9 to 9:1 and any integer values in between. In certain methods, a ratio of 1:1 cells to beads may be used. One of skill in the art will appreciate that a variety of other ratios may be suitable for use in the present invention. In particular, the ratios used will vary depending on particle size and on cell size and type.

In further methods of the present disclosure, the immune cells, such as T cells, are combined with agent-coated beads, the beads and the cells are subsequently separated, and then the cells are cultured. Alternatively, prior to culture, the agent-coated beads and cells are not separated, but are cultured together. The beads and cells may initially be concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached to contact the immune cells. The cells (for example, CD4+ T cells) and beads (for example, DYNABEADS CD3/CD28 T paramagnetic beads at a ratio of 1:1) are combined in a buffer. Again, those of ordinary skill in the art can readily appreciate any cell concentration may be used. In certain methods, it may be desirable to significantly decrease the volume in which particles and cells are mixed together (i.e., increase the concentration of cells), to ensure maximum contact of cells and particles. For example, a concentration of about 2 billion cells/ml can be used. Alternatively, greater than 100 million cells/ml can be used. A concentration of cells of 10, 15, 20, 25, 30, 35, 40, 45, or 50 million cells/ml can be used. A concentration of cells from 75, 80, 85, 90, 95, or 100 million cells/ml can be used. Concentrations of 125 or 150 million cells/ml can be used. In certain methods, cells are cultured at a density of $1\times10^6$ cells/mL.

The mixture may be cultured for several hours (about 3 hours) to about 14 days or any hourly integer value in between. The beads and immune cells may be cultured together for 2-3 days. Conditions appropriate for immune cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of immune cells. The media may comprise XVIVO-15 media supplemented with 5% human A/B serum, 1% penicillin/streptomycin (pen/strep) and 300 Units/ml of IL-2 (Miltenyi).

The engineered immune cells can be maintained under conditions necessary to support growth, for example, an appropriate temperature (e.g., 37° C.) and atmosphere (e.g., air plus 5% CO2).

Immune cells comprising receptors of the present disclosure may be autologous. Prior to expansion and genetic modification, a source of immune cells can obtained from a subject, such as a human patient. Immune cells, such as T cells, can be obtained from a number of sources, including peripheral blood mononuclear cells, bone marrow, lymph node tissue, cord blood, thymus tissue, tissue from a site of infection, ascites, pleural effusion, spleen tissue, and tumors.

In certain methods of the disclosure, any number of immune cell lines available in the art, may be used. Immune cells can be obtained from a unit of blood collected from a subject using any number of techniques known to the skilled artisan, such as Ficoll™ separation.

Cells from the circulating blood of an individual can be obtained by apheresis. The apheresis product typically contains lymphocytes, including T cells, monocytes, granulocytes, B cells, other nucleated white blood cells, red blood cells, and platelets. Cells collected by apheresis may be washed to remove the plasma fraction and to place the cells in an appropriate buffer or media for subsequent processing steps. The cells can be washed with phosphate buffered saline (PBS). The wash solution may lack calcium and magnesium or may lack many, if not all, divalent cations. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca2+-free, Mg2+-free PBS, PlasmaLyte A, or other saline solution with or without buffer. Alternatively, the undesirable components of the apheresis sample may be removed and the cells directly resuspended in culture media.

Immune cells, such as T cells, can be isolated from peripheral blood lymphocytes by lysing the red blood cells and depleting the monocytes, for example, by centrifugation through a PERCOLL™ gradient or by counterflow centrifugal elutriation. Specific subpopulations of immune cells, such as T cells, B cells, or CD4+ T cells can be further isolated by positive or negative selection techniques. For example, T cells can be isolated by incubation with anti-CD4-conjugated beads, for a time period sufficient for positive selection of the desired T cells.

Enrichment of an immune cell population, such as a T cell population, by negative selection can be accomplished with a combination of antibodies directed to surface markers unique to the negatively selected cells. One method is cell sorting and/or selection via negative magnetic immune-adherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of immune cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads.

The cells may be incubated on a rotator for varying lengths of time at varying speeds at either 2-10° C. or at room temperature.

T cells for stimulation, or PBMCs from which immune cells such as T cells are isolated, can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

Exemplary immune cells and methods for producing the same include those that have been disclosed by the present Inventors in PCT International Application Nos. PCT/US2019/037038, PCT/US2020/045250, PCT/US2020/045228, PCT/US2020/045373, and PCT/CA2016/051421, and U.S. Provisional Application Nos. 62/946,888, 62/934,419, 63/076,123, 63/068,244, 63/068,249, 63/068,245, 63/068,246, 63/065,324, and 63/037,975, which are each incorporated herein by reference.

Target Ligands

The disclosure provides receptors comprising extracellular ligand binding domains. The ligand may be an antigen and the ligand binding domain may be an antigen binding domain.

Any suitable ligand binding domain is envisaged as within the scope of the receptors described herein.

The ligand binding domain of the activating or blocking receptors may comprise an antigen binding domain comprises an antibody fragment, a Vβ only domain, a linear antibody, a single-chain variable fragment (scFv), or a single domain antibody (sdAb).

The receptors may each comprise two polypeptides each having a part of a ligand-binding domain (e.g. cognates of a heterodimeric LDB, such as a TCRα/β- or Fab-based LBD). The disclosure further provides receptors having two polypeptides, each having a part of a ligand-binding domain (e.g. cognates of a heterodimeric LDB, such as a TCRα/β- or Fab-based LBD) and one part of the ligand binding domain is fused to a hinge or transmembrane domain, while the other part of the ligand binding domain has no intracellular domain. Further variations include receptors where each polypeptide has a hinge domain, and where each polypeptide has a hinge and transmembrane domain. Some receptors may not have a hinge domain.

The ligand binding domain of the receptors may comprise a Fab fragment of an antibody.

Receptors of the present disclosure may comprise a first polypeptide that comprises an antigen-binding fragment of the heavy chain of an antibody and an intracellular domain, and a second polypeptide of the receptor comprises an antigen-binding fragment of the light chain of the antibody. Alternatively, the first polypeptide may comprise an antigen-binding fragment of the light chain of the antibody and the intracellular domain, and the second polypeptide comprises an antigen-binding fragment of the heavy chain of the antibody.

The blocking and/or activating receptors may comprise an extracellular fragment of a T cell receptor (TCR).

Any macromolecule, including virtually all proteins or peptides, can serve as an antigen for the receptors described herein. Antigens can be derived from recombinant or genomic DNA. Any DNA, which comprises a nucleotide sequence or a partial nucleotide sequence encoding a protein that elicits an immune response, encodes an antigen. An antigen need not be encoded solely by a full-length nucleotide sequence of a gene. An antigen need not be encoded by a gene. An antigen can be generated synthesized or can be derived from a biological sample, or might be macromolecule besides a polypeptide. Such a biological sample can include, but is not limited to a tissue sample, a tumor sample, a cell or a fluid with other biological components.

In the engineered receptors of the present disclosure, the antigen-binding domain may specifically bind to a target selected from etiolate receptor, αvββ integrin, BCMA, B7-H3, B7-H6, CAIX, CD19, CD20, CD22, CD30, CD33, CD37, CD44, CD44v6, CD44v7/8, CD70, CD123, CD138, CD171, CEA, DLL4, EGP-2, EGP-40, CSPG4, EGFR, ErbB2 (HER2), ErbB3 (Her3), ErbB4 (Her4), EGFRvIII, EPCAM, EphA2, EpCAM, FAP, FBP, fetal acetylcholine receptor, Fzd7, GD2, GD3, Glypican-3 (GPC3), h5T4, IL-1IR, IL13R-a2, KDR, κ light chain, λ light chain, LeY, LI CAM, MAGE-A1, mesothelin, MHC presented peptides, MUC1, MUC16, NCAM, NKG2D ligands, Notch1, Notch2/3, NYESO-1, PRAME, PSCA, PSMA, Survivin, TAG-72, TEMs, TERT, VEGFR2, and ROR1.

The antigen-binding domain may specifically bind peptide MHC (pMHC) as the antigen. Exemplary pMHC antigens include, but are not limited to, MAGE-A3 pMHC (e.g., FLWGPRALV and MPKVAELVHFL peptides), HPV E6 pMHC (e.g., TIHDIILECV peptide), HPV E7 pMHC (e.g., YMLDLQPET peptide) and NY-ESO-1 pMHC (e.g., LLEFYLAMPFA or SLLMWITQV peptides).

The antigen-binding domain may specifically bind to a target selected from CD33, CD38, a human leukocyte antigen (HLA), an organ specific antigen, a blood-brain barrier specific antigen, an Epithelial-mesenchymal transition (EMT) antigen, E-cadherin, cytokeratin, Opioid-binding protein/cell adhesion molecule (OPCML), HYLA2, Deleted in Colorectal Carcinoma (DCC), Scaffold/Matrix attachment region-binding protein 1 (SMAR1), cell surface carbohydrate and mucin type O-glycan.

The antigen-binding domain of the blocking receptor may specifically bind to an antigen from a gene with high, homogeneous surface expression across tissues. High, homogeneous surface expression across tissues allows the blocking receptor to deliver a large, even inhibitory signal. The antigen may be encoded by a gene that is absent or polymorphic in in many tumors.

Methods of distinguishing the differential expression of blocking ligands (e.g., antigens) between target and non-target cells can be used in methods and systems of the invention. For example, the presence or absence of blocking ligands in nontarget and target cells can be assayed by immunohistochemistry with an antibody that binds to the inhibitor ligand, followed by microscopy or FACS, RNA expression profiling of target cells and non-target cells, or DNA sequencing of non-target and target cells to determine if the genomic locus of the blocking ligand comprises mutations in either the target or non-target cells.

Homozygous deletions in primary tumors are rare and small, and therefore unlikely to yield blocking ligand candidates. For example, in an analysis of 2218 primary tumors across 21 human cancer types, the top 4 candidates were CDKN2A, RB1, PTEN and N3PB2. However, CDKN2A (P16) was deleted in only 5% homozygous deletion across all cancers. Homozygous HLA-A deletions were found in less than 0.2% of cancers in Cheng et al., *Nature Comm.* 8:1221 (2017), incorporated herein by reference. In contrast, deletion of a single copy of gene in cancer cells due to loss of hemizygosity occurs far more frequently.

Thus, the blocking ligand may comprise an allele of a gene that is lost in target cells due to loss of heterozygosity, and the target cells may comprise cancer cells. Cancer cells undergo frequent genome rearrangements, including duplication and deletions. These deletions can lead to the deletion of one copy of one or more genes in the cancer cells.

Loss of heterozygosity (LOH) refers to a genetic change, whereby one of the two alleles in the genome of a cell or cells is deleted, leaving a single mono-allelic (hemizygous) locus.

The blocking ligand may comprise an HLA class I allele. The major histocompatibility complex (MHC) class I is a gene complex that encodes proteins that display antigens to cells of the immune system, triggering immune response. The Human Leukocyte Antigens (HLAs) corresponding to MHC class I are HLA-A, HLA-B and HLA-C.

The blocking ligand may comprise an HLA class I allele. The blocking ligand may comprise an allele of HLA class I that is lost in a target cell through LOH. HLA-A is a group of human leukocyte antigens (HLA) of the major histocompatibility complex (MHC) that are encoded by the HLA-A locus. HLA-A is one of three major types of human MHC class I cell surface receptors. The receptor is a heterodimer comprising a heavy α chain and smaller β chain. The α chain is encoded by a variant of HLA-A, while the R chain (β2-microglobulin) is an invariant. There are several thousand variant HLA-A alleles, all of which fall within the scope of the instant disclosure.

The blocking ligand may comprise an HLA-B allele. The HLA-B gene has many possible variations (alleles). Hundreds of versions (alleles) of the HLA-B gene are known, each of which is given a particular number (such as HLAB27).

The blocking ligand may comprise an HLA-C allele. HLA-C belongs to the HLA class I heavy chain paralogues. This class I molecule is a heterodimer consisting of a heavy chain and a light chain (beta-2 microglobulin). Over one hundred HLA-C alleles have been described.

The HLA class I allele may have broad or ubiquitous RNA expression. The HLA class I allele may have a known, or generally high minor allele frequency. The HLA class I allele may not require a peptide-MHC antigen, for example when the HLA class I allele is recognized by a pan-HLA ligand binding domain.

The blocking ligand may comprise an HLA-A allele. The HLA-A allele may comprise HLA-A*02. Various single variable domains known in the art or disclosed herein that bind to and recognize HLA-A*02 are suitable for use in the present disclosure. Such scFvs include, for example and without limitation the following mouse and humanized scFv antibodies that bind HLA-A*02 in a peptide independent manner.

The blocking ligand (e.g., an antigen) may comprise a minor histocompatibility antigen (MiHA). The inhibitor ligand may comprise an allele of a MiHA that is lost in a target cell through LOH.

MiHAs are peptides derived from proteins that contain nonsynonymous differences between alleles and are displayed by common HLA alleles. The nonsynonymous differences can arise from SNPs, deletions, frameshift mutations or insertions in the coding sequence of the gene encoding the MiHA. Exemplary MiHAs can be about 9-12 amino acids in length and can bind to MHC class I and/or MHC class II proteins. Binding of the TCR to the MHC complex displaying the MiHA can activate T cells. The genetic and immunological properties of MiHAs will be known to the person of ordinary skill in the art. Candidate MiHAs are known peptides presented by known HLA class I alleles, are known to elicit T cell responses in the clinic (for example, in graft versus host disease, or transplant rejection), and allow for patient selection by simple SNP genotyping.

The MiHA may have broad or ubiquitous RNA expression. The MiHA may have high minor allele frequency. The MiHA may comprise a peptide derived from a Y chromosome gene.

The blocking ligand may comprise a Y chromosome gene, i.e. peptide encoded by a gene on the Y chromosome. The blocking ligand may comprise a peptide encoded by a Y chromosome gene that is lost in target cells through loss of Y chromosome (LoY). For example, about a third of the characterized MiHAs come from the Y chromosome. The Y chromosome contains over 200 protein coding genes, all of which are envisaged as within the scope of the instant disclosure.

As used herein, "loss of Y", or "LoY" refers a genetic change that occurs at high frequency in tumors whereby part or all of the Y chromosome is deleted, leading to a loss of Y chromosome encoded gene(s).

Loss of Y chromosome is known to occur in certain cancers. For example, there is a reported 40% somatic loss of Y chromosome in renal clear cell cancers (Arseneault et al., Sci. Rep. 7: 44876 (2017)). Similarly, clonal loss of the Y chromosome was reported in 5 out of 31 in male breast cancer subjects in Wong et al., *Oncotarget* 6(42):44927-40 (2015), incorporated herein by reference. Loss of the Y chromosome in tumors from male patients has been described as a "consistent feature" of head and neck cancer patients, as in el-Naggar et al., *Am J Clin Pathol* 105(1): 102-8 (1996), incorporated herein by reference. Further, Y chromosome loss was associated with X chromosome disomy in four of seven male patients with gastric cancer in Saal et al., *Virchows Arch B Cell Pathol* (1993), incorporated herein by reference. Thus, Y chromosome genes can be lost in a variety of cancers, and can be used as blocking ligands with the engineered receptors of the instant disclosure targeting cancer cells.

The activating ligand may be a transferrin receptor (TFRC). Human transferrin receptor is described in NCBI record No. AAA61153.1, the contents of which are incorporated herein by reference.

The activating ligand may be a tumor specific antigen (TSA). The tumor specific antigen may be mesothelin (MSLN), CEACAM5 or EGFR. The TSA may be MSLN, CEA, EGFR, DLL4, CA125, GD2, ROR1 or HER2/NEU. The activating ligand may be a pan-HLA ligand, and the activating receptor ligand binding domain is a pan-HLA binding domain, i.e. a binding domain that binds to and recognizes an antigenic determinant shared among HLA I products, such as the HLA A, B and C loci. The activating ligand may also be another class I gene product; e.g., antigens encoded by HLA-E or F. Various single variable domains known in the art are suitable for use in embodiments. Such scFvs include, for example and without limitation the following mouse and humanized pan-HLA scFv antibodies. An exemplary pan-HLA ligand is W6/32, which recognizes a conformational epitope, reacting with HLA class I alpha3 and alpha2 domains. Further exemplary antibodies with broad HLA binding are known in the art and include HC-10 and TFL-006. Exemplary activating ligands and activating receptor ligand binding domains have been disclosed by the Inventors of the present disclosure in U.S. Provisional Application No. 63/018,881, which is herein incorporated by reference in its entirety.

Exemplary ligands and ligand binding domains of activating and blocking receptors include those that have been disclosed by the present Inventors in PCT International Application Nos. PCT/US2019/037038, PCT/US2020/045250, PCT/US2020/045228, PCT/US2020/045373, and PCT/CA2016/051421, and U.S. Provisional Application Nos. 62/946,888, 62/934,419, 63/076,123, 63/068,244, 63/068,249, 63/068,245, 63/068,246, 63/065,324, and 63/037,975, which are each incorporated herein by reference.

For example, in some embodiments of the immune cells of the disclosure, a first/activating ligand is EGFR or a peptide antigen thereof, and the first/activating ligand binding domain comprises a sequence of SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, or SEQ ID NO: 391, or a sequence having at least 90%, at least 95% or at least 99% identity thereto. In some embodiments, the first ligand binding domain comprises CDRs selected from SEQ ID NOs: 131-166.

In some embodiments, the activator ligand is EGFR or a peptide antigen thereof, and the activator ligand binding domain comprises an EGFR binding domain. In some embodiments, the EGFR ligand binding domain comprises an ScFv domain. In some embodiments, the EGFR ligand binding domain comprises a sequence of SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118 or SEQ ID NO: 391. In some embodiments, the EGFR ligand binding domain comprises a sequence at least 90%, at least 95% or at least 99% identical to SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118 or SEQ ID NO: 391. In some embodiments, the EGFR ligand binding domain is encoded by a sequence comprising SEQ ID NO: 103, SEQ ID NO: 104, SEQ ID NO: 107, SEQ ID NO: 109, SEQ ID NO: 111, SEQ ID NO: 113, SEQ ID NO: 115, SEQ ID NO: 117 or SEQ ID NO: 119. In some embodiments, the EGFR ligand binding domain is encoded by a sequence having at least 80% identity, at least 85% identity, at least 90% identity, at least 95% identity or at least 99% identity to a sequence of SEQ ID NO: 103, SEQ ID NO: 104, SEQ ID NO: 107, SEQ ID NO: 109, SEQ ID NO: 111, SEQ ID NO: 113, SEQ ID NO: 115, SEQ ID NO: 117 or SEQ ID NO: 119.

In some embodiments, the activator ligand is EGFR or a peptide antigen thereof, and the activator ligand binding domain comprises an EGFR ligand binding domain. In some embodiments, the EGFR ligand binding domain comprises a VH domain selected from the group consisting of SEQ ID NO: 120, SEQ ID NO: 122, SEQ ID NO: 124, SEQ ID NO: 126, SEQ ID NO: 128 and SEQ ID NO: 130. In some embodiments, the EGFR ligand binding domain comprises a VH selected from the group consisting of SEQ ID NO: 120, SEQ ID NO: 122, SEQ ID NO: 124, SEQ ID NO: 126, SEQ ID NO: 128 and SEQ ID NO: 130 or a sequence having at least 90%, at least 95% or at least 99% identity thereto. In some embodiments, the EGFR ligand binding domain comprises a VL domain selected from the group consisting of SEQ ID NO: 121, SEQ ID NO: 123, SEQ ID NO: 125, SEQ ID NO: 127, SEQ ID NO: 129 and SEQ ID NO: 131. In some embodiments, the EGFR ligand binding domain comprises a VH selected from the group consisting of SEQ ID NO: 121, SEQ ID NO: 123, SEQ ID NO: 125, SEQ ID NO: 127, SEQ ID NO: 129 and SEQ ID NO: 131 or a sequence having at least 90%, at least 95% or at least 99% identity thereto.

In some embodiments, the activator ligand is EGFR or a peptide antigen thereof, and the activator ligand binding domain is an EGFR ligand binding domain. In some embodiments, the EGFR ligand binding domain comprises CDRs selected from SEQ ID NOs: 131-166. In some embodiments, the EGFR ligand binding domain comprises a heavy chain CDR 1 (CDR HI) selected from the group consisting of SEQ ID NOs: 132-137. In some embodiments, the EGFR ligand binding domain comprises a heavy chain CDR 2 (CDR H2) selected from the group consisting of SEQ ID NOs: 138-143. In some embodiments, the EGFR ligand binding domain comprises a heavy chain CDR 3 (CDR H3) selected from the group consisting of SEQ ID NOs: 144-149. In some embodiments, the EGFR ligand binding domain comprises a light chain CDR 1 (CDR LI) selected from the group consisting of SEQ ID NOs: 150-155. In some embodiments, the EGFR ligand binding domain comprises a light chain CDR 2 (CDR L2) selected from the group consisting of SEQ ID NOs: 156-160. In some embodiments, the EGFR ligand binding domain comprises a light chain CDR 3 (CDR L3) selected from the group consisting of SEQ ID NOs: 161-166. In some embodiments, the EGFR ligand binding domain comprises a CDR HI selected from SEQ ID NOs: 132-137, a CDR H2 selected from SEQ ID NOs: 138-143, a CDR H3 selected from SEQ ID NOs: 144-149, a CDR LI selected from SEQ ID NOs: 150-155, a CDR L2 selected from SEQ ID NOs: 156-160, and a CDR L3 selected from SEQ ID NOs: 156-160. EGFR antigen binding domain CDRs.

In some embodiments of the immune cells of the disclosure, the first/activating ligand is MSLN or a peptide antigen thereof. In some embodiments, the first/activating ligand binding domain comprises a sequence of SEQ ID NO: 86, SEQ ID NO: 88, SEQ ID NO: 90 or SEQ P) NO: 92, or a sequence having at least 90%, at least 95% or at least 99% identity thereto. In some embodiments, the MSLN ligand binding domain is encoded by a sequence comprising SEQ ID NO: 87, SEQ ID NO: 89, SEQ ID NO: 91 or SEQ ID NO: 93. In some embodiments, the MSLN ligand binding domain is encoded by a sequence having at least 80% identity, at least 85% identity, at least 90% identity, at least 95% identity or at least 99% identity to a sequence of SEQ ID NO: 87, SEQ ID NO: 89, SEQ ID NO: 91 or SEQ ID NO: 93.

In some embodiments of the immune cells of the disclosure, the first/activating ligand is CEA or a peptide antigen thereof. In some embodiments, the first/activating ligand binding domain comprises SEQ ID NO: 94, SEQ ID NO: 96, SEQ ID NO: 98, SEQ ID NO: 100, SEQ ID NO: 282, SEQ ID NO: 284, or SEQ ID NO: 286, or a sequence having at least 90%, at least 95% or at least 99% identity thereto. In some embodiments, the first/activating ligand binding domain comprises CDRs selected from SEQ ID NOs: 294-302. In some embodiments, the CEA ligand binding domain is encoded by a sequence having at least 80% identity, at least 85% identity, at least 90% identity, at least 95% identity or at least 99% identity to a sequence of SEQ ID NO: 95, SEQ ID NO: 97, SEQ ID NO: 99, SEQ ID NO: 101, SEQ ID NO: 283, SEQ ID NO: 285 or SEQ ID NO: 287.

In some embodiments, the activator ligand is CEA or a peptide antigen thereof, and the activator ligand binding domain comprises a CEA binding domain. In some embodiments, the CEA ligand binding domain comprises a CDR-H1 of EFGMN (SEQ ID NO: 294), a CDR-H2 of WINTKTGEATYVEEFKG (SEQ ID NO: 295), a CDR-H3 of WDF AYYVEAMD Y (SEQ ID NO: 296) or WDFAHYFQTMDY (SEQ ID NO: 297), a CDR-L1 of KASQNVGTNV A (SEQ ID NO: 298) or KASAAVGTYVA (SEQ ID NO: 299), a CDR-L2 of SASYRYS (SEQ ID NO: 300) or SASYRKR (SEQ ID NO: 301), and a CDR-L3 of HQ YYTYPLFT (SEQ ID NO: 302) or sequences having at least 85% or at least 95% identity thereto. In some embodiments, a CEA ScFv comprises a CDR-H1 of EFGMN (SEQ ID NO: 294), a CDR-H2 of WINTKTGEATYVEEFKG (SEQ ID NO: 295), a CDR-H3 of WDF AYYVEAMD Y (SEQ ID NO: 296) or WDFAHYFQTMDY (SEQ ID NO: 297), a CDR-L1 of KASQNVGTNV A (SEQ ID NO: 298) or KASAAVGTYVA (SEQ ID NO: 299), a CDR-L2 of SASYRYS (SEQ ID NO: 300) or SASYRKR (SEQ ID NO: 301) and a CDR-L3 of HQ YYTYPLFT (SEQ ID NO: 302).

In some embodiments, a CEA binding domain comprises a CDR-H1 of EFGMN (SEQ ID NO: 294), a CDR-H2 of WINTKTGEATYVEEFKG (SEQ ID NO: 295), a CDR-H3 of WDFAYYVEAMDY (SEQ ID NO: 296), a CDR-L1 of KASQNVGTNV A (SEQ ID NO: 298), a CDR-L2 of SASYRYS (SEQ ID NO: 300) and a CDR-L3 of HQ YYTYPLFT (SEQ ID NO: 302). In some embodiments, a CEA ScFv comprises a CDR-H1 of EFGMN (SEQ ID NO: 294), a CDR-H2 of WINTKTGEATYVEEFKG (SEQ ID NO: 295), a CDR-H3 of WDFAYYVEAMDY (SEQ ID NO: 296), a CDR-L1 of KASAAVGTYVA (SEQ ID NO: 299), a CDR-L2 of SASYRKR, and a CDR-L3 of HQ YYTYPLFT (SEQ ID NO: 302). In some embodiments, a CEA binding domain comprises a CDR-H1 of EFGMN (SEQ ID NO: 294), a CDR-H2 of WINTKTGEAT YVEEFKG (SEQ IDNO: 295), a CDR-H3 of WDFAHYFQTMD Y (SEQ ID NO: 297), a CDR-L1 of KASAAVGTYVA (SEQ ID NO: 299), a CDR-L2 of SASYRKR, and a CDR-L3 of HQ YYTYPLFT (SEQ ID NO: 302).

In some embodiments, the activator ligand is CEA or a peptide antigen thereof, and the activator receptor is a CEA CAR In some embodiments, the CEA CAR comprises sequence at least 90%, at least 95% or at least 99% identical to SEQ ID NO: 288, SEQ ID NO: 290 or SEQ ID NO: 292. In some embodiments, the CEA CAR comprises or consists essentially of SEQ ID NO: 288, SEQ ID NO: 290 or SEQ ID NO: 292. In some embodiments, the CEA CAR is encoded by a sequence comprising or consisting essentially of SEQ ID NO: 289, SEQ ID NO: 291 or SEQ ID NO: 293. In some embodiments, the CEA CAR is encoded by a sequence having at least 80% identity, at least 85% identity, at least 90% identity, at least 95% identity or at least 99% identity to SEQ ID NO: 289, SEQ ID NO: 291 or SEQ ID NO: 293.

In some embodiments of the immune cells of the disclosure, the first/activating ligand is CD19 or a peptide antigen thereof, and the first ligand binding domain comprises SEQ ID NO: 275 or SEQ ID NO: 277, or a sequence having at least 90%, at least 95% or at least 99% identity thereto.

In some embodiments of the immune cells of the disclosure, the first/activating ligand is a pan-HLA ligand. In some embodiments, the first ligand binding domain comprises a sequence of SEQ ID NO: 167, SEQ ID NO: 169, SEQ ID NO: 171, SEQ ID NO: 173, SEQ ID NO: 175, or SEQ ID NO: 177, or a sequence having at least 90%, at least 95% or at least 99% identity thereto.

In some embodiments of the immune cells of the disclosure, the second/blocking ligand comprises HA-1. In some embodiments, and wherein the second/blocking ligand binding domain comprises a TCR alpha variable domain comprising SEQ ID NO: 199 or a sequence having at least 90%, at least 95%, or at least 99% identity thereto, and a TCR beta variable domain comprising SEQ ID NO: 200 or a sequence having at least 90%, at least 95%, or at least 99% identity thereto. In some embodiments, the second/blocking ligand binding domain comprises a TCR alpha variable domain comprising SEQ ID NO: 199, and a TCR beta variable domain comprising SEQ ID NO: 200.

In some embodiments of the immune cells of the disclosure, the second/blocking ligand comprises an HLA-A*02 allele. In some embodiments, the second/blocking ligand binding domain comprises any one of SEQ ID NOs: 53-64 or a sequence having at least 90%, at least 95%, or at least 99% identity thereto. In some embodiments, the second/blocking ligand binding domain comprises CDRs selected from SEQ ID NOs: 41-52.

In some embodiments of the inhibitory/blocking receptors of the disclosure, the extracellular ligand binding domain has a higher affinity for an HA-1 (H) peptide of VLHDDLLEA (SEQ ID NO: 191) than for an HA-1(R) peptide of VLRDDLLEA (SEQ ID NO: 266). In some embodiments, the inhibitory/blocking receptor is activated by the HA-1(H) peptide of VLHDDLLEA (SEQ ID NO: 191) and is not activated, or activated to a lesser extent, by the HA-1(R) peptide of VLRDDLLEA (SEQ ID NO: 266). In some embodiments, the extracellular ligand binding domain comprises a TCR alpha variable domain comprising SEQ ID NO: 199 or a sequence having at least 90%, at least 95%, or at least 99% identity thereto, and a TCR beta variable domain comprising SEQ ID NO: 200 or a sequence having at least 90%, at least 95%, or at least 99% identity thereto. In some embodiments, the extracellular ligand binding domain comprises a TCR alpha variable domain comprising SEQ ID NO: 199 and a TCR beta variable domain comprising SEQ ID NO: 200.

In some embodiments, the activator ligand is pan-HLA ligand, and the activator ligand binding domain comprises a pan-HLA ligand binding domain. In some embodiments, the pan-HLA ligand binding domain comprises an ScFv domain. In some embodiments, the pan-HLA ligand binding domain comprises a sequence of SEQ ID NO: 167, SEQ ID NO: 169, SEQ ID NO: 171, SEQ ID NO: 173, SEQ ID NO: 175, or SEQ ID NO: 177. In some embodiments, the pan-HLA ligand binding domain comprises a sequence at least 90%, at least 95% or at least 99% identical to SEQ ID NO: 167, SEQ ID NO: 169, SEQ ID NO: 171, SEQ ID NO: 173, SEQ ID NO: 175, or SEQ ID NO: 177. In some embodiments, the pan-HLA ligand binding domain is encoded by a sequence comprising SEQ ID NO: 168, SEQ ID NO: 170, SEQ ID NO: 172, SEQ ID NO: 174, SEQ ID NO: 176, or SEQ ID NO: 178. In some embodiments, the pan-HLA ligand binding domain is encoded by a sequence having at least 80% identity, at least 85% identity, at least 90% identity, at least 95% identity or at least 99% identity to a sequence of SEQ ID NO: 168, SEQ ID NO: 170, SEQ ID NO: 172, SEQ ID NO: 174, SEQ ID NO: 176, or SEQ ID NO: 178. [0181] In some embodiments, the activator ligand is CD19 molecule (CD19) or a peptide antigen thereof, and the activator ligand binding domain comprises a CD 19 ligand binding domain. In some embodiments, the CD 19 ligand binding domain comprises an ScFv domain. In some embodiments, the CD 19 ligand binding domain comprises a sequence at least 90%, at least 95% or at least 99% identical to SEQ ID NO: 275 or SEQ ID NO: 277. In some embodiments, the CD-19 ligand binding domain comprises a sequence of SEQ ID NO: 275 or SEQ ID NO: 277. In some embodiments, the CD19 ligand binding domain is encoded by a sequence comprising SEQ ID NO: 276, or SEQ ID NO: 278. In some embodiments, the CD19 ligand binding domain is encoded by a sequence having at least 80% identity, at least 85% identity, at least 90% identity, at least 95% identity or at least 99% identity to a sequence of SEQ ID NO: 276 or SEQ ID NO: 278.

In some embodiments, activator ligand is CD19 molecule (CD19) or a peptide antigen thereof, and the activator receptor is a CAR In some embodiments, the CD 19 CAR comprises a sequence at least 90%, at least 95% or at least 99% identical to SEQ ID NO: 279 or SEQ ID NO: 281. In some embodiments, the CD 19 CAR comprises or consists essentially of SEQ ID NO: 279 or SEQ ID NO: 281. In some embodiments, the CD19 CAR is encoded by a sequence having at least 80% identity, at least 85% identity, at least 90% identity, at least 95% identity or at least 99% identity to a sequence of SEQ ID NO: 280 or SEQ P) NO: 390. In some embodiments, the CD19 CAR is encoded by a sequence comprising or consisting essentially of SEQ ID NO: 280 or SEQ ID NO: 390.

In some embodiments, the one or more ligand comprises an HLA-A allele. In some embodiments the HLA-A allele comprises HLA-A*02. Various single variable domains known in the art or disclosed herein that bind to and recognize HLA-A* 02 are suitable for use in embodiments. Such scFvs include, for example and without limitation, the following mouse and humanized scFv antibodies that bind HLA-A* 02 in a peptide-independent way, which include binding domains having at least 80% identity, at least 85% identity, at least 90% identity, at least 95% identity or at least 99% identity to any one of SEQ ID NOS: 179-190.

In some embodiments, the scFv comprises the complementarity determined regions (CDRs) of any one of SEQ ID NOS: 41-52. In some embodiments, the scFv comprises a sequence at least 95% identical to any one of SEQ P) NOS: 41-52. In some embodiments, the scFv comprises a sequence identical to any one of SEQ ID NOS: 41-52. In some embodiments, the heavy chain of the antibody comprises the heavy chain CDRs of any one of SEQ ID NOS: 53-64, and wherein the light chain of the antibody comprises the light chain CDRs of any one of SEQ ID NOS: 53-64. In some embodiments, the heavy chain of the antibody comprises a sequence at least 95% identical to the heavy chain portion of any one of SEQ ID NOS: 53-64, and wherein the light chain of the antibody comprises a sequence at least 95% identical to the light chain portion of any one of SEQ ID NOS: 53-64. [0209] In some embodiments, the heavy chain of the antibody comprises a sequence identical to the heavy chain portion of any one of SEQ ID NOS: 53-64, and wherein the light chain of the antibody comprises a sequence identical to the light chain portion of any one of SEQ ID NOS: 53-64.

In some embodiments, a ligand as used herein comprises a minor histocompatibility antigen (MiHA). In some embodiments, the blocking ligand comprises an allele of a MiHA that is lost in a target cell through LOH. Exemplary, but non-limiting, examples of MiHAs that are envisaged as within the scope of the instant invention include those having the sequence of any one of SEQ ID NOS: 273, 303-325, 327-356, 358-389, 34, and 23-25.

Exemplary ligand binding domains that selectively bind to HA-1 variant H peptide (VLHDDLLEA (SEQ ID NO: 191)) include the sequences of SEQ ID NO: 194, 201, 202, 196, and 198. TCR alpha and TCR beta sequences in SEQ ID NO: 193 are separated by a P2A self-cleaving polypeptide of sequence ATNFSLLKQAGDVEENPGP (SEQ ID NO: 192) with an N terminal GSG linker.

In some embodiments, the TCR alpha and TCR beta variable domains separated by a self-cleaving polypeptide sequence comprise SEQ ID NO: 193, or a sequence having at least 90%, at least 95%, or at least 99% identity thereto. In some embodiments, the TCR alpha and TCR beta variable domains are encoded by a sequence of SEQ ID NO: 194, or a sequence having at least 80% identity, at least 90%, at least 95%, or at least 99% identity thereto. In some embodiments, the TCR alpha variable domain comprises SEQ ID NO: 199 or a sequence having at least 90%, at least 95%, or at least 99% identity thereto. In some embodiments, the TCR beta variable domain comprises SEQ ID NO: 200 or a sequence having at least 90%, at least 95%, or at least 99% identity thereto.

In some embodiments, the first or second ligand binding domain comprises a sequence of any one of SEQ ID NO: 210, SEQ ID NO: 212, SEQ ID NO: 214, SEQ ID NO: 216, SEQ ID NO: 218, SEQ ID NO: 220, SEQ ID NO: 222 Or SEQ ID NO: 224, or a sequence having at least 90%, at least 95% or at least 99% identity thereto.

It will be appreciated by the person of ordinary skill that first, activator ligand binding domains for the first receptor may be isolated or derived from any source known in the art, including, but not limited to, art recognized T cell receptors, chimeric antigen receptors and antibody binding domains.

Methods of Treatment

The present disclosure provides methods of treating a subject in need thereof, comprising administering to the subject a therapeutically effective amount of the engineered immune cells of the present disclosure.

The engineered immune cells of the present disclosure may be used to treat a subject that has cancer. The cancer may comprise a liquid tumor or a solid tumor. Exemplary liquid tumors include leukemias and lymphomas. Further cancers that are liquid tumors can be those that occur, for example, in blood, bone marrow, and lymph nodes, and can include, for example, leukemia, myeloid leukemia, lymphocytic leukemia, lymphoma, Hodgkin's lymphoma, melanoma, and multiple myeloma. Leukemias include, for example, acute lymphoblastic leukemia (ALL), acute myeloid leukemia (AML), chronic lymphocytic leukemia (CLL), chronic myelogenous leukemia (CML), and hairy cell leukemia. Exemplary solid tumors include sarcomas and carcinomas. Cancers can arise in virtually an organ in the body, including blood, bone marrow, lung, breast, colon, bone, central nervous system, pancreas, prostate and ovary. Further cancers that are solid tumors include, for example, prostate cancer, testicular cancer, breast cancer, brain cancer, pancreatic cancer, colon cancer, thyroid cancer, stomach cancer, lung cancer, ovarian cancer, Kaposi's sarcoma, skin cancer, squamous cell skin cancer, renal cancer, head and neck cancers, throat cancer, squamous carcinomas that form on the moist mucosal linings of the nose, mouth, throat, bladder cancer, osteosarcoma, cervical cancer, endometrial cancer, esophageal cancer, liver cancer, and kidney cancer. In some embodiments, the condition treated by the methods described herein is metastasis of melanoma cells, prostate cancer cells, testicular cancer cells, breast cancer cells, brain cancer cells, pancreatic cancer cells, colon cancer cells, thyroid cancer cells, stomach cancer cells, lung cancer cells, ovarian cancer cells, Kaposi's sarcoma cells, skin cancer cells, renal cancer cells, head or neck cancer cells, throat cancer cells, squamous carcinoma cells, bladder cancer cells, osteosarcoma cells, cervical cancer cells, endometrial cancer cells, esophageal cancer cells, liver cancer cells, or kidney cancer cells.

Treating cancer with the engineered immune cells of the present disclosure can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer with the engineered immune cells of the present disclosure can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer using the engineered immune cells of the present disclosure may result in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer with the engineered immune cells of the present disclosure can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer with the engineered immune cells of the present disclosure can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer with the engineered immune cells can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer with the engineered immune cells can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer with the engineered immune cells can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer with the engineered immune cells can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer with the engineered immune cells can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder with the engineered immune cells can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder with the engineered immune cells can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder with the engineered immune cells can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder with the engineered immune cells can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

Exemplary methods of treatment and conditions to be treated using the cells of the present invention including those that have been disclosed by the present Inventors in PCT International Application Nos. PCT/US2019/037038, PCT/US2020/045250, PCT/US2020/045228, PCT/US2020/045373, and PCT/CA2016/051421, and U.S. Provisional Application Nos. 62/946,888, 62/934,419, 63/076,123, 63/068,244, 63/068,249, 63/068,245, 63/068,246, 63/065,324, and 63/037,975, which are each incorporated herein by reference.

EXAMPLES

Example 1

Figure 4:
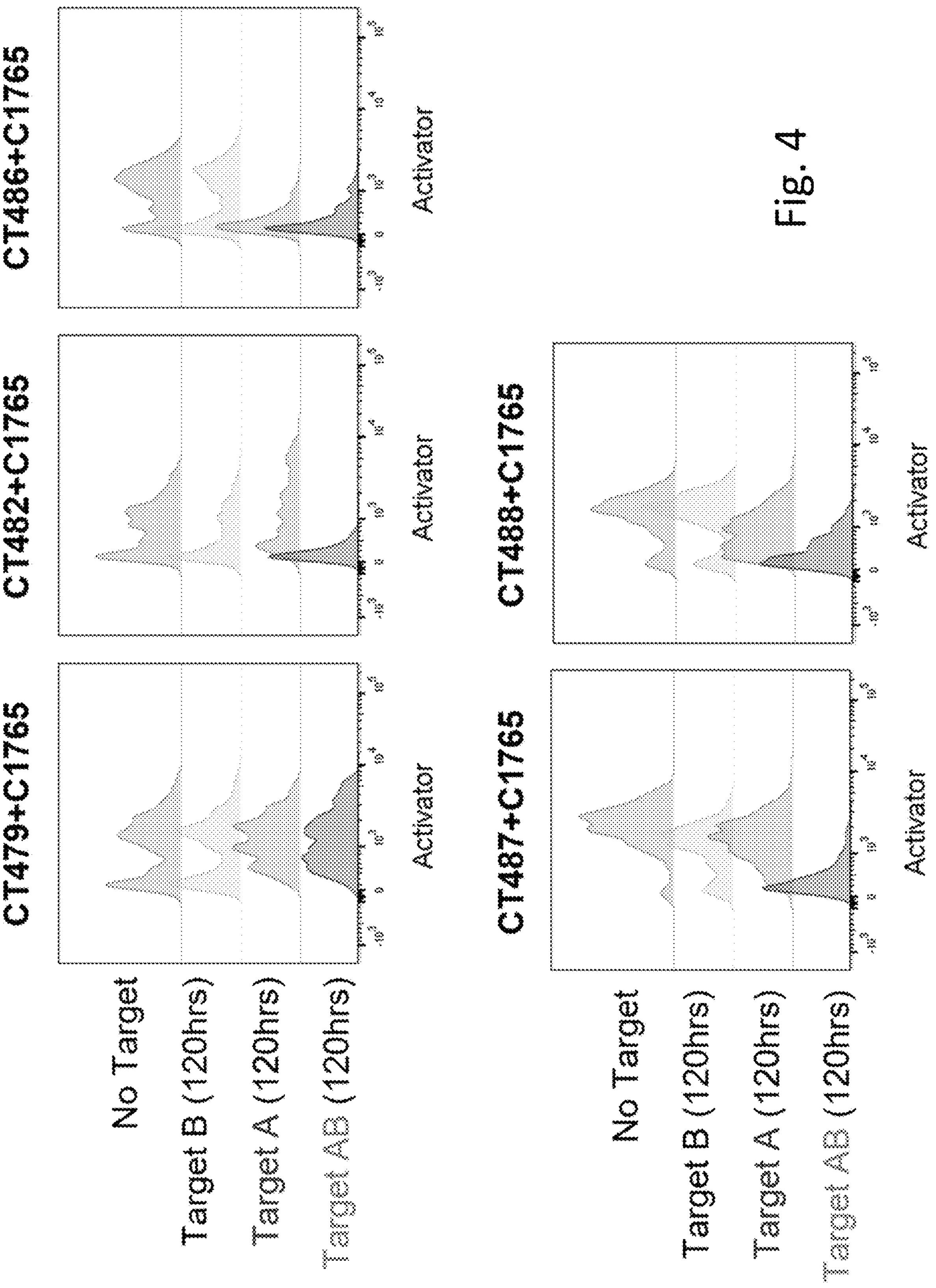
FIGS. 4-6 provide experimental results showing reduced expression of activating receptors.

FIG. 4 provides experimental results showing that, for the engineered immune cells of the present disclosure expressing activating and blocking receptors, surface levels of the activating receptor decrease when the immune cells are in the presence of non-target cells expressing both the activating and blocking ligand.

Figure 5:
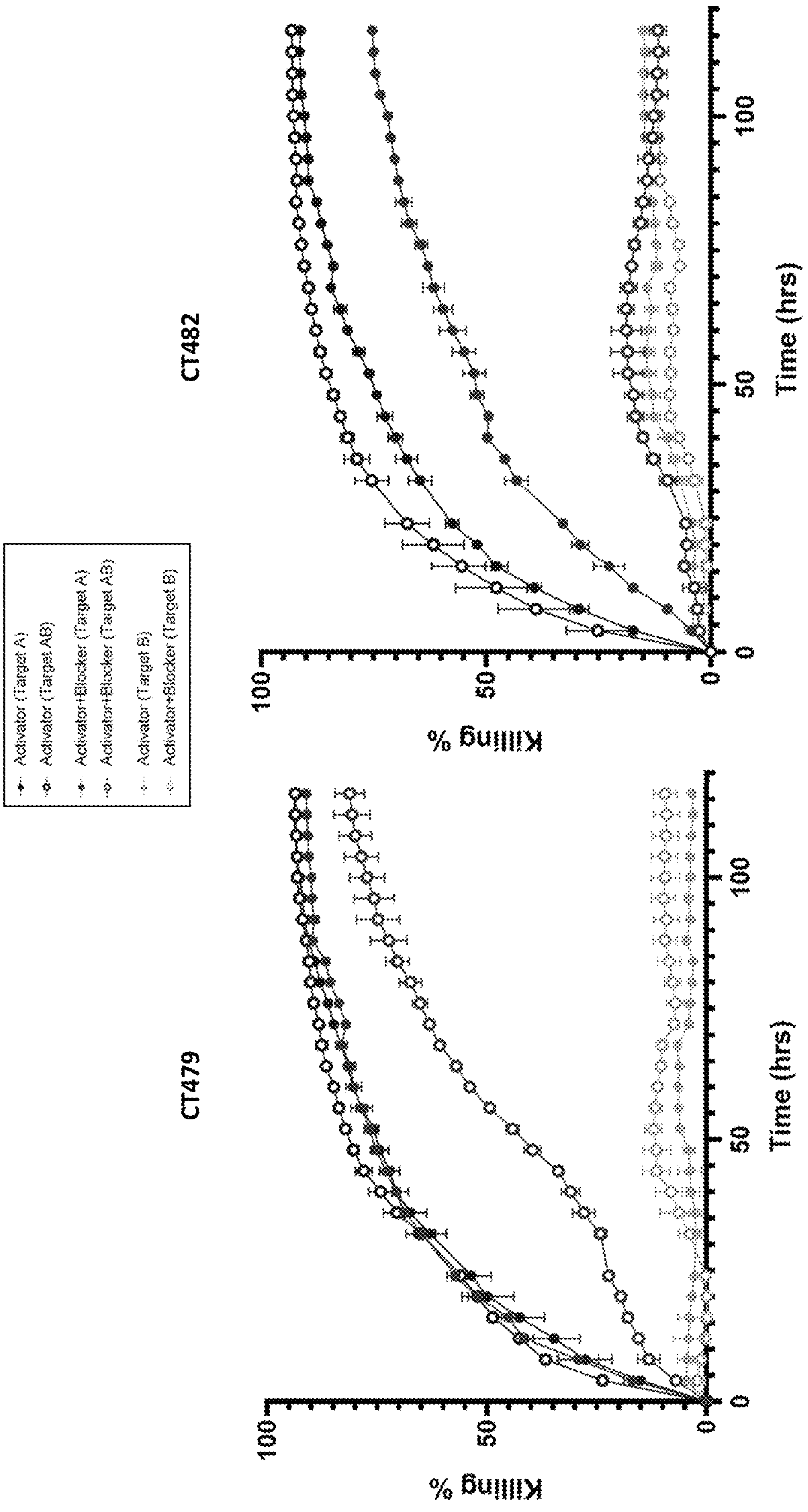
Figure 6:
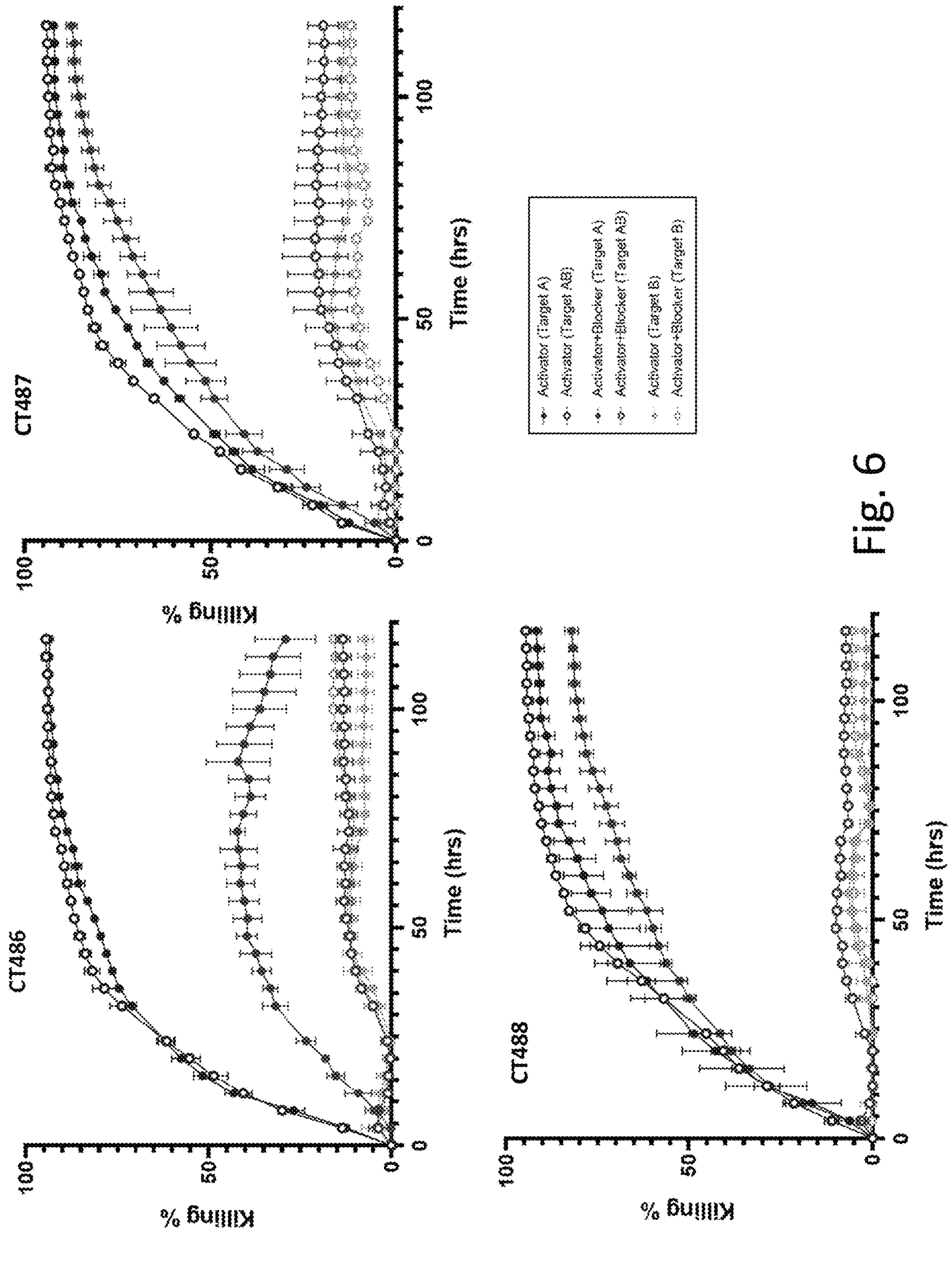
Figure 7:
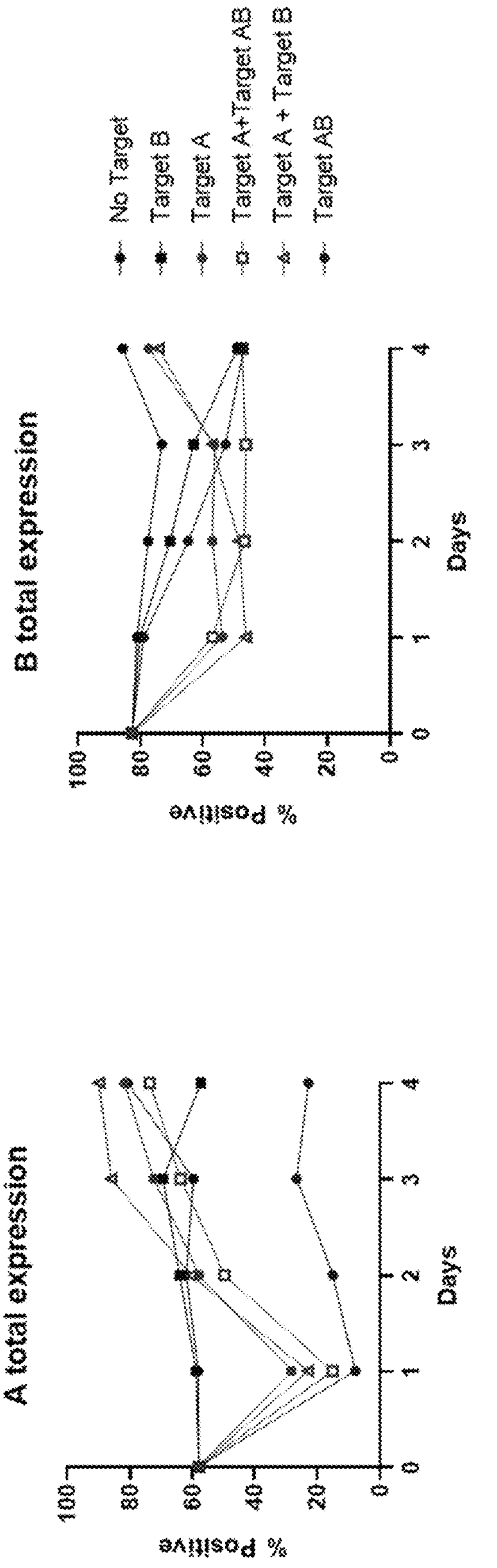
FIG. 7 provides experimental results showing reduced expression of activating receptors.
Figure 8:
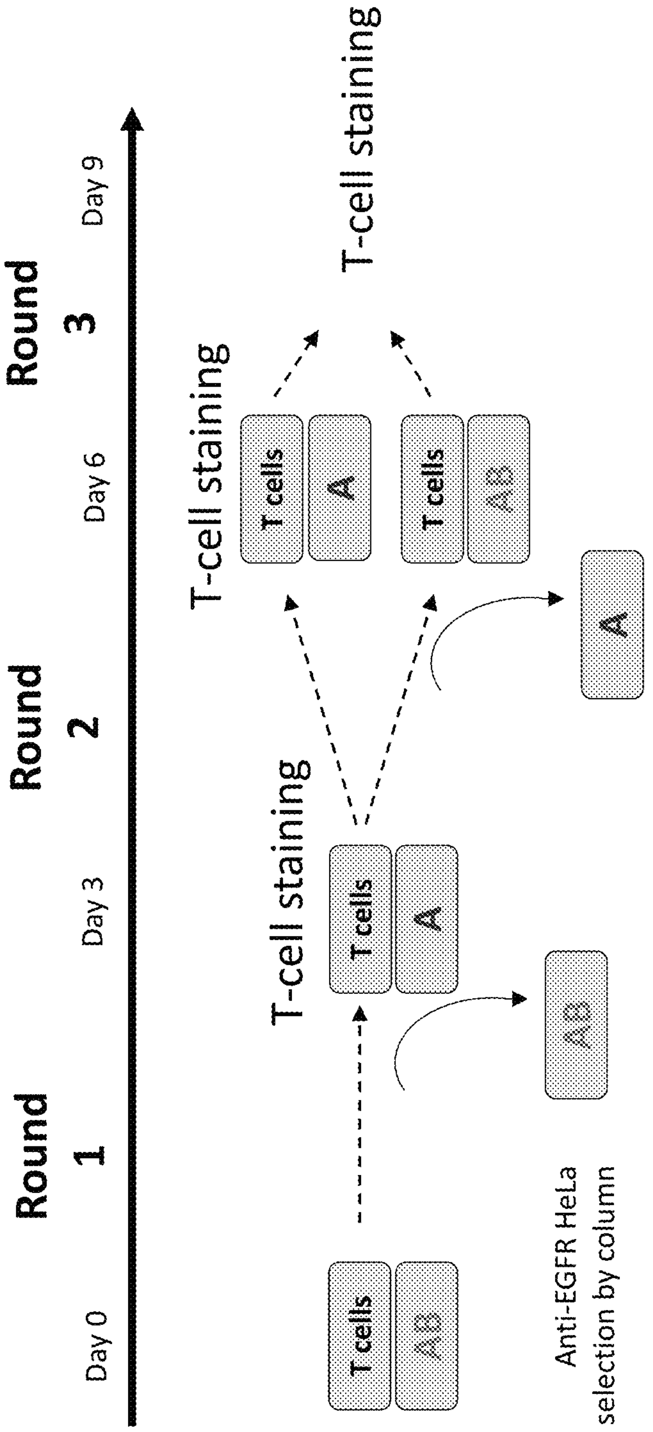
FIG. 8 shows a schematic for an experiment to show the reversibility of reduced expression of activating receptors.
Figure 9:
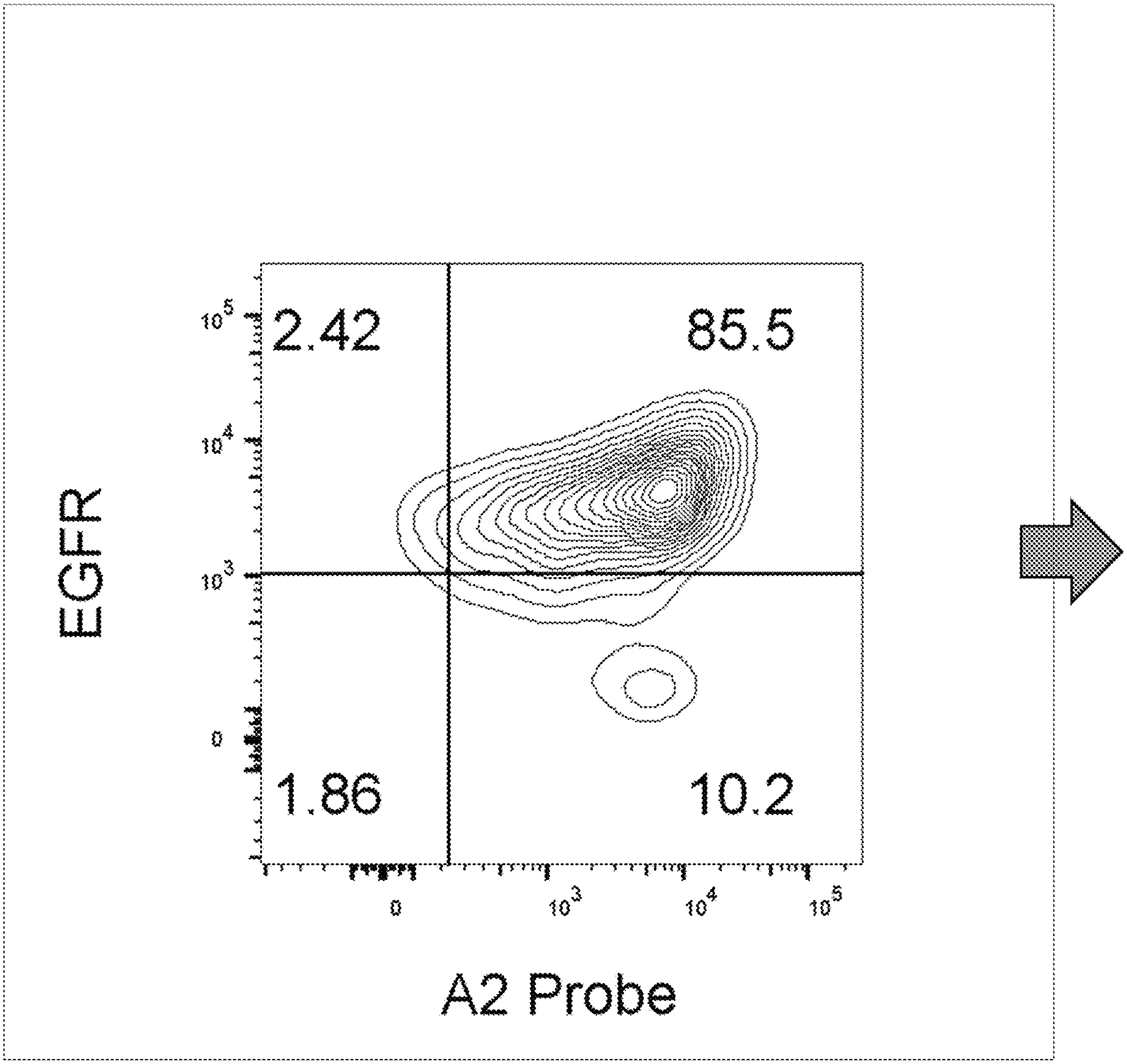
FIGS. 9-12 provide experimental results showing reversibly reduced expression of activating receptors.
Figure 10:
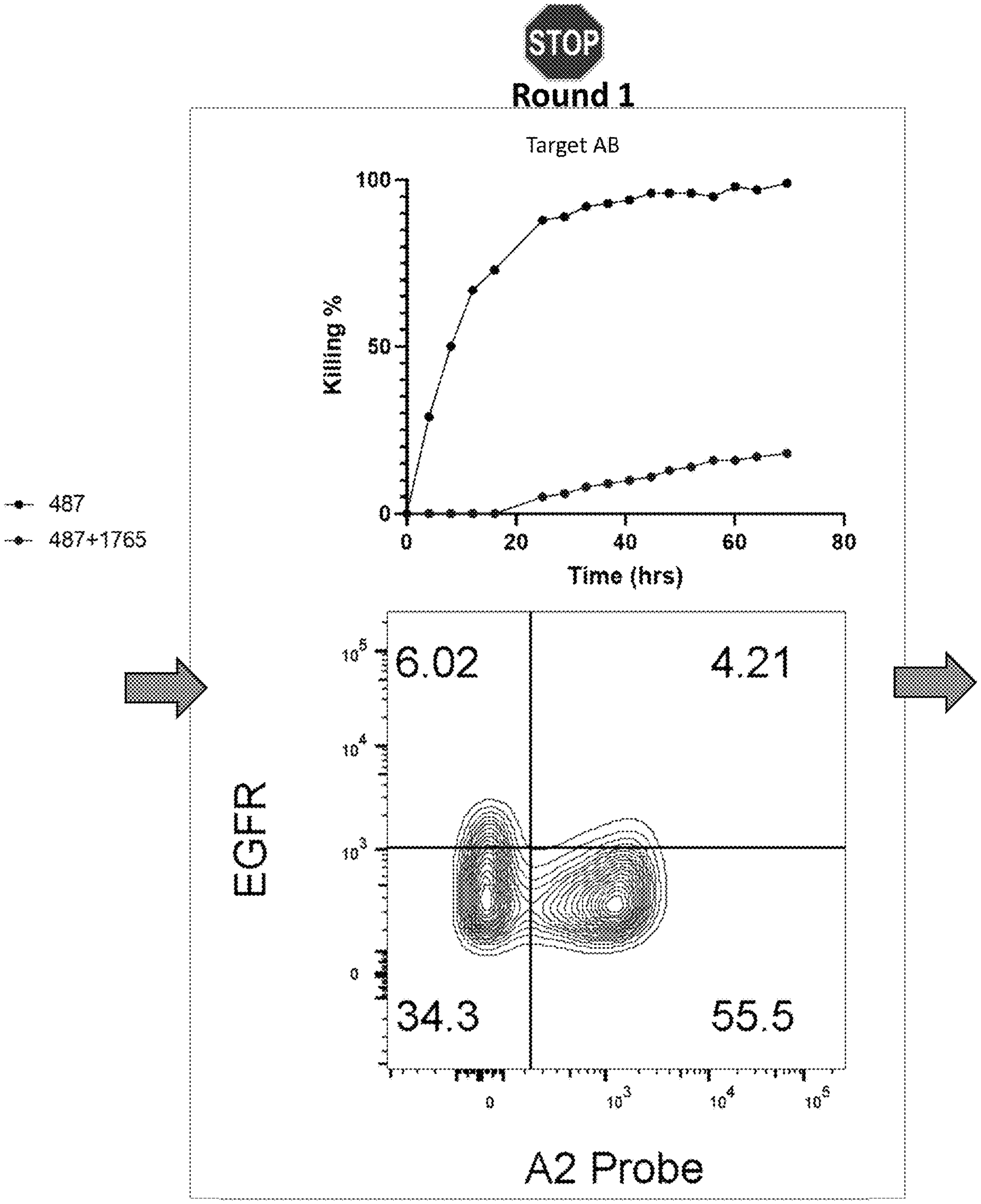
Figure 11:
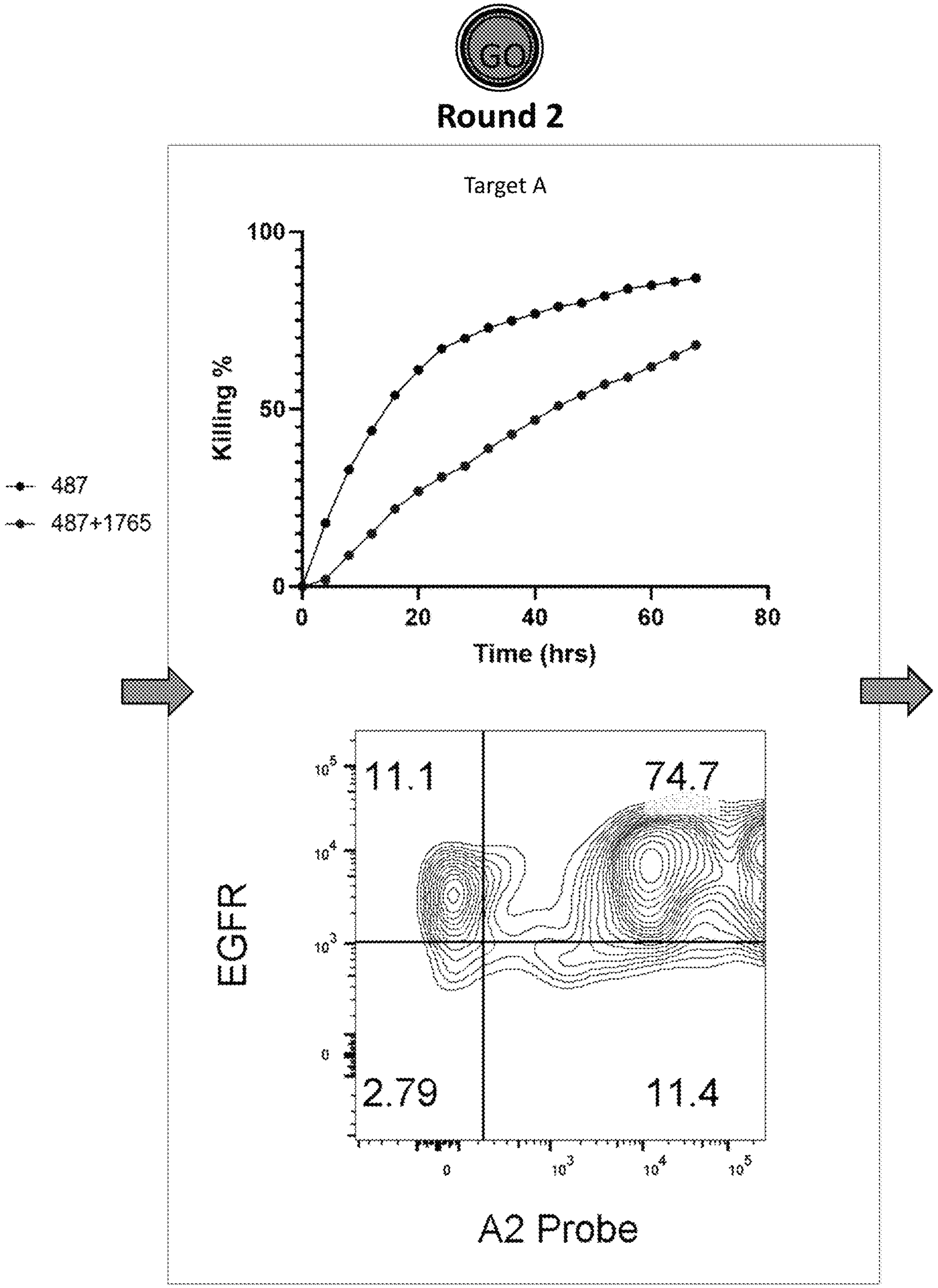
Figure 12:
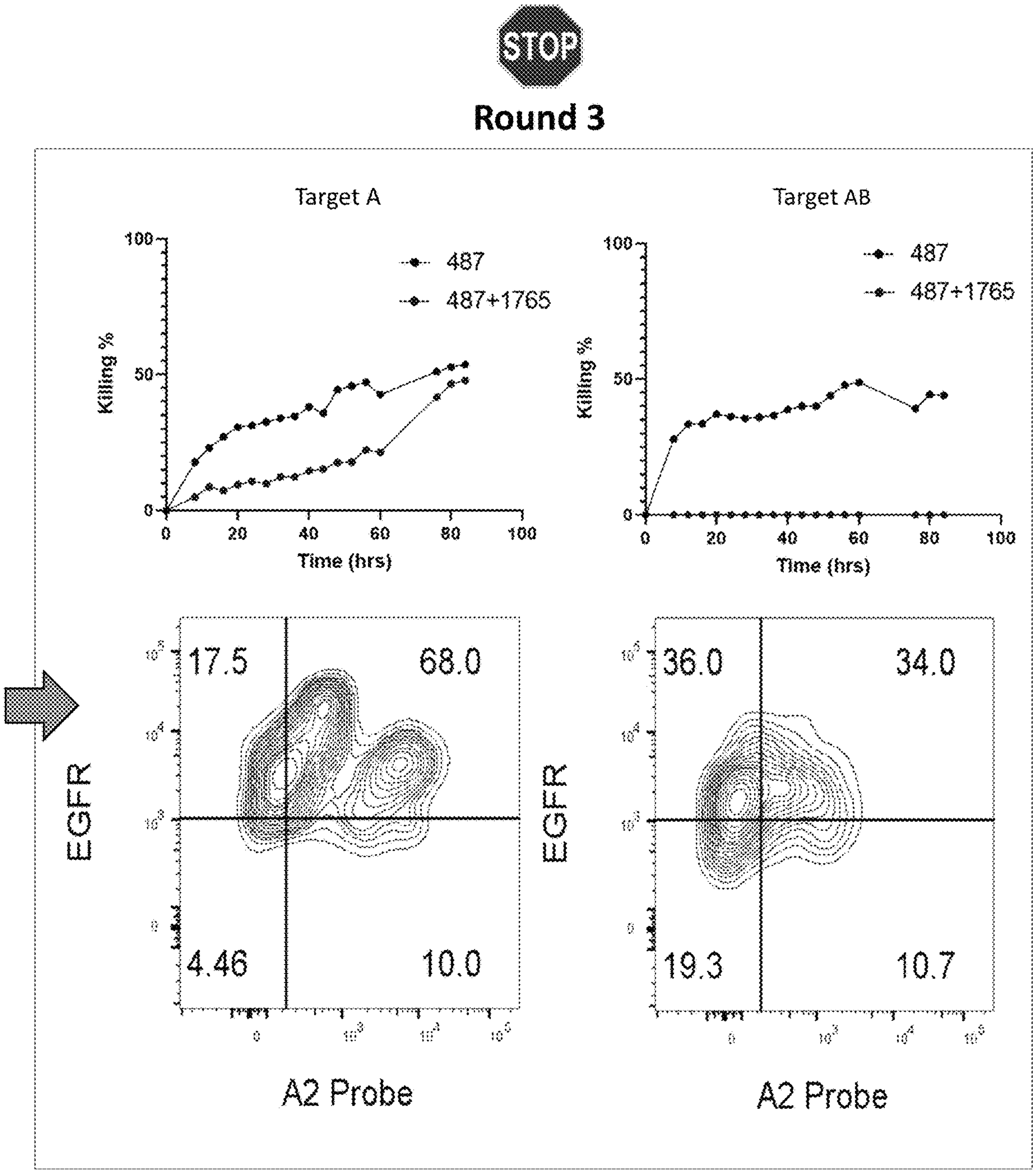
Figure 13:
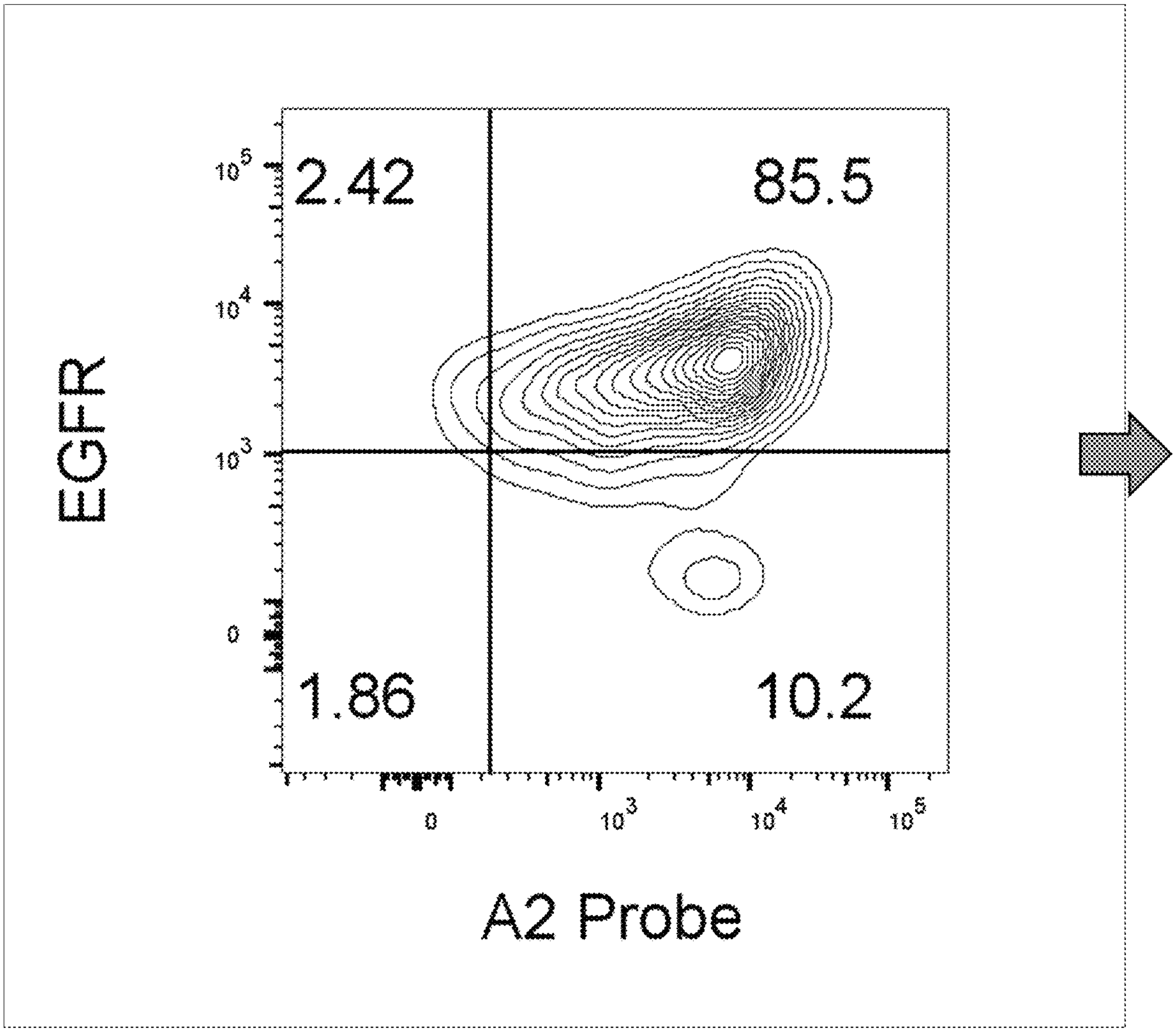
FIGS. 13-16 provide experimental results showing reversibly reduced expression of activating receptors.
Figure 14:
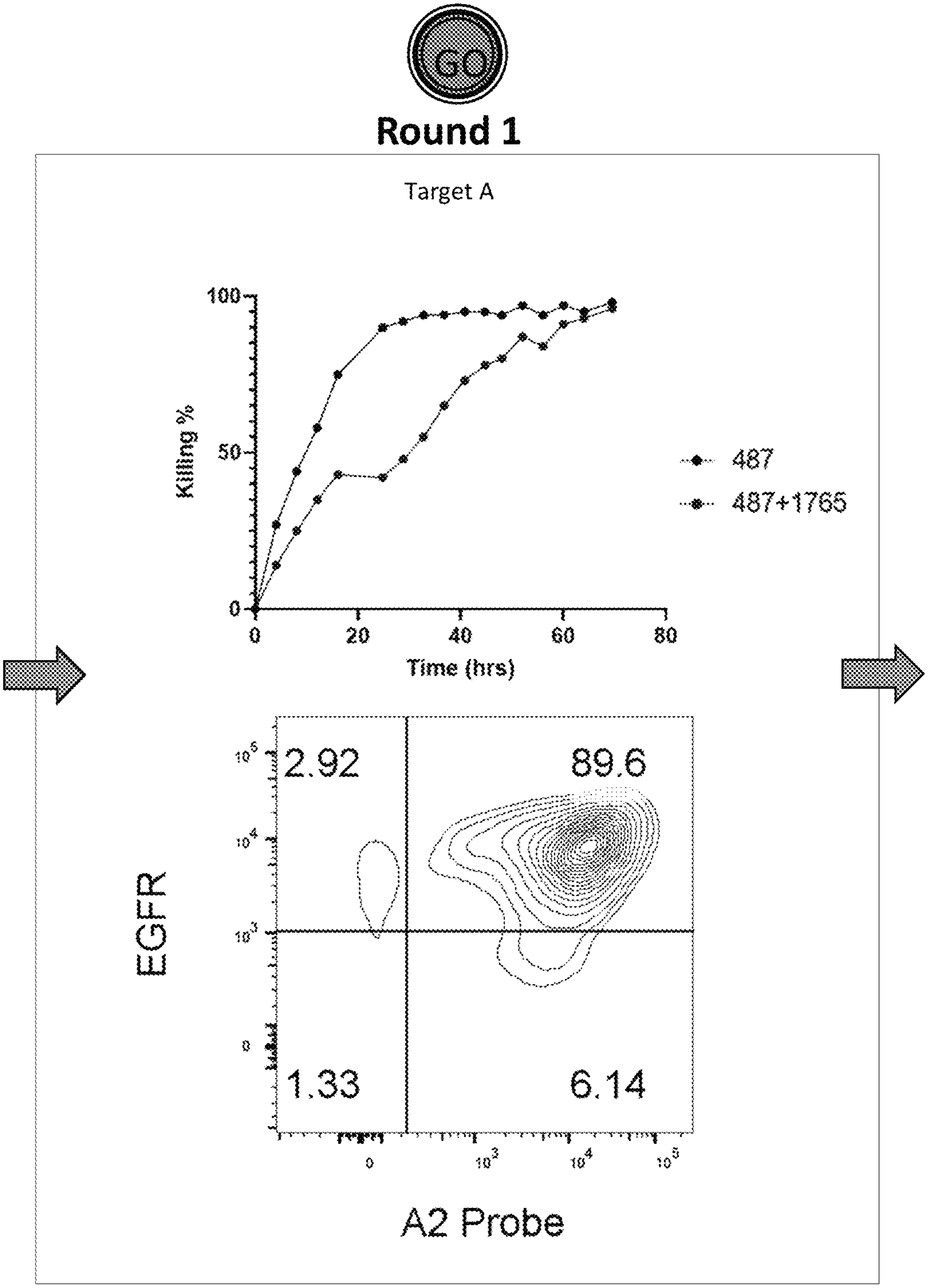
Figure 15:
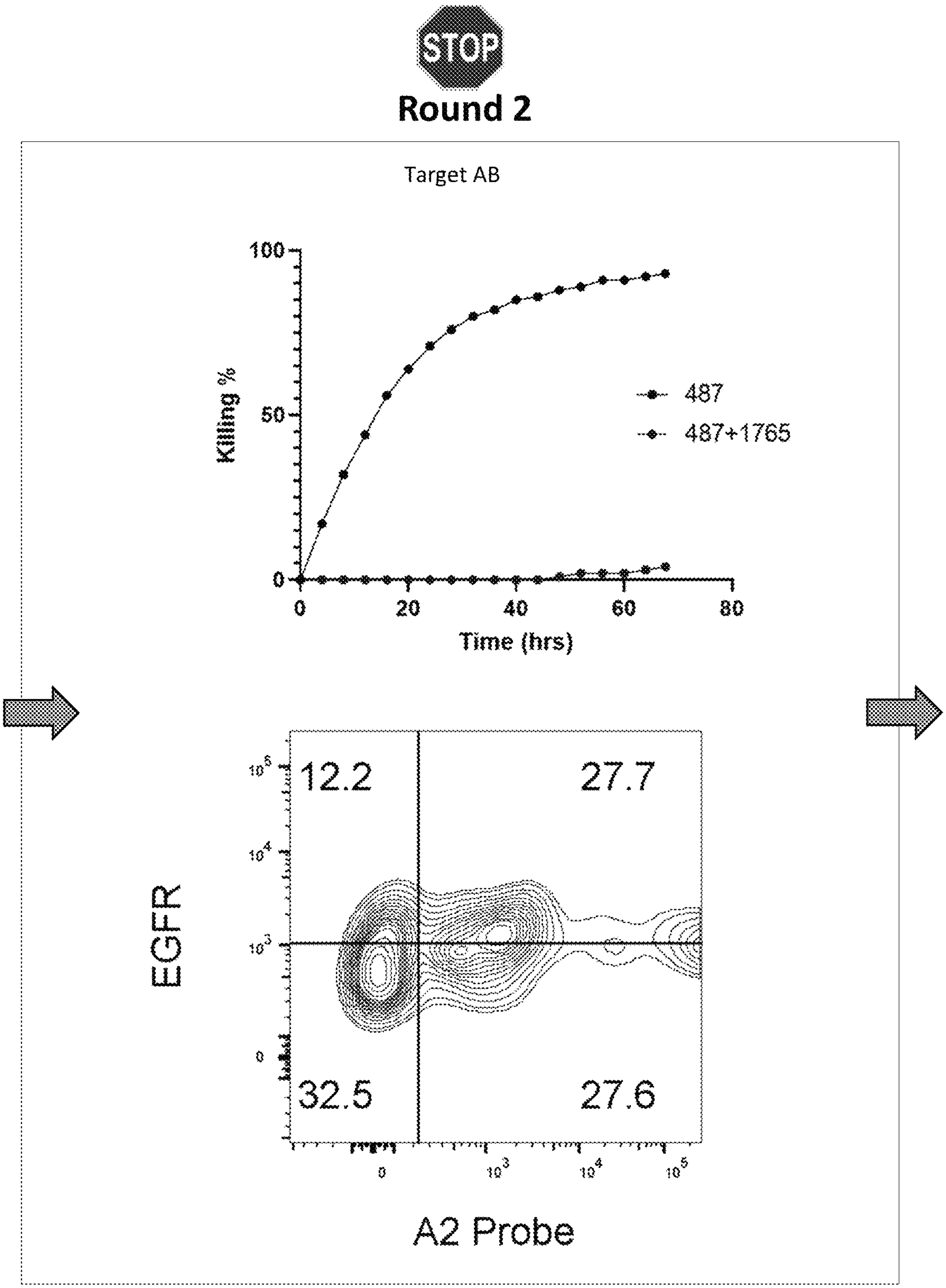
Figure 16:
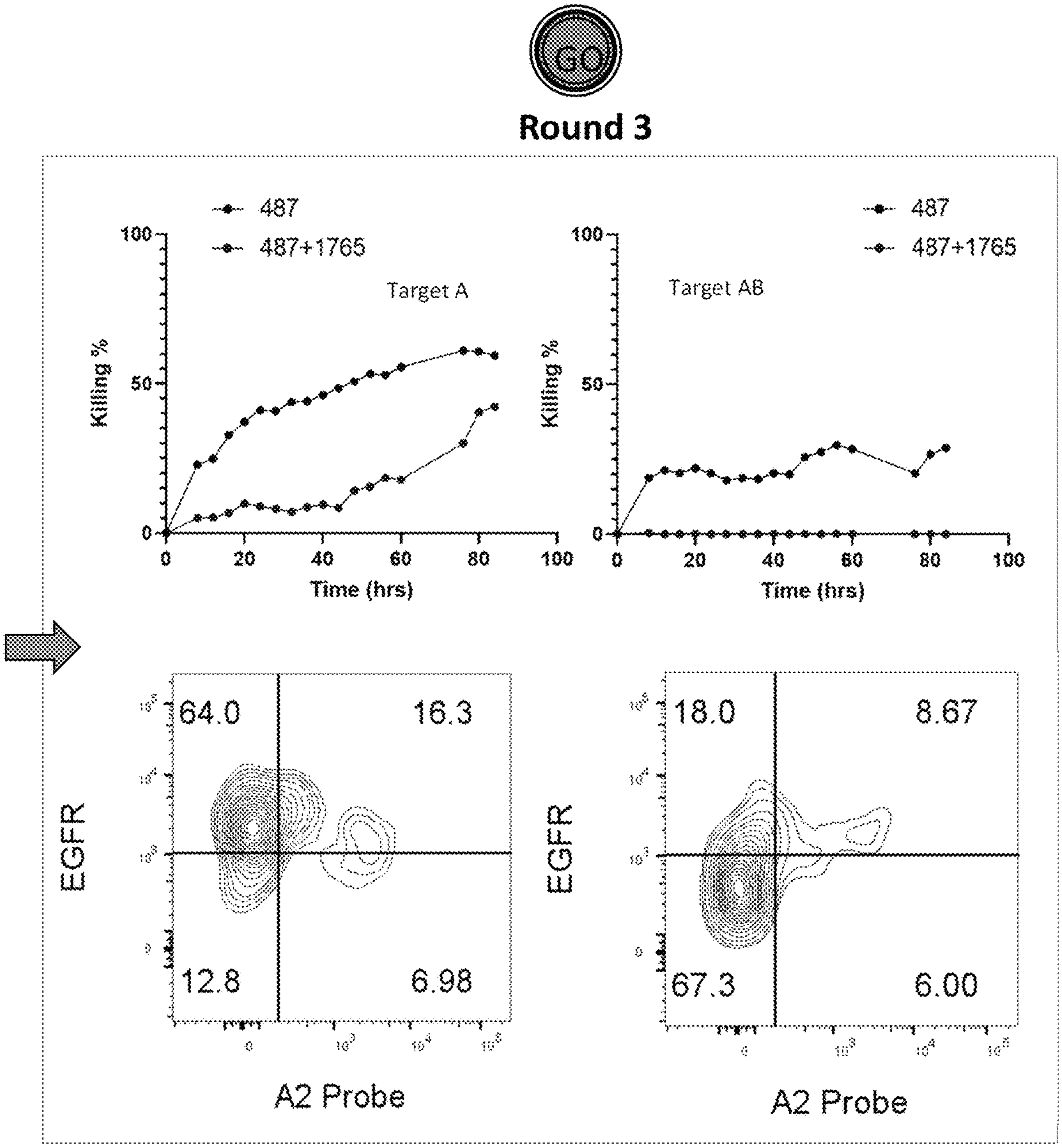

FIGS. 5-7 provides experimental results showing that this reduced surface expression of the activating receptors corresponds with the ability of the immune cells to kill other cells. Thus, advantageously, when the immune cells are in limited or no contact with target cells, their ability to kill is diminished, thereby reducing non-target effects.

Example 2

Another surprising facet of the immune cells of the present invention is that the reduced surface expression of the activating receptors only occurs when the immune cells contact non-target cells expressing both the activating and blocking ligands. This is shown in FIG. 7.

Example 3

FIGS. 8-16 provide an experimental protocol and results that indicate the reduced expression of activating receptors is reversible upon contact with target cells.

Example 4

Figure 17:
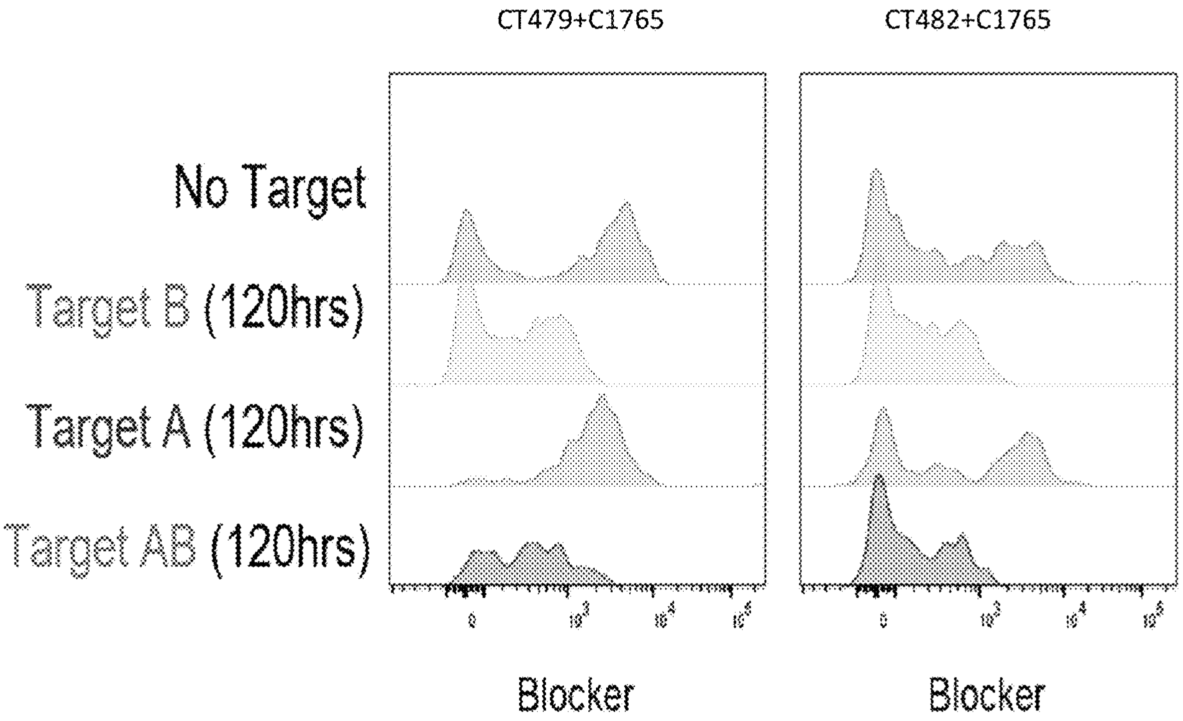
FIGS. 17-19 shows experimental results indicating that the blocking receptor does not undergo reduced surface expression in an appreciable amount in the presence of non-target cells.
Figure 18:
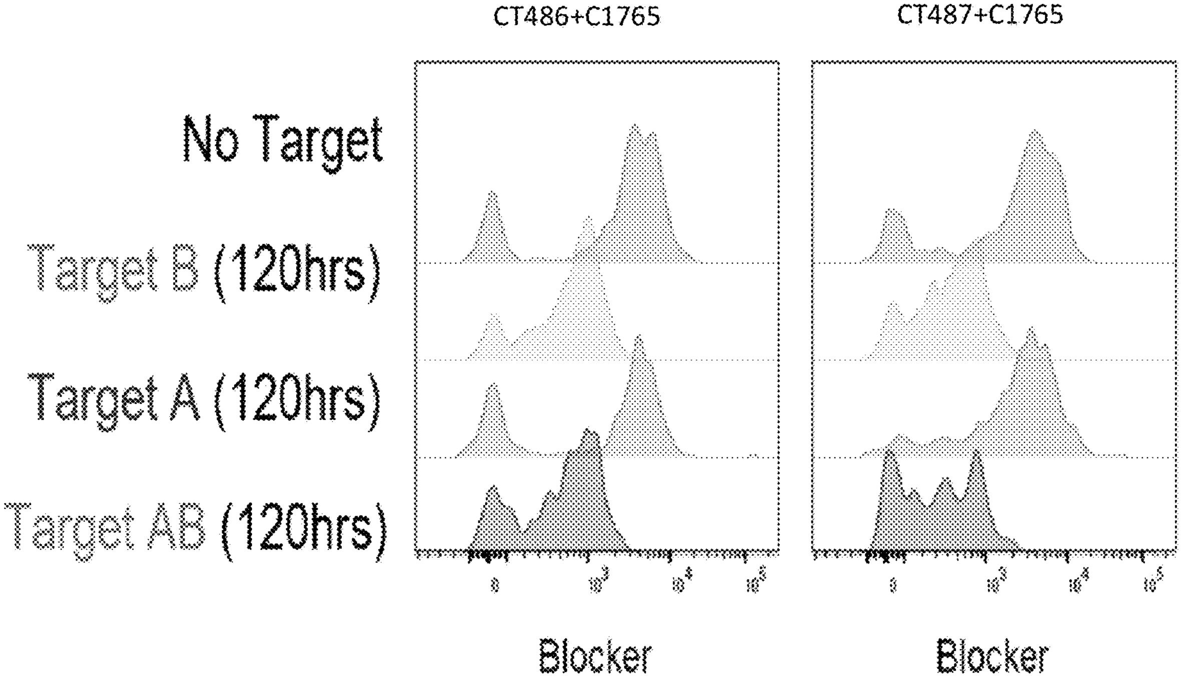
Figure 19:
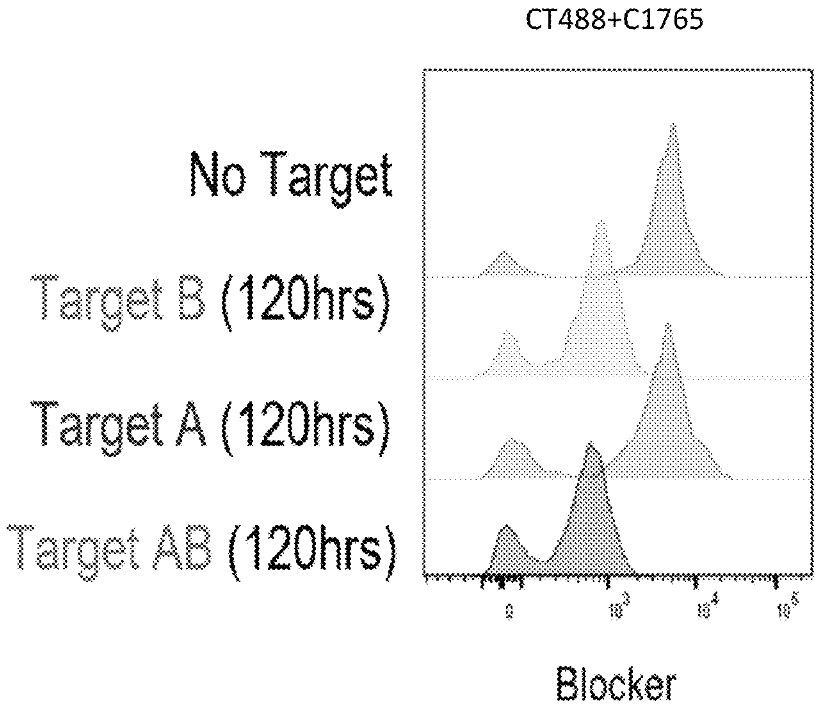

FIGS. 17-19 provide experimental results showing that, unlike the activating receptor, the blocking receptor does not undergo reduced surface expression in an appreciable amount in the presence of non-target cells.

Example 5

FIG. 22 shows experimental results indicating that the blocking receptor provides a blocking signal that dominates and inhibits the activating signal from the activating receptor.

Jurkat cells were transfected with either an activating receptor (MP1-CAR) for a MAGE-A3 activating ligand or the activating receptor and a blocking receptor (ESO-Tmod) for a NY-ESO-1 blocking ligand.

Panel A shows the NFAT-luciferase signal of Jurkat cells transfected with either the activator alone or in combination with the blocker, after 6 hours of co-culture with activator and blocker peptide-loaded T2 cells. The T2 cells were loaded with titrated amounts of activator MAGE-A3 peptide and a fixed amount of blocker NY-ESO-1 peptide concentration. This reveals the activation dose-response of the transfected cells.

Panel B shows the NFAT-luciferase signal of Jurkat cells transfected with either the activator alone or in combination with the blocker, after 6 hours of co-culture with activator and blocker peptide-loaded T2 cells. The T2 cells were loaded with titrated amounts of blocker NY-ESO-1 peptide and a fixed amount of activator MAGE-A3 peptide concentration above the Emax concentration (~0.1 μM). This reveals the inhibition dose-response of the transfected cells.

Panel C shows the NFAT-luciferase signal of Jurkat cells transfected with either the activator alone or in combination with the blocker, after 6 hours of co-culture with activator and blocker peptide-loaded T2 cells. The x-value blocker NY-ESO-1 peptide concentrations from panel B were normalized to the constant activator MAGE peptide concentrations used for each curve and plotted on the x-axis. The ratio of blocker peptide to activator peptide required for 50% blocking (IC50) are indicated for each curve. The B:A peptide ratio required is less than 1 indicating that, for this pair of activator CAR and blocker, similar (or fewer) blocker pMHC antigens may be sufficient on target cells to block activator pMHC antigens.

Since this ratio is less than 1, it can be inferred that the blocking signal dominates and inhibits the activating signal. Thus, a single blocking receptor can provide a blocking signal of sufficient strength to inhibit the activating signal of one or more activating receptors. As such, the quantity of activating and blocking ligands expressed by a non-target cell can form part of the basis for determining the appropriate relative amounts of activating and blocking receptors that should be expressed by an immune cell of the disclosure.

Example 6

FIG. 23 provides experimental results showing that the blocking receptors are ligand-dependent. For both CAR and TCR activating receptors, blocking receptors had minimal ligand-independent blocking activity. This impact is shown by the minimal effect on the $EC_{50}$ of the activating receptors by the blocking receptor in the presence/absence of the blocking ligand.

Example 7

FIG. 25 provides experimental results showing the relative impact hinge length and flexibility has on the strength of a blocking receptor as a function of the $EC_{50}$ of the activating receptor.

Example 8

FIG. 26 shows the large relative impact of the LBD on the activating receptor's structure activity relationship when compared with the effects provided by different hinges, transmembrane and intracellular domains. In this study, 45 separate activating receptors were created using various combinations of ligand binding domains, hinges, and intracellular domains. For each receptor one of five ligand binding domains that bind to the same activating ligand were selected. Despite all binding to the same target ligand, the identity of the ligand binding domain caused differences in the $EC_{50}$ of the activating receptors that spanned orders of magnitude. The ligand binding domain was shown to have greater than 10× the impact on the receptors' $EC_{50}$ compared to the hinge, transmembrane and intracellular domains.

Example 9

FIGS. 33-34 show the impact receptor cross-talk can have on the ability of the blocking receptor to inhibit the activation signal. Engineered immune cells were created with one of five different activating receptors. Though the activating receptors differed between the cells, each targeted the same activating ligand, epidermal growth factor receptor (EGFR), using a different LBD. As shown by five graph panels FIGS. 33-34, each of the different activating receptors provided the immune cells with equivalent abilities to kill target cells. Then, immune cells were created that had one of the five activating receptors and the same blocking receptor. Addition of the blocker caused some of the immune cells, like CT486-containing cells, to decrease their ability to kill target cells.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

SEQUENCE LISTING

```
Sequence total quantity: 391
SEQ ID NO: 1            moltype = AA  length = 45
FEATURE                 Location/Qualifiers
REGION                  1..45
                        note = CD8alpha hinge
source                  1..45
                        mol_type = protein
                        organism = synthetic construct
SEQUENCE: 1
TTTPAPRPPT PAPTIASQPL SLRPEACRPA AGGAVHTRGL DFACD                 45

SEQ ID NO: 2            moltype = DNA  length = 135
FEATURE                 Location/Qualifiers
misc_feature            1..135
                        note = CD8alpha hinge
source                  1..135
                        mol_type = other DNA
                        organism = synthetic construct
SEQUENCE: 2
accacgacgc cagcgccgcg accaccaaca ccggcgccca ccatcgcgtc gcagcccctg  60
tccctgcgcc cagaggcgtg ccggccagcg gcggggggcg cagtgcacac gagggggctg  120
gacttcgcct gtgat                                                  135

SEQ ID NO: 3            moltype = AA  length = 41
FEATURE                 Location/Qualifiers
REGION                  1..41
                        note = CD28 hinge
source                  1..41
                        mol_type = protein
                        organism = synthetic construct
SEQUENCE: 3
CTIEVMYPPP YLDNEKSNGT IIHVKGKHLC PSPLFPGPSK P                     41

SEQ ID NO: 4            moltype = DNA  length = 123
FEATURE                 Location/Qualifiers
misc_feature            1..123
                        note = CD28 hinge
source                  1..123
                        mol_type = other DNA
                        organism = synthetic construct
SEQUENCE: 4
tgtaccattg aagttatgta tcctcctcct tacctagaca atgagaagag caatggaacc  60
attatccatg tgaaagggaa acacctttgt ccaagtcccc tatttcccgg accttctaag  120
ccc                                                               123

SEQ ID NO: 5            moltype = AA  length = 27
FEATURE                 Location/Qualifiers
REGION                  1..27
                        note = CD28 transmembrane domain
source                  1..27
                        mol_type = protein
                        organism = synthetic construct
SEQUENCE: 5
FWVLVVVGGV LACYSLLVTV AFIIFWV                                     27

SEQ ID NO: 6            moltype = DNA  length = 81
FEATURE                 Location/Qualifiers
misc_feature            1..81
                        note = CD28 transmembrane domain
source                  1..81
                        mol_type = other DNA
                        organism = synthetic construct
SEQUENCE: 6
ttctgggtgc tggtcgttgt gggcggcgtg ctggcctgct acagcctgct ggtgacagtg  60
gccttcatca tcttttgggt g                                           81

SEQ ID NO: 7            moltype = AA  length = 25
FEATURE                 Location/Qualifiers
REGION                  1..25
                        note = IL-2R beta transmembrane domain
source                  1..25
                        mol_type = protein
                        organism = synthetic construct
SEQUENCE: 7
IPWLGHLLVG LSGAFGFIIL VYLLI                                       25

SEQ ID NO: 8            moltype = DNA  length = 75
FEATURE                 Location/Qualifiers
```

-continued

```
misc_feature           1..75
                       note = IL-2R beta transmembrane domain
source                 1..75
                       mol_type = other DNA
                       organism = synthetic construct
SEQUENCE: 8
attccgtggc tcggccacct cctcgtgggc ctcagcgggg cttttggctt catcatctta  60
gtgtacttgc tgatc                                                    75

SEQ ID NO: 9           moltype = AA  length = 112
FEATURE                Location/Qualifiers
REGION                 1..112
                       note = CD3 zeta activation domain
source                 1..112
                       mol_type = protein
                       organism = synthetic construct
SEQUENCE: 9
RVKFSRSADA PAYKQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 10          moltype = DNA  length = 336
FEATURE                Location/Qualifiers
misc_feature           1..336
                       note = CD3 zeta activation domain
source                 1..336
                       mol_type = other DNA
                       organism = synthetic construct
SEQUENCE: 10
agagtgaagt tcagcaggag cgcagacgcc cccgcgtaca agcagggcca gaaccagctc  60
tataacgagc tcaatctagg acgaagagag gagtacgatg ttttggacaa gcgtagaggc  120
cgggaccctg agatgggggg aaagccgaga aggaagaacc ctcaggaagg cctgtacaat  180
gaactgcaga aagataagat ggcggaggcc tacagtgaga ttgggatgaa aggcgagcgc  240
cggaggggca aggggcacga tggcctttac cagggactca gtacagccac caaggacacc  300
tacgacgccc ttcacatgca ggccctgccc cctcgc                             336

SEQ ID NO: 11          moltype = AA  length = 43
FEATURE                Location/Qualifiers
REGION                 1..43
                       note = CD3 zeta activation domain
source                 1..43
                       mol_type = protein
                       organism = synthetic construct
SEQUENCE: 11
RVKFSRSADA PAYQQGQNQL YNELNLGRRE EYDVLHMQAL PPR                     43

SEQ ID NO: 12          moltype = DNA  length = 129
FEATURE                Location/Qualifiers
misc_feature           1..129
                       note = CD3 zeta activation domain
source                 1..129
                       mol_type = other DNA
                       organism = synthetic construct
SEQUENCE: 12
agagtgaagt tcagcaggag cgcagacgcc cccgcgtacc agcagggcca gaaccagctc  60
tataacgagc tcaatctagg acgaagagag gagtacgatg ttttgcacat gcaggccctg  120
ccccctcgc                                                           129

SEQ ID NO: 13          moltype = AA  length = 41
FEATURE                Location/Qualifiers
REGION                 1..41
                       note = CD28 co-stimulatory domain
source                 1..41
                       mol_type = protein
                       organism = synthetic construct
SEQUENCE: 13
RSKRSRLLHS DYMNMTPRRP GPTRKHYQPY APPRDFAAYR S                       41

SEQ ID NO: 14          moltype = DNA  length = 123
FEATURE                Location/Qualifiers
misc_feature           1..123
                       note = CD28 co-stimulatory domain
source                 1..123
                       mol_type = other DNA
                       organism = synthetic construct
SEQUENCE: 14
aggagcaagc ggagcagact gctgcacagc gactacatga acatgacccc ccggaggcct  60
ggccccaccc ggaagcacta ccagccctac gccccctccca gggatttcgc cgcctaccgg  120
agc                                                                 123
```

-continued

```
SEQ ID NO: 15          moltype = AA  length = 94
FEATURE                Location/Qualifiers
REGION                 1..94
                       note = IL-2-Rbeta intracellular domain
source                 1..94
                       mol_type = protein
                       organism = synthetic construct
SEQUENCE: 15
NCRNTGPWLK KVLKCNTPDP SKFFSQLSSE HGGDVQKWLS SPFPSSSFSP GGLAPEISPL  60
EVLERDKVTQ LLPLNTDAYL SLQELQGQDP THLV                              94

SEQ ID NO: 16          moltype = DNA  length = 282
FEATURE                Location/Qualifiers
misc_feature           1..282
                       note = IL-2-Rbeta intracellular domain
source                 1..282
                       mol_type = other DNA
                       organism = synthetic construct
SEQUENCE: 16
aactgcagga acaccgggcc atggctgaag aaggtcctga agtgtaacac cccagacccc  60
tcgaagttct tttcccagct gagctcagag catggaggcg acgtccagaa gtggctctct  120
tcgcccttcc cctcatcgtc cttcagccct ggcggcctgg cacctgagat ctcgccacta  180
gaagtgctgg agagggacaa ggtgacgcag ctgctccccc tgaacactga tgcctacttg  240
tctctccaag aactccaggg tcaggaccca actcacttgg tg                     282

SEQ ID NO: 17          moltype = AA  length = 4
FEATURE                Location/Qualifiers
REGION                 1..4
                       note = STAT5 recruitment motif
source                 1..4
                       mol_type = protein
                       organism = synthetic construct
SEQUENCE: 17
YLSL                                                               4

SEQ ID NO: 18          moltype = AA  length = 760
FEATURE                Location/Qualifiers
source                 1..760
                       mol_type = protein
                       organism = Homo sapiens
SEQUENCE: 18
MMDQARSAFS NLFGGEPLSY TRFSLARQVD GDNSHVEMKL AVDEEENADN NTKANVTKPK  60
RCSGSICYGT IAVIVFFLIG FMIGYLGYCK GVEPKTECER LAGTESPVRE EPGEDFPAAR  120
RLYWDDLKRK LSEKLDSTDF TSTIKLLNEN SYVPREAGSQ KDENLALYVE NQFREFKLSK  180
VWRDQHFVKI QVKDSAQNSV IIVDKNGRLV YLVENPGGYV AYSKAATVTG KLVHANFGTK  240
KDFEDLYTPV NGSIVIVRAG KITFAEKVAN AESLNAIGVL IYMDQTKFPI VNAELSFFGH  300
AHLGTGDPYT PGFPSFNHTQ FPPSRSSGLP NIPVQTISRA AAEKLFGNME GDCPSDWKTD  360
STCRMVTSES KNVKLTVSNV LKEIKILNIF GVIKGFVEPD HYVVVGAQRD AWGPGAAKSG  420
VGTALLLKLA QMFSDMVLKD GFQPSRSIIF ASWSAGDFGS VGATEWLEGY LSSLHLKAFT  480
YINLDKAVLG TSNFKVSASP LLYTLIEKTM QNVKHPVTGQ FLYQDSNWAS KVEKLTLDNA  540
AFPFLAYSGI PAVSFCFCED TDYPYLGTTM DTYKELIERI PELNKVARAA AEVAGQFVIK  600
LTHDVELNLD YERYNSQLLS FVRDLNQYRA DIKEMGLSLQ WLYSARGDFF RATSRLTTDF  660
GNAEKTDRFV MKKLNDRVMR VEYHFLSPYV SPKESPFRHV FWGSGSHTLP ALLENLKLRK  720
QNNGAFNETL FRNQLALATW TIQGAANALS GDVWDIDNEF                        760

SEQ ID NO: 19          moltype = DNA  length = 300
FEATURE                Location/Qualifiers
misc_feature           1..300
                       note = CD3 epsilon intracellular domain
source                 1..300
                       mol_type = other DNA
                       organism = synthetic construct
SEQUENCE: 19
aagaatagaa aggccaaggc caagcctgtg acacgaggag cgggtgctgg cggcaggcaa  60
aggggacaaa acaaggagag gccaccacct gttcccaacc cagactatga gcccatccgg  120
aaaggccagc gggacctgta ttctggcctg aatcagcgca gaatcggcgg aagcaggagc  180
aagcggagca gactgctgca cagcgactac atgaacatga ccccccggag gcctggcccc  240
acccggaagc actaccagcc ctacgcccct cccagggatt tcgccgccta ccggagctag  300

SEQ ID NO: 20          moltype = DNA  length = 69
FEATURE                Location/Qualifiers
misc_feature           1..69
                       note = TCR beta transmembrane domain
source                 1..69
                       mol_type = other DNA
                       organism = synthetic construct
SEQUENCE: 20
accatcctct atgagatctt gctagggaag gccaccttgt atgccgtgct ggtcagtgcc  60
ctcgtgctg                                                          69
```

```
SEQ ID NO: 21           moltype =   length =
SEQUENCE: 21
000

SEQ ID NO: 22           moltype = DNA  length = 270
FEATURE                 Location/Qualifiers
misc_feature            1..270
                        note = CD3 gamma intracellular domain
source                  1..270
                        mol_type = other DNA
                        organism = synthetic construct
SEQUENCE: 22
ggacaggatg gagttcgcca gtcgagagct tcagacaagc agactctgtt gcccaatgac  60
cagctctacc agcccctcaa ggatcgagaa gatgaccagt acagccacct tcaaggaaac  120
cagttgagga ggaatggcgg aagcaggagc aagcggagca gactgctgca cagcgactac  180
atgaacatga ccccccggag gcctggcccc acccggaagc actaccagcc ctacgcccct  240
cccagggatt tcgccgccta ccggagctag                                    270

SEQ ID NO: 23           moltype = AA  length = 10
FEATURE                 Location/Qualifiers
REGION                  1..10
                        note = UTY peptide
SITE                    1
                        note = X - X is R or G
SITE                    6
                        note = X - X is E or A
SITE                    8
                        note = X - X is V or P
source                  1..10
                        mol_type = protein
                        organism = synthetic construct
SEQUENCE: 23
XESEEXSXSL                                                          10

SEQ ID NO: 24           moltype = AA  length = 9
FEATURE                 Location/Qualifiers
REGION                  1..9
                        note = RPSY peptide
SITE                    8
                        note = X - X is V or L
source                  1..9
                        mol_type = protein
                        organism = synthetic construct
SEQUENCE: 24
TIRYPDPXI                                                           9

SEQ ID NO: 25           moltype = AA  length = 8
FEATURE                 Location/Qualifiers
REGION                  1..8
                        note = UTY peptide
SITE                    5
                        note = X - X is H or R
SITE                    7
                        note = X - X is D or N
source                  1..8
                        mol_type = protein
                        organism = synthetic construct
SEQUENCE: 25
LPHNXTXL                                                            8

SEQ ID NO: 26           moltype = AA  length = 23
FEATURE                 Location/Qualifiers
REGION                  1..23
                        note = TCR alpha transmembrane domain
source                  1..23
                        mol_type = protein
                        organism = synthetic construct
SEQUENCE: 26
VIGFRILLLK VAGFNLLMTL RLW                                           23

SEQ ID NO: 27           moltype = DNA  length = 69
FEATURE                 Location/Qualifiers
misc_feature            1..69
                        note = TCR alpha transmembrane domain
source                  1..69
                        mol_type = other DNA
                        organism = synthetic construct
SEQUENCE: 27
```

```
gtgattgggt tccgaatcct cctcctgaaa gtggccgggt ttaatctgct catgacgctg  60
cggctgtgg                                                          69

SEQ ID NO: 28          moltype = AA  length = 23
FEATURE                Location/Qualifiers
REGION                 1..23
                       note = TCR beta transmembrane domain
source                 1..23
                       mol_type = protein
                       organism = synthetic construct
SEQUENCE: 28
TILYEILLGK ATLYAVLVSA LVL                                          23

SEQ ID NO: 29          moltype = AA  length = 21
FEATURE                Location/Qualifiers
REGION                 1..21
                       note = CD3 zeta transmembrane domain
source                 1..21
                       mol_type = protein
                       organism = synthetic construct
SEQUENCE: 29
LCYLLDGILF IYGVILTALF L                                            21

SEQ ID NO: 30          moltype = AA  length = 89
FEATURE                Location/Qualifiers
REGION                 1..89
                       note = CD3 delta intracellular domain
source                 1..89
                       mol_type = protein
                       organism = synthetic construct
SEQUENCE: 30
GHETGRLSGA ADTQALLRND QVYQPLRDRD DAQYSHLGGN WARNKGGSRS KRSRLLHSDY  60
MNMTPRRPGP TRKHYQPYAP PRDFAAYRS                                    89

SEQ ID NO: 31          moltype = DNA  length = 269
FEATURE                Location/Qualifiers
misc_feature           1..269
                       note = CD3 delta intracellular domain
source                 1..269
                       mol_type = other DNA
                       organism = synthetic construct
SEQUENCE: 31
ggacatgaga ctggaaggct gtctggggct gccgacacac aagctctgtt gaggaatgac  60
caggtctatc agcccctccg agatcgagat gatgctcagt acagccacct tggaggaaac  120
tgggctcgga acaagggcgg aagcaggagc aagcggagca gactgctgca cagcgactac  180
atgaacatga ccccccggag gcctggcccc acccggaagc actaccagcc ctacgcccct  240
cccagggatt tcgccgccta ccggagcta                                    269

SEQ ID NO: 32          moltype = AA  length = 99
FEATURE                Location/Qualifiers
REGION                 1..99
                       note = CD3 epsilon intracellular domain
source                 1..99
                       mol_type = protein
                       organism = synthetic construct
SEQUENCE: 32
KNRKAKAKPV TRGAGAGGRQ RGQNKERPPP VPNPDYEPIR KGQRDLYSGL NQRRIGGSRS  60
KRSRLLHSDY MNMTPRRPGP TRKHYQPYAP PRDFAAYRS                         99

SEQ ID NO: 33          moltype = AA  length = 89
FEATURE                Location/Qualifiers
REGION                 1..89
                       note = CD3 gamma intracellular domain
source                 1..89
                       mol_type = protein
                       organism = synthetic construct
SEQUENCE: 33
GQDGVRQSRA SDKQTLLPND QLYQPLKDRE DDQYSHLQGN QLRRNGGSRS KRSRLLHSDY  60
MNMTPRRPGP TRKHYQPYAP PRDFAAYRS                                    89

SEQ ID NO: 34          moltype = AA  length = 11
FEATURE                Location/Qualifiers
REGION                 1..11
                       note = SMCY peptide
SITE                   3
                       note = X - X is S or A
SITE                   8
                       note = X - X is R or Q
source                 1..11
```

```
                        mol_type = protein
                        organism = synthetic construct
SEQUENCE: 34
SPXVDKAXAE L                                                 11

SEQ ID NO: 35           moltype = AA  length = 10
FEATURE                 Location/Qualifiers
REGION                  1..10
                        note = TCR beta intracellular domain
source                  1..10
                        mol_type = protein
                        organism = synthetic construct
SEQUENCE: 35
MAMVKRKDSR                                                   10

SEQ ID NO: 36           moltype = DNA  length = 30
FEATURE                 Location/Qualifiers
misc_feature            1..30
                        note = TCR beta intracellular domain
source                  1..30
                        mol_type = other DNA
                        organism = synthetic construct
SEQUENCE: 36
atggccatgg tcaagagaaa ggattccaga                             30

SEQ ID NO: 37           moltype = AA  length = 41
FEATURE                 Location/Qualifiers
REGION                  1..41
                        note = CD28 intracellular domain
source                  1..41
                        mol_type = protein
                        organism = synthetic construct
SEQUENCE: 37
RSKRSRLLHS DYMNMTPRRP GPTRKHYQPY APPRDFAAYR S                41

SEQ ID NO: 38           moltype = DNA  length = 123
FEATURE                 Location/Qualifiers
misc_feature            1..123
                        note = CD28 intracellular domain
source                  1..123
                        mol_type = other DNA
                        organism = synthetic construct
SEQUENCE: 38
aggagcaagc ggagcagact gctgcacagc gactacatga acatgacccc ccggaggcct  60
ggccccaccc ggaagcacta ccagccctac gccccctccca gggatttcgc cgcctaccgg  120
agc                                                          123

SEQ ID NO: 39           moltype = AA  length = 42
FEATURE                 Location/Qualifiers
REGION                  1..42
                        note = 4-1BB intracellular domain
source                  1..42
                        mol_type = protein
                        organism = synthetic construct
SEQUENCE: 39
KRGRKKLLYI FKQPFMRPVQ TTQEEDGCSC RFPEEEEGGC EL               42

SEQ ID NO: 40           moltype = DNA  length = 126
FEATURE                 Location/Qualifiers
misc_feature            1..126
                        note = 4-1BB intracellular domain
source                  1..126
                        mol_type = other DNA
                        organism = synthetic construct
SEQUENCE: 40
aaacggggca gaaagaaact cctgtatata ttcaaacaac catttatgag gccagtacaa  60
actactcaag aggaagatgg ctgtagctgc cgatttccag aagaagaaga aggaggatgt  120
gaactg                                                       126

SEQ ID NO: 41           moltype = AA  length = 16
FEATURE                 Location/Qualifiers
REGION                  1..16
                        note = HLA-A*02 CDR-L1
source                  1..16
                        mol_type = protein
                        organism = synthetic construct
SEQUENCE: 41
RSSQSIVHSN GNTYLE                                            16
```

```
SEQ ID NO: 42          moltype = AA  length = 12
FEATURE                Location/Qualifiers
REGION                 1..12
                       note = HLA-A*02 CDR-L2
source                 1..12
                       mol_type = protein
                       organism = synthetic construct
SEQUENCE: 42
KVSNRFSGVP DR                                                12

SEQ ID NO: 43          moltype = AA  length = 9
FEATURE                Location/Qualifiers
REGION                 1..9
                       note = HLA-A*02 CDR-L3
source                 1..9
                       mol_type = protein
                       organism = synthetic construct
SEQUENCE: 43
FQGSHVPRT                                                    9

SEQ ID NO: 44          moltype = AA  length = 12
FEATURE                Location/Qualifiers
REGION                 1..12
                       note = HLA-A*02 CDR-H1
source                 1..12
                       mol_type = protein
                       organism = synthetic construct
SEQUENCE: 44
ASGYTFTSYH IH                                                12

SEQ ID NO: 45          moltype = AA  length = 18
FEATURE                Location/Qualifiers
REGION                 1..18
                       note = HLA-A*02 CDR-H2
source                 1..18
                       mol_type = protein
                       organism = synthetic construct
SEQUENCE: 45
WIYPGNVNTE YNEKFKGK                                          18

SEQ ID NO: 46          moltype = AA  length = 9
FEATURE                Location/Qualifiers
REGION                 1..9
                       note = HLA-A*02 CDR-H3
source                 1..9
                       mol_type = protein
                       organism = synthetic construct
SEQUENCE: 46
EEITYAMDY                                                    9

SEQ ID NO: 47          moltype = AA  length = 16
FEATURE                Location/Qualifiers
REGION                 1..16
                       note = HLA-A*02 CDR-L1
source                 1..16
                       mol_type = protein
                       organism = synthetic construct
SEQUENCE: 47
RSSQSIVHSN GNTYLD                                            16

SEQ ID NO: 48          moltype = AA  length = 12
FEATURE                Location/Qualifiers
REGION                 1..12
                       note = HLA-A*02 CDR-L2
source                 1..12
                       mol_type = protein
                       organism = synthetic construct
SEQUENCE: 48
KVSNRFSGVP DR                                                12

SEQ ID NO: 49          moltype = AA  length = 9
FEATURE                Location/Qualifiers
REGION                 1..9
                       note = HLA-A*02 CDR-L3
source                 1..9
                       mol_type = protein
                       organism = synthetic construct
SEQUENCE: 49
MQGSHVPRT                                                    9
```

```
SEQ ID NO: 50           moltype = AA  length = 11
FEATURE                 Location/Qualifiers
REGION                  1..11
                        note = HLA-A*02 CDR-H1
source                  1..11
                        mol_type = protein
                        organism = synthetic construct
SEQUENCE: 50
SGYTFTSYHM H                                                       11

SEQ ID NO: 51           moltype = AA  length = 17
FEATURE                 Location/Qualifiers
REGION                  1..17
                        note = HLA-A*02 CDR-H2
source                  1..17
                        mol_type = protein
                        organism = synthetic construct
SEQUENCE: 51
WIYPGDGSTQ YNEKFKG                                                 17

SEQ ID NO: 52           moltype = AA  length = 9
FEATURE                 Location/Qualifiers
REGION                  1..9
                        note = HLA-A*02 CDR-H3
source                  1..9
                        mol_type = protein
                        organism = synthetic construct
SEQUENCE: 52
EGTYYAMDY                                                          9

SEQ ID NO: 53           moltype = AA  length = 247
FEATURE                 Location/Qualifiers
REGION                  1..247
                        note = HLA-A*02 ScFv
source                  1..247
                        mol_type = protein
                        organism = synthetic construct
SEQUENCE: 53
DVLMTQTPLS LPVSLGDQAS ISCRSSQSIV HSNGNTYLEW YLQKPGQSPK LLIYKVSNRF  60
SGVPDRFSGS GSGTDFTLKI SRVEAEDLGV YYCFQGSHVP RTSGGGTKLE IKGGGGSGGG  120
GSGGGGSGGQ VQLQQSGPEL VKPGASVRIS CKASGYTFTS YHIHWVKQRP GQGLEWIGWI  180
YPGNVNTEYN EKFKGKATLT ADKSSSTAYM HLSSLTSEDS AVYFCAREEI TYAMDYWGQG  240
TSVTVSS                                                            247

SEQ ID NO: 54           moltype = AA  length = 247
FEATURE                 Location/Qualifiers
REGION                  1..247
                        note = HLA-A*02 ScFv
source                  1..247
                        mol_type = protein
                        organism = synthetic construct
SEQUENCE: 54
QVQLVQSGAE VKKPGSSVKV SCKASGYTFT SYHIHWVRQA PGQGLEWMGW IYPGNVNTEY  60
NEKFKGKATI TADKSTSTAY MELSSLRSED TAVYYCAREE ITYAMDYWGQ GTTVTVSSGG  120
GGSGGGGSGG GGSGGEIVLT QSPGTLSLSP GERATLSCRS SQSIVHSNGN TYLEWYQQKP  180
GQAPRLLIYK VSNRFSGIPD RFSGSGSGTD FTLTISRLEP EDFAVYYCFQ GSHVPRTFGG  240
GTKVEIK                                                            247

SEQ ID NO: 55           moltype = AA  length = 247
FEATURE                 Location/Qualifiers
REGION                  1..247
                        note = HLA-A*02 ScFv
source                  1..247
                        mol_type = protein
                        organism = synthetic construct
SEQUENCE: 55
QVQLVQSGAE VKKPGSSVKV SCKASGYTFT SYHIHWVRQA PGQGLEWMGW IYPGNVNTEY  60
NEKFKGKATI TADKSTSTAY MELSSLRSED TAVYYCAREE ITYAMDYWGQ GTTVTVSSGG  120
GGSGGGGSGG GGSGGDIVMT QTPLSLPVTP GEPASISCRS SQSIVHSNGN TYLEWYLQKP  180
GQSPQLLIYK VSNRFSGVPD RFSGSGSGTD FTLKISRVEA EDVGVYYCFQ GSHVPRTFGG  240
GTKVEIK                                                            247

SEQ ID NO: 56           moltype = AA  length = 247
FEATURE                 Location/Qualifiers
REGION                  1..247
                        note = HLA-A*02 ScFv
source                  1..247
                        mol_type = protein
```

```
                         organism = synthetic construct
SEQUENCE: 56
EVQLVESGGG LVKPGGSLRL SCAASGYTFT SYHIHWVRQA PGKGLEWVGW IYPGNVNTEY  60
NEKFKGRFTI SRDDSKNTLY LQMNSLKTED TAVYYCAREE ITYAMDYWGQ GTTVTVSSGG  120
GGSGGGGSGG GGSGGDIQMT QSPSSLSASV GDRVTITCRS SQSIVHSNGN TYLEWYQQKP  180
GKAPKLLIYK VSNRFSGVPS RFSGSGSGTD FTLTISSLQP EDFATYYCFQ GSHVPRTFGG  240
GTKVEIK                                                            247

SEQ ID NO: 57            moltype = AA  length = 247
FEATURE                  Location/Qualifiers
REGION                   1..247
                         note = HLA-A*02 ScFv
source                   1..247
                         mol_type = protein
                         organism = synthetic construct
SEQUENCE: 57
QVQLVQSGAE VKKPGSSVKV SCKASGYTFT SYHIHWVRQA PGQGLEWIGW IYPGNVNTEY  60
NEKFKGKATI TADESTNTAY MELSSLRSED TAVYYCAREE ITYAMDYWGQ GTLVTVSSGG  120
GGSGGGGSGG GGSGGDIQMT QSPSTLSASV GDRVTITCRS SQSIVHSNGN TYLEWYQQKP  180
GKAPKLLIYK VSNRFSGVPA RFSGSGSGTE FTLTISSLQP DDFATYYCFQ GSHVPRTFGQ  240
GTKVEVK                                                            247

SEQ ID NO: 58            moltype = AA  length = 247
FEATURE                  Location/Qualifiers
REGION                   1..247
                         note = HLA-A*02 ScFv
source                   1..247
                         mol_type = protein
                         organism = synthetic construct
SEQUENCE: 58
QVQLVQSGAE VKKPGSSVKV SCKASGYTFT SYHMHWVRQA PGQGLEWIGY IYPGNVNTEY  60
NEKFKGKATL TADKSTNTAY MELSSLRSED TAVYFCAREE ITYAMDYWGQ GTLVTVSSGG  120
GGSGGGGSGG GGSGGDVQMT QSPSTLSASV GDRVTITCSS SQSIVHSNGN TYMEWYQQKP  180
GKAPKLLIYK VSNRFSGVPD RFSGSGSGTE FTLTISSLQP DDFATYYCHQ GSHVPRTFGQ  240
GTKVEVK                                                            247

SEQ ID NO: 59            moltype = AA  length = 247
FEATURE                  Location/Qualifiers
REGION                   1..247
                         note = HLA-A*02 ScFv
source                   1..247
                         mol_type = protein
                         organism = synthetic construct
SEQUENCE: 59
QVQLQQSGPE LVKPGASVKM SCKASGYTFT SYHIQWVKQR PGQGLEWIGW IYPGDGSTQY  60
NEKFKGKTTL TADKSSSTAY MLLSSLTSED SAIYFCAREG TYYAMDYWGQ GTSVTVSSGG  120
GGSGGGGSGG GGSGGDVLMT QTPLSLPVSL GDQVSISCRS SQSIVHSNGN TYLEWYLQKP  180
GQSPKLLIYK VSNRFSGVPD RFSGSGSGTD FTLKISRVEA EDLGVYYCFQ GSHVPRTFGG  240
GTKLEIK                                                            247

SEQ ID NO: 60            moltype = AA  length = 247
FEATURE                  Location/Qualifiers
REGION                   1..247
                         note = HLA-A*02 ScFv
source                   1..247
                         mol_type = protein
                         organism = synthetic construct
SEQUENCE: 60
QLQLQESGPG LVKPSETLSL TCTVSGYTFT SYHIQWIRQP PGKGLEWIGW IYPGDGSTQY  60
NEKFKGRATI SVDTSKNQFS LNLDSVSAAD TAIYYCAREG TYYAMDYWGK GSTVTVSSGG  120
GGSGGGGSGG GGSGGDIQMT QSPSSLSASV GDRVTITCRS SQSIVHSNGN TYLEWYQQKP  180
GKAPKLLIYK VSNRFSGVPS RFSGSGSGTD FTFTISSLQP EDIATYYCFQ GSHVPRTFGP  240
GTKVDIK                                                            247

SEQ ID NO: 61            moltype = AA  length = 247
FEATURE                  Location/Qualifiers
REGION                   1..247
                         note = HLA-A*02 ScFv
source                   1..247
                         mol_type = protein
                         organism = synthetic construct
SEQUENCE: 61
EVQLVQSGAE LKKPGSSVKV SCKASGYTFT SYHIQWVKQA PGQGLEWIGW IYPGDGSTQY  60
NEKFKGKATL TVDKSTNTAY MELSSLRSED TAVYYCAREG TYYAMDYWGQ GTLVTVSSGG  120
GGSGGGGSGG GGSGGDIQMT QSPSTLSASV GDRVTITCRS SQSIVHSNGN TYLEWYQQKP  180
GKAPKLLIYK VSNRFSGVPS RFSGSGSGTD FTLTISSLQP DDFATYYCFQ GSHVPRTFGQ  240
GTKVEVK                                                            247

SEQ ID NO: 62            moltype = AA  length = 247
```

```
FEATURE                Location/Qualifiers
REGION                 1..247
                       note = HLA-A*02 ScFv
source                 1..247
                       mol_type = protein
                       organism = synthetic construct
SEQUENCE: 62
QVQLVQSGAE VKKPGSSVKV SCKASGYTFT SYHIQWVRQA PGQGLEWMGW IYPGDGSTQY  60
NEKFKGRVTI TADKSTSTAY MELSSLRSED TAVYYCAREG TYYAMDYWGQ GTTVTVSSGG  120
GGSGGGGSGG GGSGGEIVLT QSPGTLSLSP GERATLSCRS SQSIVHSNGN TYLEWYQQKP  180
GQAPRLLIYK VSNRFSGIPD RFSGSGSGTD FTLTISRLEP EDFAVYYCFQ GSHVPRTFGG  240
GTKVEIK                                                            247

SEQ ID NO: 63          moltype = AA  length = 247
FEATURE                Location/Qualifiers
REGION                 1..247
                       note = HLA-A*02 ScFv
source                 1..247
                       mol_type = protein
                       organism = synthetic construct
SEQUENCE: 63
QVTLKQSGAE VKKPGSSVKV SCTASGYTFT SYHVSWVRQA PGQGLEWLGR IYPGDGSTQY  60
NEKFKGKVTI TADKSMDTSF MELTSLTSED TAVYYCAREG TYYAMDLWGQ GTLVTVSSGG  120
GGSGGGGSGG GGSGGEIVLT QSPGTLSLSP GERATLSCRS SQSIVHSNGN TYLAWYQQKP  180
GQAPRLLISK VSNRFSGVPD RFSGSGSGTD FTLTISRLEP EDFAVYYCQQ GSHVPRTFGG  240
GTKVEIK                                                            247

SEQ ID NO: 64          moltype = AA  length = 247
FEATURE                Location/Qualifiers
REGION                 1..247
                       note = HLA-A*02 ScFv
source                 1..247
                       mol_type = protein
                       organism = synthetic construct
SEQUENCE: 64
QVQLVQSGAE VKKPGASVKV SCKASGYTFT SYHMHWVRQA PGQRLEWMGW IYPGDGSTQY  60
NEKFKGKVTI TRDTSASTAY MELSSLRSED TAVYYCAREG TYYAMDYWGQ GTLVTVSSGG  120
GGSGGGGSGG GGSGGDIVMT QTPLSLPVTP GEPASISCRS SQSIVHSNGN TYLDWYLQKP  180
GQSPQLLIYK VSNRFSGVPD RFSGSGSGTD FTLKISRVEA EDVGVYYCMQ GSHVPRTFGG  240
GTKVEIK                                                            247

SEQ ID NO: 65          moltype = AA  length = 670
FEATURE                Location/Qualifiers
source                 1..670
                       mol_type = protein
                       organism = Homo sapiens
SEQUENCE: 65
MTPILTVLIC LGLSLGPRTH VQAGHLPKPT LWAEPGSVIT QGSPVTLRCQ GGQETQEYRL  60
YREKKTALWI TRIPQELVKK GQFPIPSITW EHAGRYRCYY GSDTAGRSES SDPLELVVTG  120
AYIKPTLSAQ PSPVVNSGGN VILQCDSQVA FDGFSLCKEG EDEHPQCLNS QPHARGSSRA  180
IFSVGPVSPS RRWWYRCYAY DSNSPYEWSL PSDLLELLVL GVSKKPSLSV QPGPIVAPEE  240
TLTLQCGSDA GYNRFVLYKD GERDFLQLAG AQPQAGLSQA NFTLGPVSRS YGGQYRCYGA  300
HNLSSEWSAP SDPLDILIAG QFYDRVSLSV QPGPTVASGE NVTLLCQSQG WMQTFLLTKE  360
GAADDPWRLR STYQSQKYQA EFPMGPVTSA HAGTYRCYGS QSSKPYLLTH PSDPLELVVS  420
GPSGGPSSPT TGPTSTSGPE DQPLTPTGSD PQSGLGRHLG VVIGILVAVI LLLLLLLLLF  480
LILRHRRQGK HWTSTQRKAD FQHPAGAVGP EPTDRGLQWR SSPAADAQEE NLYAAVKHTQ  540
PEDGVEMDTR SPHDEDPQAV TYAEVKHSRP RREMASPPSP LSGEFLDTKD RQAEEDRQMD  600
TEAAASEAPQ DVTYAQLHSL TLRREATEPP PSQEGPSPAV PSIYATLAIH PSQEGPSPAV  660
PSIYATLAIH                                                         670

SEQ ID NO: 66          moltype = DNA  length = 3229
FEATURE                Location/Qualifiers
source                 1..3229
                       mol_type = other DNA
                       organism = Homo sapiens
SEQUENCE: 66
aaatgagttt taaaaaggct tgtccaggaa gcacatatgg gagctggtca ctctgcattt  60
tgggccctcc tggaggtgtt tagaccttcc gagagagaaa ctgagacaca tgagagggaa  120
gaaatgactc agtggtgaga ccctgtggag tcccacccac aaccagcaca ctgtgaccca  180
ctgcacaaac ctctagccca cagctcactt cctcctttaa gaagagaaga gaaaagagga  240
gaggagagga ggaacagaaa agaaaagaaa agaaaaagtg ggaaacaaat aatctaagaa  300
tgaggagaaa gcaagaagag tgacccccctt gtgggcactc cattggtttt atggcgcctc  360
tactttctgg agtttgtgta aaacaaaaat attatggtct ttgtgcacat ttacatcaag  420
ctcagcctgg gcggcacagc cagatgcgag atgcgtctct gctgatctga gtctgcctgc  480
agcatggacc tgggtcttcc ctgaagcatc tccagggctg gagggacgac tgccatgcac  540
cgagggctca tccatccaca gagcagggca gtgggaggag acgccatgac ccccatcctc  600
acggtcctga tctgtctcgg gctgagtctg ggcccccgga cccacgtgca ggcagggcac  660
ctccccaagc ccaccctctg ggctgaacca ggctctgtga tcacccaggg gagtcctgtg  720
accctcaggt gtcagggggg ccaggagacc caggagtacc gtctatatag agaaaagaaa  780
```

-continued

```
acagcaccct ggattacacg gatcccacag gagcttgtga agaagggcca gttccccatc  840
ccatccatca cctgggaaca cacagggcgg tatcgctgtt actatggtag cgacactgca  900
ggccgctcag agagcagtga ccccctggag ctggtggtga caggagccta catcaaaccc  960
accctctcag cccagcccag ccccgtggtg aactcaggag ggaatgtaac cctccagtgt  1020
gactcacagg tggcatttga tggcttcatt ctgtgtaagg aaggagaaga tgaacaccca  1080
caatgcctga actcccagcc ccatgcccgt gggtcgtccc gcgccatctt ctccgtgggc  1140
cccgtgagcc cgagtcgcag gtggtggtac aggtgctatg cttatgactc gaactctccc  1200
tatgagtggt ctctacccag tgatctcctg gagctcctgg tcctaggtgt ttctaagaag  1260
ccatcactct cagtgcagcc aggtcctatc gtggcccctg aggagaccct gactctgcag  1320
tgtggctctg atgctggcta caacagattt gttctgtata aggacgggga acgtgacttc  1380
cttcagctcg ctggcgcaca gccccaggct gggctctccc aggccaactt caccctgggc  1440
cctgtgagcc gctcctacgg gggccagtac agatgctacg gtgcacacaa cctctcctcc  1500
gagtggtcgg cccccagcga ccccctggac atcctgatcg caggacagtt ctatgacaga  1560
gtctccctct cggtgcagcc gggccccacg gtggcctcag gagagaacgt gaccctgctg  1620
tgtcagtcac agggatggat gcaaactttc cttctgacca aggagggggc agctgatgac  1680
ccatggcgtc taagatcaac gtaccaatct caaaaatacc aggctgaatt ccccatgggt  1740
cctgtgacct cagcccatgc ggggacctac aggtgctacg gctcacagag ctccaaaccc  1800
tacctgctga ctcaccccag tgacccccctg gagctcgtgg tctcaggacc gtctgggggc  1860
cccagctccc cgacaacagg ccccacctcc acatctggcc ctgaggacca gcccctcacc  1920
cccaccgggt cggatcccca gagtggtctg ggaaggcacc tgggggttgt gatcggcatc  1980
ttggtggccg tcatcctact gctcctcctc ctcctcctcc tcttcctcat cctccgacat  2040
cgacgtcagg gcaaacactg gacatcgacc cagagaaagg ctgatttcca acatcctgca  2100
ggggctgtgg ggccagagcc cacagacaga ggcctgcagt ggaggtccag cccagctgcc  2160
gatgcccagg aagaaaacct ctatgctgcc gtgaagcaca cacagcctga ggatggggtg  2220
gagatggaca ctcggagccc acacgatgaa gacccccagg cagtgacgta tgccgaggtg  2280
aaacactcca gacctaggag agaaatggcc tctcctcctt ccccactgtc tggggaattc  2340
ctggacacaa aggacagaca ggcggaagag gacaggcaga tggacactga ggctgctgca  2400
tctgaagccc cccaggatgt gacctacgcc cagctgcaca gcttgaccct cagacgggag  2460
gcaactgagc ctcctccatc ccaggaaggg ccctctccag ctgtgcccag catctacgcc  2520
actctggcca tccactagcc cagggggga cgcagacccc acactccatg gagtctggaa  2580
tgcatgggag ctgccccccc agtggacacc attggacccc acccagcctg gatctacccc  2640
aggagactct gggaactttt aggggtcact caattctgca gtataaataa ctaatgtctc  2700
tacaattttg aaataaagca acagacttct caataatcaa tgaagtagct gagaaaacta  2760
agtcagaaag tgcattaaac tgaatcacaa tgtaaatatt acacatcaag cgatgaaact  2820
ggaaaactac aagccacgaa tgaatgaatt aggaaagaaa aaaagtagga aatgaatgat  2880
cttggctttc ctataagaaa tttagggcag ggcacggtgg ctcacgcctg taattccagc  2940
actttgggag gccgaggcgg gcagatcacg agttcaggag atcgagacca tcttggccaa  3000
catggtgaaa ccctgtctct cctaaaaata caaaaattag ctggatgtgg tggcagtgcc  3060
tgtaatccca gctatttggg aggctgaggc aggagaatcg cttgaaccag ggagtcagag  3120
gtttcagtga gccaagatcg caccactgct ctccagcctg gcgacagagg gagactccat  3180
ctcaaattaa aaaaaaaaaa aaaaaagaaa gaaaaaaaaa aaaaaaaaa             3229

SEQ ID NO: 67          moltype = AA  length = 6
FEATURE                Location/Qualifiers
REGION                 1..6
                       note = ITIM
source                 1..6
                       mol_type = protein
                       organism = synthetic construct
SEQUENCE: 67
NLYAAV                                                             6

SEQ ID NO: 68          moltype = AA  length = 6
FEATURE                Location/Qualifiers
REGION                 1..6
                       note = ITIM
source                 1..6
                       mol_type = protein
                       organism = synthetic construct
SEQUENCE: 68
VTYAEV                                                             6

SEQ ID NO: 69          moltype = AA  length = 6
FEATURE                Location/Qualifiers
REGION                 1..6
                       note = ITIM
source                 1..6
                       mol_type = protein
                       organism = synthetic construct
SEQUENCE: 69
VTYAQL                                                             6

SEQ ID NO: 70          moltype = AA  length = 6
FEATURE                Location/Qualifiers
REGION                 1..6
                       note = ITIM
source                 1..6
                       mol_type = protein
                       organism = synthetic construct
```

```
SEQUENCE: 70
SIYATL                                                              6

SEQ ID NO: 71          moltype = AA  length = 35
FEATURE                Location/Qualifiers
REGION                 1..35
                       note = ITIM 1-2
source                 1..35
                       mol_type = protein
                       organism = synthetic construct
SEQUENCE: 71
NLYAAVKHTQ PEDGVEMDTR SPHDEDPQAV TYAEV                              35

SEQ ID NO: 72          moltype = AA  length = 58
FEATURE                Location/Qualifiers
REGION                 1..58
                       note = ITIM 2-3
source                 1..58
                       mol_type = protein
                       organism = synthetic construct
SEQUENCE: 72
VTYAEVKHSR PRREMASPPS PLSGEFLDTK DRQAEEDRQM DTEAAASEAP QDVTYAQL    58

SEQ ID NO: 73          moltype = AA  length = 36
FEATURE                Location/Qualifiers
REGION                 1..36
                       note = ITIM 3-4
source                 1..36
                       mol_type = protein
                       organism = synthetic construct
SEQUENCE: 73
VTYAQLHSLT LRREATEPPP SQEGPSPAVP SIYATL                             36

SEQ ID NO: 74          moltype = AA  length = 87
FEATURE                Location/Qualifiers
REGION                 1..87
                       note = ITIM 1-3
source                 1..87
                       mol_type = protein
                       organism = synthetic construct
SEQUENCE: 74
NLYAAVKHTQ PEDGVEMDTR SPHDEDPQAV TYAEVKHSRP RREMASPPSP LSGEFLDTKD  60
RQAEEDRQMD TEAAASEAPQ DVTYAQL                                       87

SEQ ID NO: 75          moltype = AA  length = 88
FEATURE                Location/Qualifiers
REGION                 1..88
                       note = ITIM 2-4
source                 1..88
                       mol_type = protein
                       organism = synthetic construct
SEQUENCE: 75
VTYAEVKHSR PRREMASPPS PLSGEFLDTK DRQAEEDRQM DTEAAASEAP QDVTYAQLHS  60
LTLRREATEP PPSQEGPSPA VPSIYATL                                      88

SEQ ID NO: 76          moltype = AA  length = 117
FEATURE                Location/Qualifiers
REGION                 1..117
                       note = ITIM 1-4
source                 1..117
                       mol_type = protein
                       organism = synthetic construct
SEQUENCE: 76
NLYAAVKHTQ PEDGVEMDTR SPHDEDPQAV TYAEVKHSRP RREMASPPSP LSGEFLDTKD  60
RQAEEDRQMD TEAAASEAPQ DVTYAQLHSL TLRREATEPP PSQEGPSPAV PSIYATL     117

SEQ ID NO: 77          moltype = AA  length = 20
FEATURE                Location/Qualifiers
REGION                 1..20
                       note = D3D4 domain
source                 1..20
                       mol_type = protein
                       organism = synthetic construct
SEQUENCE: 77
YGSQSSKPYL LTHPSDPLEL                                               20

SEQ ID NO: 78          moltype = AA  length = 43
FEATURE                Location/Qualifiers
REGION                 1..43
```

```
                        note = short hinge
source                  1..43
                        mol_type = protein
                        organism = synthetic construct
SEQUENCE: 78
VVSGPSGGPS SPTTGPTSTS GPEDQPLTPT GSDPQSGLGR HLG                     43

SEQ ID NO: 79           moltype = AA  length = 86
FEATURE                 Location/Qualifiers
REGION                  1..86
                        note = hinge- transmembrane
source                  1..86
                        mol_type = protein
                        organism = synthetic construct
SEQUENCE: 79
YGSQSSKPYL LTHPSDPLEL VVSGPSGGPS SPTTGPTSTS GPEDQPLTPT GSDPQSGLGR  60
HLGVVIGILV AVILLLLLLL LLFLIL                                        86

SEQ ID NO: 80           moltype = AA  length = 190
FEATURE                 Location/Qualifiers
REGION                  1..190
                        note = hinge-transmembrane-intracellular domain
source                  1..190
                        mol_type = protein
                        organism = synthetic construct
SEQUENCE: 80
VVIGILVAVI LLLLLLLLLF LILRHRRQGK HWTSTQRKAD FQHPAGAVGP EPTDRGLQWR  60
SSPAADAQEE NLYAAVKHTQ PEDGVEMDTR SPHDEDPQAV TYAEVKHSRP RREMASPPSP  120
LSGEFLDTKD RQAEEDRQMD TEAAASEAPQ DVTYAQLHSL TLRREATEPP PSQEGPSPAV  180
PSIYATLAIH                                                          190

SEQ ID NO: 81           moltype = AA  length = 167
FEATURE                 Location/Qualifiers
REGION                  1..167
                        note = LILRB1 intracellular domain
source                  1..167
                        mol_type = protein
                        organism = synthetic construct
SEQUENCE: 81
RHRRQGKHWT STQRKADFQH PAGAVGPEPT DRGLQWRSSP AADAQEENLY AAVKHTQPED  60
GVEMDTRSPH DEDPQAVTYA EVKHSRPRRE MASPPSPLSG EFLDTKDRQA EEDRQMDTEA  120
AASEAPQDVT YAQLHSLTLR REATEPPPSQ EGPSPAVPSI YATLAIH                 167

SEQ ID NO: 82           moltype = AA  length = 253
FEATURE                 Location/Qualifiers
REGION                  1..253
                        note = LILRB1 hinge-transmemebrane-intracellular domain
source                  1..253
                        mol_type = protein
                        organism = synthetic construct
SEQUENCE: 82
YGSQSSKPYL LTHPSDPLEL VVSGPSGGPS SPTTGPTSTS GPEDQPLTPT GSDPQSGLGR  60
HLGVVIGILV AVILLLLLLL LLFLILRHRR QGKHWTSTQR KADFQHPAGA VGPEPTDRGL  120
QWRSSPAADA QEENLYAAVK HTQPEDGVEM DTRSPHDEDP QAVTYAEVKH SRPRREMASP  180
PSPLSGEFLD TKDRQAEEDR QMDTEAAASE APQDVTYAQL HSLTLRREAT EPPPSQEGPS  240
PAVPSIYATL AIH                                                      253

SEQ ID NO: 83           moltype = AA  length = 233
FEATURE                 Location/Qualifiers
REGION                  1..233
                        note = LILRB1 hinge-TM-intracellular domain
source                  1..233
                        mol_type = protein
                        organism = synthetic construct
SEQUENCE: 83
VVSGPSGGPS SPTTGPTSTS GPEDQPLTPT GSDPQSGLGR HLGVVIGILV AVILLLLLLL  60
LLFLILRHRR QGKHWTSTQR KADFQHPAGA VGPEPTDRGL QWRSSPAADA QEENLYAAVK  120
HTQPEDGVEM DTRSPHDEDP QAVTYAEVKH SRPRREMASP PSPLSGEFLD TKDRQAEEDR  180
QMDTEAAASE APQDVTYAQL HSLTLRREAT EPPPSQEGPS PAVPSIYATL AIH          233

SEQ ID NO: 84           moltype = AA  length = 63
FEATURE                 Location/Qualifiers
REGION                  1..63
                        note = LILRB1 hinge domain
source                  1..63
                        mol_type = protein
                        organism = synthetic construct
SEQUENCE: 84
YGSQSSKPYL LTHPSDPLEL VVSGPSGGPS SPTTGPTSTS GPEDQPLTPT GSDPQSGLGR  60
```

```
HLG                                                                63

SEQ ID NO: 85          moltype = AA  length = 23
FEATURE                Location/Qualifiers
REGION                 1..23
                       note = LILRB1 transmembrane domain
source                 1..23
                       mol_type = protein
                       organism = synthetic construct
SEQUENCE: 85
VVIGILVAVI LLLLLLLLLF LIL                                          23

SEQ ID NO: 86          moltype = AA  length = 237
FEATURE                Location/Qualifiers
REGION                 1..237
                       note = MSLN binding domain
source                 1..237
                       mol_type = protein
                       organism = synthetic construct
SEQUENCE: 86
QVQLVQSGAE VEKPGASVKV SCKASGYTFT DYYMHWVRQA PGQGLEWMGW INPNSGGTNY  60
AQKFQGRVTM TRDTSISTAY MELSRLRSDD TAVYYCASGW DFDYWGQGTL VTVSSGGGGS  120
GGGGSGGGGS GGDIVMTQSS SLSASVGDRV TITCRASQSI RYYLSWYQQK PGKAPKLLIY  180
TASILQNGVP SRFSGSGSGT DFTLTISSLQ PEDFATYYCL QTYTTPDFGP GTKVEIK     237

SEQ ID NO: 87          moltype = DNA  length = 711
FEATURE                Location/Qualifiers
misc_feature           1..711
                       note = MSLN binding domain
source                 1..711
                       mol_type = other DNA
                       organism = synthetic construct
SEQUENCE: 87
caggtgcagc tggtgcagtc tggggctgag gtggagaagc ctggggcctc agtgaaggtc  60
tcctgcaagg cttctggata caccttcacc gactactata tgcactgggt gcgacaggcc  120
cctggacaag ggcttgagtg gatgggatgg atcaacccta acagtggtgg cacaaactat  180
gcacagaagt ttcagggcag ggtcaccatg accagggaca cgtccatcag cacagcctac  240
atggagctga gcaggctgag atctgacgac acggccgtgt attactgtgc gtctggctgg  300
gactttgact actggggcca gggaaccctg gtcaccgtgt cctcaggcgg aggtggaagc  360
ggagggggag gatctggcgg cggaggaagc ggaggcgaca tcgtgatgac ccagtcttcc  420
tccctgtctg catctgtcgg agacagagtc accatcactt gccgggccag tcagagcatt  480
aggtactatt taagttggta tcagcagaaa ccaggaaaag cccctaagct cctgatctat  540
actgcatcca ttttacaaaa tggggtccca tcaaggttca gtggcagtgg atctgggaca  600
gatttcactc tcaccatcag cagcctgcaa cctgaggatt ttgcaactta ttactgcctc  660
cagacttaca ctactccgga ctttggccca gggaccaagg tggaaatcaa a           711

SEQ ID NO: 88          moltype = AA  length = 246
FEATURE                Location/Qualifiers
REGION                 1..246
                       note = MSLN binding domain
source                 1..246
                       mol_type = protein
                       organism = synthetic construct
SEQUENCE: 88
QVQLVQSGAE VRAPGASVKI SCKASGFTFR GYYIHWVRQA PGQGLEWMGI INPSGGSRAY  60
AQKFQGRVTM TRDTSTSTVY MELSSLRSDD TAMYYCARTA SCGGDCYYLD YWGQGTLVTV  120
SSGGGGSGGG GSGGGGSGGD IQMTQSPPTL SASVGDRVTI TCRASENVNI WLAWYQQKPG  180
KAPKLLIYKS SSLASGVPSR FSGSGSGAEF TLTISSLQPD DFATYYCQQY QSYPLTFGGG  240
TKVEIK                                                             246

SEQ ID NO: 89          moltype = DNA  length = 738
FEATURE                Location/Qualifiers
misc_feature           1..738
                       note = MSLN binding domain
source                 1..738
                       mol_type = other DNA
                       organism = synthetic construct
SEQUENCE: 89
caggtgcagc tggtgcagtc tggggctgag gtgagggcac ctggggcctc agtgaagatt  60
tcctgcaagg cttctggatt caccttcaga ggctactata tccactgggt gcgacaggcc  120
cctggacaag ggcttgagtg gatgggaatc atcaacccta gtggtggtag cagagcctac  180
gcacagaagt tccagggcag ggtcaccatg accagggaca cttccacgag cacagtctac  240
atggagctga gcagcctgag atctgacgac acggccatgt attactgtgc gagaaccgca  300
agttgtggtg gtgactgcta ctaccttgac tactggggcc agggaaccct ggtcaccgtg  360
tcctcaggcg gaggtggaag cggaggggga ggatctggcg gcggaggaag cggaggcgac  420
atccagatga cccagtctcc tcccaccctg tctgcatctg taggagacag agtcaccatc  480
acttgccggg ccagtgagaa tgttaatatc tggttggcct ggtatcagca gaaaccaggg  540
aaagccccta agctcctgat ctataagtca tccagtttag caagtggggt cccatcaagg  600
ttcagtggca gtggatctgg ggcagaattc actctcacca tcagcagcct gcagcctgat  660
```

```
gattttgcaa cttattactg ccaacagtat caaagttacc ccctcacttt cggcggaggg  720
accaaggtgg aaatcaaa                                                738

SEQ ID NO: 90           moltype = AA  length = 242
FEATURE                 Location/Qualifiers
REGION                  1..242
                        note = MSLN binding domain
source                  1..242
                        mol_type = protein
                        organism = synthetic construct
SEQUENCE: 90
QVQLVQSGAE VKKPGASVKV SCKASGYSFT GYTMNWVRQA PGQRLEWMGL ITPYNGASSY  60
NQKFRGRVTI TRDTSASTAY MELSSLRSED TAVYYCARGG YDGRGFDYWG QGTTVTVSSG  120
GGGSGGGGSG GGGSGGDIQM TQSPSSLSAS VGDRVTITCS ASSSVSYMHW YQQKPGKAPK  180
RLIYDTSKLA SGVPSRFSGS GSGTEFTLTI SSLQPEDFAT YYCQQWSGYP LTFGQGTKLE  240
IK                                                                 242

SEQ ID NO: 91           moltype = DNA  length = 726
FEATURE                 Location/Qualifiers
misc_feature            1..726
                        note = MSLN binding domain
source                  1..726
                        mol_type = other DNA
                        organism = synthetic construct
SEQUENCE: 91
caggtgcagc tggtgcagtc tggggctgag gtgaagaagc ctggggcctc agtgaaggtt  60
tcctgcaagg cttctggata ctcattcacc ggctacacca tgaactgggt gaggcaggcc  120
cctggacaaa gacttgagtg gatgggactt atcacccctt acaatggtgc ttctagctac  180
aaccagaagt tcaggggcag ggtcacaatc actagagaca cgtcagccag cacagcctac  240
atggagctct ccagcctgag atctgaagac actgcagtct attactgtgc aagggggggt  300
tacgacggga ggggttttga ctactggggc cagggaacca cggtcaccgt gtcctcaggc  360
ggaggtggaa gcggaggggg aggatctggc ggcggaggaa gcggaggcga catccagatg  420
acccagtctc cttcaagctt gtctgcatct gtaggagaca gggtcaccat cacttgcagt  480
gccagctcaa gtgtaagtta catgcactgg tatcagcaga aaccaggcaa ggcccctaag  540
agattgatct atgacacatc caaattagca agtggggtcc caagtcgctt cagtggcagt  600
ggatctggga ccgaattcac tctcaccatc agcagcttgc agcctgagga ttttgcaact  660
tattactgcc agcagtggag tggttaccct ctcacgttcg gtcaggggac aaagttggaa  720
atcaaa                                                             726

SEQ ID NO: 92           moltype = AA  length = 242
FEATURE                 Location/Qualifiers
REGION                  1..242
                        note = MSLN binding domain
source                  1..242
                        mol_type = protein
                        organism = synthetic construct
SEQUENCE: 92
QVQLQQSGPE LEKPGASVKI SCKASGYSFT GYTMNWVKQS HGKSLEWIGL ITPYNGASSY  60
NQKFRGKATL TVDKSSSTAY MDLLSLTSED SAVYFCARGG YDGRGFDYWG QGTTVTVSSG  120
GGGSGGGGSG GGGSGGDIEL TQSPAIMSAS PGEKVTMTCS ASSSVSYMHW YQQKSGTSPK  180
RWIYDTSKLA SGVPGRFSGS GSGNSYSLTI SSVEAEDDAT YYCQQWSGYP LTFGAGTKLE  240
IK                                                                 242

SEQ ID NO: 93           moltype = DNA  length = 726
FEATURE                 Location/Qualifiers
misc_feature            1..726
                        note = MSLN binding domain
source                  1..726
                        mol_type = other DNA
                        organism = synthetic construct
SEQUENCE: 93
caggtgcagc tgcagcagtc tgggcctgag ctggagaagc ctggggcctc agtgaagatt  60
tcctgcaagg cttctggata ctcattcacc ggctacacca tgaactgggt gaagcagagc  120
catggaaaaa gccttgagtg gattggactt atcacccctt acaatggtgc ttctagctac  180
aaccagaagt tcaggggcaa ggccacatta actgtagaca agtcatccag cacagcctac  240
atggacctcc tcagcctgac atctgaagac tctgcagtct atttctgtgc aagggggggt  300
tacgacggga ggggttttga ctactggggc cagggaacca cggtcaccgt gtcctcaggc  360
ggaggtggaa gcggaggggg aggatctggc ggcggaggaa gcggaggcga catcgagctc  420
acccagtctc ctgcaatcat gtctgcatct ccaggagaga aggtcaccat gacttgcagt  480
gccagctcaa gtgtaagtta catgcactgg tatcagcaga aatcaggcac ctcccctaag  540
agatggatct atgacacatc caaattggca agtggggtcc caggtcgctt cagtggcagt  600
ggatctggga actcttactc tctcaccatc agcagcgtgg aggctgagga tgatgcaact  660
tattactgcc agcagtggag tggttaccct ctcacgttcg gtgctgggac aaagttggaa  720
atcaaa                                                             726

SEQ ID NO: 94           moltype = AA  length = 243
FEATURE                 Location/Qualifiers
REGION                  1..243
                        note = CEA binding domain
```

```
source                1..243
                      mol_type = protein
                      organism = synthetic construct
SEQUENCE: 94
QVQLQQSGAE LVRSGTSVKL SCTASGFNIK DSYMHWLRQG PEQGLEWIGW IDPENGDTEY  60
APKFQGKATF TTDTSSNTAY LQLSSLTSED TAVYYCNEGT PTGPYYFDYW GQGTTVTVSS  120
GGGGSGGGGS GGGGSGGENV LTQSPAIMSA SPGEKVTITC SASSSVSYMH WFQQKPGTSP  180
KLWIYSTSNL ASGVPARFSG SGSGTSYSLT ISRMEAEDAA TYYCQQRSSY PLTFGAGTKL  240
ELK                                                               243

SEQ ID NO: 95         moltype = DNA  length = 729
FEATURE               Location/Qualifiers
misc_feature          1..729
                      note = CEA binding domain
source                1..729
                      mol_type = other DNA
                      organism = synthetic construct
SEQUENCE: 95
caggtccagc tgcagcagtc tggggcagag cttgtgaggt cagggacctc agtcaagttg  60
tcctgcacag cttctggctt caacattaaa gactcctata tgcactggtt gaggcagggg  120
cctgaacagg gcctggagtg gattggatgg attgatcctg agaatggtga tactgaatat  180
gccccgaagt tccagggcaa ggccactttt actacagaca catcctccaa cacagcctac  240
ctgcagctca gcagcctgac atctgaggac actgccgtct attactgtaa tgaagggaca  300
ccgacagggc catactattt tgactactgg ggtcaaggaa ccacagtcac cgtgtcctca  360
ggcggaggtg gaagcggagg gggaggatct ggcggcggag gaagcggagg cgagaacgtt  420
ctcacccagt ctccagcaat catgtctgca tctccagggg agaaggtcac cataacctgc  480
agtgccagct caagtgtaag ttacatgcac tggttccagc agaagccagg cacttctccc  540
aaactctgga tttatagcac atccaacctg gcttctggag tccctgctcg cttcagtggc  600
agtggatctg ggacctctta ctctctcaca atcagccgaa tggaggctga agatgctgcc  660
acttattact gccagcaaag gagtagttac ccgctcacgt tcggtgctgg gaccaagctg  720
gagctgaaa                                                         729

SEQ ID NO: 96         moltype = AA  length = 243
FEATURE               Location/Qualifiers
REGION                1..243
                      note = CEA binding domain
source                1..243
                      mol_type = protein
                      organism = synthetic construct
SEQUENCE: 96
QVQLVQSGAE VKKPGASVKV SCKASGFNIK DSYMHWVRQA PGQGLEWMGW IDPENGDTEY  60
APKFQGRVTM TTDTSTSTAY MELRSLRSDD TAVYYCNEGT PTGPYYFDYW GQGTTVTVSS  120
GGGGSGGGGS GGGGSGGEIV LTQSPATLSL SPGERATLSC SASSSVSYMH WYQQKPGLAP  180
RLLIYSTSNL ASGIPDRFSG SGSGTDFTLT ISRLEPEDFA VYYCQQRSSY PLTFGQGTKL  240
EIK                                                               243

SEQ ID NO: 97         moltype = DNA  length = 729
FEATURE               Location/Qualifiers
misc_feature          1..729
                      note = CEA binding domain
source                1..729
                      mol_type = other DNA
                      organism = synthetic construct
SEQUENCE: 97
caggtccagc tggtgcagtc tggggcagag gtgaagaaac caggggcctc agtcaaggtg  60
tcctgcaaag cttctggctt caacattaaa gactcctata tgcactgggt gaggcaggcg  120
cctggacagg gcctggagtg gatgggatgg attgatcctg agaatggtga tactgaatat  180
gccccgaagt tccagggcag ggtcactatg actacagaca catccacctc cacagcctac  240
atggagctca ggagcctgag atctgacgac actgccgtct attactgtaa tgaagggaca  300
ccgacagggc catactattt tgactactgg ggtcaaggaa ccacagtcac cgtgtcctca  360
ggcggaggtg gaagcggagg gggaggatct ggcggcggag gaagcggagg cgagatcgtt  420
ctcacccagt ctccagcaac cttgtctctg tctccagggg agagggccac cctaagctgc  480
agtgccagct caagtgtaag ttacatgcac tggtaccagc agaagccagg ccttgctccc  540
agactcctga tttatagcac atccaacctg gcttctggaa tccctgatcg cttcagtggc  600
agtggatctg ggaccgattt cactctcaca atcagccgac tggagcctga agatttcgcc  660
gtttattact gccagcaaag gagtagttac ccgctcacgt tcggtcaggg gaccaagctg  720
gagatcaaa                                                         729

SEQ ID NO: 98         moltype = AA  length = 243
FEATURE               Location/Qualifiers
REGION                1..243
                      note = CEA binding domain
source                1..243
                      mol_type = protein
                      organism = synthetic construct
SEQUENCE: 98
EVQLAESGGG LVQPGGSLRL SCAASGFTFS SDAMSWVRQA PGKGLEWVSA ISGSGGSTYY  60
ADSVKGRFTI SRDNSKNTLY LQMNSLRAED TAVYYCAKSN EFLFDYWGQG TLVTVSSGGG  120
GSGGGGSGGG GSGGSSELTQ DPAVSVALGQ TVRITCQGDS LRSSYASWYR QRPGQAPVLV  180
```

```
IYGKNNRPSG IPDRFSGSSS GNTASLTITG AQAEDEADYY WNSSYAWLPY VVFGGGTKLT  240
VLG                                                               243

SEQ ID NO: 99          moltype = DNA  length = 729
FEATURE                Location/Qualifiers
misc_feature           1..729
                       note = CEA binding domain
source                 1..729
                       mol_type = other DNA
                       organism = synthetic construct
SEQUENCE: 99
gaggtgcagc tggcggagtc tgggggaggc ttggtacagc ctgggggtc cctgagactc  60
tcctgtgcag cctctggatt cacctttagc agcgatgcca tgagctgggt ccgccaggct  120
ccagggaagg ggctggagtg ggtctcagct attagtggta gtggtggtag cacatactac  180
gcagactccg tgaagggccg gttcaccatc tccagagaca attccaagaa cacgctgtat  240
ctgcaaatga acagcctgag agccgaggac acggccgtgt attactgtgc aaagtctaat  300
gagtttcttt ttgactactg gggccaaggt accctggtca ccgtgtcgag tggcggaggt  360
ggaagcggag ggggaggatc tggcggcgga ggaagcggag gctcttctga gctgactcag  420
gaccctgctg tgtctgtggc cttgggacag acagtcagga tcacatgcca aggagacagc  480
ctcagaagct cttatgcaag ctggtaccgg cagaggccag gacaggcccc tgtacttgtc  540
atctatggta aaaacaaccg gccctcaggg atcccagacc gattctctgg ctccagctca  600
ggaaacacag cttccttgac catcactggg gctcaggcgg aagatgaggc tgactattac  660
tggaactcca gctacgcttg gctgccctac gtggtattcg gcggagggac caagctgacc  720
gtcctaggt                                                         729

SEQ ID NO: 100         moltype = AA  length = 243
FEATURE                Location/Qualifiers
REGION                 1..243
                       note = CEA binding domain
source                 1..243
                       mol_type = protein
                       organism = synthetic construct
SEQUENCE: 100
QVQLEQSGAG VVKPGASVKL SCKASGFNIK DSYMHWLRQG PGQRLEWIGW IDPENGDTEY  60
APKFQGKATF TTDTSANTAY LGLSSLRPED TAVYYCNEGT PTGPYYFDYW GQGTLVTVSS  120
GGGGSGGGGS GGGGSGGENV LTQSPSSMSV SVGDRVNIAC SASSSVPYMH WLQQKPGKSP  180
KLLIYLTSNL ASGVPSRFSG SGSGTDYSLT ISSVQPEDAA TYYCQQRSSY PLTFGGGTKL  240
EIK                                                               243

SEQ ID NO: 101         moltype = DNA  length = 729
FEATURE                Location/Qualifiers
misc_feature           1..729
                       note = CEA binding domain
source                 1..729
                       mol_type = other DNA
                       organism = synthetic construct
SEQUENCE: 101
caggtccagc tggagcagtc tggggcaggg gttgtgaagc caggggcctc agtcaagttg  60
tcctgcaaag cttctggctt caacattaaa gactcctata tgcactggtt gaggcagggg  120
cctggacagc gcctggagtg gattggatgg attgatcctg agaatggtga tactgaatat  180
gccccgaagt tccagggcaa ggccactttt actacagaca catccgccaa cacagcctac  240
ctggggctca gcagcctgag acctgaggac actgccgtct attactgtaa tgaagggaca  300
ccgacagggc catactattt tgactactgg ggtcaaggaa ccctagtcac cgtgtcctca  360
ggcggaggtg gaagcggagg gggaggatct ggcggcggag gaagcggagg cgagaacgtt  420
ctcacccagt ctccaagctc tatgtctgta tctgtcgggg acagggtcaa catcgcctgc  480
agtgccagct caagtgtacc ttacatgcac tggctccagc agaagccagg caaatctccc  540
aaactcctga tttatctcac atccaacctg gcttctggag tccctagccg cttcagtggc  600
agtggatctg ggaccgatta ctctctcaca atcagctcag tgcagcctga agatgctgcc  660
acttattact gccagcaaag gagtagttac ccgctcacgt tcggtggtgg gaccaagctg  720
gagatcaaa                                                         729

SEQ ID NO: 102         moltype = AA  length = 249
FEATURE                Location/Qualifiers
REGION                 1..249
                       note = EGFR ScFv
source                 1..249
                       mol_type = protein
                       organism = synthetic construct
SEQUENCE: 102
QVQLVESGGG VVQPGRSLRL SCAASGFTFS TYGMHWVRQA PGKGLEWVAV IWDDGSYKYY  60
GDSVKGRFTI SRDNSKNTLY LQMNSLRAED TAVYYCARDG ITMVRGVMKD YFDYWGQGTL  120
VTVSSGGGGS GGGGSGGGGS GGAIQLTQSP SSLSASVGDR VTITCRASQD ISSALVWYQQ  180
KPGKAPKLLI YDASSLESGV PSRFSGSESG TDFTLTISSL QPEDFATYYC QQFNSYPLTF  240
GGGTKVEIK                                                         249

SEQ ID NO: 103         moltype = DNA  length = 747
FEATURE                Location/Qualifiers
misc_feature           1..747
                       note = EGFR ScFv
```

```
source                  1..747
                        mol_type = other DNA
                        organism = synthetic construct
SEQUENCE: 103
caggtgcagc tggtggagtc tgggggaggc gtggtccagc ctgggaggtc cctgagactc  60
tcctgtgcag cgtctggatt caccttcagt acctatggca tgcactgggt ccgccaggct  120
ccaggcaagg ggctggagtg ggtggcagtt atatgggatg atggaagtta taaatactat  180
ggagactccg tgaagggccg attcaccatc tccagagaca attccaagaa cacgctgtat  240
ctgcaaatga acagcctgag agccgaggac acggctgtgt attactgtgc gagagatggt  300
attactatgg ttcggggagt tatgaaggac tactttgact actggggcca gggaaccctg  360
gtcaccgtct cctcaggcgg aggtggaagc ggagggggag gatctggcgg cggaggaagc  420
ggaggcgcca tccagttgac ccagtctcca tcctccctgt ctgcatctgt aggagacaga  480
gtcaccatca cttgccgggc aagtcaggac attagcagtg ctttagtctg gtatcagcag  540
aaaccaggga aagctcctaa gctcctgatc tatgatgcct ccagtttgga aagtggggtc  600
ccatcaaggt tcagcggcag tgaatctggg acagatttca ctctcaccat cagcagcctg  660
cagcctgaag attttgcaac ttattactgt caacagttta atagttaccc gctcactttc  720
ggcggaggga ccaaggtgga gatcaaa                                       747

SEQ ID NO: 104          moltype = AA  length = 249
FEATURE                 Location/Qualifiers
REGION                  1..249
                        note = EGFR ScFv
source                  1..249
                        mol_type = protein
                        organism = synthetic construct
SEQUENCE: 104
AIQLTQSPSS LSASVGDRVT ITCRASQDIS SALVWYQQKP GKAPKLLIYD ASSLESGVPS  60
RFSGSESGTD FTLTISSLQP EDFATYYCQQ FNSYPLTFGG GTKVEIKGGG GSGGGGSGGG  120
GSGGQVQLVE SGGGVVQPGR SLRLSCAASG FTFSTYGMHW VRQAPGKGLE WVAVIWDDGS  180
YKYYGDSVKG RFTISRDNSK NTLYLQMNSL RAEDTAVYYC ARDGITMVRG VMKDYFDYWG  240
QGTLVTVSS                                                           249

SEQ ID NO: 105          moltype = DNA  length = 747
FEATURE                 Location/Qualifiers
misc_feature            1..747
                        note = EGFR ScFv
source                  1..747
                        mol_type = other DNA
                        organism = synthetic construct
SEQUENCE: 105
gccatccagt tgacccagtc tccatcctcc ctgtctgcat ctgtaggaga cagagtcacc  60
atcacttgcc gggcaagtca ggacattagc agtgctttag tctggtatca gcagaaacca  120
gggaaagctc ctaagctcct gatctatgat gcctccagtt tggaaagtgg ggtcccatca  180
aggttcagcg gcagtgaatc tgggacagat ttcactctca ccatcagcag cctgcagcct  240
gaagattttg caacttatta ctgtcaacag tttaatagtt acccgctcac tttcggcgga  300
gggaccaagg tggagatcaa aggcggaggt ggaagcggag ggggaggatc tggcggcgga  360
ggaagcggag gccaggtgca gctggtggag tctgggggag gcgtggtcca gcctgggagg  420
tccctgagac tctcctgtgc agcgtctgga ttcaccttca gtacctatgg catgcactgg  480
gtccgccagg ctccaggcaa ggggctggag tgggtggcag ttatatggga tgatggaagt  540
tataaatact atggagactc cgtgaagggc cgattcacca tctccagaga caattccaag  600
aacacgctgt atctgcaaat gaacagcctg agagccgagg acacggctgt gtattactgt  660
gcgagagatg gtattactat ggttcgggga gttatgaagg actactttga ctactggggc  720
cagggaaccc tggtcaccgt ctcctca                                       747

SEQ ID NO: 106          moltype = AA  length = 247
FEATURE                 Location/Qualifiers
REGION                  1..247
                        note = EGFR ScFv
source                  1..247
                        mol_type = protein
                        organism = synthetic construct
SEQUENCE: 106
QIQLVQSGPE LKKPGETVKI SCKASGYTFT EYPIHWVKQA PGKGFKWMGM IYTDIGKPTY  60
AEEFKGRFAF SLETSASTAY LQINNLKNED TATYFCVRDR YDSLFDYWGQ GTTLTVSSGG  120
GGSGGGGSGG GGSGGDVVMT QTPLSLPVSL GDQASISCRS SQSLVHSNGN TYLHWYLQKP  180
GQSPKLLIYK VSNRFSGVPD RFSGSGSGTD FTLKISRVEA EDLGVYFCSQ STHVPWTFGG  240
GTKLEIK                                                             247

SEQ ID NO: 107          moltype = DNA  length = 741
FEATURE                 Location/Qualifiers
misc_feature            1..741
                        note = EGFR ScFv
source                  1..741
                        mol_type = other DNA
                        organism = synthetic construct
SEQUENCE: 107
cagatccagt tggtgcagtc tggacctgag ctgaagaagc ctggagagac agtcaagatc  60
tcctgcaagg cctctgggta taccttcaca gaatatccaa tacactgggt gaagcaggct  120
ccaggaaagg gtttcaagtg gatgggcatg atatacaccg acattggaaa gccaacatat  180
```

```
gctgaagagt tcaagggacg gtttgccttc tctttggaga cctctgccag cactgcctat  240
ttgcagatca acaacctcaa gaatgaggac acggctacat atttctgtgt aagagatcga  300
tatgattccc tctttgacta ctggggccaa ggcaccactc tcacagtctc ctcaggcgga  360
ggtggaagcg gagggggagg atctggcggc ggaggaagcg gaggcgatgt tgtgatgacc  420
caaactccac tctccctgcc tgtcagtctt ggagatcaag cctccatctc ttgcagatct  480
agtcagagcc ttgtacacag taatggaaac acctatttac attggtacct gcagaagcca  540
ggccagtctc caaagctcct gatctacaaa gtttccaacc gattttctgg ggtcccagac  600
aggttcagtg gcagtggatc agggacagat ttcacactca agatcagcag agtggaggct  660
gaggatctgg gagtttattt ctgctctcaa agtacacatg ttccgtggac gttcggtgga  720
ggcaccaagc tggaaatcaa a                                             741

SEQ ID NO: 108         moltype = AA  length = 247
FEATURE                Location/Qualifiers
REGION                 1..247
                       note = EGFR ScFv
source                 1..247
                       mol_type = protein
                       organism = synthetic construct
SEQUENCE: 108
DVVMTQTPLS LPVSLGDQAS ISCRSSQSLV HSNGNTYLHW YLQKPGQSPK LLIYKVSNRF  60
SGVPDRFSGS GSGTDFTLKI SRVEAEDLGV YFCSQSTHVP WTFGGGTKLE IKGGGGSGGG  120
GSGGGGSGGQ IQLVQSGPEL KKPGETVKIS CKASGYTFTE YPIHWVKQAP GKGFKWMGMI  180
YTDIGKPTYA EEFKGRFAFS LETSASTAYL QINNLKNEDT ATYFCVRDRY DSLFDYWGQG  240
TTLTVSS                                                             247

SEQ ID NO: 109         moltype = DNA  length = 741
FEATURE                Location/Qualifiers
misc_feature           1..741
                       note = EGFR ScFv
source                 1..741
                       mol_type = other DNA
                       organism = synthetic construct
SEQUENCE: 109
gatgttgtga tgacccaaac tccactctcc ctgcctgtca gtcttggaga tcaagcctcc  60
atctcttgca gatctagtca gagccttgta cacagtaatg gaaacaccta tttacattgg  120
tacctgcaga agccaggcca gtctccaaag ctcctgatct acaaagtttc caaccgattt  180
tctggggtcc cagacaggtt cagtggcagt ggatcaggga cagatttcac actcaagatc  240
agcagagtgg aggctgagga tctgggagtt tatttctgct ctcaaagtac acatgttccg  300
tggacgttcg gtggaggcac caagctggaa atcaaaggcg gaggtggaag cggaggggga  360
ggatctggcg gcggaggaag cggaggccag atccagttgg tgcagtctgg acctgagctg  420
aagaagcctg gagagacagt caagatctcc tgcaaggcct ctgggtatac cttcacagaa  480
tatccaatac actgggtgaa gcaggctcca ggaaagggtt tcaagtggat gggcatgata  540
tacaccgaca ttggaaagcc aacatatgct gaagagttca agggacggtt tgccttctct  600
ttggagacct ctgccagcac tgcctatttg cagatcaaca acctcaagaa tgaggacacg  660
gctacatatt tctgtgtaag agatcgatat gattccctct ttgactactg gggccaaggc  720
accactctca cagtctcctc a                                             741

SEQ ID NO: 110         moltype = AA  length = 249
FEATURE                Location/Qualifiers
REGION                 1..249
                       note = EGFR ScFv
source                 1..249
                       mol_type = protein
                       organism = synthetic construct
SEQUENCE: 110
EMQLVESGGG FVKPGGSLKL SCAASGFAFS HYDMSWVRQT PKQRLEWVAY IASGGDITYY  60
ADTVKGRFTI SRDNAQNTLY LQMSSLKSED TAMFYCSRSS YGNNGDALDF WGQGTSVTVS  120
SGGGGSGGGG SGGGGSGGDV VMTQTPLSLP VSLGDQASIS CRSSQSLVHS NGNTYLHWYL  180
QKPGQSPKLL IYKVSNRFSG VPDRFSGSGS GTDFTLKISR VEAEDLGVYF CSQSTHVLTF  240
GSGTKLEIK                                                           249

SEQ ID NO: 111         moltype = DNA  length = 747
FEATURE                Location/Qualifiers
misc_feature           1..747
                       note = EGFR ScFv
source                 1..747
                       mol_type = other DNA
                       organism = synthetic construct
SEQUENCE: 111
gaaatgcagc tggtggagtc tgggggaggc ttcgtgaagc ctggagggtc cctgaaactc  60
tcatgtgcag cctctggatt cgctttcagt cactatgaca tgtcttgggt tcgccagact  120
ccgaagcaga ggctggagtg ggtcgcatac attgctagtg gtggtgatat cacctactat  180
gcagacactg tgaagggccg attcaccatc tccagagaca atgcccagaa caccctgtac  240
ctgcaaatga gcagtctgaa gtctgaggac acagccatgt tttactgttc acgatcctcc  300
tatggtaaca acggagatgc cctggacttc tggggtcaag gtacctcagt caccgtctcc  360
tcaggcggag gtggaagcgg agggggagga tctggcggcg gaggaagcgg aggcgatgtt  420
gtgatgaccc aaactccact ctccctgcct gtcagtcttg gagatcaagc ctccatctct  480
tgcagatcta gtcagagcct tgttcacagt aatggaaaca cctatttaca ttggtacctg  540
cagaagccag gccagtctcc aaagctcctg atctacaaag tttccaaccg attttctggg  600
```

```
gtcccagaca ggttcagtgg cagtggatca gggacagatt tcacactcaa gatcagcaga  660
gtggaggctg aggatctggg agtttatttc tgctctcaaa gtacacatgt tctcacgttc  720
ggctcgggga caaagttgga aataaaa                                       747

SEQ ID NO: 112         moltype = AA  length = 249
FEATURE                Location/Qualifiers
REGION                 1..249
                       note = EGFR ScFv
source                 1..249
                       mol_type = protein
                       organism = synthetic construct
SEQUENCE: 112
DVVMTQTPLS LPVSLGDQAS ISCRSSQSLV HSNGNTYLHW YLQKPGQSPK LLIYKVSNRF  60
SGVPDRFSGS GSGTDFTLKI SRVEAEDLGV YFCSQSTHVL TFGSGTKLEI KGGGGSGGGG  120
SGGGGSGGEM QLVESGGGFV KPGGSLKLSC AASGFAFSHY DMSWVRQTPK QRLEWVAYIA  180
SGGDITYYAD TVKGRFTISR DNAQNTLYLQ MSSLKSEDTA MFYCSRSSYG NNGDALDFWG  240
QGTSVTVSS                                                           249

SEQ ID NO: 113         moltype = DNA  length = 747
FEATURE                Location/Qualifiers
misc_feature           1..747
                       note = EGFR ScFv
source                 1..747
                       mol_type = other DNA
                       organism = synthetic construct
SEQUENCE: 113
gatgttgtga tgacccaaac tccactctcc ctgcctgtca gtcttggaga tcaagcctcc  60
atctcttgca gatctagtca gagccttgtt cacagtaatg gaaacaccta tttacattgg  120
tacctgcaga agccaggcca gtctccaaag ctcctgatct acaaagtttc caaccgattt  180
tctggggtcc cagacaggtt cagtggcagt ggatcaggga cagatttcac actcaagatc  240
agcagagtgg aggctgagga tctgggagtt tatttctgct ctcaaagtac acatgttctc  300
acgttcggct cggggacaaa gttggaaata aaaggcggag gtggaagcgg agggggagga  360
tctggcggcg gaggaagcgg aggcgaaatg cagctggtgg agtctggggg aggcttcgtg  420
aagcctggag ggtccctgaa actctcatgt gcagcctctg gattcgcttt cagtcactat  480
gacatgtctt gggttcgcca gactccgaag cagaggctgg agtgggtcgc atacattgct  540
agtggtggtg atatcaccta ctatgcagac actgtgaagg gccgattcac catctccaga  600
gacaatgccc agaacaccct gtacctgcaa atgagcagtc tgaagtctga ggacacagcc  660
atgttttact gttcacgatc ctcctatggt aacaacggag atgccctgga cttctggggt  720
caaggtacct cagtcaccgt ctcctca                                       747

SEQ ID NO: 114         moltype = AA  length = 243
FEATURE                Location/Qualifiers
REGION                 1..243
                       note = EGFR ScFv
source                 1..243
                       mol_type = protein
                       organism = synthetic construct
SEQUENCE: 114
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSNDT AIYYCARALT YYDYEFAYWG QGTLVTVSAG  120
GGGSGGGGSG GGGSGGDILL TQSPVILSVS PGERVSFSCR ASQSIGTNIH WYQQRTNGSP  180
RLLIKYASES ISGIPSRFSG SGSGTDFTLS INSVESEDIA DYYCQQNNNW PTTFGAGTKL  240
ELK                                                                 243

SEQ ID NO: 115         moltype = DNA  length = 729
FEATURE                Location/Qualifiers
misc_feature           1..729
                       note = EGFR ScFv
source                 1..729
                       mol_type = other DNA
                       organism = synthetic construct
SEQUENCE: 115
caggtgcagc tgaagcagtc cggccccggc ctggtgcagc cctcccagtc cctgtccatc  60
acctgcaccg tgtccggctt ctccctgacc aactacggcg tgcactgggt gcggcagtcc  120
cccggcaagg gcctggagtg gctgggcgtg atctggtccg gcggcaacac cgactacaac  180
acccccttca cctcccggct gtccatcaac aaggacaact ccaagtccca ggtgttcttc  240
aagatgaact ccctgcagtc caacgacacc gccatctact actgcgcccg ggccctgacc  300
tactacgact acgagttcgc ctactggggc cagggcaccc tggtgaccgt gtccgccggc  360
ggaggtggaa gcggaggggg aggatctggc ggcggaggaa gcggaggcga catcctgctg  420
acccagtccc ccgtgatcct gtccgtgtcc cccggcgagc gggtgtcctt ctcctgccgg  480
gcctcccagt ccatcggcac caacatccac tggtaccagc agcggaccaa cggctccccc  540
cggctgctga tcaagtacgc ctccgagtcc atctccggca tcccctcccg gttctccggc  600
tccggctccg gcaccgactt caccctgtcc atcaactccg tggagtccga ggacatcgcc  660
gactactact gccagcagaa caacaactgg cccaccacct tcggcgccgg caccaagctg  720
gagctgaag                                                           729

SEQ ID NO: 116         moltype = AA  length = 244
FEATURE                Location/Qualifiers
REGION                 1..244
```

```
                        note = EGFR ScFv
source                  1..244
                        mol_type = protein
                        organism = synthetic construct
SEQUENCE: 116
QVQLVQSGAE VKKPGASVKV SCKASGYTFT SHWMHWVRQA PGQGLEWIGE FNPSNGRTNY  60
NEKFKSKATM TVDTSTNTAY MELSSLRSED TAVYYCASRD YDYDGRYFDY WGQGTLVTVS  120
SGGGGSGGGG SGGGGSGGDI QMTQSPSSLS ASVGDRVTIT CSASSSVTYM YWYQQKPGKA  180
PKLLIYDTSN LASGVPSRFS GSGSGTDYTF TISSLQPEDI ATYYCQQWSS HIFTFGQGTK  240
VEIK                                                               244

SEQ ID NO: 117          moltype = DNA  length = 731
FEATURE                 Location/Qualifiers
misc_feature            1..731
                        note = EGFR ScFv
source                  1..731
                        mol_type = other DNA
                        organism = synthetic construct
SEQUENCE: 117
aggtgcagct ggtgcagtcc ggcgccgagg tgaagaagcc cggcgcctcc gtgaaggtgt  60
cctgcaaggc ctccggctac accttcacct cccactggat gcactgggtg cggcaggccc  120
ccggccaggg cctggagtgg atcggcgagt tcaacccctc caacggccgg accaactaca  180
acgagaagtt caagtccaag gccaccatga ccgtggacac ctccaccaac accgcctaca  240
tggagctgtc ctccctgcgg tccgaggaca ccgccgtgta ctactgcgcc tcccgggact  300
acgactacga cggccggtac ttcgactact ggggccaggg caccctggtg accgtgtcct  360
ccggcggagg tggaagcgga gggggaggat ctggcggcgg aggaagcgga ggcgacatcc  420
agatgaccca gtcccctcc tccctgtccg cctccgtggg cgaccgggtg accatcacct  480
gctccgcctc ctcctccgtg acctacatgt actggtacca gcagaagccc ggcaaggccc  540
ccaagctgct gatctacgac acctccaacc tggcctccgg cgtgccctcc cggttctccg  600
gctccggctc cggcaccgac tacaccttca ccatctcctc cctgcagccc gaggacatcg  660
ccacctacta ctgccagcag tggtcctccc acatcttcac cttcggccag ggcaccaagg  720
tggagatcaa g                                                       731

SEQ ID NO: 118          moltype = AA  length = 243
FEATURE                 Location/Qualifiers
REGION                  1..243
                        note = EGFR ScFv
source                  1..243
                        mol_type = protein
                        organism = synthetic construct
SEQUENCE: 118
QVQLQESGPG LVKPSETLSL TCTVSGGSVS SGDYYWTWIR QSPGKGLEWI GHIYYSGNTN  60
YNPSLKSRLT ISIDTSKTQF SLKLSSVTAA DTAIYYCVRD RVTGAFDIWG QGTMVTVSSG  120
GGGSGGGGSG GGGSGGDIQM TQSPSSLSAS VGDRVTITCQ ASQDISNYLN WYQQKPGKAP  180
KLLIYDASNL ETGVPSRFSG SGSGTDFTFT ISSLQPEDIA TYFCQHFDHL PLAFGGGTKV  240
EIK                                                                243

SEQ ID NO: 119          moltype = DNA  length = 729
FEATURE                 Location/Qualifiers
misc_feature            1..729
                        note = EGFR ScFv
source                  1..729
                        mol_type = other DNA
                        organism = synthetic construct
SEQUENCE: 119
caggtgcagc tgcaggagtc cggccccggc ctggtgaagc cctccgagac cctgtccctg  60
acctgcaccg tgtccggcgg ctccgtgtcc tccggcgact actactggac ctggatccgg  120
cagtcccccg gcaagggcct ggagtggatc ggccacatct actactccgg caacaccaac  180
tacaacccct ccctgaagtc ccggctgacc atctccatcg acacctccaa gacccagttc  240
tccctgaagc tgtcctccgt gaccgccgcc gacaccgcca tctactactg cgtgcgggac  300
cgggtgaccg gcgccttcga catctggggc cagggcacca tggtgaccgt gtcctccggc  360
ggaggtggaa gcggaggggg aggatctggc ggcggaggaa gcggaggcga catccagatg  420
acccagtccc cctcctccct gtccgcctcc gtgggcgacc gggtgaccat cacctgccag  480
gcctcccagg acatctccaa ctacctgaac tggtaccagc agaagcccgg caaggccccc  540
aagctgctga tctacgacgc ctccaacctg gagaccggcg tgccctcccg gttctccggc  600
tccggctccg gcaccgactt caccttcacc atctcctccc tgcagcccga ggacatcgcc  660
acctacttct gccagcactt cgaccacctg cccctggcct tcggcggcgg caccaaggtg  720
gagatcaag                                                          729

SEQ ID NO: 120          moltype = AA  length = 125
FEATURE                 Location/Qualifiers
REGION                  1..125
                        note = EGFR VH
source                  1..125
                        mol_type = protein
                        organism = synthetic construct
SEQUENCE: 120
QVQLVESGGG VVQPGRSLRL SCAASGFTFS TYGMHWVRQA PGKGLEWVAV IWDDGSYKYY  60
GDSVKGRFTI SRDNSKNTLY LQMNSLRAED TAVYYCARDG ITMVRGVMKD YFDYWGQGTL  120
```

```
VTVSS                                                            125

SEQ ID NO: 121          moltype = AA  length = 107
FEATURE                 Location/Qualifiers
REGION                  1..107
                        note = EGFR VL
source                  1..107
                        mol_type = protein
                        organism = synthetic construct
SEQUENCE: 121
AIQLTQSPSS LSASVGDRVT ITCRASQDIS SALVWYQQKP GKAPKLLIYD ASSLESGVPS  60
RFSGSESGTD FTLTISSLQP EDFATYYCQQ FNSYPLTFGG GTKVEIK               107

SEQ ID NO: 122          moltype = AA  length = 118
FEATURE                 Location/Qualifiers
REGION                  1..118
                        note = EGFR VH
source                  1..118
                        mol_type = protein
                        organism = synthetic construct
SEQUENCE: 122
QIQLVQSGPE LKKPGETVKI SCKASGYTFT EYPIHWVKQA PGKGFKWMGM IYTDIGKPTY  60
AEEFKGRFAF SLETSASTAY LQINNLKNED TATYFCVRDR YDSLFDYWGQ GTTLTVSS    118

SEQ ID NO: 123          moltype = AA  length = 112
FEATURE                 Location/Qualifiers
REGION                  1..112
                        note = EGFR VL
source                  1..112
                        mol_type = protein
                        organism = synthetic construct
SEQUENCE: 123
DVVMTQTPLS LPVSLGDQAS ISCRSSQSLV HSNGNTYLHW YLQKPGQSPK LLIYKVSNRF  60
SGVPDRFSGS GSGTDFTLKI SRVEAEDLGV YFCSQSTHVP WTFGGGTKLE IK        112

SEQ ID NO: 124          moltype = AA  length = 121
FEATURE                 Location/Qualifiers
REGION                  1..121
                        note = EGFR VH
source                  1..121
                        mol_type = protein
                        organism = synthetic construct
SEQUENCE: 124
EMQLVESGGG FVKPGGSLKL SCAASGFAFS HYDMSWVRQT PKQRLEWVAY IASGGDITYY  60
ADTVKGRFTI SRDNAQNTLY LQMSSLKSED TAMFYCSRSS YGNNGDALDF WGQGTSVTVS  120
S                                                                121

SEQ ID NO: 125          moltype = AA  length = 111
FEATURE                 Location/Qualifiers
REGION                  1..111
                        note = EGFR VL
source                  1..111
                        mol_type = protein
                        organism = synthetic construct
SEQUENCE: 125
DVVMTQTPLS LPVSLGDQAS ISCRSSQSLV HSNGNTYLHW YLQKPGQSPK LLIYKVSNRF  60
SGVPDRFSGS GSGTDFTLKI SRVEAEDLGV YFCSQSTHVL TFGSGTKLEI K         111

SEQ ID NO: 126          moltype = AA  length = 119
FEATURE                 Location/Qualifiers
REGION                  1..119
                        note = EGR VH
source                  1..119
                        mol_type = protein
                        organism = synthetic construct
SEQUENCE: 126
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSNDT AIYYCARALT YYDYEFAYWG QGTLVTVSA   119

SEQ ID NO: 127          moltype = AA  length = 107
FEATURE                 Location/Qualifiers
REGION                  1..107
                        note = EGFR VL
source                  1..107
                        mol_type = protein
                        organism = synthetic construct
SEQUENCE: 127
DILLTQSPVI LSVSPGERVS FSCRASQSIG TNIHWYQQRT NGSPRLLIKY ASESISGIPS  60
RFSGSGSGTD FTLSINSVES EDIADYYCQQ NNNWPTTFGA GTKLELK               107
```

```
SEQ ID NO: 128         moltype = AA  length = 121
FEATURE                Location/Qualifiers
REGION                 1..121
                       note = EGFR VH
source                 1..121
                       mol_type = protein
                       organism = synthetic construct
SEQUENCE: 128
QVQLVQSGAE VKKPGASVKV SCKASGYTFT SHWMHWVRQA PGQGLEWIGE FNPSNGRTNY  60
NEKFKSKATM TVDTSTNTAY MELSSLRSED TAVYYCASRD YDYDGRYFDY WGQGTLVTVS  120
S                                                                  121

SEQ ID NO: 129         moltype = AA  length = 106
FEATURE                Location/Qualifiers
REGION                 1..106
                       note = EGFR VL
source                 1..106
                       mol_type = protein
                       organism = synthetic construct
SEQUENCE: 129
DIQMTQSPSS LSASVGDRVT ITCSASSSVT YMYWYQQKPG KAPKLLIYDT SNLASGVPSR  60
FSGSGSGTDY TFTISSLQPE DIATYYCQQW SSHIFTFGQG TKVEIK                 106

SEQ ID NO: 130         moltype = AA  length = 119
FEATURE                Location/Qualifiers
REGION                 1..119
                       note = EGFR VH
source                 1..119
                       mol_type = protein
                       organism = synthetic construct
SEQUENCE: 130
QVQLQESGPG LVKPSETLSL TCTVSGGSVS SGDYYWTWIR QSPGKGLEWI GHIYYSGNTN  60
YNPSLKSRLT ISIDTSKTQF SLKLSSVTAA DTAIYYCVRD RVTGAFDIWG QGTMVTVSS   119

SEQ ID NO: 131         moltype = AA  length = 107
FEATURE                Location/Qualifiers
REGION                 1..107
                       note = EGFR VL
source                 1..107
                       mol_type = protein
                       organism = synthetic construct
SEQUENCE: 131
DIQMTQSPSS LSASVGDRVT ITCQASQDIS NYLNWYQQKP GKAPKLLIYD ASNLETGVPS  60
RFSGSGSGTD FTFTISSLQP EDIATYFCQH FDHLPLAFGG GTKVEIK                107

SEQ ID NO: 132         moltype = AA  length = 5
FEATURE                Location/Qualifiers
REGION                 1..5
                       note = EGFR CDR-H1
source                 1..5
                       mol_type = protein
                       organism = synthetic construct
SEQUENCE: 132
TYGMH                                                              5

SEQ ID NO: 133         moltype = AA  length = 5
FEATURE                Location/Qualifiers
REGION                 1..5
                       note = EGFR CDR-H1
source                 1..5
                       mol_type = protein
                       organism = synthetic construct
SEQUENCE: 133
EYPIH                                                              5

SEQ ID NO: 134         moltype = AA  length = 5
FEATURE                Location/Qualifiers
REGION                 1..5
                       note = EGFR CDR-H1
source                 1..5
                       mol_type = protein
                       organism = synthetic construct
SEQUENCE: 134
HYDMS                                                              5

SEQ ID NO: 135         moltype = AA  length = 5
FEATURE                Location/Qualifiers
REGION                 1..5
```

```
                        note = EGFR CDR-H1
source                  1..5
                        mol_type = protein
                        organism = synthetic construct
SEQUENCE: 135
NYGVH                                                                5

SEQ ID NO: 136          moltype = AA  length = 5
FEATURE                 Location/Qualifiers
REGION                  1..5
                        note = EGFR CDR-H1
source                  1..5
                        mol_type = protein
                        organism = synthetic construct
SEQUENCE: 136
SHWMH                                                                5

SEQ ID NO: 137          moltype = AA  length = 7
FEATURE                 Location/Qualifiers
REGION                  1..7
                        note = EGFR CDR-H1
source                  1..7
                        mol_type = protein
                        organism = synthetic construct
SEQUENCE: 137
SGDYYWT                                                              7

SEQ ID NO: 138          moltype = AA  length = 17
FEATURE                 Location/Qualifiers
REGION                  1..17
                        note = EGFR CDR-H2
source                  1..17
                        mol_type = protein
                        organism = synthetic construct
SEQUENCE: 138
VIWDDGSYKY YGDSVKG                                                   17

SEQ ID NO: 139          moltype = AA  length = 17
FEATURE                 Location/Qualifiers
REGION                  1..17
                        note = EGFR CDR-H2
source                  1..17
                        mol_type = protein
                        organism = synthetic construct
SEQUENCE: 139
MIYTDIGKPT YAEEFKG                                                   17

SEQ ID NO: 140          moltype = AA  length = 17
FEATURE                 Location/Qualifiers
REGION                  1..17
                        note = EGFR CDR-H2
source                  1..17
                        mol_type = protein
                        organism = synthetic construct
SEQUENCE: 140
YIASGGDITY YADTVKG                                                   17

SEQ ID NO: 141          moltype = AA  length = 16
FEATURE                 Location/Qualifiers
REGION                  1..16
                        note = EGFR CDR-H2
source                  1..16
                        mol_type = protein
                        organism = synthetic construct
SEQUENCE: 141
VIWSGGNTDY NTPFTS                                                    16

SEQ ID NO: 142          moltype = AA  length = 17
FEATURE                 Location/Qualifiers
REGION                  1..17
                        note = EGFR CDR-H2
source                  1..17
                        mol_type = protein
                        organism = synthetic construct
SEQUENCE: 142
EFNPSNGRTN YNEKFKS                                                   17

SEQ ID NO: 143          moltype = AA  length = 16
FEATURE                 Location/Qualifiers
```

```
REGION              1..16
                    note = EGFR CDR-H2
source              1..16
                    mol_type = protein
                    organism = synthetic construct
SEQUENCE: 143
HIYYSGNTNY NPSLKS                                                   16

SEQ ID NO: 144      moltype = AA  length = 16
FEATURE             Location/Qualifiers
REGION              1..16
                    note = EGFR CDR-H3
source              1..16
                    mol_type = protein
                    organism = synthetic construct
SEQUENCE: 144
DGITMVRGVM KDYFDY                                                   16

SEQ ID NO: 145      moltype = AA  length = 9
FEATURE             Location/Qualifiers
REGION              1..9
                    note = EGFR CDR-H3
source              1..9
                    mol_type = protein
                    organism = synthetic construct
SEQUENCE: 145
DRYDSLFDY                                                           9

SEQ ID NO: 146      moltype = AA  length = 12
FEATURE             Location/Qualifiers
REGION              1..12
                    note = EGFR CDR-H3
source              1..12
                    mol_type = protein
                    organism = synthetic construct
SEQUENCE: 146
SSYGNNGDAL DF                                                       12

SEQ ID NO: 147      moltype = AA  length = 11
FEATURE             Location/Qualifiers
REGION              1..11
                    note = EGFR CDR-H3
source              1..11
                    mol_type = protein
                    organism = synthetic construct
SEQUENCE: 147
ALTYYDYEFA Y                                                        11

SEQ ID NO: 148      moltype = AA  length = 12
FEATURE             Location/Qualifiers
REGION              1..12
                    note = EGFR CDR-H3
source              1..12
                    mol_type = protein
                    organism = synthetic construct
SEQUENCE: 148
RDYDYDGRYF DY                                                       12

SEQ ID NO: 149      moltype = AA  length = 9
FEATURE             Location/Qualifiers
REGION              1..9
                    note = EGFR CDR-H3
source              1..9
                    mol_type = protein
                    organism = synthetic construct
SEQUENCE: 149
DRVTGAFDI                                                           9

SEQ ID NO: 150      moltype = AA  length = 11
FEATURE             Location/Qualifiers
REGION              1..11
                    note = EGFR CDR-L1
source              1..11
                    mol_type = protein
                    organism = synthetic construct
SEQUENCE: 150
RASQDISSAL V                                                        11

SEQ ID NO: 151      moltype = AA  length = 16
```

```
FEATURE                 Location/Qualifiers
REGION                  1..16
                        note = EGFR CDR-L1
source                  1..16
                        mol_type = protein
                        organism = synthetic construct
SEQUENCE: 151
RSSQSLVHSN GNTYLH                                                    16

SEQ ID NO: 152          moltype = AA  length = 16
FEATURE                 Location/Qualifiers
REGION                  1..16
                        note = EGFRR CDR-L1
source                  1..16
                        mol_type = protein
                        organism = synthetic construct
SEQUENCE: 152
RSSQSLVHSN GNTYLH                                                    16

SEQ ID NO: 153          moltype = AA  length = 11
FEATURE                 Location/Qualifiers
REGION                  1..11
                        note = EGFR CDR-L1
source                  1..11
                        mol_type = protein
                        organism = synthetic construct
SEQUENCE: 153
RASQSIGTNI H                                                         11

SEQ ID NO: 154          moltype = AA  length = 10
FEATURE                 Location/Qualifiers
REGION                  1..10
                        note = EGFR CDR-L1
source                  1..10
                        mol_type = protein
                        organism = synthetic construct
SEQUENCE: 154
SASSSVTYMY                                                           10

SEQ ID NO: 155          moltype = AA  length = 11
FEATURE                 Location/Qualifiers
REGION                  1..11
                        note = EGFR CDR-L1
source                  1..11
                        mol_type = protein
                        organism = synthetic construct
SEQUENCE: 155
QASQDISNYL N                                                         11

SEQ ID NO: 156          moltype = AA  length = 7
FEATURE                 Location/Qualifiers
REGION                  1..7
                        note = EGFR CDR-L2
source                  1..7
                        mol_type = protein
                        organism = synthetic construct
SEQUENCE: 156
DASSLES                                                              7

SEQ ID NO: 157          moltype = AA  length = 7
FEATURE                 Location/Qualifiers
REGION                  1..7
                        note = EGFR CDR-L2
source                  1..7
                        mol_type = protein
                        organism = synthetic construct
SEQUENCE: 157
KVSNRFS                                                              7

SEQ ID NO: 158          moltype = AA  length = 7
FEATURE                 Location/Qualifiers
REGION                  1..7
                        note = EGFR CDR-L2
source                  1..7
                        mol_type = protein
                        organism = synthetic construct
SEQUENCE: 158
YASESIS                                                              7
```

```
SEQ ID NO: 159          moltype = AA  length = 7
FEATURE                 Location/Qualifiers
REGION                  1..7
                        note = EGFR CDR-L2
source                  1..7
                        mol_type = protein
                        organism = synthetic construct
SEQUENCE: 159
DTSNLAS                                                                 7

SEQ ID NO: 160          moltype = AA  length = 7
FEATURE                 Location/Qualifiers
REGION                  1..7
                        note = EGFR CDR-L2
source                  1..7
                        mol_type = protein
                        organism = synthetic construct
SEQUENCE: 160
DASNLET                                                                 7

SEQ ID NO: 161          moltype = AA  length = 9
FEATURE                 Location/Qualifiers
REGION                  1..9
                        note = EGFR CDR-L3
source                  1..9
                        mol_type = protein
                        organism = synthetic construct
SEQUENCE: 161
QQFNSYPLT                                                               9

SEQ ID NO: 162          moltype = AA  length = 9
FEATURE                 Location/Qualifiers
REGION                  1..9
                        note = EGFR CDR-L3
source                  1..9
                        mol_type = protein
                        organism = synthetic construct
SEQUENCE: 162
SQSTHVPWT                                                               9

SEQ ID NO: 163          moltype = AA  length = 8
FEATURE                 Location/Qualifiers
REGION                  1..8
                        note = EGFR CDR-L3
source                  1..8
                        mol_type = protein
                        organism = synthetic construct
SEQUENCE: 163
SQSTHVLT                                                                8

SEQ ID NO: 164          moltype = AA  length = 9
FEATURE                 Location/Qualifiers
REGION                  1..9
                        note = EGFR CDR-L3
source                  1..9
                        mol_type = protein
                        organism = synthetic construct
SEQUENCE: 164
QQNNNWPTT                                                               9

SEQ ID NO: 165          moltype = AA  length = 9
FEATURE                 Location/Qualifiers
REGION                  1..9
                        note = EGFR CDR-L3
source                  1..9
                        mol_type = protein
                        organism = synthetic construct
SEQUENCE: 165
QQWSSHIFT                                                               9

SEQ ID NO: 166          moltype = AA  length = 9
FEATURE                 Location/Qualifiers
REGION                  1..9
                        note = EGFR CDR-L3
source                  1..9
                        mol_type = protein
                        organism = synthetic construct
SEQUENCE: 166
QHFDHLPLA                                                               9
```

```
SEQ ID NO: 167         moltype = AA  length = 246
FEATURE                Location/Qualifiers
REGION                 1..246
                       note = pan-HLA ScFv
source                 1..246
                       mol_type = protein
                       organism = synthetic construct
SEQUENCE: 167
QVQLKQSGPG LVQPSQSLSL TCTVSGFSLT SYGVHWVRQP PGKGLEWLGV IWSGGSTDYN  60
AAFISRLSIR KDNSKSQVFF KMNSLQADDT AIYYCARTFT TSTSAWFAYW GQGTLVTVSA  120
GGGGSGGGGS GGGGSGGSIV MTQTPKFLLV SAGDRVTITC KASQSVSNDV AWYQQKPGQS  180
PICLLIYYAS NRYTGVPDRF TGSGYGTDFT FTISTVQAED LAVYFCQQDY SSPPWTFGGG  240
TKLEIR                                                             246

SEQ ID NO: 168         moltype = DNA  length = 738
FEATURE                Location/Qualifiers
misc_feature           1..738
                       note = pan-HLA ScFv
source                 1..738
                       mol_type = other DNA
                       organism = synthetic construct
SEQUENCE: 168
caggtgcagc tgaagcagtc aggacctggc ctagtgcagc cctcacagag cctgtccctg  60
acctgcacag tctctggttt ctcattaact agttatggcg tacactgggt tcgccagcct  120
ccaggaaagg gtctggagtg gctgggagtg atctggagtg gtggaagcac agactataat  180
gctgctttca tatccagact gagcatcagg aaggacaact ccaagagcca agtcttcttt  240
aaaatgaaca gtctgcaagc tgatgacaca gccatatact actgtgccag aacctttact  300
acgtctacct cggcctggtt tgcttactgg ggccaaggga ctctggtcac tgtctctgca  360
ggcggaggtg gaagcggagg gggaggatct ggcggcggag gaagcggagg cagcatcgtg  420
atgacccaga ctccaaaatt cctgcttgtg tctgcgggag acagagtcac catcacttgc  480
aaggcgagtc agtctgtgag caacgacgta gcttggtatc agcagaaacc agggcaatct  540
cctatctgtc tcctgatcta ctatgcatct aatcggtata caggggtccc tgataggttc  600
accggaagtg gatatgggac agatttcact ttcaccatca gcaccgtgca ggctgaagat  660
cttgcagtat atttctgtca acaggattat agtagtcctc cgtggacttt cggcggaggg  720
accaagttgg agatcaga                                                738

SEQ ID NO: 169         moltype = AA  length = 245
FEATURE                Location/Qualifiers
REGION                 1..245
                       note = pan-HLA ScFv
source                 1..245
                       mol_type = protein
                       organism = synthetic construct
SEQUENCE: 169
QVQLQESGPG LVKPSQTLSL TCTVSGFSLT SYGVHWIRQP PGKGLEWIGV IWSGGSTDYN  60
AAFISRVTIS VDTSKNQFSL KLSSVTAADT AVYYCARTFT TSTSAWFAYW GQGTLVTVSS  120
GGGGSGGGGS GGGGSGGDIV MTQSPDSLAV SLGERATINC KASQSVSNDV AWYQQKPGQP  180
PKLLIYYASN RYTGVPDRFS GSGSGTDFTL TISSLQAEDV AVYYCQQDYS SPPWTFGGGT  240
KVEIK                                                              245

SEQ ID NO: 170         moltype = DNA  length = 735
FEATURE                Location/Qualifiers
misc_feature           1..735
                       note = pan-HLA ScFv
source                 1..735
                       mol_type = other DNA
                       organism = synthetic construct
SEQUENCE: 170
caggtgcagc tgcaggagtc cggacctggc ctagtgaagc cctcacagac cctgtccctg  60
acctgcacag tctctggttt ctcattaact agctatggtg tacactggat tagacagcct  120
ccaggaaagg gtctggagtg gattggagtg atctggagtg gtggaagcac agactataat  180
gctgctttca tatccagagt gaccatcagc gtggacacct ccaagaacca attctccctt  240
aaactgagca gtgtgacagc tgccgacaca gccgtatact actgtgccag aacctttact  300
acgtctacct cggcctggtt tgcttactgg ggccaaggga ctctggtcac tgtctcttca  360
ggcggaggtg gaagcggagg gggaggatct ggcggcggag gaagcggagg cgacatcgtg  420
atgacccaga gtccagattc cctggctgtg tctctgggag agagagccac catcaattgc  480
aaggcgagtc agtctgtgag caacgacgta gcttggtatc agcagaaacc agggcaacct  540
cctaaactcc tgatctacta tgcatctaat cggtatacag gggtccctga taggttcagc  600
ggaagtggat ctgggacaga tttcactctc accatcagca gcctgcaggc tgaagatgtt  660
gcagtatatt actgtcaaca ggattatagt agtcctccgt ggactttcgg cggagggacc  720
aaggtggaga tcaaa                                                   735

SEQ ID NO: 171         moltype = AA  length = 245
FEATURE                Location/Qualifiers
REGION                 1..245
                       note = pan-HLA ScFv
source                 1..245
                       mol_type = protein
```

```
                        organism = synthetic construct
SEQUENCE: 171
EVQLLESGGG LVQPGGSLRL SCAASGFSLT SYGVHWVRQA PGKGLEWVSV IWSGGSTDYN  60
AAFISRFTIS RDNSKNTLYL QMNSLRAEDT AVYYCARTFT TSTSAWFAYW GQGTLVTVSS  120
GGGGSGGGGS GGGGSGGDIQ MTQSPSSLSA SVGDRVTITC KASQSVSNDV AWYQQKPGKA  180
PKLLIYYASN RYTGVPSRFS GSGSGTDFTF TISSLQPEDI ATYYCQQDYS SPPWTFGGGT  240
KVEIK                                                              245

SEQ ID NO: 172          moltype = DNA  length = 735
FEATURE                 Location/Qualifiers
misc_feature            1..735
                        note = pan-HLA ScFv
source                  1..735
                        mol_type = other DNA
                        organism = synthetic construct
SEQUENCE: 172
gaggtgcagc tgctggagtc cggaggtggc ctagtgcagc ccggagggag cctgcgcctg  60
agctgcgcag cctctggttt ctcattaact agctatggtg tacactgggt tagacaggct  120
ccaggaaagg gtctggagtg ggttagcgtg atctggagtg gtggaagcac agactataat  180
gctgctttca tatccagatt taccatcagc cgggacaact ccaagaacac actctacctt  240
caaatgaaca gtttgagagc tgaagacaca gccgtatact actgtgccag aacctttact  300
acgtctacct cggcctggtt tgcttactgg ggccaaggga ctctggtcac tgtctcttca  360
ggcggaggtg gaagcggagg gggaggatct ggcggcggag gaagcggagg cgacatccag  420
atgacccaga gtccaagctc cctgtctgcg tctgtgggag acagagtcac catcacttgc  480
aaggcgagtc agtctgtgag caacgacgta gcttggtatc agcagaaacc agggaaagct  540
cctaaactcc tgatctacta tgcatctaat cggtatacag ggtccctag taggttcagc  600
ggaagtggat ctgggacaga tttcactttc accatcagca gcctgcagcc tgaagatatt  660
gcaacatatt actgtcaaca ggattatagt agtcctccgt ggactttcgg cggagggacc  720
aaggtggaga tcaaa                                                   735

SEQ ID NO: 173          moltype = AA  length = 245
FEATURE                 Location/Qualifiers
REGION                  1..245
                        note = pan-HLA ScFv
source                  1..245
                        mol_type = protein
                        organism = synthetic construct
SEQUENCE: 173
QVQLQESGPG LVKPSETLSL TCTVSGFSLT SYGVHWIRQP PGKGLEWIGV IWSGGSTDYN  60
AAFISRVTIS RDTSKNQFSL KLSSVTAADT AVYYCARTFT TSTSAWFAYW GQGTLVTVSS  120
GGGGSGGGGS GGGGSGGDIV MTQTPLSLSV TPGQPASISC KASQSVSNDV AWYLQKPGQS  180
PQLLIYYASN RYTGVPDRFS GSGSGTDFTL KISRVEAEDV GVYYCQQDYS SPPWTFGGGT  240
KVEIK                                                              245

SEQ ID NO: 174          moltype = DNA  length = 735
FEATURE                 Location/Qualifiers
misc_feature            1..735
                        note = pan-HLA ScFv
source                  1..735
                        mol_type = other DNA
                        organism = synthetic construct
SEQUENCE: 174
caggtgcagc tgcaggagtc cggacctggc ctagtgaagc cctcagaaac cctgtccctg  60
acctgcacag tctctggttt ctcattaact agctatggtg tacactggat tagacagcct  120
ccaggaaagg gtctggagtg gattggagtg atctggagtg gtggaagcac agactataat  180
gctgctttca tatccagagt gaccatcagc agggacacct ccaagaacca attctccctt  240
aaactgagca gtgtgacagc tgccgacaca gccgtatact actgtgccag aacctttact  300
acgtctacct cggcctggtt tgcttactgg ggccaaggga ctctggtcac tgtctcttca  360
ggcggaggtg gaagcggagg gggaggatct ggcggcggag gaagcggagg cgacatcgtg  420
atgacccaga ctccactttc cctgtctgtg actccgggac agccagccag catcagttgc  480
aaggcgagtc agtctgtgag caacgacgta gcttggtatc tgcagaaacc agggcaatct  540
cctcaactcc tgatctacta tgcatctaat cggtatacag ggtccctga taggttcagc  600
ggaagtggat ctgggacaga tttcactttg aagatcagca gggtggaggc tgaagatgtt  660
ggagtatatt actgtcaaca ggattatagt agtcctccgt ggactttcgg cggagggacc  720
aaggtggaga tcaaa                                                   735

SEQ ID NO: 175          moltype = AA  length = 245
FEATURE                 Location/Qualifiers
REGION                  1..245
                        note = pan-HLA ScFv
source                  1..245
                        mol_type = protein
                        organism = synthetic construct
SEQUENCE: 175
QVQLVESGGG VVQPGRSLRL SCAVSGFSLT SYGMHWVRQA PGKGLEWVAV IWSGGSTDYN  60
AAFISRFTIS RDNSKNTLYL QMNSLRAEDT AVYYCAKTFT TSTSAWFAYW GQGTLVTVSS  120
GGGGSGGGGS GGGGSGGEIV LTQSPATLSL SPGERATLSC RASQSVSNDL AWYQQKPGQA  180
PRLLIYYASN RYTGVPDRFS GSGSGTDFTL TISSLEPEDF AVYYCQQDYS SPPWTFGQGT  240
KVEIK                                                              245
```

```
SEQ ID NO: 176          moltype = DNA  length = 735
FEATURE                 Location/Qualifiers
misc_feature            1..735
                        note = pan-HLA ScFv
source                  1..735
                        mol_type = other DNA
                        organism = synthetic construct
SEQUENCE: 176
caggtgcagc tggtggagtc cggaggtggc gtagtgcagc ccggaaggag cctgcgcctg  60
agctgcgcag tctctggttt ctcattaact agctatggta tgcactgggt tagacaggct  120
ccaggaaagg gtctggagtg ggttgcagtg atctggagtg gtggaagcac agactataat  180
gctgctttca tatccagatt taccatcagc cgggacaact ccaagaacac actctacctt  240
caaatgaaca gtttgagagc tgaagacaca gccgtatact actgtgccaa aacctttact  300
acgtctacct cggcctggtt tgcttactgg ggccaaggga ctctggtcac tgtctcttca  360
ggcggaggtg gaagcggagg gggaggatct ggcggcggag gaagcggagg cgagatcgtg  420
ctgacccaga gtccagctac cctgtctctg tctccgggag agagagccac cctcagttgc  480
agggcgagtc agtctgtgag caacgaccta gcttggtatc agcagaaacc agggcaagct  540
cctagactcc tgatctacta tgcatctaat cggtatacag gggtccctga taggttcagc  600
ggaagtggat ctgggacaga tttcactctc accatcagca gcctggagcc tgaagatttt  660
gcagtatatt actgtcaaca ggattatagt agtcctccgt ggactttcgg ccaagggacc  720
aaggtggaga tcaaa                                                   735

SEQ ID NO: 177          moltype = AA  length = 245
FEATURE                 Location/Qualifiers
REGION                  1..245
                        note = pan-HLA ScFv
source                  1..245
                        mol_type = protein
                        organism = synthetic construct
SEQUENCE: 177
QVQLVESGGG VVQPGRSLRL SCAVSGFSLT SYGMHWVRQA PGKGLEWVAV IWSGGSTDYN  60
AAFISRFTIS RDNSKNTLYL QMNSLRAEDT AVYYCARTFT TSTSAWFAYW GQGTLVTVSS  120
GGGGSGGGGS GGGGSGGDIQ MTQSPSSLSA SVGDRVTITC QASQSVSNDL NWYQQKPGKA  180
PKLLIYYASN RYTGVPDRFS GSGSGTDFTF TISSLQPEDI ATYYCQQDYS SPPWTFGGGT  240
KVEIK                                                              245

SEQ ID NO: 178          moltype = DNA  length = 735
FEATURE                 Location/Qualifiers
misc_feature            1..735
                        note = pan-HLA ScFv
source                  1..735
                        mol_type = other DNA
                        organism = synthetic construct
SEQUENCE: 178
caggtgcagc tggtggagtc cggaggtggc gtagtgcagc ccggaaggag cctgcgcctg  60
agctgcgcag tctctggttt ctcattaact agctatggta tgcactgggt tagacaggct  120
ccaggaaagg gtctggagtg ggttgcagtg atctggagtg gtggaagcac agactataat  180
gctgctttca tatccagatt taccatcagc cgggacaact ccaagaacac actctacctt  240
caaatgaaca gtttgagagc tgaagacaca gccgtatact actgtgccag aacctttact  300
acgtctacct cggcctggtt tgcttactgg ggccaaggga ctctggtcac tgtctcttca  360
ggcggaggtg gaagcggagg gggaggatct ggcggcggag gaagcggagg cgacatccag  420
atgacccaga gtccaagctc cctgtctgcg tctgtgggag acagagtcac catcacttgc  480
caggcgagtc agtctgtgag caacgaccta aattggtatc agcagaaacc agggaaagct  540
cctaaactcc tgatctacta tgcatctaat cggtatacag gggtccctga taggttcagc  600
ggaagtggat ctgggacaga tttcactttc accatcagca gcctgcagcc tgaagatatt  660
gcaacatatt actgtcaaca ggattatagt agtcctccgt ggactttcgg cggagggacc  720
aaggtggaga tcaaa                                                   735

SEQ ID NO: 179          moltype = DNA  length = 741
FEATURE                 Location/Qualifiers
misc_feature            1..741
                        note = HLA-A*02 antigen binding domain
source                  1..741
                        mol_type = other DNA
                        organism = synthetic construct
SEQUENCE: 179
gatgttttga tgacccaaac tccactctcc ctgcctgtca gtcttggaga tcaagcctcc  60
atctcttgca gatctagtca gagcattgta catagtaatg gaaacaccta tttagaatgg  120
tacctgcaga aaccaggcca gtctccaaag ctcctgatct acaaagtttc caaccgattt  180
tctggggtcc cagacaggtt cagtggcagt ggatcaggga cagatttcac actcaagatc  240
agtagagtgg aggctgagga tctgggagtt tattactgct ttcaaggttc acatgttcct  300
cggacgtccg gtggaggcac caagctggaa atcaaaggcg gaggtggaag cggaggggga  360
ggatctggcg gcggaggaag cggaggccag gtccagctgc agcagtctgg acctgagctg  420
gtgaagcctg gggcttcagt gaggatatcc tgcaaggctt ctggctacac cttcacaagt  480
taccatatac attgggtgaa gcagaggcct ggacagggac ttgagtggat tggatggatt  540
tatcctggaa atgttaatac tgagtacaat gagaagttca agggcaaggc cacactgact  600
gcagacaaat cgtccagcac agcctacatg cacctcagca gcctgacctc tgaggactct  660
gcggtctatt tctgtgccag agaggagatt acctatgcta tggactactg gggtcaagga  720
```

```
acctcagtca ccgtgtcctc a                                           741

SEQ ID NO: 180         moltype = DNA  length = 741
FEATURE                Location/Qualifiers
misc_feature           1..741
                       note = HLA-A*02 antigen binding domain
source                 1..741
                       mol_type = other DNA
                       organism = synthetic construct
SEQUENCE: 180
caggtgcagc tggtgcagtc tggggctgag gtgaagaagc ctgggtcctc agtgaaggtt  60
tcctgcaagg cttctggata caccttcact agctatcata tacattgggt gcgccaggcc  120
cccggacaag ggcttgagtg gatgggatgg atctaccctg gcaatgttaa cacagaatat  180
aatgagaagt tcaagggcaa agccaccatt accgcggaca aatccacgag cacagcctac  240
atggagctga gcagcctgag atctgaagac acggctgtgt attactgtgc gagggaggaa  300
attacctacg ctatggacta ctggggccag ggaaccacag tcaccgtgtc ctcaggcgga  360
ggtggaagcg gagggggagg atctggcggc ggaggaagcg gaggcgagat tgtattgacc  420
cagagcccag gcaccctgag cctctctcca ggagagcggg ccaccctcag ttgtagatcc  480
agtcagagta ttgtacacag taatgggaac acctatttgg aatggtatca gcagaaacca  540
ggtcaagccc caagattgct catctacaaa gtctctaaca gatttagtgg tattccagac  600
aggttcagcg gttccggaag tggtactgat ttcaccctca cgatctccag gctcgagcca  660
gaagatttcg ccgtttatta ctgttttcaa ggttcacatg tgccgcgcac attcggtggg  720
ggtactaaag tagaaatcaa a                                           741

SEQ ID NO: 181         moltype = DNA  length = 741
FEATURE                Location/Qualifiers
misc_feature           1..741
                       note = HLA-A*02 antigen binding domain
source                 1..741
                       mol_type = other DNA
                       organism = synthetic construct
SEQUENCE: 181
caggtgcagc tggtgcagtc tggggctgag gtgaagaagc ctgggtcctc agtgaaggtt  60
tcctgcaagg cttctggata caccttcact agctatcata tacattgggt gcgccaggcc  120
cccggacaag ggcttgagtg gatgggatgg atctaccctg gcaatgttaa cacagaatat  180
aatgagaagt tcaagggcaa agccaccatt accgcggaca aatccacgag cacagcctac  240
atggagctga gcagcctgag atctgaagac acggctgtgt attactgtgc gagggaggaa  300
attacctacg ctatggacta ctggggccag ggaaccacag tcaccgtgtc ctcaggcgga  360
ggtggaagcg gagggggagg atctggcggc ggaggaagcg gaggcgacat tgtaatgacc  420
cagaccccac tcagcctgcc cgtcactcca ggagagccgg ccagcatcag ttgtagatcc  480
agtcagagta ttgtacacag taatgggaac acctatttgg aatggtatct gcagaaacca  540
ggtcaatccc cacaattgct catctacaaa gtctctaaca gatttagtgg tgtaccagac  600
aggttcagcg gttccggaag tggtactgat ttcaccctca agatctccag ggtcgaggca  660
gaagatgtcg gcgtttatta ctgttttcaa ggttcacatg tgccgcgcac attcggtggg  720
ggtactaaag tagaaatcaa a                                           741

SEQ ID NO: 182         moltype = DNA  length = 741
FEATURE                Location/Qualifiers
misc_feature           1..741
                       note = HLA-A*02 antigen binding domain
source                 1..741
                       mol_type = other DNA
                       organism = synthetic construct
SEQUENCE: 182
gaggtgcagc tggtggagtc tgggggtggg ctggtgaagc ctggggggctc actgaggctt  60
tcctgcgcgg cttctggata caccttcact agctatcata tacattgggt gcgccaggcc  120
cccggaaaag ggcttgagtg ggtgggatgg atctaccctg gcaatgttaa cacagaatat  180
aatgagaagt tcaagggcag attcaccatt agcagggacg attccaagaa cacactctac  240
ctgcagatga acagcctgaa aactgaagac acggctgtgt attactgtgc gagggaggaa  300
attacctacg ctatggacta ctggggccag ggaaccacag tcaccgtgtc ctcaggcgga  360
ggtggaagcg gagggggagg atctggcggc ggaggaagcg gaggcgacat tcaaatgacc  420
cagagcccat ccagcctgag cgcatctgta ggtgaccggg tcaccatcac ttgtagatcc  480
agtcagagta ttgtacacag taatgggaac acctatttgg aatggtatca gcagaaacca  540
ggtaaagccc caaaattgct catctacaaa gtctctaaca gatttagtgg tgtaccaagc  600
aggttcagcg gttccggaag tggtactgat ttcaccctca cgatctcctc tctccagcca  660
gaagatttcg ccacttatta ctgttttcaa ggttcacatg tgccgcgcac attcggtggg  720
ggtactaaag tagaaatcaa a                                           741

SEQ ID NO: 183         moltype = DNA  length = 741
FEATURE                Location/Qualifiers
misc_feature           1..741
                       note = HLA-A*02 antigen binding domain
source                 1..741
                       mol_type = other DNA
                       organism = synthetic construct
SEQUENCE: 183
caggtgcagc tggtgcagtc tggggctgag gtgaagaagc ctgggtcctc agtgaaggtt  60
tcctgcaagg cttctggata caccttcact agctatcata tacattgggt gcgccaggcc  120
cccggacaag ggcttgagtg gatcggatgg atctaccctg gcaatgttaa cacagaatat  180
```

```
aatgagaagt tcaagggcaa agccaccatt accgcggacg aatccacgaa cacagcctac  240
atggagctga gcagcctgag atctgaagac acggctgtgt attactgtgc gagggaggaa  300
attacctacg ctatggacta ctggggccag ggaaccctgg tcaccgtgtc ctcaggcgga  360
ggtggaagcg gagggggagg atctggcggc ggaggaagcg gaggcgacat tcaaatgacc  420
cagagcccat ccaccctgag cgcatctgta ggtgaccggg tcaccatcac ttgtagatcc  480
agtcagagta ttgtacacag taatgggaac acctatttgg aatggtatca gcagaaacca  540
ggtaaagccc caaaattgct catctacaaa gtctctaaca gatttagtgg tgtaccagcc  600
aggttcagcg gttccggaag tggtactgaa ttcaccctca cgatctcctc tctccagcca  660
gatgatttcg ccacttatta ctgttttcaa ggttcacatg tgccgcgcac attcggtcag  720
ggtactaaag tagaagtcaa a                                            741

SEQ ID NO: 184         moltype = DNA  length = 741
FEATURE                Location/Qualifiers
misc_feature           1..741
                       note = HLA-A*02 antigen binding domain
source                 1..741
                       mol_type = other DNA
                       organism = synthetic construct
SEQUENCE: 184
caggtgcagc tggtgcagtc tggggctgag gtgaagaagc ctgggtcctc agtgaaggtt  60
tcctgcaagg cttctggata caccttcact agctatcata tgcattgggt gcgccaggcc  120
cccggacaag ggcttgagtg gatcggatac atctaccctg gcaatgttaa cacagaatat  180
aatgagaagt tcaagggcaa agccaccctt accgcggaca aatccacgaa cacagcctac  240
atggagctga gcagcctgag atctgaagac acggctgtgt atttctgtgc gagggaggaa  300
attacctacg ctatggacta ctggggccag ggaaccctgg tcaccgtgtc ctcaggcgga  360
ggtggaagcg gagggggagg atctggcggc ggaggaagcg gaggcgacgt tcaaatgacc  420
cagagcccat ccaccctgag cgcatctgta ggtgaccggg tcaccatcac ttgtagctcc  480
agtcagagta ttgtacacag taatgggaac acctatatgg aatggtatca gcagaaacca  540
ggtaaagccc caaaattgct catctacaaa gtctctaaca gatttagtgg tgtaccagac  600
aggttcagcg gttccggaag tggtactgaa ttcaccctca cgatctcctc tctccagcca  660
gatgatttcg ccacttatta ctgtcatcaa ggttcacatg tgccgcgcac attcggtcag  720
ggtactaaag tagaagtcaa a                                            741

SEQ ID NO: 185         moltype = DNA  length = 741
FEATURE                Location/Qualifiers
misc_feature           1..741
                       note = HLA-A*02 antigen binding domain
source                 1..741
                       mol_type = other DNA
                       organism = synthetic construct
SEQUENCE: 185
caggtgcagc tgcagcagtc tgggcctgag ctggtgaagc ctggggcctc agtgaagatg  60
tcctgcaagg cttctggata caccttcact agctatcata tccagtgggt gaagcagagg  120
cctggacaag ggcttgagtg gatcggatgg atctaccctg gcgatggtag tacacagtat  180
aatgagaagt tcaagggcaa aaccaccctt accgcggaca aatcctccag cacagcctac  240
atgttgctga gcagcctgac ctctgaagac tctgctatct atttctgtgc gagggagggg  300
acctactacg ctatggacta ctggggccag ggaacctcag tcaccgtgtc ctcaggcgga  360
ggtggaagcg gagggggagg atctggcggc ggaggaagcg gaggcgatgt tttgatgacc  420
cagactccac tctccctgcc tgtctctctt ggagaccaag tctccatctc ttgtagatcc  480
agtcagagta ttgtacacag taatgggaac acctatttag aatggtatct gcagaaacca  540
ggtcagtctc caaagttgct catctacaaa gtctctaaca gatttagtgg tgtaccagac  600
aggttcagcg gttccggaag tggtactgat ttcaccctca agatctcgag agtggaggct  660
gaggatctgg gagtttatta ctgttttcaa ggttcacatg tgccgcgcac attcggtgga  720
ggtactaaac tggaaatcaa a                                            741

SEQ ID NO: 186         moltype = DNA  length = 741
FEATURE                Location/Qualifiers
misc_feature           1..741
                       note = HLA-A*02 antigen binding domain
source                 1..741
                       mol_type = other DNA
                       organism = synthetic construct
SEQUENCE: 186
cagctgcagc tgcaggagtc tgggcccggg ctggtgaagc cttcggaaac gctgagcctc  60
acctgcacgg tttctggata caccttcacc agctatcata tccagtggat ccgacagccc  120
cctggaaaag ggcttgagtg gatcggatgg atctaccctg gcgatggttc aacacagtac  180
aatgagaagt tcaagggcag agccacgatt agcgtggaca catccaagaa ccaattctcc  240
ctgaacctgg acagcgtgag tgctgcggac acggccattt attactgtgc gagagaggga  300
acttactacg ctatggacta ctggggcaaa gggagcacgg tcaccgtgtc ctcaggcgga  360
ggtggaagcg gagggggagg atctggcggc ggaggaagcg gaggcgacat ccagatgacc  420
cagagcccaa gctccctgag tgcgtccgtg ggcgaccgcg tgaccatcac ttgcagatcc  480
tctcagtcca tcgtgcactc caacggcaac acgtacctcg agtggtacca gcagaagccc  540
gggaaggccc cgaaactgct catctacaag gtgagcaacc ggttctccgg cgtccccagc  600
cgcttctcag ggtccggctc ggggacggat ttcaccttca cgattagcag cttgcagccc  660
gaagacatcg ccacgtacta ctgctttcag ggaagtcacg tgccgcgtac cttcgggccg  720
ggcacgaaag tggatattaa g                                            741

SEQ ID NO: 187         moltype = DNA  length = 741
FEATURE                Location/Qualifiers
```

```
misc_feature            1..741
                        note = HLA-A*02 antigen binding domain
source                  1..741
                        mol_type = other DNA
                        organism = synthetic construct
SEQUENCE: 187
gaggtgcagc tggtgcagtc tggggccgag ctgaagaagc ctgggtcctc ggtgaaggtg  60
tcctgcaagg cttctggata caccttcacc agctatcata tccagtgggt aaaacaggcc  120
cctggacaag ggcttgagtg gatcggatgg atctaccctg gcgatggttc aacacagtac  180
aatgagaagt tcaagggcaa agccacgctt accgtggaca aatccacgaa cacagcctac  240
atggagctga gcagcctgag atctgaggac acggccgtat attactgtgc gagagaggga  300
acttactacg ctatggacta ctggggccaa gggaccctgg tcaccgtgtc ctcaggcgga  360
ggtggaagcg gagggggagg atctggcggc ggaggaagcg gaggcgacat ccagatgacc  420
cagagcccat ccaccctgag tgcgtccgtg ggcgaccgcg tgaccatcac ttgcagatcc  480
tctcagtcca tcgtgcactc caacggcaac acgtacctcg agtggtacca gcagaagccc  540
gggaaggccc cgaaactgct catctacaag gtgagcaacc ggttctccgg cgtccccagc  600
cgcttctcag ggtccggctc ggggacggat ttcaccctca cgattagcag cttgcagccc  660
gatgacttcg ccacgtacta ctgctttcag ggaagtcacg tgccgcgtac cttcgggcag  720
ggcacgaaag tggaagttaa g                                            741

SEQ ID NO: 188          moltype = DNA  length = 741
FEATURE                 Location/Qualifiers
misc_feature            1..741
                        note = HLA-A*02 antigen binding domain
source                  1..741
                        mol_type = other DNA
                        organism = synthetic construct
SEQUENCE: 188
caggtgcagc tggtgcagtc tggggccgag gtgaagaagc ctgggtcctc ggtgaaggtg  60
tcctgcaagg cttctggata caccttcacc agctatcata tccagtgggt acgacaggcc  120
cctggacaag ggcttgagtg gatgggatgg atctaccctg gcgatggttc aacacagtac  180
aatgagaagt tcaagggcag agtcacgatt accgcggaca aatccacgag cacagcctac  240
atggagctga gcagcctgag atctgaggac acggccgtat attactgtgc gagagaggga  300
acttactacg ctatggacta ctggggccaa gggaccacgg tcaccgtgtc ctcaggcgga  360
ggtggaagcg gagggggagg atctggcggc ggaggaagcg gaggcgagat cgtcctgacc  420
cagagcccag ggaccctgag tttgtccccg ggcgagcgcg cgaccctcag ttgcagatcc  480
tctcagtcca tcgtgcactc caacggcaac acgtacctcg agtggtacca gcagaagccc  540
gggcaggccc cgcgactgct catctacaag gtgagcaacc ggttctccgg catccccgac  600
cgcttctcag ggtccggctc ggggacggat ttcaccctca cgattagccg cttggagccc  660
gaagacttcg ccgtgtacta ctgctttcag ggaagtcacg tgccgcgtac cttcgggggg  720
ggcacgaaag tggaaattaa g                                            741

SEQ ID NO: 189          moltype = DNA  length = 741
FEATURE                 Location/Qualifiers
misc_feature            1..741
                        note = HLA-A*02 antigen binding domain
source                  1..741
                        mol_type = other DNA
                        organism = synthetic construct
SEQUENCE: 189
caggtgaccc tgaagcagtc tggggccgag gtgaagaagc ctgggtcctc ggtgaaggtg  60
tcctgcacgg cttctggata caccttcacc agctatcatg tcagctgggt acgacaggcc  120
cctggacaag ggcttgagtg gttgggaagg atctaccctg gcgatggttc aacacagtac  180
aatgagaagt tcaagggcaa agtcacgatt accgcggaca aatccatgga cacatccttc  240
atggagctga ccagcctgac atctgaggac acggccgtat attactgtgc gagagaggga  300
acttactacg ctatggacct ctggggccaa gggaccctgg tcaccgtgtc ctcaggcgga  360
ggtggaagcg gagggggagg atctggcggc ggaggaagcg gaggcgagat cgtcctgacc  420
cagagcccag ggaccctgag tttgtccccg ggcgagcgcg cgaccctcag ttgcagatcc  480
tctcagtcca tcgtgcactc caacggcaac acgtacctcg cgtggtacca gcagaagccc  540
gggcaggccc cgcgactgct catctccaag gtgagcaacc ggttctccgg cgtccccgac  600
cgcttctcag ggtccggctc ggggacggat ttcaccctca cgattagccg cttggagccc  660
gaagacttcg ccgtgtacta ctgccaacag ggaagtcacg tgccgcgtac cttcgggggg  720
ggcacgaaag tggaaattaa g                                            741

SEQ ID NO: 190          moltype = DNA  length = 741
FEATURE                 Location/Qualifiers
misc_feature            1..741
                        note = HLA-A*02 antigen binding domain
source                  1..741
                        mol_type = other DNA
                        organism = synthetic construct
SEQUENCE: 190
caggtgcagc tggtgcagtc tggggccgag gtgaagaagc ctggggcctc ggtgaaggtg  60
tcctgcaagg cttctggata caccttcacc agctatcata tgcactgggt acgacaggcc  120
cctggacaaa ggcttgagtg gatgggatgg atctaccctg gcgatggttc aacacagtac  180
aatgagaagt tcaagggcaa agtcacgatt acccgggaca catccgcgag cacagcctac  240
atggagctga gcagcctgag atctgaggac acggccgtat attactgtgc gagagaggga  300
acttactacg ctatggacta ctggggccaa gggaccctgg tcaccgtgtc ctcaggcgga  360
ggtggaagcg gagggggagg atctggcggc ggaggaagcg gaggcgacat cgtcatgacc  420
```

```
cagaccccac tgtccctgcc tgtgaccccg ggcgagcccg cgagcatcag ttgcagatcc  480
tctcagtcca tcgtgcactc caacggcaac acgtacctcg actggtacct gcagaagccc  540
gggcagtccc cgcaactgct catctacaag gtgagcaacc ggttctccgg cgtccccgac  600
cgcttctcag ggtccggctc ggggacggat ttcaccctca agattagccg cgtggaggcc  660
gaagacgtcg gcgtgtacta ctgcatgcag ggaagtcacg tgccgcgtac cttcgggggg  720
ggcacgaaag tggaaattaa g                                            741

SEQ ID NO: 191         moltype = AA  length = 9
FEATURE                Location/Qualifiers
REGION                 1..9
                       note = HA-1 variant H peptide
source                 1..9
                       mol_type = protein
                       organism = synthetic construct
SEQUENCE: 191
VLHDDLLEA                                                          9

SEQ ID NO: 192         moltype = AA  length = 19
FEATURE                Location/Qualifiers
REGION                 1..19
                       note = P2A self cleaving peptide
source                 1..19
                       mol_type = protein
                       organism = synthetic construct
SEQUENCE: 192
ATNFSLLKQA GDVEENPGP                                               19

SEQ ID NO: 193         moltype = AA  length = 608
FEATURE                Location/Qualifiers
REGION                 1..608
                       note = HA-1H TCR alpha and beta
source                 1..608
                       mol_type = protein
                       organism = synthetic construct
SEQUENCE: 193
MVKIRQFLLA ILWLQLSCVS AAKNEVEQSP QNLTAQEGEF ITINCSYSVG ISALHWLQQH  60
PGGGIVSLFM LSSGKKKHGR LIATINIQEK HSSLHITASH PRDSAVYICA VRSVSGAGSY  120
QLTFGKGTKL SVIPNIQNPD PAVYQLRDSK SSDKSVCLFT DFDSQTNVSQ SKDSDVYITD  180
KCVLDMRSMD FKSNSAVAWS NKSDFACANA FNNSIIPEDT FFPSPESSCD VKLVEKSFET  240
DTNLNFQNLS VIGFRILLLK VAGFNLLMTL RLWSSGSGAT NFSLLKQAGD VEENPGPMGT  300
SLLCWMALCL LGADHADTGV SQNPRHKITK RGQNVTFRCD PISEHNRLYW YRQTLGQGPE  360
FLTYFQNEAQ LEKSRLLSDR FSAERPKGSF STLEIQRTEQ GDSAMYLCAS SIDSFNEQFF  420
GPGTRLTVLE DLKNVFPPEV AVFEPSEAEI SHTQKATLVC LATGFYPDHV ELSWWVNGKE  480
VHSGVCTDPQ PLKEQPALND SRYCLSSRLR VSATFWQNPR NHFRCQVQFY GLSENDEWTQ  540
DRAKPVTQIV SAEAWGRADC GFTSESYQQG VLSATILYEI LLGKATLYAV LVSALVLMAM  600
VKRKDSRG                                                           608

SEQ ID NO: 194         moltype = DNA  length = 1827
FEATURE                Location/Qualifiers
misc_feature           1..1827
                       note = HA-1(H) TCR alpha and beta
source                 1..1827
                       mol_type = other DNA
                       organism = synthetic construct
SEQUENCE: 194
atggtgaaga tccggcaatt tttgttggct attttgtggc ttcagctaag ctgtgtaagt  60
gccgccaaaa atgaagtgga gcagagtcct cagaacctga ctgcccagga aggagaattt  120
atcacaatca actgcagtta ctcggtagga ataagtgcct tacactggct gcaacagcat  180
ccaggaggag gcattgtttc cttgtttatg ctgagctcag ggaagaagaa gcatggaaga  240
ttaattgcca caataaacat acaggaaaag cacagctccc tgcacatcac agcctcccat  300
cccagagact ctgccgtcta catctgtgct gtcagaagcg tgtccggggc cggctcctac  360
cagctcacct ttgggaaggg gaccaaatta tcagtcattc caaatatcca gaaccctgac  420
cctgccgtgt accagctgag agactctaaa tccagtgaca agtctgtctg cctattcacc  480
gattttgatt ctcaaacaaa tgtgtcacaa agtaaggatt ctgatgtgta tatcacagac  540
aaatgtgtgc tagacatgag gtctatggac ttcaagagca acagtgctgt ggcctggagc  600
aacaaatctg actttgcatg tgcaaacgcc ttcaacaaca gcattattcc agaagacacc  660
ttcttcccca gcccagaaag ttcctgtgat gtcaagctgg tcgagaaaag ctttgaaaca  720
gatacgaacc taaactttca aaacctgtca gtgattgggt tccgaatcct cctcctgaaa  780
gtggccgggt ttaatctgct catgacgctg cggctgtggt ccagcggatc cggagccacc  840
aacttcagcc tgctgaagca ggccggcgac gtggaggaga accccggccc catgggcacc  900
agcctcctct gctggatggc cctgtgtctc ctgggggcag atcacgcaga tactggagtc  960
tcccagaacc ccagacacaa gatcacaaag aggggacaga atgtaacttt caggtgtgat  1020
ccaatttctg aacacaaccg cctttattgg taccgacaga ccctggggca gggcccagag  1080
tttctgactt acttccagaa tgaagctcaa ctagaaaaat caaggctgct cagtgatcgg  1140
ttctctgcag agaggcctaa gggatctttc tccaccttgg agatccagcg cacagagcag  1200
ggggactcgg ccatgtatct ctgtgccagc agcatcgact ccttcaacga gcagttcttc  1260
gggccgggca ccaggctcac ggtcctcgag gacctgaaaa acgtgttccc acccgaggtc  1320
gctgtgtttg agccatcaga agcagagatc tcccacaccc aaaaggccac actggtgtgc  1380
ctggccacag gcttctaccc cgaccacgtg gagctgagct ggtgggtgaa tgggaaggag  1440
```

```
gtgcacagtg gggtctgcac agacccgcag cccctcaagg agcagcccgc cctcaatgac  1500
tccagatact gcctgagcag ccgcctgagg gtgtcggcca ccttctggca gaaccccgc  1560
aaccacttcc gctgtcaagt ccagttctac gggctctcgg agaatgacga gtggacccag  1620
gatagggcca aacctgtcac ccagatcgtc agcgccgagg cctggggtag agcagactgt  1680
ggcttcacct ccgagtctta ccagcaaggg gtcctgtctg ccaccatcct ctatgagatc  1740
ttgctaggga aggccacctt gtatgccgtg ctggtcagtg ccctcgtgct gatggccatg  1800
gtcaagagaa aggattccag aggctag                                      1827

SEQ ID NO: 195         moltype = AA  length = 440
FEATURE                Location/Qualifiers
REGION                 1..440
                       note = Ftcr alpha LIR1 HA-1H
source                 1..440
                       mol_type = protein
                       organism = synthetic construct
SEQUENCE: 195
MVKIRQFLLA ILWLQLSCVS AAKNEVEQSP QNLTAQEGEF ITINCSYSVG ISALHWLQQH  60
PGGGIVSLFM LSSGKKKHGR LIATINIQEK HSSLHITASH PRDSAVYICA VRSVSGAGSY  120
QLTFGKGTKL SVIPNIQNPD PAVYQLRDSK SSDKSVCLFT DFDSQTNVSQ SKDSDVYITD  180
KCVLDMRSMD FKSNSAVAWS NKSDFACANA FNNSIIPEDT FFPSPESSCD VKLVEKSFET  240
DTNLNFQNLS VVIGILVAVI LLLLLLLLLF LILRHRRQGK HWTSTQRKAD FQHPAGAVGP  300
EPTDRGLQWR SSPAADAQEE NLYAAVKHTQ PEDGVEMDTR SPHDEDPQAV TYAEVKHSRP  360
RREMASPPSP LSGEFLDTKD RQAEEDRQMD TEAAASEAPQ DVTYAQLHSL TLRREATEPP  420
PSQEGPSPAV PSIYATLAIH                                              440

SEQ ID NO: 196         moltype = DNA  length = 1279
FEATURE                Location/Qualifiers
misc_feature           1..1279
                       note = Ftcr alpha LIR1 HA-1H
source                 1..1279
                       mol_type = other DNA
                       organism = synthetic construct
SEQUENCE: 196
atggtgaaga tccggcaatt tttgttggct attttgtggc ttcagctaag ctgtgtaagt  60
gccgccaaaa atgaagtgga gcagagtcct cagaacctga ctgcccagga aggagaattt  120
atcacaatca actgcagtta ctcggtagga ataagtgcct tacactggct gcaacagcat  180
ccaggaggag gcattgtttc cttgtttatg ctgagctcag ggaagaagaa gcatggaaga  240
ttaattgcca caataaacat acaggaaaag cacagctccc tgcacatcac agcctcccat  300
cccagagact ctgccgtcta catctgtgct gtcagaagcg tgtccggggc cggctcctac  360
cagctcacct ttgggaaggg gaccaaatta tcagtcattc caaatatcca gaaccctgac  420
cctgccgtgt accagctgag agactctaaa tccagtgaca agtctgtctg cctattcacc  480
gattttgatt ctcaaacaaa tgtgtcacaa agtaaggatt ctgatgtgta tatcacagac  540
aaatgtgtgc tagacatgag gtctatggac ttcaagagca acagtgctgt ggcctggagc  600
aacaaatctg actttgcatg tgcaaacgcc ttcaacaaca gcattattcc agaagacacc  660
ttcttcccca gcccagaaag ttcctgtgat gtcaagctgg tcgagaaaag ctttgaaaca  720
gatacgaacc taaactttca aaacctgtca gttgtgatcg gcatcttggt ggccgtcatc  780
ctactgctcc tcctcctcct cctcctcttc ctcatcctcc gacatcgacg tcagggcaaa  840
cactggacat cgacccagag aaaggctgat ttccaacatc ctgcaggggc tgtggggcca  900
gagcccacag acagaggcct gcagtggagg tccagcccag ctgccgatgc ccaggaagaa  960
aacctctatg ctgccgtgaa gcacacacag cctgaggatg gggtggagat ggacactcgg  1020
agcccacacg atgaagaccc ccaggcagtg acgtatgccg aggtgaaaca ctccagacct  1080
aggagagaaa tggcctctcc tccttcccca ctgtctgggg aattcctgga cacaaaggac  1140
agacaggcgg aagaggacag gcagatggac actgaggctg ctgcatctga agcccccccag  1200
gatgtgacct acgcccagct gcacagcttg accctcagac gggaggcaac tgagcctcct  1260
ccatcccagg aagggccct                                               1279

SEQ ID NO: 197         moltype = AA  length = 466
FEATURE                Location/Qualifiers
REGION                 1..466
                       note = Ftcr beta LIR1 HA-1H
source                 1..466
                       mol_type = protein
                       organism = synthetic construct
SEQUENCE: 197
MGTSLLCWMA LCLLGADHAD TGVSQNPRHK ITKRGQNVTF RCDPISEHNR LYWYRQTLGQ  60
GPEFLTYFQN EAQLEKSRLL SDRFSAERPK GSFSTLEIQR TEQGDSAMYL CASSIDSFNE  120
QFFGPGTRLT VLEDLKNVFP PEVAVFEPSE AEISHTQKAT LVCLATGFYP DHVELSWWVN  180
GKEVHSGVCT DPQPLKEQPA LNDSRYCLSS RLRVSATFWQ NPRNHFRCQV QFYGLSENDE  240
WTQDRAKPVT QIVSAEAWGR ADCGFTSESY QQGVLSVVIG ILVAVILLLL LLLLLFLILR  300
HRRQGKHWTS TQRKADFQHP AGAVGPEPTD RGLQWRSSPA ADAQEENLYA AVKHTQPEDG  360
VEMDTRSPHD EDPQAVTYAE VKHSRPRREM ASPPSPLSGE FLDTKDRQAE EDRQMDTEAA  420
ASEAPQDVTY AQLHSLTLRR EATEPPPSQE GPSPAVPSIY ATLAIH                  466

SEQ ID NO: 198         moltype = DNA  length = 1401
FEATURE                Location/Qualifiers
misc_feature           1..1401
                       note = Ftcr beta LIR1 HA-1H
source                 1..1401
                       mol_type = other DNA
```

```
                         organism = synthetic construct
SEQUENCE: 198
atgggcacca gcctcctctg ctggatggcc ctgtgtctcc tgggggcaga tcacgcagat  60
actggagtct cccagaaccc cagacacaag atcacaaaga ggggacagaa tgtaactttc  120
aggtgtgatc caatttctga acacaaccgc ctttattggt accgacagac cctggggcag  180
ggcccagagt ttctgactta cttccagaat gaagctcaac tagaaaaatc aaggctgctc  240
agtgatcggt tctctgcaga gaggcctaag ggatctttct ccaccttgga gatccagcgc  300
acagagcagg gggactcggc catgtatctc tgtgccagca gcatcgactc cttcaacgag  360
cagttcttcg ggccgggcac caggctcacg gtcctcgagg acctgaaaaa cgtgttccca  420
cccgaggtcg ctgtgtttga gccatcagaa gcagagatct cccacaccca aaaggccaca  480
ctggtgtgcc tggccacagg cttctacccc gaccacgtgg agctgagctg gtgggtgaat  540
gggaaggagg tgcacagtgg ggtctgcaca gacccgcagc ccctcaagga gcagcccgcc  600
ctcaatgact ccagatactg cctgagcagc cgcctgaggg tgtcggccac cttctggcag  660
aacccccgca accacttccg ctgtcaagtc cagttctacg ggctctcgga gaatgacgag  720
tggacccagg atagggccaa acctgtcacc cagatcgtca gcgccgaggc ctggggtaga  780
gcagactgtg gcttcacctc cgagtcttac cagcaagggg tcctgtctgt tgtgatcggc  840
atcttggtgg ccgtcatcct actgctcctc ctcctcctcc tcctcttcct catcctccga  900
catcgacgtc agggcaaaca ctggacatcg acccagagaa aggctgattt ccaacatcct  960
gcaggggctg tggggccaga gcccacagac agaggcctgc agtggaggtc cagcccagct  1020
gccgatgccc aggaagaaaa cctctatgct gccgtgaagc acacacagcc tgaggatggg  1080
gtggagatgg acactcggag cccacacgat gaagaccccc aggcagtgac gtatgccgag  1140
gtgaaacact ccagacctag gagagaaatg cctctcctc cttccccact gtctggggaa  1200
ttcctggaca caaaggacag acaggcggaa gaggacaggc agatggacac tgaggctgct  1260
gcatctgaag ccccccagga tgtgacctac gcccagctgc acagcttgac cctcagacgg  1320
gaggcaactg agcctcctcc atcccaggaa gggccctctc cagctgtgcc cagcatctac  1380
gccactctgg ccatccacta g                                          1401

SEQ ID NO: 199           moltype = AA  length = 250
FEATURE                  Location/Qualifiers
REGION                   1..250
                         note = HA-1H TCR alpha
source                   1..250
                         mol_type = protein
                         organism = synthetic construct
SEQUENCE: 199
MVKIRQFLLA ILWLQLSCVS AAKNEVEQSP QNLTAQEGEF ITINCSYSVG ISALHWLQQH  60
PGGGIVSLFM LSSGKKKHGR LIATINIQEK HSSLHITASH PRDSAVYICA VRSVSGAGSY  120
QLTFGKGTKL SVIPNIQNPD PAVYQLRDSK SSDKSVCLFT DFDSQTNVSQ SKDSDVYITD  180
KCVLDMRSMD FKSNSAVAWS NKSDFACANA FNNSIIPEDT FFPSPESSCD VKLVEKSFET  240
DTNLNFQNLS                                                        250

SEQ ID NO: 200           moltype = AA  length = 276
FEATURE                  Location/Qualifiers
REGION                   1..276
                         note = HA-1H TCR beta
source                   1..276
                         mol_type = protein
                         organism = synthetic construct
SEQUENCE: 200
MGTSLLCWMA LCLLGADHAD TGVSQNPRHK ITKRGQNVTF RCDPISEHNR LYWYRQTLGQ  60
GPEFLTYFQN EAQLEKSRLL SDRFSAERPK GSFSTLEIQR TEQGDSAMYL CASSIDSFNE  120
QFFGPGTRLT VLEDLKNVFP PEVAVFEPSE AEISHTQKAT LVCLATGFYP DHVELSWWVN  180
GKEVHSGVCT DPQPLKEQPA LNDSRYCLSS RLRVSATFWQ NPRNHFRCQV QFYGLSENDE  240
WTQDRAKPVT QIVSAEAWGR ADCGFTSESY QQGVLS                            276

SEQ ID NO: 201           moltype = DNA  length = 750
FEATURE                  Location/Qualifiers
misc_feature             1..750
                         note = HA-1H TCR alpha
source                   1..750
                         mol_type = other DNA
                         organism = synthetic construct
SEQUENCE: 201
atggtgaaga tccggcaatt tttgttggct attttgtggc ttcagctaag ctgtgtaagt  60
gccgccaaaa atgaagtgga gcagagtcct cagaacctga ctgcccagga aggagaattt  120
atcacaatca actgcagtta ctcggtagga ataagtgcct tacactggct gcaacagcat  180
ccaggaggag gcattgtttc cttgtttatg ctgagctcag ggaagaagaa gcatggaaga  240
ttaattgcca caataaacat acaggaaaag cacagctccc tgcacatcac agcctcccat  300
cccagagact ctgccgtcta catctgtgct gtcagaagcg tgtccggggc cggctcctac  360
cagctcacct ttgggaaggg gaccaaatta tcagtcattc caaatatcca gaaccctgac  420
cctgccgtgt accagctgag agactctaaa tccagtgaca agtctgtctg cctattcacc  480
gattttgatt ctcaaacaaa tgtgtcacaa agtaaggatt ctgatgtgta tatcacagac  540
aaatgtgtgc tagacatgag gtctatggac ttcaagagca acagtgctgt ggcctggagc  600
aacaaatctg actttgcatg tgcaaacgcc ttcaacaaca gcattattcc agaagacacc  660
ttcttcccca gcccagaaag ttcctgtgat gtcaagctgg tcgagaaaag ctttgaaaca  720
gatacgaacc taaactttca aaacctgtca                                  750

SEQ ID NO: 202           moltype = DNA  length = 828
FEATURE                  Location/Qualifiers
```

```
misc_feature           1..828
                       note = HA-1H TCR beta
source                 1..828
                       mol_type = other DNA
                       organism = synthetic construct
SEQUENCE: 202
atgggcacca gcctcctctg ctggatggcc ctgtgtctcc tgggggcaga tcacgcagat  60
actggagtct cccagaaccc cagacacaag atcacaaaga ggggacagaa tgtaactttc  120
aggtgtgatc caatttctga acacaaccgc ctttattggt accgacagac cctggggcag  180
ggcccagagt ttctgactta cttccagaat gaagctcaac tagaaaaatc aaggctgctc  240
agtgatcggt tctctgcaga gaggcctaag ggatctttct ccaccttgga gatccagcgc  300
acagagcagg gggactcggc catgtatctc tgtgccagca gcatcgactc cttcaacgag  360
cagttcttcg ggccgggcac caggctcacg gtcctcgagg acctgaaaaa cgtgttccca  420
cccgaggtcg ctgtgtttga gccatcagaa gcagagatct cccacaccca aaaggccaca  480
ctggtgtgcc tggccacagg cttctacccc gaccacgtgg agctgagctg gtgggtgaat  540
gggaaggagg tgcacagtgg ggtctgcaca gacccgcagc ccctcaagga gcagcccgcc  600
ctcaatgact ccagatactg cctgagcagc cgcctgaggg tgtcggccac cttctggcag  660
aacccccgca accacttccg ctgtcaagtc cagttctacg ggctctcgga gaatgacgag  720
tggacccagg atagggccaa acctgtcacc cagatcgtca gcgccgaggc ctggggtaga  780
gcagactgtg gcttcacctc cgagtcttac cagcaagggg tcctgtct               828

SEQ ID NO: 203         moltype = AA  length = 13
FEATURE                Location/Qualifiers
REGION                 1..13
                       note = NY-ESO CDR
source                 1..13
                       mol_type = protein
                       organism = synthetic construct
SEQUENCE: 203
CASSLGLGYE QYF                                                     13

SEQ ID NO: 204         moltype = AA  length = 20
FEATURE                Location/Qualifiers
REGION                 1..20
                       note = NY-ESO CDR
source                 1..20
                       mol_type = protein
                       organism = synthetic construct
SEQUENCE: 204
CASSLGGPRG LAGLRGDEQF                                              20

SEQ ID NO: 205         moltype = AA  length = 12
FEATURE                Location/Qualifiers
REGION                 1..12
                       note = NY-ESO CDR
source                 1..12
                       mol_type = protein
                       organism = synthetic construct
SEQUENCE: 205
CASSLRRDNE QF                                                      12

SEQ ID NO: 206         moltype = AA  length = 19
FEATURE                Location/Qualifiers
REGION                 1..19
                       note = MAGE-A3 CDR
source                 1..19
                       mol_type = protein
                       organism = synthetic construct
SEQUENCE: 206
CASSLEVLLG ADFPDTQYF                                               19

SEQ ID NO: 207         moltype = AA  length = 18
FEATURE                Location/Qualifiers
REGION                 1..18
                       note = MAGE-A3 CDR
source                 1..18
                       mol_type = protein
                       organism = synthetic construct
SEQUENCE: 207
CASSFPAGHG ADLDNEQF                                                18

SEQ ID NO: 208         moltype = AA  length = 14
FEATURE                Location/Qualifiers
REGION                 1..14
                       note = MAGE-A3 CDR
source                 1..14
                       mol_type = protein
                       organism = synthetic construct
SEQUENCE: 208
```

```
CASSEITGRI GEQF                                             14

SEQ ID NO: 209          moltype = AA  length = 18
FEATURE                 Location/Qualifiers
REGION                  1..18
                        note = MAGE-A3 CDR
source                  1..18
                        mol_type = protein
                        organism = synthetic construct
SEQUENCE: 209
CASSLGGDEL GADGNEQF                                         18

SEQ ID NO: 210          moltype = AA  length = 241
FEATURE                 Location/Qualifiers
REGION                  1..241
                        note = NY-ESO-1 ScFv
source                  1..241
                        mol_type = protein
                        organism = synthetic construct
SEQUENCE: 210
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPLTFGG GTKVEIKGGG GSGGGGSGGG  120
GSGGEVQLVE SGGGLVQPGG SLRLSCAASG FTVYDYMSWV RQAPGKGLEW VSVIYSGGST  180
YYADSVKGRF TISRDNSKNT LYLQMNSLRA EDTAVYYCAR YSYYYYYMDV WGKGTTVTVS  240
S                                                           241

SEQ ID NO: 211          moltype = DNA  length = 723
FEATURE                 Location/Qualifiers
misc_feature            1..723
                        note = NY-ESO-1 ScFv
source                  1..723
                        mol_type = other DNA
                        organism = synthetic construct
SEQUENCE: 211
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta cccctctcac tttcggcggc  300
ggaacaaagg tggagatcaa gggcggaggt ggaagcggag ggggaggatc tggcggcgga  360
ggaagcggag gcgaagtgca gctggtggaa agcggcggag gcctggtgca gcctggcggc  420
agcctgagac tgtcttgcgc cgccagcggc ttcaccgtgt acgactacat gagctgggtc  480
cgccaggccc ctggcaaggg actggaatgg gtgtccgtga tctacagcgg cggcagcacc  540
tactacgccg acagcgtgaa gggtcgattc accatcagcc gggacaacag caagaacacc  600
ctgtacctgc agatgaacag cctgcgggcc gaggacaccg ccgtgtatta ctgtgcgagg  660
tactcctact actactacta catggacgtc tggggcaaag ggaccacggt caccgtgtcc  720
tca                                                         723

SEQ ID NO: 212          moltype = AA  length = 244
FEATURE                 Location/Qualifiers
REGION                  1..244
                        note = MAGE-A3 antigen binding domain
source                  1..244
                        mol_type = protein
                        organism = synthetic construct
SEQUENCE: 212
QVQLQESGPG LVKPSDTLSL TCAVSGYSIS SSNWWGWIRQ PPGKGLEWIG YIYYSGSTYY  60
NPSLKSRVTM SVDTSKNQFS LKLSSVTAVD TAVYYCARIP FGDWWYFDLW GRGTLVTVSS  120
GGGGSGGGGS GGGGSGGDIQ MTQSPSSLSA SVGDRVTITC RASQSISSYL NWYQQKPGKA  180
PKLLIYAASS LQSGVPSRFS GSGSGTDFTL TISSLQPEDF ATYYCQQSYS FVLTFGGGTK  240
VEIK                                                        244

SEQ ID NO: 213          moltype = DNA  length = 732
FEATURE                 Location/Qualifiers
misc_feature            1..732
                        note = MAGE-A3 antigen binding domain
source                  1..732
                        mol_type = other DNA
                        organism = synthetic construct
SEQUENCE: 213
caggtgcagc tgcaggaaag cggccctggc ctggtgaaac ccagcgacac cctgagcctg  60
acctgcgccg tgtccggcta cagcatcagc agcagcaatt ggtggggctg gatcagacag  120
ccccctggca agggcctgga atggatcggc tacatctact acagcggcag cacctactac  180
aaccccagcc tgaagtccag agtgaccatg agcgtggaca ccagcaagaa ccagttcagc  240
ctgaagctga gcagcgtgac cgccgtcgat accgctgtgt attactgtgc gagaataccc  300
tttggggatt ggtggtactt cgatctctgg ggccgtggca ccctggtcac tgtgtcctca  360
ggcggaggtg gaagcggagg gggaggatct ggcggcggag gaagcggagg cgacatccag  420
atgacccaga gccccagcag cctgagcgcc agcgtgggcg acagagtgac catcacctgt  480
cgggccagcc agtcgatcag cagctacctg aactggtatc agcagaagcc cggcaaggcc  540
```

```
cccaagctgc tgatctacgc cgccagctcc ctgcagagcg gcgtgccaag cagattcagc  600
ggcagcggct ccggcaccga cttcaccctg accatcagca gcctgcagcc cgaggacttc  660
gccacctact actgccagca gagttacagt ttcgttctca ctttcggcgg agggaccaag  720
gtggagatca aa                                                      732

SEQ ID NO: 214         moltype = AA  length = 248
FEATURE                Location/Qualifiers
REGION                 1..248
                       note = MAGE-A3 antigen binding domain
source                 1..248
                       mol_type = protein
                       organism = synthetic construct
SEQUENCE: 214
QVQLVQSGAE VKKPGASVKV SCKVSGYTLT ELSMHWVRQA PGKGLEWMGG FDPEDGETIY  60
AQKFQGRVTM TEDTSTDTAY MELSSLRSED TAVYYCATDL YSSSWYCDAF DIWGQGTMVT  120
VSSGGGGSGG GGSGGGGSGG DIQMTQSPSS LSASVGDRVT ITCRASQSIS SYLNWYQQKP  180
GKAPKLLIYA ASSLQSGVPS RFSGSGSGTD FTLTISSLQP EDFATYYCQQ SWASTPLTFG  240
GGTKVEIK                                                           248

SEQ ID NO: 215         moltype = DNA  length = 744
FEATURE                Location/Qualifiers
misc_feature           1..744
                       note = MAGE-A3 antigen binding domain
source                 1..744
                       mol_type = other DNA
                       organism = synthetic construct
SEQUENCE: 215
caggtgcagc tggtgcagtc tggcgccgaa gtgaagaaac ctggcgcctc cgtgaaggtg  60
tcctgcaagg tgtccggcta caccctgacc gagctgtcga tgcactgggt ccgccaggca  120
cctggcaagg gactggaatg gatgggcggc tttgaccccg aggacggcga gacaatctac  180
gcccagaaat tccagggcag agtgaccatg accgaggaca ccagcaccga caccgcctac  240
atggaactga gcagcctgcg gagcgaggac accgctgtgt attactgtgc aacagatctg  300
tatagcagca gctggtactg tgatgctttt gatatctggg gccaagggac aatggtcacc  360
gtgtcctcag gcggaggtgg aagcggaggg ggaggatctg gcggcggagg aagcggaggc  420
gacatccaga tgacccagag ccccagcagc ctgagcgcca gcgtgggcga cagagtgacc  480
atcacctgtc gggccagcca gtcgatcagc agctacctga actggtatca gcagaagccc  540
ggcaaggccc ccaagctgct gatctacgcc gccagctccc tgcagagcgg cgtgccaagc  600
agattcagcg gcagcggctc cggcaccgac ttcaccctga ccatcagcag cctgcagccc  660
gaggacttcg ccacctacta ctgccagcag agttgggcca gcacccctct cactttcggc  720
ggagggacca aggtggagat caaa                                         744

SEQ ID NO: 216         moltype = AA  length = 245
FEATURE                Location/Qualifiers
REGION                 1..245
                       note = HPV E6 antigen binding domain
source                 1..245
                       mol_type = protein
                       organism = synthetic construct
SEQUENCE: 216
EVQLVESGGG LVQPGGSLRL SCAASGFTFS SYWMHWVRQA PGKGLVWVSR INSDGSSTSY  60
ADSVKGRFTI SRDNAKNTLY LQMNSLRAED TAVYYCAREN GVVKWYFDLW GRGTLVTVSS  120
GGGGSGGGGS GGGGSGGDIQ MTQSPSSLSA SVGDRVTITC RASQSISSYL NWYQQKPGKA  180
PKLLIYAASS LQSGVPSRFS GSGSGTDFTL TISSLQPEDF ATYYCQQSYS TPLFPFGGGT  240
KVEIK                                                              245

SEQ ID NO: 217         moltype = DNA  length = 735
FEATURE                Location/Qualifiers
misc_feature           1..735
                       note = HPV E6 antigen binding domain
source                 1..735
                       mol_type = other DNA
                       organism = synthetic construct
SEQUENCE: 217
gaagtgcagc tggtggaaag cggcggaggc ctggtgcagc ctggcggcag cctgagactg  60
tcttgcgccg ccagcggctt caccttcagc agctactgga tgcactgggt ccgccaggcc  120
cctggcaagg gactggtctg ggtgtctcga atcaacagcg acggcagcag caccagctac  180
gccgacagcg tgaagggccg gttcaccatc agccgggaca acgccaagaa caccctgtac  240
ctgcagatga acagcctgcg ggccgaggac accgccgtgt attactgtgc cagggagaac  300
ggcgtggtga agtggtactt cgacctgtgg ggccgtggca ccctggtcac tgtgtcctca  360
ggcggaggtg gaagcggagg gggaggatct ggcggcggag gaagcggagg cgacatccag  420
atgacccaga gccccagcag cctgagcgcc agcgtgggcg acagagtgac catcacctgt  480
cgggccagcc agtcgatcag cagctacctg aactggtatc agcagaagcc cggcaaggcc  540
cccaagctgc tgatctacgc cgccagctcc ctgcagagcg gcgtgccaag cagattcagc  600
ggcagcggct ccggcaccga cttcaccctg accatcagca gcctgcagcc cgaggacttc  660
gccacctact actgccagca gagttacagt acccctctct ttcccttcgg cggagggacc  720
aaggtggaga tcaaa                                                   735

SEQ ID NO: 218         moltype = AA  length = 247
FEATURE                Location/Qualifiers
```

```
REGION                  1..247
                        note = HPV E6 antigen binding domain
source                  1..247
                        mol_type = protein
                        organism = synthetic construct
SEQUENCE: 218
EVQLVESGGG LVQPGRSLRL SCAASGFTFD DYAMHWVRQA PGKGLEWVSG ISWNSGSIGY  60
ADSVKGRFTI SRDNAKNSLY LQMNSLRAED TALYYCAKDG RGSPFYGGAF DIWGQGTMVT  120
VSSGGGGSGG GGSGGGGSGG DIQMTQSPSS LSASVGDRVT ITCRASQSIS SYLNWYQQKP  180
GKAPKLLIYA ASSLQSGVPS RFSGSGSGTD FTLTISSLQP EDFATYYCQQ SYSTPLTFGG  240
GTKVEIK                                                            247

SEQ ID NO: 219          moltype = DNA  length = 741
FEATURE                 Location/Qualifiers
misc_feature            1..741
                        note = HPV E6 antigen binding domain
source                  1..741
                        mol_type = other DNA
                        organism = synthetic construct
SEQUENCE: 219
gaagtgcagc tggtggaaag cggcggaggc ctggtgcagc ccggtcgaag cctgagactg  60
agctgcgccg ccagcggctt cacctttgac gactacgcca tgcactgggt ccgccaggcc  120
cctggcaagg gactggaatg ggtgtccggc atcagctgga acagcggcag catcggctac  180
gccgacagcg tgaagggccg gttcaccatc agccgggaca acgccaagaa cagcctgtac  240
ctgcagatga acagcctgcg ggccgaggac accgccttgt attactgtgc caaggacggc  300
aggggctccc ccttctacgg cggcgccttc gacatctggg gccaagggac aatggtcacc  360
gtgtcctcag gcggaggtgg aagcggaggg ggaggatctg gcggcggagg aagcggaggc  420
gacatccaga tgacccagtc tccatcctcc ctgtctgcat ctgtaggaga cagagtcacc  480
atcacttgcc gggcaagtca gagcattagc agctatttaa attggtatca gcagaaacca  540
gggaaagccc ctaagctcct gatctatgct gcatccagtt tgcaaagtgg ggtcccatca  600
aggttcagtg gcagtggatc tgggacagat ttcactctca ccatcagcag tctgcaacct  660
gaagattttg caacttacta ctgtcaacag agttacagta cccctctcac tttcggcggc  720
ggaacaaagg tggagatcaa g                                            741

SEQ ID NO: 220          moltype = AA  length = 251
FEATURE                 Location/Qualifiers
REGION                  1..251
                        note = HPV E7 antigen binding domain
source                  1..251
                        mol_type = protein
                        organism = synthetic construct
SEQUENCE: 220
EVQLVESGGG LVKPGGSLRL SCAASGFTFS NAWMSWVRQA PGKGLEWVGR IKSKTDGGTT  60
DYAAPVKGRF TISRDDSKNT LYLQMNSLKT EDTAVYYCTT SYDYLLNPYR WNWFDPWGQG  120
TLVTVSSGGG GSGGGGSGGG GSGGDIQMTQ SPSSLSASVG DRVTITCRAS QSISSYLNWY  180
QQKPGKAPKL LIYAASSLQS GVPSRFSGSG SGTDFTLTIS SLQPEDFATY YCQQSYSTPL  240
TFGGGTKVEI K                                                       251

SEQ ID NO: 221          moltype = DNA  length = 753
FEATURE                 Location/Qualifiers
misc_feature            1..753
                        note = HPV E7 antigen binding domain
source                  1..753
                        mol_type = other DNA
                        organism = synthetic construct
SEQUENCE: 221
gaagtgcagc tggtggaaag cggcggaggc ctggtgaaac ctggcggcag cctgagactg  60
agctgcgccg ccagcggctt caccttctcg aacgcctgga tgagctgggt ccgccaggcc  120
cctggcaagg gactggaatg ggtcggacgg atcaagagca agaccgacgg cggcaccacc  180
gactacgctg cccccgtgaa gggccggttc accatcagcc gggacgacag caagaacacc  240
ctgtacctgc agatgaacag cctgaaaacc gaggacaccg ccgtgtatta ctgtaccacc  300
tcctacgatt accttctcaa tccttatcgt tggaactggt tcgacccctg gggccaggga  360
accctggtca ccgtgtcctc aggcggaggt ggaagcggag ggggaggatc tggcggcgga  420
ggaagcggcg gagacatcca gatgacccag tctccatcct ccctgtctgc atctgtagga  480
gacagagtca ccatcacttg ccgggcaagt cagagcatta gcagctattt aaattggtat  540
cagcagaaac cagggaaagc ccctaagctc ctgatctatg ctgcatccag tttgcaaagt  600
ggggtcccat caaggttcag tggcagtgga tctgggacag atttcactct caccatcagc  660
agtctgcaac ctgaagattt tgcaacttac tactgtcaac agagttacag tacccctctc  720
actttcggcg gcggaacaaa ggtggagatc aag                               753

SEQ ID NO: 222          moltype = AA  length = 246
FEATURE                 Location/Qualifiers
REGION                  1..246
                        note = MAGE-A3 antigen binding domain
source                  1..246
                        mol_type = protein
                        organism = synthetic construct
SEQUENCE: 222
QVQLVQSGAE VKKPGSSVKV SCKASGGTFS SYAISWVRQA PGQGLEWMGG IIPIFGTANY  60
```

```
AQKFQGRVTI TADESTSTAY MELSSLRSED TAVYYCARDM DTFSMVTLFD YWGQGTLVTV  120
SSGGGGSGGG GSGGGGSGGD IQMTQSPSSL SASVGDRVTI TCRASQSISS YLNWYQQKPG  180
KAPKLLIYAA SSLQSGVPSR FSGSGSGTDF TLTISSLQPE DFATYYCQQS YSWPLTFGGG  240
TKVEIK                                                             246

SEQ ID NO: 223          moltype = DNA  length = 738
FEATURE                 Location/Qualifiers
misc_feature            1..738
                        note = MAGE-A3 antigen binding domain
source                  1..738
                        mol_type = other DNA
                        organism = synthetic construct
SEQUENCE: 223
caggtgcagc tggtgcagtc tggcgccgaa gtgaagaaac ccggcagcag cgtgaaggtg  60
tcctgcaagg ccagcggcgg caccttcagc agctacgcca tcagctgggt ccgccaggct  120
cctggacagg gactggaatg gatgggcggc atcatcccca tcttcggcac cgccaactac  180
gcccagaaat tccagggcag agtgaccatc accgccgacg agagcaccag caccgcctac  240
atggaactga gcagccttcg aagcgaggac accgctgtgt attactgtgc cagggacatg  300
gacaccttct ccatggtgac cctgttcgac tactggggcc agggcaccct ggtcaccgtg  360
tcctcaggcg gaggtggaag cggaggggga ggatctggcg gcggaggaag cggaggcgac  420
atccagatga cccagagccc cagcagcctg agcgccagcg tgggcgacag agtgaccatc  480
acctgtcggg ccagccagtc gatcagcagc tacctgaact ggtatcagca gaagcccggc  540
aaggcccccca agctgctgat ctacgccgcc agctccctgc agagcggcgt gccaagcaga  600
ttcagcggca gcggctccgg caccgacttc accctgacca tcagcagcct gcagcccgag  660
gacttcgcca cctactactg ccagcagagt tacagttggc ctctcacttt cggcggaggg  720
accaaggtgg agatcaaa                                                738

SEQ ID NO: 224          moltype = AA  length = 245
FEATURE                 Location/Qualifiers
REGION                  1..245
                        note = KRAS G12V antigen binding domain
source                  1..245
                        mol_type = protein
                        organism = synthetic construct
SEQUENCE: 224
QVTLRESGPA LVKPTQTLTL TCTFSGFSLS TSGMCVSWIR QPPGKALEWL ALIDWDDDKY  60
YSTSLKTRLT ISKDTSKNQV VLTMTNMDPV DTATYYCARS YDELYYFDYW GQGTLVTVSS  120
GGGGSGGGGS GGGGSGGDIQ MTQSPSSLSA SVGDRVTITC RASQSIWTSY LNWYQQKPGK  180
APKLLIYAAS SLQSGVPSRF SGSGSGTDFT LTISSLQPED FATYYCQQSY STPLTFGGGT  240
KVEIK                                                              245

SEQ ID NO: 225          moltype = DNA  length = 735
FEATURE                 Location/Qualifiers
misc_feature            1..735
                        note = KRAS G12V antigen binding domain
source                  1..735
                        mol_type = other DNA
                        organism = synthetic construct
SEQUENCE: 225
caggtcacac tgagagagtc cggccctgcc ctggtgaaac ccacccagac cctgaccctg  60
acatgcacct tcagcggctt cagcctgagc accagcggga tgtgcgtgtc ctggattcga  120
cagccccctg gcaaggccct ggaatggctg gccctgattg actgggacga cgacaagtac  180
tacagcacca gcctgaaaac ccggctgacc atcagcaagg acaccagcaa gaaccaggtg  240
gtgctgacca tgaccaacat ggaccccgtg gacaccgcca cgtattactg tgcacggagt  300
tacgacgagc tctactactt tgactactgg ggccagggaa ccctggtcac cgtgtcctca  360
ggcggaggtg gaagcggagg gggaggatct ggcggcggag gaagcggagg cgacatccag  420
atgacccaga gccccagctc cctctctgca tctgtgggcg acagagtgac catcacctgt  480
cgggccagcc agtcgatctg gaccagctac ctgaactggt atcagcagaa gcccggcaag  540
gcccccaagc tgctgatcta cgccgccagc tccctgcaga gcggcgtgcc aagcagattc  600
agcggcagcg gctccggcac cgacttcacc ctgaccatca gcagcctgca gcccgaggac  660
ttcgccacct actactgcca gcagagttac agtacccctc tcactttcgg cggagggacc  720
aaggtggaga tcaaa                                                   735

SEQ ID NO: 226          moltype = AA  length = 5
FEATURE                 Location/Qualifiers
REGION                  1..5
                        note = linker
source                  1..5
                        mol_type = protein
                        organism = synthetic construct
SEQUENCE: 226
GGGGS                                                              5

SEQ ID NO: 227          moltype = AA  length = 10
FEATURE                 Location/Qualifiers
REGION                  1..10
                        note = linker
source                  1..10
                        mol_type = protein
```

```
                         organism = synthetic construct
SEQUENCE: 227
GGGGSGGGGS                                                     10

SEQ ID NO: 228           moltype = AA  length = 15
FEATURE                  Location/Qualifiers
REGION                   1..15
                         note = linker
source                   1..15
                         mol_type = protein
                         organism = synthetic construct
SEQUENCE: 228
GGGGSGGGGS GGGGS                                               15

SEQ ID NO: 229           moltype = AA  length = 15
FEATURE                  Location/Qualifiers
REGION                   1..15
                         note = linker
source                   1..15
                         mol_type = protein
                         organism = synthetic construct
SEQUENCE: 229
GGGGSGGGGS GGGGS                                               15

SEQ ID NO: 230           moltype = AA  length = 20
FEATURE                  Location/Qualifiers
REGION                   1..20
                         note = linker
source                   1..20
                         mol_type = protein
                         organism = synthetic construct
SEQUENCE: 230
GGGGSGGGGS GGGGSGGGGS                                          20

SEQ ID NO: 231           moltype = AA  length = 4
FEATURE                  Location/Qualifiers
REGION                   1..4
                         note = linker
source                   1..4
                         mol_type = protein
                         organism = synthetic construct
SEQUENCE: 231
GGGS                                                           4

SEQ ID NO: 232           moltype = AA  length = 247
FEATURE                  Location/Qualifiers
REGION                   1..247
                         note = KRAS ScFv
source                   1..247
                         mol_type = protein
                         organism = synthetic construct
SEQUENCE: 232
QVQLVESGGG LVKPGGSLRL SCAASGFTFS DYYMSWIRQA PGKGLEWVSY ISSSGSTIYY  60
ADSVKGRFTI SRDNAKNSLY LQMNSLRAED TAVYYCARDF TRDYYYYYYM DVWGKGTTVT  120
VSSGGGGSGG GGSGGGGSGG DIQMTQSPSS LSASVGDRVT ITCRASQSIS SYLNWYQQKP  180
GKAPKLLIYA ASSLQSGVPS RFSGSGSGTD FTLTISSLQP EDFATYYCQQ SYSTPLTFGG  240
GTKVEIK                                                        247

SEQ ID NO: 233           moltype = DNA  length = 741
FEATURE                  Location/Qualifiers
misc_feature             1..741
                         note = KRAS ScFv
source                   1..741
                         mol_type = other DNA
                         organism = synthetic construct
SEQUENCE: 233
caggtgcagc tggtggaaag cggcggaggc ctggtgaaac ctggcggcag cctgagactg  60
agctgcgccg ccagcggctt caccttcagc gactactaca tgagctggat cagacaggcc  120
cctggcaagg gactggaatg ggtgtcctac atcagcagca gcggctcgac catctactac  180
gccgacagcg tgaagggccg gttcaccatc agccgggaca acgccaagaa cagcctgtac  240
ctgcagatga acagcctgcg ggccgaggac accgccgtgt attactgtgc cagggacttc  300
accagggact actactacta ctactacatg gacgtgtggg gcaaagggac cacggtcacc  360
gtgtcctcag gcggaggtgg aagcggaggg ggaggatctg gcggcggagg aagcggaggc  420
gacatccaga tgacccagtc tccatcctcc ctgtctgcat ctgtaggaga cagagtcacc  480
atcacttgcc gggcaagtca gagcattagc agctatttaa attggtatca gcagaaacca  540
gggaaagccc ctaagctcct gatctatgct gcatccagtt tgcaaagtgg ggtcccatca  600
aggttcagtg gcagtggatc tgggacagat ttcactctca ccatcagcag tctgcaacct  660
gaagattttg caacttacta ctgtcaacag agttacagta cccctctcac tttcggcggc  720
ggaacaaagg tggagatcaa g                                        741
```

```
SEQ ID NO: 234          moltype = AA  length = 244
FEATURE                 Location/Qualifiers
REGION                  1..244
                        note = KRAS ScFv
source                  1..244
                        mol_type = protein
                        organism = synthetic construct
SEQUENCE: 234
QVTLRESGPA LVKPTQTLTL TCTFSGFSLS TSGMCVSWIR QPPGKALEWL ALIDWDDDKY  60
YSTSLKTRLT ISKDTSKNQV VLTMTNMDPV DTATYYCARS YDELYYFDYW GQGTLVTVSS  120
GGGGSGGGGS GGGGSGGDIQ MTQSPSSLSA SVGDRVTITC RASQSISSYL NWYQQKPGKA  180
PKLLIYAASS LQSGVPSRFS GSGSGTDFTL TISSLQPEDF ATYYCQQSYS TPLTFGGGTK  240
VEIK                                                              244

SEQ ID NO: 235          moltype = DNA  length = 732
FEATURE                 Location/Qualifiers
misc_feature            1..732
                        note = KRAS ScFv
source                  1..732
                        mol_type = other DNA
                        organism = synthetic construct
SEQUENCE: 235
caggtcacac tgagagagtc cggccctgcc ctggtgaaac ccacccagac cctgaccctg  60
acatgcacct tcagcggctt cagcctgagc accagcggga tgtgcgtgtc ctggattcga  120
cagccccctg gcaaggccct ggaatggctg gccctgattg actgggacga cgacaagtac  180
tacagcacca gcctgaaaac ccggctgacc atcagcaagg acaccagcaa gaaccaggtg  240
gtgctgacca tgaccaacat ggaccccgtg gacaccgcca cgtattactg tgcacggagt  300
tacgacgagc tctactactt tgactactgg ggccagggaa ccctggtcac cgtgtcctca  360
ggcggaggtg gaagcggagg gggaggatct ggcggcggag gaagcggagg cgacatccag  420
atgacccagt ctccatcctc cctgtctgca tctgtaggag acagagtcac catcacttgc  480
cgggcaagtc agagcattag cagctattta aattggtatc agcagaaacc agggaaagcc  540
cctaagctcc tgatctatgc tgcatccagt ttgcaaagtg gggtcccatc aaggttcagt  600
ggcagtggat ctgggacaga tttcactctc accatcagca gtctgcaacc tgaagatttt  660
gcaacttact actgtcaaca gagttacagt acccctctca ctttcggcgg cggaacaaag  720
gtggagatca ag                                                     732

SEQ ID NO: 236          moltype = AA  length = 245
FEATURE                 Location/Qualifiers
REGION                  1..245
                        note = KRAS ScFv
source                  1..245
                        mol_type = protein
                        organism = synthetic construct
SEQUENCE: 236
QVTLRESGPA LVKPTQTLTL TCTFSGFSLS TSGMCVSWIR QPPGKALEWL ALIDWDDDKY  60
YSTSLKTRLT ISKDTSKNQV VLTMTNMDPV DTATYYCARS YDELYYFDYW GQGTLVTVSS  120
GGGGSGGGGS GGGGSGGDIQ MTQSPSSLSA SVGDRVTITC RASQSIWTSY LNWYQQKPGK  180
APKLLIYAAS SLQSGVPSRF SGSGSGTDFT LTISSLQPED FATYYCQQSY STPLTFGGGT  240
KVEIK                                                             245

SEQ ID NO: 237          moltype = DNA  length = 735
FEATURE                 Location/Qualifiers
misc_feature            1..735
                        note = KRAS ScFv
source                  1..735
                        mol_type = other DNA
                        organism = synthetic construct
SEQUENCE: 237
caggtcacac tgagagagtc cggccctgcc ctggtgaaac ccacccagac cctgaccctg  60
acatgcacct tcagcggctt cagcctgagc accagcggga tgtgcgtgtc ctggattcga  120
cagccccctg gcaaggccct ggaatggctg gccctgattg actgggacga cgacaagtac  180
tacagcacca gcctgaaaac ccggctgacc atcagcaagg acaccagcaa gaaccaggtg  240
gtgctgacca tgaccaacat ggaccccgtg gacaccgcca cgtattactg tgcacggagt  300
tacgacgagc tctactactt tgactactgg ggccagggaa ccctggtcac cgtgtcctca  360
ggcggaggtg gaagcggagg gggaggatct ggcggcggag gaagcggagg cgacatccag  420
atgacccaga gccccagctc cctctctgca tctgtgggcg acagagtgac catcacctgt  480
cgggccagcc agtcgatctg gaccagctac ctgaactggt atcagcagaa gcccggcaag  540
gcccccaagc tgctgatcta cgccgccagc tccctgcaga gcggcgtgcc aagcagattc  600
agcggcagcg gctccggcac cgacttcacc ctgaccatca gcagcctgca gcccgaggac  660
ttcgccacct actactgcca gcagagttac agtacccctc tcactttcgg cggagggacc  720
aaggtggaga tcaaa                                                  735

SEQ ID NO: 238          moltype = AA  length = 244
FEATURE                 Location/Qualifiers
REGION                  1..244
                        note = KRAS ScFv
source                  1..244
                        mol_type = protein
```

```
                         organism = synthetic construct
SEQUENCE: 238
QVTLRESGPA LVKPTQTLTL TCTFSGFSLS TSGMCVSWIR QPPGKALEWL ALIDWDDDKY  60
YSTSLKTRLT ISKDTSKNQV VLTMTNMDPV DTATYYCARS YDELYYFDYW GQGTLVTVSS  120
GGGGSGGGGS GGGGSGGDIQ MTQSPSSLSA SVGDRVTITC RASQSISSYL NWYQQKPGKA  180
PKLLIYAASS LQSGVPSRFS GSGSGTDFTL TISSLQPEDF ATYYCQQSYS TRLTFGGGTK  240
VEIK                                                              244

SEQ ID NO: 239          moltype = DNA  length = 732
FEATURE                 Location/Qualifiers
misc_feature            1..732
                        note = KRAS ScFv
source                  1..732
                        mol_type = other DNA
                        organism = synthetic construct
SEQUENCE: 239
caggtcacac tgagagagtc cggccctgcc ctggtgaaac ccacccagac cctgaccctg  60
acatgcacct tcagcggctt cagcctgagc accagcggga tgtgcgtgtc ctggattcga  120
cagcccccctg gcaaggccct ggaatggctg gccctgattg actgggacga cgacaagtac  180
tacagcacca gcctgaaaac ccggctgacc atcagcaagg acaccagcaa gaaccaggtg  240
gtgctgacca tgaccaacat ggaccccgtg gacaccgcca cgtattactg tgcacggagt  300
tacgacgagc tctactactt tgactactgg ggccagggaa ccctggtcac cgtgtcctca  360
ggcggaggtg gaagcggagg gggaggatct ggcggcggag gaagcggagg cgacatccag  420
atgacccaga gccccagctc cctctctgca tctgtgggcg acagagtgac catcacctgt  480
cgggccagcc agtcgatcag cagctacctg aactggtatc agcagaagcc cggcaaggcc  540
cccaagctgc tgatctacgc cgccagctcc ctgcagagcg gcgtgccaag cagattcagc  600
ggcagcggct ccggcaccga cttcaccctg accatcagca gcctgcagcc cgaggacttc  660
gccacctact actgccagca gagttacagt acccggctca ctttcggcgg agggaccaag  720
gtggagatca aa                                                     732

SEQ ID NO: 240          moltype = AA  length = 244
FEATURE                 Location/Qualifiers
REGION                  1..244
                        note = KRAS TCR alpha
source                  1..244
                        mol_type = protein
                        organism = synthetic construct
SEQUENCE: 240
MQRNLGAVLG ILWVQICWVR GDQVEQSPSA LSLHEGTDSA LRCNFTTTMR SVQWFRQNSR  60
GSLISLFYLA SGTKENGRLK SAFDSKERRY STLHIRDAQL EDSGTYFCAA DSSNTGYQNF  120
YFGKGTSLTV IPNIQNPEPA VYQLKDPRSQ DSTLCLFTDF DSQINVPKTM ESGTFITDKC  180
VLDMKAMDSK SNGAIAWSNQ TSFTCQDIFK ETNATYPSSD VPCDATLTEK SFETDMNLNF  240
QNLS                                                              244

SEQ ID NO: 241          moltype = DNA  length = 732
FEATURE                 Location/Qualifiers
misc_feature            1..732
                        note = KRAS TCR alpha
source                  1..732
                        mol_type = other DNA
                        organism = synthetic construct
SEQUENCE: 241
atgcagagga acctgggagc tgtgctgggg attctgtggg tgcagatttg ctgggtgaga  60
ggggatcagg tggagcagag tccttcagcc ctgagcctcc acgagggaac cgattctgct  120
ctgagatgca attttacgac caccatgagg agtgtgcagt ggttccgaca gaattccagg  180
ggcagcctca tcagtttgtt ctacttggct tcaggaacaa aggagaatgg gaggctaaag  240
tcagcatttg attctaagga gcggcgctac agcaccctgc acatcaggga tgcccagctg  300
gaggactcag gcacttactt ctgtgctgct gactcttcga acacgggtta ccagaacttc  360
tattttggga aaggaacaag tttgactgtc attccaaaca tccagaaccc agaacctgct  420
gtgtaccagt taaaagatcc tcggtctcag gacagcaccc tctgcctgtt caccgacttt  480
gactcccaaa tcaatgtgcc gaaaaccatg gaatctggaa cgttcatcac tgacaaatgt  540
gtgctggaca tgaaagctat ggattccaag agcaatgggg ccattgcctg gagcaaccag  600
acaagcttca cctgccaaga tatcttcaaa gagaccaacg ccacctaccc cagttcagac  660
gttccctgtg atgccacgtt gaccgagaaa agctttgaaa cagatatgaa cctgaacttt  720
caaaacctgt ct                                                     732

SEQ ID NO: 242          moltype = AA  length = 283
FEATURE                 Location/Qualifiers
REGION                  1..283
                        note = KRAS TCR beta
source                  1..283
                        mol_type = protein
                        organism = synthetic construct
SEQUENCE: 242
MSNTAFPDPA WNTTLLSWVA LFLLGTSSAN SGVVQSPRYI IKGKGERSIL KCIPISGHLS  60
VAWYQQTQGQ ELKFFIQHYD KMERDKGNLP SRFSVQQFDD YHSEMNMSAL ELEDSAVYFC  120
ASSLTDPLDS DYTFGSGTRL LVIEDLRNVT PPKVSLFEPS KAEIANKQKA TLVCLARGFF  180
PDHVELSWWV NGKEVHSGVC TDPQAYKESN YSYCLSSRLR VSATFWHNPR NHFRCQVQFH  240
GLSEEDKWPE GSPKPVTQNI SAEAWGRADC GITSASYQQG VLS                   283
```

```
SEQ ID NO: 243          moltype = DNA  length = 849
FEATURE                 Location/Qualifiers
misc_feature            1..849
                        note = KRAS TCR beta
source                  1..849
                        mol_type = other DNA
                        organism = synthetic construct
SEQUENCE: 243
atgtctaaca ctgccttccc tgaccccgcc tggaacacca ccctgctatc ttgggttgct  60
ctctttctcc tgggaacaag ttcagcaaat tctggggttg tccagtctcc aagatacata  120
atcaaaggaa agggagaaag gtccattcta aaatgtattc ccatctctgg acatctctct  180
gtggcctggt atcaacagac tcaggggcag gaactaaagt tcttcattca gcattatgat  240
aaaatggaga gagataaagg aaacctgccc agcagattct cagtccaaca gtttgatgac  300
tatcactctg agatgaacat gagtgccttg gagctagagg actctgccgt gtacttctgt  360
gccagctctc tcacagatcc gctagactcc gactacacct tcggctcagg gaccaggctt  420
ttggtaatag aggatctgag aaatgtgact ccacccaagg tctccttgtt tgagccatca  480
aaagcagaga ttgcaaacaa acaaaaggct accctcgtgt gcttggccag gggcttcttc  540
cctgaccacg tggagctgag ctggtgggtg aatggcaagg aggtccacag tggggtctgc  600
acggaccctc aggcctacaa ggagagcaat tatagctact gcctgagcag ccgcctgagg  660
gtctctgcta ccttctggca caatcctcgc aaccacttcc gctgccaagt gcagttccat  720
gggctttcag aggaggacaa gtggccagag ggctcaccca aacctgtcac acagaacatc  780
agtgcagagg cctggggccg agcagactgt gggattacct cagcatccta tcaacaaggg  840
gtcttgtct                                                          849

SEQ ID NO: 244          moltype = AA  length = 283
FEATURE                 Location/Qualifiers
REGION                  1..283
                        note = KRAS TCR beta
source                  1..283
                        mol_type = protein
                        organism = synthetic construct
SEQUENCE: 244
MSNTAFPDPA WNTTLLSWVA LFLLGTSSAN SGVVQSPRYI IKGKGERSIL KCIPISGHLS  60
VAWYQQTQGQ ELKFFIQHYD KMERDKGNLP SRFSVQQFDD YHSEMNMSAL ELEDSAVYFC  120
ASSLTDPLDS DYTFGSGTRL LVIEDLRNVT PPKVSLFEPS KAEIANKQKA TLVCLARGFF  180
PDHVELSWWV NGKEVHSGVC TDPQAYKESN YSYCLSSRLR VSATFWHNPR NHFRCQVQFH  240
GLSEEDKWPE GSPKPVTQNI SAEAWGRADC GITSASYQQG VLS                    283

SEQ ID NO: 245          moltype = DNA  length = 849
FEATURE                 Location/Qualifiers
misc_feature            1..849
                        note = KRAS TCR beta
source                  1..849
                        mol_type = other DNA
                        organism = synthetic construct
SEQUENCE: 245
atgtctaaca ctgccttccc tgaccccgcc tggaacacca ccctgctatc ttgggttgct  60
ctctttctcc tgggaacaag ttcagcaaat tctggggttg tccagtctcc aagatacata  120
atcaaaggaa agggagaaag gtccattcta aaatgtattc ccatctctgg acatctctct  180
gtggcctggt atcaacagac tcaggggcag gaactaaagt tcttcattca gcattatgat  240
aaaatggaga gagataaagg aaacctgccc agcagattct cagtccaaca gtttgatgac  300
tatcactctg agatgaacat gagtgccttg gagctagagg actctgccgt gtacttctgt  360
gccagctctc tcacagatcc gctagactcc gactacacct tcggctcagg gaccaggctt  420
ttggtaatag aggatctgag aaatgtgact ccacccaagg tctccttgtt tgagccatca  480
aaagcagaga ttgcaaacaa acaaaaggct accctcgtgt gcttggccag gggcttcttc  540
cctgaccacg tggagctgag ctggtgggtg aatggcaagg aggtccacag tggggtctgc  600
acggaccctc aggcctacaa ggagagcaat tatagctact gcctgagcag ccgcctgagg  660
gtctctgcta ccttctggca caatcctcgc aaccacttcc gctgccaagt gcagttccat  720
gggctttcag aggaggacaa gtggccagag ggctcaccca aacctgtcac acagaacatc  780
agtgcagagg cctggggccg agcagactgt gggattacct cagcatccta tcaacaaggg  840
gtcttgtct                                                          849

SEQ ID NO: 246          moltype = AA  length = 248
FEATURE                 Location/Qualifiers
REGION                  1..248
                        note = KRAS TCRa
source                  1..248
                        mol_type = protein
                        organism = synthetic construct
SEQUENCE: 246
MKTVTGPLFL CFWLQLNCVS RGEQVEQRPP HLSVREGDSA VITCTYTDPN SYYFFWYKQE  60
PGASLQLLMK VFSSTEINEG QGFTVLLNKK DKRLSLNLTA AHPGDSAAYF CAVSGGTNSA  120
GNKLTFGIGT RVLVRPDIQN PEPAVYQLKD PRSQDSTLCL FTDFDSQINV PKTMESGTFI  180
TDKCVLDMKA MDSKSNGAIA WSNQTSFTCQ DIFKETNATY PSSDVPCDAT LTEKSFETDM  240
NLNFQNLS                                                           248

SEQ ID NO: 247          moltype = DNA  length = 744
FEATURE                 Location/Qualifiers
```

```
misc_feature          1..744
                      note = KRAS TCRa
source                1..744
                      mol_type = other DNA
                      organism = synthetic construct
SEQUENCE: 247
atgaagacgg tgactggacc tttgttcctg tgcttctggc tgcagctgaa ctgtgtgagc  60
agaggcgagc aggtggagca gcgccctcct cacctgagtg tccgggaggg agacagtgcc  120
gttatcacct gcacctacac agaccctaac agttattact tcttctggta caagcaagag  180
ccgggggcaa gtcttcagtt gcttatgaag gttttctcaa gtacggaaat aaacgaagga  240
caaggattca ctgtcctact gaacaagaaa gacaaacgac tctctctgaa cctcacagct  300
gcccatcctg ggactcagc cgcgtacttc tgcgcagtca gtggagggac taacagtgca  360
gggaacaagc taacttttgg aattggaacc agggtgctgg tcaggccaga catccagaac  420
ccagaacctg ctgtgtacca gttaaaagat cctcggtctc aggacagcac cctctgcctg  480
ttcaccgact ttgactccca aatcaatgtg ccgaaaacca tggaatctgg aacgttcatc  540
actgacaaat gtgtgctgga catgaaagct atggattcca agagcaatgg ggccattgcc  600
tggagcaacc agacaagctt cacctgccaa gatatcttca aagagaccaa cgccacctac  660
cccagttcag acgttccctg tgatgccacg ttgaccgaga aaagctttga aacagatatg  720
aacctgaact ttcaaaacct gtct                                         744

SEQ ID NO: 248        moltype = AA  length = 272
FEATURE               Location/Qualifiers
REGION                1..272
                      note = KRAS TCRb
source                1..272
                      mol_type = protein
                      organism = synthetic construct
SEQUENCE: 248
MGCRLLSCVA FCLLGIGPLE TAVFQTPNYH VTQVGNEVSF NCKQTLGHDT MYWYKQDSKK  60
LLKIMFSYNN KQLIVNETVP RRFSPQSSDK AHLNLRIKSV EPEDSAVYLC ASSRDWGPAE  120
QFFGPGTRLT VLEDLRNVTP PKVSLFEPSK AEIANKQKAT LVCLARGFFP DHVELSWWVN  180
GKEVHSGVCT DPQAYKESNY SYCLSSRLRV SATFWHNPRN HFRCQVQFHG LSEEDKWPEG  240
SPKPVTQNIS AEAWGRADCG ITSASYHQGV LS                                272

SEQ ID NO: 249        moltype = DNA  length = 816
FEATURE               Location/Qualifiers
misc_feature          1..816
                      note = KRAS TCRb
source                1..816
                      mol_type = other DNA
                      organism = synthetic construct
SEQUENCE: 249
atgggctgta ggctcctaag ctgtgtggcc ttctgcctct tgggaatagg ccctttggag  60
acagctgttt tccagactcc aaactatcat gtcacacagg tgggaaatga agtgtctttc  120
aattgtaagc aaactctggg ccacgatact atgtattggt acaagcaaga ctctaagaaa  180
ttgctgaaga ttatgtttag ctacaataat aagcaactca ttgtaaacga aacagttcca  240
aggcgcttct cacctcagtc ttcagataaa gctcatttga atcttcgaat caagtctgta  300
gagccggagg actctgctgt gtatctctgt gccagcagtc gggactgggg gcctgctgag  360
cagttcttcg gaccagggac acgactcacc gtcctagagg atctgagaaa tgtgactcca  420
cccaaggtct ccttgtttga gccatcaaaa gcagagattg caaacaaaca aaaggctacc  480
ctcgtgtgct tggccagggg cttcttccct gaccacgtgg agctgagctg gtgggtgaat  540
ggcaaggagg tccacagtgg ggtctgcacg gaccctcagg cctacaagga gagcaattat  600
agctactgcc tgagcagccg cctgagggtc tctgctacct tctggcacaa tcctcgaaac  660
cacttccgct gccaagtgca gttccatggg ctttcagagg aggacaagtg gccagagggc  720
tcacccaaac ctgtcacaca gaacatcagt gcagaggcct ggggccgagc agactgtgga  780
atcacttcag catcctatca tcagggggtt ctgtct                            816

SEQ ID NO: 250        moltype = AA  length = 272
FEATURE               Location/Qualifiers
REGION                1..272
                      note = KRAS TCRb
source                1..272
                      mol_type = protein
                      organism = synthetic construct
SEQUENCE: 250
MGCRLLSCVA FCLLGIGPLE TAVFQTPNYH VTQVGNEVSF NCKQTLGHDT MYWYKQDSKK  60
LLKIMFSYNN KQLIVNETVP RRFSPQSSDK AHLNLRIKSV EPEDSAVYLC ASSRDWGPAE  120
QFFGPGTRLT VLEDLRNVTP PKVSLFEPSK AEIANKQKAT LVCLARGFFP DHVELSWWVN  180
GKEVHSGVCT DPQAYKESNY SYCLSSRLRV SATFWHNPRN HFRCQVQFHG LSEEDKWPEG  240
SPKPVTQNIS AEAWGRADCG ITSASYHQGV LS                                272

SEQ ID NO: 251        moltype = DNA  length = 816
FEATURE               Location/Qualifiers
misc_feature          1..816
                      note = KRAS TCRb
source                1..816
                      mol_type = other DNA
                      organism = synthetic construct
SEQUENCE: 251
```

```
atgggctgta ggctcctaag ctgtgtggcc ttctgcctct tgggaatagg ccctttggag  60
acagctgttt tccagactcc aaactatcat gtcacacagg tgggaaatga agtgtctttc  120
aattgtaagc aaactctggg ccacgatact atgtattggt acaagcaaga ctctaagaaa  180
ttgctgaaga ttatgtttag ctacaataat aagcaactca ttgtaaacga aacagttcca  240
aggcgcttct cacctcagtc ttcagataaa gctcatttga atcttcgaat caagtctgta  300
gagccggagg actctgctgt gtatctctgt gccagcagtc gggactgggg gcctgctgag  360
cagttcttcg gaccagggac acgactcacc gtcctagagg atctgagaaa tgtgactcca  420
cccaaggtct ccttgtttga gccatcaaaa gcagagattg caaacaaaca aaaggctacc  480
ctcgtgtgct tggccagggg cttcttccct gaccacgtgg agctgagctg gtgggtgaat  540
ggcaaggagg tccacagtgg ggtctgcacg gaccctcagg cctacaagga gagcaattat  600
agctactgcc tgagcagccg cctgagggtc tctgctacct tctggcacaa tcctcgaaac  660
cacttccgct gccaagtgca gttccatggg ctttcagagg aggacaagtg gccagagggc  720
tcacccaaac ctgtcacaca gaacatcagt gcagaggcct ggggccgagc agactgtgga  780
atcacttcag catcctatca tcagggggtt ctgtct                           816

SEQ ID NO: 252          moltype = AA  length = 244
FEATURE                 Location/Qualifiers
REGION                  1..244
                        note = TCRa control
source                  1..244
                        mol_type = protein
                        organism = synthetic construct
SEQUENCE: 252
MQRNLGAVLG ILWVQICWVR GDQVEQSPSA LSLHEGTDSA LRCNFTTTMR SVQWFRQNSR  60
GSLISLFYLA SGTKENGRLK SAFDSKERRY STLHIRDAQL EDSGTYFCAA DSSNTGYQNF  120
YFGKGTSLTV IPNIQNPEPA VYQLKDPRSQ DSTLCLFTDF DSQINVPKTM ESGTFITDKC  180
VLDMKAMDSK SNGAIAWSNQ TSFTCQDIFK ETNATYPSSD VPCDATLTEK SFETDMNLNF  240
QNLS                                                              244

SEQ ID NO: 253          moltype = DNA  length = 732
FEATURE                 Location/Qualifiers
misc_feature            1..732
                        note = TCRa control
source                  1..732
                        mol_type = other DNA
                        organism = synthetic construct
SEQUENCE: 253
atgcagagga acctgggagc tgtgctgggg attctgtggg tgcagatttg ctgggtgaga  60
ggggatcagg tggagcagag tccttcagcc ctgagcctcc acgagggaac cgattctgct  120
ctgagatgca attttacgac caccatgagg agtgtgcagt ggttccgaca gaattccagg  180
ggcagcctca tcagtttgtt ctacttggct tcaggaacaa aggagaatgg gaggctaaag  240
tcagcatttg attctaagga gcggcgctac agcaccctgc acatcaggga tgcccagctg  300
gaggactcag gcacttactt ctgtgctgct gactcttcga acacgggtta ccagaacttc  360
tattttggga aaggaacaag tttgactgtc attccaaaca tccagaaccc agaacctgct  420
gtgtaccagt taaaagatcc tcggtctcag gacagcaccc tctgcctgtt caccgacttt  480
gactcccaaa tcaatgtgcc gaaaaccatg gaatctggaa cgttcatcac tgacaaatgt  540
gtgctggaca tgaaagctat ggattccaag agcaatgggg ccattgcctg gagcaaccag  600
acaagcttca cctgccaaga tatcttcaaa gagaccaacg ccacctaccc cagttcagac  660
gttccctgtg atgccacgtt gaccgagaaa agctttgaaa cagatatgaa cctgaacttt  720
caaaacctgt ct                                                     732

SEQ ID NO: 254          moltype = AA  length = 248
FEATURE                 Location/Qualifiers
REGION                  1..248
                        note = TCRa control
source                  1..248
                        mol_type = protein
                        organism = synthetic construct
SEQUENCE: 254
MKTVTGPLFL CFWLQLNCVS RGEQVEQRPP HLSVREGDSA VITCTYTDPN SYYFFWYKQE  60
PGASLQLLMK VFSSTEINEG QGFTVLLNKK DKRLSLNLTA AHPGDSAAYF CAVSGGTNSA  120
GNKLTFGIGT RVLVRPDIQN PEPAVYQLKD PRSQDSTLCL FTDFDSQINV PKTMESGTFI  180
TDKCVLDMKA MDSKSNGAIA WSNQTSFTCQ DIFKETNATY PSSDVPCDAT LTEKSFETDM  240
NLNFQNLS                                                          248

SEQ ID NO: 255          moltype = DNA  length = 744
FEATURE                 Location/Qualifiers
misc_feature            1..744
                        note = TCRa control
source                  1..744
                        mol_type = other DNA
                        organism = synthetic construct
SEQUENCE: 255
atgaagacgg tgactggacc tttgttcctg tgcttctggc tgcagctgaa ctgtgtgagc  60
agaggcgagc aggtggagca gcgccctcct cacctgagtg tccgggaggg agacagtgcc  120
gttatcacct gcacctacac agaccctaac agttattact tcttctggta caagcaagag  180
ccgggggcaa gtcttcagtt gcttatgaag gttttctcaa gtacggaaat aaacgaagga  240
caaggattca ctgtcctact gaacaagaaa gacaaacgac tctctctgaa cctcacagct  300
gcccatcctg gggactcagc cgcgtacttc tgcgcagtca gtggagggac taacagtgca  360
```

```
gggaacaagc taacttttgg aattggaacc agggtgctgg tcaggccaga catccagaac  420
ccagaacctg ctgtgtacca gttaaaagat cctcggtctc aggacagcac cctctgcctg  480
ttcaccgact ttgactccca aatcaatgtg ccgaaaacca tggaatctgg aacgttcatc  540
actgacaaat gtgtgctgga catgaaagct atggattcca agagcaatgg ggccattgcc  600
tggagcaacc agacaagctt cacctgccaa gatatcttca aagagaccaa cgccacctac  660
cccagttcag acgttccctg tgatgccacg ttgaccgaga aaagctttga aacagatatg  720
aacctgaact ttcaaaacct gtct                                          744

SEQ ID NO: 256          moltype = AA  length = 9
FEATURE                 Location/Qualifiers
REGION                  1..9
                        note = mH-Y-2Db peptide
source                  1..9
                        mol_type = protein
                        organism = synthetic construct
SEQUENCE: 256
KCSRNRQYL                                                           9

SEQ ID NO: 257          moltype = AA  length = 614
FEATURE                 Location/Qualifiers
REGION                  1..614
                        note = H-Y TCR alpha and beta
source                  1..614
                        mol_type = protein
                        organism = synthetic construct
SEQUENCE: 257
MFPVTILLLS AFFSLRGNSA QSVDQPDAHV TLSEGASLEL RCSYSYSAAP YLFWYVQYPG  60
QSLQFLLKYI TGDTVVKGTK GFEAEFRKSN SSFNLKKSPA HWSDSAKYFC ALEGQDQGGS  120
AKLIFGEGTK LTVSSPDIQN PEPAVYQLKD PRSQDSTLCL FTDFDSQINV PKTMESGTFI  180
TDKTVLDMKA MDSKSNGAIA WSNQTSFTCQ DIFKETNATY PSSDVPCDAT LTEKSFETDM  240
NLNFQNLSVM GLRILLLKVA GFNLLMTLRL WSSRAKRSGS GATNFSLLKQ AGDVEENPGP  300
MSNTAFPDPA WNTTLLSWVA LFLLGTKHME AAVTQSPRNK VAVTGGKVTL SCNQTNNHNN  360
MYWYRQDTGH GLRLIHYSYG AGSTEKGDIP DGYKASRPSQ ENFSLILELA TPSQTSVYFC  420
ASGDNSAETL YFGPGTRLTV LEDLRNVTPP KVSLFEPSKA EIANKQKATL VCLARGFFPD  480
HVELSWWVNG KEVHSGVSTD PQAYKESNYS YCLSSRLRVS ATFWHNPRNH FRCQVQFHGL  540
SEEDKWPEGS PKPVTQNISA EAWGRADCGI TSASYHQGVL SATILYEILL GKATLYAVLV  600
SGLVLMAMVK KKNS                                                     614

SEQ ID NO: 258          moltype = DNA  length = 1845
FEATURE                 Location/Qualifiers
misc_feature            1..1845
                        note = H-Y TCR alpha and beta
source                  1..1845
                        mol_type = other DNA
                        organism = synthetic construct
SEQUENCE: 258
atgttccccg ttaccatatt gctcctgagt gctttcttca gtttgcgagg gaactctgcc  60
caatctgtcg atcagccaga tgcacacgtt accctttccg agggtgcgtc acttgaactg  120
aggtgttcct atagctactc agcagcccct tatctgtttt ggtacgtaca atacccaggg  180
cagagtctcc aatttctcct taaatatata accggggaca ctgtagtgaa ggggactaaa  240
ggttttgaag cagagtttag gaagagcaac agctccttca accttaagaa gtcacccgca  300
cactggtcag actccgcgaa atacttctgt gctctggaag ggcaagacca gggtggaagt  360
gccaaattga tatttggtga gggtactaaa ttgactgtta gctcaccaga catccagaac  420
ccagaacctg ctgtgtacca gttaaaagat cctcggtctc aggacagcac cctctgcctg  480
ttcaccgact ttgactccca aatcaatgtg ccgaaaacca tggaatctgg aacgttcatc  540
actgacaaaa ctgtgctgga catgaaagct atggattcca agagcaatgg ggccattgcc  600
tggagcaacc agacaagctt cacctgccaa gatatcttca aagagaccaa cgccacctac  660
cccagttcag acgttccctg tgatgccacg ttgaccgaga aaagctttga aacagatatg  720
aacctaaact ttcaaaacct gtcagttatg ggactccgaa tcctcctgct gaaagtagcg  780
ggatttaacc tgctcatgac gctgaggctg tggtccagtc gggccaagcg gtccggatcc  840
ggagccacca acttcagcct gctgaagcag gccggcgacg tggaggagaa ccccggcccc  900
atgtctaata ctgcatttcc agatccggcc tggaatacta cactccttag ttgggttgcc  960
ctcttcctcc ttggcacgaa gcacatggaa gccgccgtca cccagagtcc gagaaacaaa  1020
gtagcggtca ccggcggtaa ggtaacattg agttgtaacc aaacgaacaa ccataacaat  1080
atgtactggt atagacaaga cacaggccat ggcttgcgcc tgattcacta cagctatgga  1140
gcggggagta cggagaaggg tgatattccc gatggctata aagcctctcg gcctagccag  1200
gagaatttta gtttgatcct ggagctcgca acccccagtc agactagcgt ctacttttgt  1260
gcctcaggcg acaatagtgc ggaaaccctt tacttcggcc ctgggacaag acttacagtt  1320
ctagaggatc tgagaaatgt gactccaccc aaggtctcct tgtttgagcc atcaaaagca  1380
gagattgcaa acaaacaaaa ggctaccctc gtgtgcttgg ccaggggctt cttccctgac  1440
cacgtggagc tgagctggtg ggtgaatggc aaggaggtcc acagtggggt cagcacggac  1500
cctcaggcct acaaggagag caattatagc tactgcctga gcagccgcct gagggtctct  1560
gctaccttct ggcacaatcc tcgaaaccac ttccgctgcc aagtgcagtt ccatgggctt  1620
tcagaggagg acaagtggcc agagggctca cccaaacctg tcacacagaa catcagtgca  1680
gaggcctggg gccgagcaga ctgtggaatc acttcagcat cctatcatca gggggttctg  1740
tctgcaacca tcctctatga gatcctactg ggaaggccaa ccctatatgc tgtgctggtc  1800
agtggcctgg tgctgatggc catggtcaag aaaaaaaatt cctag                   1845

SEQ ID NO: 259          moltype = AA  length = 619
```

```
FEATURE                 Location/Qualifiers
REGION                  1..619
                        note = H-Y TCR alpha and beta
source                  1..619
                        mol_type = protein
                        organism = synthetic construct
SEQUENCE: 259
MFPVTILLLS AFFSLRGNSA QSVDQPDAHV TLSEGASLEL RCSYSYSAAP YLFWYVQYPG  60
QSLQFLLKYI TGDTVVKGTK GFEAEFRKSN SSFNLKKSPA HWSDSAKYFC ALEGQDQGGS  120
AKLIFGEGTK LTVSSPYIQN PDPAVYQLRD SKSSDKSVCL FTDFDSQTNV SQSKDSDVYI  180
TDKCVLDMRS MDFKSNSAVA WSNKSDFACA NAFNNSIIPE DTFFPSPESS CDVKLVEKSF  240
ETDTNLNFQN LSVIGFRILL LKVAGFNLLM TLRLWSSGSG ATNFSLLKQA GDVEENPGPM  300
SNTAFPDPAW NTTLLSWVAL FLLGTKHMEA AVTQSPRNKV AVTGGKVTLS CNQTNNHNNM  360
YWYRQDTGHG LRLIHYSYGA GSTEKGDIPD GYKASRPSQE NFSLILELAT PSQTSVYFCA  420
SGDNSAETLY FGPGTRLTVL EDLKNVFPPE VAVFEPSEAE ISHTQKATLV CLATGFYPDH  480
VELSWWVNGK EVHSGVCTDP QPLKEQPALN DSRYCLSSRL RVSATFWQNP RNHFRCQVQF  540
YGLSENDEWT QDRAKPVTQI VSAEAWGRAD CGFTSESYQQ GVLSATILYE ILLGKATLYA  600
VLVSALVLMA MVKRKDSRG                                               619

SEQ ID NO: 260          moltype = DNA  length = 1860
FEATURE                 Location/Qualifiers
misc_feature            1..1860
                        note = H-Y TCR alpha and beta
source                  1..1860
                        mol_type = other DNA
                        organism = synthetic construct
SEQUENCE: 260
atgttccccg ttaccatatt gctcctgagt gctttcttca gtttgcgagg gaactctgcc  60
caatctgtcg atcagccaga tgcacacgtt accctttccg agggtgcgtc acttgaactg  120
aggtgttcct atagctactc agcagcccct tatctgtttt ggtacgtaca atacccaggg  180
cagagtctcc aatttctcct taaatatata accggggaca ctgtagtgaa ggggactaaa  240
ggttttgaag cagagtttag gaagagcaac agctccttca accttaagaa gtcacccgca  300
cactggtcag actccgcgaa atacttctgt gctctggaag ggcaagacca gggtggaagt  360
gccaaattga tatttggtga gggtactaaa ttgactgtta gctcaccgta tatccagaac  420
cctgaccctg ccgtgtacca gctgagagac tctaaatcca gtgacaagtc tgtctgccta  480
ttcaccgatt ttgattctca aacaaatgtg tcacaaagta aggattctga tgtgtatatc  540
acagacaaat gtgtgctaga catgaggtct atggacttca agagcaacag tgctgtggcc  600
tggagcaaca aatctgactt tgcatgtgca aacgccttca acaacagcat tattccagaa  660
gacaccttct tccccagccc agaaagttcc tgtgatgtca agctggtcga gaaaagcttt  720
gaaacagata cgaacctaaa ctttcaaaac ctgtcagtga ttgggttccg aatcctcctc  780
ctgaaagtgg ccgggtttaa tctgctcatg acgctgcggc tgtggtccag cggatccgga  840
gccaccaact tcagcctgct gaagcaggcc ggcgacgtgg aggagaaccc cggccccatg  900
tctaatactg catttccaga tccggcctgg aatactacac tccttagttg ggttgccctc  960
ttcctccttg gcacgaagca catggaagcc gccgtcaccc agagtccgag aaacaaagta  1020
gcggtcaccg gcggtaaggt aacattgagt tgtaaccaaa cgaacaacca taacaatatg  1080
tactggtata gacaagacac aggccatggc ttgcgcctga ttcactacag ctatggagcg  1140
gggagtacgg agaagggtga tattcccgat ggctataaag cctctcggcc tagccaggag  1200
aattttagtt tgatcctgga gctcgcaacc cccagtcaga ctagcgtcta cttttgtgcc  1260
tcaggcgaca atagtgcgga aaccctttac ttcggccctg ggacaagact tacagttctg  1320
gaggacctga aaaacgtgtt cccacccgag gtcgctgtgt ttgagccatc agaagcagag  1380
atctcccaca cccaaaaggc cacactggtg tgcctggcca caggcttcta ccccgaccac  1440
gtggagctga gctggtgggt gaatgggaag gaggtgcaca gtggggtctg cacagacccg  1500
cagcccctca aggagcagcc cgccctcaat gactccagat actgcctgag cagccgcctg  1560
agggtgtcgg ccaccttctg gcagaacccc cgcaaccact tccgctgtca agtccagttc  1620
tacgggctct cggagaatga cgagtggacc caggataggg ccaaacctgt cacccagatc  1680
gtcagcgccg aggcctgggg tagagcagac tgtggcttca cctccgagtc ttaccagcaa  1740
ggggtcctgt ctgccaccat cctctatgag atcttgctag ggaaggccac cttgtatgcc  1800
gtgctggtca gtgccctcgt gctgatggcc atggtcaaga gaaaggattc cagaggctag  1860

SEQ ID NO: 261          moltype = AA  length = 614
FEATURE                 Location/Qualifiers
REGION                  1..614
                        note = H-Y TCR alpha and beta
source                  1..614
                        mol_type = protein
                        organism = synthetic construct
SEQUENCE: 261
MFPVTILLLS AFFSLRGNSA QSVDQPDAHV TLSEGASLEL RCSYSYSAAP YLFWYVQYPG  60
QSLQFLLKYI TGDTVVKGTK GFEAEFRKSN SSFNLKKSPA HWSDSAKYFC ALEGQDQGGS  120
AKLIFGEGTK LTVSSPDIQN PEPAVYQLKD PRSQDSTLCL FTDFDSQINV PKTMESGTFI  180
TDKTVLDMKA MDSKSNGAIA WSNQTSFTCQ DIFKETNATY PSSDVPCDAT LTEKSFETDM  240
NLNFQNLSVM GLRILLLKVA GFNLLMTLRL WSSRAKRSGS GATNFSLLKQ AGDVEENPGP  300
MSNTAFPDPA WNTTLLSWVA LFLLGTKHME AAVTQSPRNK VAVTGGKVTL SCNQTNNHNN  360
MYWYRQDTGH GLRLIHYSYG AGSTEKGDIP DGYKASRPSQ ENFSLILELA TPSQTSVYFC  420
ASGDNSAETL YFGPGTRLLV LEDLRNVTPP KVSLFEPSKA EIANKQKATL VCLARGFFPD  480
HVELSWWVNG KEVHSGVSTD PQAYKESNYS YCLSSRLRVS ATFWHNPRNH FRCQVQFHGL  540
SEEDKWPEGS PKPVTQNISA EAWGRADCGI TSASYHQGVL SATILYEILL GKATLYAVLV  600
SGLVLMAMVK KKNS                                                    614
```

```
SEQ ID NO: 262          moltype = DNA  length = 1845
FEATURE                 Location/Qualifiers
misc_feature            1..1845
                        note = H-Y TCR alpha and beta
source                  1..1845
                        mol_type = other DNA
                        organism = synthetic construct
SEQUENCE: 262
atgttccccg ttaccatatt gctcctgagt gctttcttca gtttgcgagg gaactctgcc  60
caatctgtcg atcagccaga tgcacacgtt accctttccg agggtgcgtc acttgaactg  120
aggtgttcct atagctactc agcagcccct tatctgtttt ggtacgtaca atacccaggg  180
cagagtctcc aatttctcct taaatatata accggggaca ctgtagtgaa ggggactaaa  240
ggttttgaag cagagtttag gaagagcaac agctccttca accttaagaa gtcacccgca  300
cactggtcag actccgcgaa atacttctgt gctctggaag ggcaagacca gggtggaagt  360
gccaaattga tatttggtga gggtactaaa ttgactgtta gctcaccaga catccagaac  420
ccagaacctg ctgtgtacca gttaaaagat cctcggtctc aggacagcac cctctgcctg  480
ttcaccgact ttgactccca aatcaatgtg ccgaaaacca tggaatctgg aacgttcatc  540
actgacaaaa ctgtgctgga catgaaagct atggattcca agagcaatgg ggccattgcc  600
tggagcaacc agacaagctt cacctgccaa gatatcttca aagagaccaa cgccacctac  660
cccagttcag acgttccctg tgatgccacg ttgaccgaga aaagctttga aacagatatg  720
aacctaaact ttcaaaacct gtcagttatg ggactccgaa tcctcctgct gaaagtagcg  780
ggatttaacc tgctcatgac gctgaggctg tggtccagtc gggccaagcg gtccggatcc  840
ggagccacca acttcagcct gctgaagcag gccggcgacg tggaggagaa ccccggcccc  900
atgtctaata ctgcatttcc agatccggcc tggaatacta cactccttag ttgggttgcc  960
ctcttcctcc ttggcacgaa gcacatggaa gccgccgtca cccagagtcc gagaaacaaa  1020
gtagcggtca ccggcggtaa ggtaacattg agttgtaacc aaacgaacaa ccataacaat  1080
atgtactggt atagacaaga cacaggccat ggcttgcgcc tgattcacta cagctatgga  1140
gcggggagta cggagaaggg tgatattccc gatggctata aagcctctcg gcctagccag  1200
gagaatttta gtttgatcct ggagctcgca acccccagtc agactagcgt ctacttttgt  1260
gcctcaggcg acaatagtgc ggaaaccctt tacttcggcc ctgggacaag acttttggtt  1320
ctagaggatc tgagaaatgt gactccaccc aaggtctcct tgtttgagcc atcaaaagca  1380
gagattgcaa acaaacaaaa ggctaccctc gtgtgcttgg ccaggggctt cttccctgac  1440
cacgtggagc tgagctggtg ggtgaatggc aaggaggtcc acagtggggt cagcacggac  1500
cctcaggcct acaaggagag caattatagc tactgcctga gcagccgcct gagggtctct  1560
gctaccttct ggcacaatcc tcgaaaccac ttccgctgcc aagtgcagtt ccatgggctt  1620
tcagaggagg acaagtggcc agagggctca cccaaacctg tcacacagaa catcagtgca  1680
gaggcctggg gccgagcaga ctgtggaatc acttcagcat cctatcatca gggggttctg  1740
tctgcaacca tcctctatga gatcctactg ggaaggccca ccctatatgc tgtgctggtc  1800
agtggcctgg tgctgatggc catggtcaag aaaaaaaatt cctag                 1845

SEQ ID NO: 263          moltype = AA  length = 619
FEATURE                 Location/Qualifiers
REGION                  1..619
                        note = H-Y TCR alpha and beta
source                  1..619
                        mol_type = protein
                        organism = synthetic construct
SEQUENCE: 263
MFPVTILLLS AFFSLRGNSA QSVDQPDAHV TLSEGASLEL RCSYSYSAAP YLFWYVQYPG  60
QSLQFLLKYI TGDTVVKGTK GFEAEFRKSN SSFNLKKSPA HWSDSAKYFC ALEGQDQGGS  120
AKLIFGEGTK LTVSSPYIQN PDPAVYQLRD SKSSDKSVCL FTDFDSQTNV SQSKDSDVYI  180
TDKCVLDMRS MDFKSNSAVA WSNKSDFACA NAFNNSIIPE DTFFPSPESS CDVKLVEKSF  240
ETDTNLNFQN LSVIGFRILL LKVAGFNLLM TLRLWSSGSG ATNFSLLKQA GDVEENPGPM  300
SNTAFPDPAW NTTLLSWVAL FLLGTKHMEA AVTQSPRNKV AVTGGKVTLS CNQTNNHNNM  360
YWYRQDTGHG LRLIHYSYGA GSTEKGDIPD GYKASRPSQE NFSLILELAT PSQTSVYFCA  420
SGDNSAETLY FGPGTRLLVL EDLKNVFPPE VAVFEPSEAE ISHTQKATLV CLATGFYPDH  480
VELSWWVNGK EVHSGVCTDP QPLKEQPALN DSRYCLSSRL RVSATFWQNP RNHFRCQVQF  540
YGLSENDEWT QDRAKPVTQI VSAEAWGRAD CGFTSESYQQ GVLSATILYE ILLGKATLYA  600
VLVSALVLMA MVKRKDSRG                                              619

SEQ ID NO: 264          moltype = DNA  length = 1860
FEATURE                 Location/Qualifiers
misc_feature            1..1860
                        note = H-Y TCR alpha and beta
source                  1..1860
                        mol_type = other DNA
                        organism = synthetic construct
SEQUENCE: 264
atgttccccg ttaccatatt gctcctgagt gctttcttca gtttgcgagg gaactctgcc  60
caatctgtcg atcagccaga tgcacacgtt accctttccg agggtgcgtc acttgaactg  120
aggtgttcct atagctactc agcagcccct tatctgtttt ggtacgtaca atacccaggg  180
cagagtctcc aatttctcct taaatatata accggggaca ctgtagtgaa ggggactaaa  240
ggttttgaag cagagtttag gaagagcaac agctccttca accttaagaa gtcacccgca  300
cactggtcag actccgcgaa atacttctgt gctctggaag ggcaagacca gggtggaagt  360
gccaaattga tatttggtga gggtactaaa ttgactgtta gctcaccgta tatccagaac  420
cctgaccctg ccgtgtacca gctgagagac tctaaatcca gtgacaagtc tgtctgccta  480
ttcaccgatt ttgattctca aacaaatgtg tcacaaagta aggattctga tgtgtatatc  540
acagacaaat gtgtgctaga catgaggtct atggacttca agagcaacag tgctgtggcc  600
tggagcaaca aatctgactt tgcatgtgca aacgccttca acaacagcat tattccagaa  660
```

```
gacaccttct tccccagccc agaaagttcc tgtgatgtca agctggtcga gaaaagcttt  720
gaaacagata cgaacctaaa ctttcaaaac ctgtcagtga ttgggttccg aatcctcctc  780
ctgaaagtgg ccgggtttaa tctgctcatg acgctgcggc tgtggtccag cggatccgga  840
gccaccaact tcagcctgct gaagcaggcc ggcgacgtgg aggagaaccc cggccccatg  900
tctaatactg catttccaga tccggcctgg aatactacac tccttagttg ggttgccctc  960
ttcctccttg gcacgaagca catggaagcc gccgtcaccc agagtccgag aaacaaagta  1020
gcggtcaccg gcggtaaggt aacattgagt tgtaaccaaa cgaacaacca taacaatatg  1080
tactggtata gacaagacac aggccatggc ttgcgcctga ttcactacag ctatggagcg  1140
gggagtacgg agaagggtga tattcccgat ggctataaag cctctcggcc tagccaggag  1200
aattttagtt tgatcctgga gctcgcaacc cccagtcaga ctagcgtcta cttttgtgcc  1260
tcaggcgaca atagtgcgga aaccctttac ttcggccctg ggacaagact tttggttctg  1320
gaggacctga aaaacgtgtt cccacccgag gtcgctgtgt ttgagccatc agaagcagag  1380
atctcccaca cccaaaaggc cacactggtg tgcctggcca caggcttcta ccccgaccac  1440
gtggagctga gctggtgggt gaatgggaag gaggtgcaca gtggggtctg cacagacccg  1500
cagcccctca aggagcagcc cgccctcaat gactccagat actgcctgag cagccgcctg  1560
agggtgtcgg ccaccttctg gcagaacccc cgcaaccact tccgctgtca agtccagttc  1620
tacgggctct cggagaatga cgagtggacc caggataggg ccaaacctgt cacccagatc  1680
gtcagcgccg aggcctgggg tagagcagac tgtggcttca cctccgagtc ttaccagcaa  1740
ggggtcctgt ctgccaccat cctctatgag atcttgctag ggaaggccac cttgtatgcc  1800
gtgctggtca gtgccctcgt gctgatggcc atggtcaaga gaaaggattc cagaggctag  1860

SEQ ID NO: 265         moltype = AA  length = 9
FEATURE                Location/Qualifiers
REGION                 1..9
                       note = NY-ESO-1
source                 1..9
                       mol_type = protein
                       organism = synthetic construct
SEQUENCE: 265
SLLMWITQV                                                          9

SEQ ID NO: 266         moltype = AA  length = 9
FEATURE                Location/Qualifiers
REGION                 1..9
                       note = HA-1(R) peptide
source                 1..9
                       mol_type = protein
                       organism = synthetic construct
SEQUENCE: 266
VLRDDLLEA                                                          9

SEQ ID NO: 267         moltype = AA  length = 607
FEATURE                Location/Qualifiers
REGION                 1..607
                       note = NY-ESO-1 TCR alpha and beta
source                 1..607
                       mol_type = protein
                       organism = synthetic construct
SEQUENCE: 267
METLLGLLIL WLQLQWVSSK QEVTQIPAAL SVPEGENLVL NCSFTDSAIY NLQWFRQDPG  60
KGLTSLLLIQ SSQREQTSGR LNASLDKSSG RSTLYIAASQ PGDSATYLCA VRPLYGGSYI  120
PTFGRGTSLI VHPYIQNPDP AVYQLRDSKS SDKSVCLFTD FDSQTNVSQS KDSDVYITDK  180
CVLDMRSMDF KSNSAVAWSN KSDFACANAF NNSIIPEDTF FPSPESSCDV KLVEKSFETD  240
TNLNFQNLSV IGFRILLLKV AGFNLLMTLR LWSSGSGATN FSLLKQAGDV EENPGPMSIG  300
LLCCAALSLL WAGPVNAGVT QTPKFQVLKT GQSMTLQCAQ DMNHEYMSWY RQDPGMGLRL  360
IHYSVGAGIT DQGEVPNGYN VSRSTTEDFP LRLLSAAPSQ TSVYFCASSY VGNTGELFFG  420
EGSRLTVLED LKNVFPPEVA VFEPSEAEIS HTQKATLVCL ATGFYPDHVE LSWWVNGKEV  480
HSGVCTDPQP LKEQPALNDS RYCLSSRLRV SATFWQNPRN HFRCQVQFYG LSENDEWTQD  540
RAKPVTQIVS AEAWGRADCG FTSESYQQGV LSATILYEIL LGKATLYAVL VSALVLMAMV  600
KRKDSRG                                                            607

SEQ ID NO: 268         moltype = DNA  length = 1824
FEATURE                Location/Qualifiers
misc_feature           1..1824
                       note = NY-ESO-1 TCR alpha and beta
source                 1..1824
                       mol_type = other DNA
                       organism = synthetic construct
SEQUENCE: 268
atggagacac tcttgggcct gcttatcctt tggctgcagc tgcaatgggt gagcagcaaa  60
caggaggtga cgcagattcc tgcagctctg agtgtcccag aaggagaaaa cttggttctg  120
aactgcagtt tcactgatag cgctatttac aacctccagt ggtttaggca ggaccctggg  180
aaaggactca catctctgtt gcttattcag tcaagtcaga gagagcaaac aagtggaaga  240
cttaatgcct cgctggataa atcatcagga cgtagtactt tatacattgc agcttctcag  300
cctggtgact cagccaccta cctctgtgct gtgaggcccc tctacggagg aagctacata  360
cctacatttg gaagaggaac cagccttatt gttcatccgt atatccagaa ccctgaccct  420
gccgtgtacc agctgagaga ctctaaatcc agtgacaagt ctgtctgcct attcaccgat  480
tttgattctc aaacaaatgt gtcacaaagt aaggattctg atgtgtatat cacagacaaa  540
tgtgtgctag acatgaggtc tatggacttc aagagcaaca gtgctgtggc ctggagcaac  600
```

```
aaatctgact ttgcatgtgc aaacgccttc aacaacagca ttattccaga agacaccttc  660
ttccccagcc cagaaagttc ctgtgatgtc aagctggtcg agaaaagctt tgaaacagat  720
acgaacctaa actttcaaaa cctgtcagtg attgggttcc gaatcctcct cctgaaagtg  780
gccgggttta atctgctcat gacgctgcgg ctgtggtcca gcggatccgg agccaccaac  840
ttcagcctgc tgaagcaggc cggcgacgtg gaggagaacc ccggccccat gagcatcggc  900
ctcctgtgct gtgcagcctt gtctctcctg tgggcaggtc cagtgaatgc tggtgtcact  960
cagaccccaa aattccaggt cctgaagaca ggacagagca tgacactgca gtgtgcccag  1020
gatatgaacc atgaatacat gtcctggtat cgacaagacc caggcatggg gctgaggctg  1080
attcattact cagttggtgc tggtatcact gaccaaggag aagtccccaa tggctacaat  1140
gtctccagat caaccacaga ggatttcccg ctcaggctgc tgtcggctgc tccctcccag  1200
acatctgtgt acttctgtgc cagcagttac gtcgggaaca ccggggagct gtttttttgga  1260
gaaggctcta ggctgaccgt actggaggac ctgaaaaacg tgttcccacc cgaggtcgct  1320
gtgtttgagc catcagaagc agagatctcc cacacccaaa aggccacact ggtgtgcctg  1380
gccacaggct tctaccccga ccacgtggag ctgagctggt gggtgaatgg gaaggaggtg  1440
cacagtgggg tctgcacaga cccgcagccc ctcaaggagc agcccgccct caatgactcc  1500
agatactgcc tgagcagccg cctgagggtg tcggccacct tctggcagaa cccccgcaac  1560
cacttccgct gtcaagtcca gttctacggg ctctcggaga atgacgagtg gacccaggat  1620
agggccaaac ctgtcaccca gatcgtcagc gccgaggcct ggggtagagc agactgtggc  1680
ttcacctccg agtcttacca gcaaggggtc ctgtctgcca ccatcctcta tgagatcttg  1740
ctagggaagg ccaccttgta tgccgtgctg gtcagtgccc tcgtgctgat ggccatggtc  1800
aagagaaagg attccagagg ctag                                        1824
```

```
SEQ ID NO: 269          moltype = AA  length = 612
FEATURE                 Location/Qualifiers
REGION                  1..612
                        note = KRAS TCR
source                  1..612
                        mol_type = protein
                        organism = synthetic construct
SEQUENCE: 269
MQRNLGAVLG ILWVQICWVR GDQVEQSPSA LSLHEGTDSA LRCNFTTTMR SVQWFRQNSR  60
GSLISLFYLA SGTKENGRLK SAFDSKERRY STLHIRDAQL EDSGTYFCAA DSSNTGYQNF  120
YFGKGTSLTV IPNIQNPEPA VYQLKDPRSQ DSTLCLFTDF DSQINVPKTM ESGTFITDKT  180
VLDMKAMDSK SNGAIAWSNQ TSFTCQDIFK ETNATYPSSD VPCDATLTEK SFETDMNLNF  240
QNLSVMGLRI LLLKVAGFNL LMTLRLWSSR AKRSGSGATN FSLLKQAGDV EENPGPMSNT  300
AFPDPAWNTT LLSWVALFLL GTSSANSGVV QSPRYIIKGK GERSILKCIP ISGHLSVAWY  360
QQTQGQELKF FIQHYDKMER DKGNLPSRFS VQQFDDYHSE MNMSALELED SAVYFCASSL  420
TDPLDSDYTF GSGTRLLVIE DLRNVTPPKV SLFEPSKAEI ANKQKATLVC LARGFFPDHV  480
ELSWWVNGKE VHSGVSTDPQ AYKESNYSYC LSSRLRVSAT FWHNPRNHFR CQVQFHGLSE  540
EDKWPEGSPK PVTQNISAEA WGRADCGITS ASYQQGVLSA TILYEILLGK ATLYAVLVST  600
LVVMAMVKRK NS                                                     612
```

```
SEQ ID NO: 270          moltype = DNA  length = 1839
FEATURE                 Location/Qualifiers
misc_feature            1..1839
                        note = KRAS TCR
source                  1..1839
                        mol_type = other DNA
                        organism = synthetic construct
SEQUENCE: 270
atgcagagga acctgggagc tgtgctgggg attctgtggg tgcagatttg ctgggtgaga  60
ggggatcagg tggagcagag tccttcagcc ctgagcctcc acgagggaac cgattctgct  120
ctgagatgca attttacgac caccatgagg agtgtgcagt ggttccgaca gaattccagg  180
ggcagcctca tcagtttgtt ctacttggct tcaggaacaa aggagaatgg gaggctaaag  240
tcagcatttg attctaagga gcggcgctac agcaccctgc acatcaggga tgcccagctg  300
gaggactcag gcacttactt ctgtgctgct gactcttcga acacgggtta ccagaacttc  360
tattttggga aaggaacaag tttgactgtc attccaaaca tccagaaccc agaacctgct  420
gtgtaccagt taaaagatcc tcggtctcag gacagcaccc tctgcctgtt caccgacttt  480
gactcccaaa tcaatgtgcc gaaaaccatg gaatctggaa cgttcatcac tgacaaaact  540
gtgctggaca tgaaagctat ggattccaag agcaatgggg ccattgcctg gagcaaccag  600
acaagcttca cctgccaaga tatcttcaaa gagaccaacg ccacctaccc cagttcagac  660
gttccctgtg atgccacgtt gaccgagaaa agctttgaaa cagatatgaa cctgaacttt  720
caaaacctgt cagttatggg actccgaatc ctcctgctga aagtagcggg atttaacctg  780
ctcatgacgc tgaggctgtg gtccagtcgg gccaagcggt ccggatccgg agccaccaac  840
ttcagcctgc tgaagcaggc cggcgacgtg gaggagaacc ccggccccat gtctaacact  900
gccttccctg accccgcctg gaacaccacc ctgctatctt gggttgctct ctttctcctg  960
ggaacaagtt cagcaaattc tggggttgtc cagtctccaa gatacataat caaaggaaag  1020
ggagaaaggt ccattctaaa atgtattccc atctctggac atctctctgt ggcctggtat  1080
caacagactc aggggcagga actaaagttc ttcattcagc attatgataa aatggagaga  1140
gataaaggaa acctgcccag cagattctca gtccaacagt ttgatgacta tcactctgag  1200
atgaacatga gtgccttgga gctagaggac tctgccgtgt acttctgtgc cagctctctc  1260
acagatccgc tagactccga ctacaccttc ggctcaggga ccaggctttt ggtaatagag  1320
gatctgagaa atgtgactcc acccaaggtc tccttgtttg agccatcaaa agcagagatt  1380
gcaaacaaac aaaaggctac cctcgtgtgc ttggccaggg gcttcttccc tgaccacgtg  1440
gagctgagct ggtgggtgaa tggcaaggag gtccacagtg gggtcagcac ggaccctcag  1500
gcctacaagg agagcaatta tagctactgc ctgagcagcc gcctgagggt ctctgctacc  1560
ttctggcaca atcctcgcaa ccacttccgc tgccaagtgc agttccatgg gctttcagag  1620
gaggacaagt ggccagaggg ctcacccaaa cctgtcacac agaacatcag tgcagaggcc  1680
tggggccgag cagactgtgg gattacctca gcatcctatc aacaaggggt cttgtctgcc  1740
```

-continued

```
accatcctct atgagatcct gctagggaaa gccaccctgt atgctgtgct tgtcagtaca  1800
ctggtggtga tggctatggt caaaagaaag aattcatag                         1839

SEQ ID NO: 271         moltype = AA  length = 18
FEATURE                Location/Qualifiers
REGION                 1..18
                       note = T2A self cleaving peptide
source                 1..18
                       mol_type = protein
                       organism = synthetic construct
SEQUENCE: 271
EGRGSLLTCG DVEENPGP                                                18

SEQ ID NO: 272         moltype = AA  length = 20
FEATURE                Location/Qualifiers
REGION                 1..20
                       note = E2A self cleaving peptide
source                 1..20
                       mol_type = protein
                       organism = synthetic construct
SEQUENCE: 272
QCTNYALLKL AGDVESNPGP                                              20

SEQ ID NO: 273         moltype = AA  length = 22
FEATURE                Location/Qualifiers
REGION                 1..22
                       note = F2A self cleaving peptide
source                 1..22
                       mol_type = protein
                       organism = synthetic construct
SEQUENCE: 273
VKQTLNFDLL KLAGDVESNP GP                                           22

SEQ ID NO: 274         moltype =   length =
SEQUENCE: 274
000

SEQ ID NO: 275         moltype = AA  length = 242
FEATURE                Location/Qualifiers
REGION                 1..242
                       note = CD19 ScFv
source                 1..242
                       mol_type = protein
                       organism = synthetic construct
SEQUENCE: 275
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGGG GSGGGGSGGG  120
GSEVKLQESG PGLVAPSQSL SVTCTVSGVS LPDYGVSWIR QPPRKGLEWL GVIWGSETTY  180
YNSALKSRLT IIKDNSKSQV FLKMNSLQTD DTAIYYCAKH YYYGGSYAMD YWGQGTSVTV  240
SS                                                                 242

SEQ ID NO: 276         moltype = DNA  length = 726
FEATURE                Location/Qualifiers
misc_feature           1..726
                       note = CD19 ScFv
source                 1..726
                       mol_type = other DNA
                       organism = synthetic construct
SEQUENCE: 276
gacatccaga tgacacagac tacatcctcc ctgtctgcct ctctgggaga cagagtcacc  60
atcagttgca gggcaagtca ggacattagt aaatatttaa attggtatca gcagaaacca  120
gatggaactg ttaaactcct gatctaccat acatcaagat tacactcagg agtcccatca  180
aggttcagtg gcagtgggtc tggaacagat tattctctca ccattagcaa cctggagcaa  240
gaagatattg ccacttactt ttgccaacag ggtaatacgc ttccgtacac gttcggaggg  300
gggaccaagc tggagatcac aggtggcggt ggctcgggcg gtggtgggtc gggtggcggc  360
ggatctgagg tgaaactgca ggagtcagga cctggcctgg tggcgccctc acagagcctg  420
tccgtcacat gcactgtctc aggggtctca ttacccgact atggtgtaag ctggattcgc  480
cagcctccac gaaagggtct ggagtggctg ggagtaatat ggggtagtga aaccacatac  540
tataattcag ctctcaaatc cagactgacc atcatcaagg acaactccaa gagccaagtt  600
ttcttaaaaa tgaacagtct gcaaactgat gacacagcca tttactactg tgccaaacat  660
tattactacg gtggtagcta tgctatggac tactggggcc aaggaacctc agtcaccgtg  720
tcctca                                                             726

SEQ ID NO: 277         moltype = AA  length = 244
FEATURE                Location/Qualifiers
REGION                 1..244
                       note = CD19 ScFv
source                 1..244
                       mol_type = protein
```

```
                        organism = synthetic construct
SEQUENCE: 277
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGGG GSGGGGSGGG  120
GSGGEVKLQE SGPGLVAPSQ SLSVTCTVSG VSLPDYGVSW IRQPPRKGLE WLGVIWGSET  180
TYYNSALKSR LTIIKDNSKS QVFLKMNSLQ TDDTAIYYCA KHYYYGGSYA MDYWGQGTSV  240
TVSS                                                              244

SEQ ID NO: 278          moltype = DNA  length = 732
FEATURE                 Location/Qualifiers
misc_feature            1..732
                        note = CD19 ScFv
source                  1..732
                        mol_type = other DNA
                        organism = synthetic construct
SEQUENCE: 278
gacatccaga tgacacagac tacatcctcc ctgtctgcct ctctgggaga cagagtcacc  60
atcagttgca gggcaagtca ggacattagt aaatatttaa attggtatca gcagaaacca  120
gatggaactg ttaaactcct gatctaccat acatcaagat tacactcagg agtcccatca  180
aggttcagtg gcagtgggtc tggaacagat tattctctca ccattagcaa cctggagcaa  240
gaagatattg ccacttactt ttgccaacag ggtaatacgc ttccgtacac gttcggaggg  300
gggaccaagc tggagatcac aggcggaggt ggaagcggag ggggaggatc tggcggcgga  360
ggaagcggag gcgaggtgaa actgcaggag tcaggacctg gcctggtggc gccctcacag  420
agcctgtccg tcacatgcac tgtctcaggg gtctcattac ccgactatgg tgtaagctgg  480
attcgccagc ctccacgaaa gggtctggag tggctgggag taatatgggg tagtgaaacc  540
acatactata attcagctct caaatccaga ctgaccatca tcaaggacaa ctccaagagc  600
caagttttct taaaaatgaa cagtctgcaa actgatgaca cagccattta ctactgtgcc  660
aaacattatt actacggtgg tagctatgct atggactact ggggccaagg aacctcagtc  720
accgtgtcct ca                                                     732

SEQ ID NO: 279          moltype = AA  length = 509
FEATURE                 Location/Qualifiers
REGION                  1..509
                        note = CD19 CAR
source                  1..509
                        mol_type = protein
                        organism = synthetic construct
SEQUENCE: 279
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGGG GSGGGGSGGG  120
GSEVKLQESG PGLVAPSQSL SVTCTVSGVS LPDYGVSWIR QPPRKGLEWL GVIWGSETTY  180
YNSALKSRLT IIKDNSKSQV FLKMNSLQTD DTAIYYCAKH YYYGGSYAMD YWGQGTSVTV  240
SSTTTPAPRP PTPAPTIASQ PLSLRPEACR PAAGGAVHTR GLDFACDFWV LVVVGGVLAC  300
YSLLVTVAFI IFWVRSKRSR LLHSDYMNMT PRRPGPTRKH YQPYAPPRDF AAYRSKRGRK  360
KLLYIFKQPF MRPVQTTQEE DGCSCRFPEE EEGGCELRVK FSRSADAPAY KQGQNQLYNE  420
LNLGRREEYD VLDKRRGRDP EMGGKPRRKN PQEGLYNELQ KDKMAEAYSE IGMKGERRRG  480
KGHDGLYQGL STATKDTYDA LHMQALPPR                                   509

SEQ ID NO: 280          moltype = DNA  length = 1527
FEATURE                 Location/Qualifiers
misc_feature            1..1527
                        note = CD19 CAR
source                  1..1527
                        mol_type = other DNA
                        organism = synthetic construct
SEQUENCE: 280
gacatccaga tgacacagac tacatcctcc ctgtctgcct ctctgggaga cagagtcacc  60
atcagttgca gggcaagtca ggacattagt aaatatttaa attggtatca gcagaaacca  120
gatggaactg ttaaactcct gatctaccat acatcaagat tacactcagg agtcccatca  180
aggttcagtg gcagtgggtc tggaacagat tattctctca ccattagcaa cctggagcaa  240
gaagatattg ccacttactt ttgccaacag ggtaatacgc ttccgtacac gttcggaggg  300
gggaccaagc tggagatcac aggtggcggt ggctcgggcg gtggtgggtc gggtggcggc  360
ggatctgagg tgaaactgca ggagtcagga cctggcctgg tggcgccctc acagagcctg  420
tccgtcacat gcactgtctc aggggtctca ttacccgact atggtgtaag ctggattcgc  480
cagcctccac gaaagggtct ggagtggctg ggagtaatat ggggtagtga aaccacatac  540
tataattcag ctctcaaatc cagactgacc atcatcaagg acaactccaa gagccaagtt  600
ttcttaaaaa tgaacagtct gcaaactgat gacacagcca tttactactg tgccaaacat  660
tattactacg gtggtagcta tgctatggac tactggggcc aaggaacctc agtcaccgtg  720
tcctcaacca cgacgccagc gccgcgacca ccaacaccgg cgcccaccat cgcgtcgcag  780
cccctgtccc tgcgcccaga ggcgtgccgg ccagcggcgg ggggcgcagt gcacacgagg  840
gggctggact tcgcctgtga tttctgggtg ctggtcgttg tgggcggcgt gctggcctgc  900
tacagcctgc tggtgacagt ggccttcatc atcttttggg tgaggagcaa gcggagcaga  960
ctgctgcaca gcgactacat gaacatgacc ccccggaggc ctggccccac ccggaagcac  1020
taccagccct acgcccctcc cagggatttc gccgcctacc ggagcaaacg gggcagaaag  1080
aaactcctgt atatattcaa acaaccattt atgaggccag tacaaactac tcaagaggaa  1140
gatggctgta gctgccgatt tccagaagaa gaagaaggag gatgtgaact gagagtgaag  1200
ttcagcagga gcgcagacgc ccccgcgtac aagcagggcc agaaccagct ctataacgag  1260
ctcaatctag gacgaagaga ggagtacgat gttttggaca agcgtagagg ccgggaccct  1320
gagatggggg gaaagccgag aaggaagaac cctcaggaag gcctgtacaa tgaactgcag  1380
```

```
aaagataaga tggcggaggc ctacagtgag attgggatga aaggcgagcg ccggaggggc  1440
aaggggcacg atggccttta ccagggactc agtacagcca ccaaggacac ctacgacgcc  1500
cttcacatgc aggccctgcc ccctcgc                                      1527

SEQ ID NO: 281          moltype = AA  length = 509
FEATURE                 Location/Qualifiers
REGION                  1..509
                        note = CD19 CAR
source                  1..509
                        mol_type = protein
                        organism = synthetic construct
SEQUENCE: 281
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGGG GSGGGGSGGG  120
GSEVKLQESG PGLVAPSQSL SVTCTVSGVS LPDYGVSWIR QPPRKGLEWL GVIWGSETTY  180
YNSALKSRLT IIKDNSKSQV FLKMNSLQTD DTAIYYCAKH YYYGGSYAMD YWGQGTSVTV  240
SSTTTPAPRP PTPAPTIASQ PLSLRPEACR PAAGGAVHTR GLDFACDFWV LVVVGGVLAC  300
YSLLVTVAFI IFWVRSKRSR LLHSDYMNMT PRRPGPTRKH YQPYAPPRDF AAYRSKRGRK  360
KLLYIFKQPF MRPVQTTQEE DGCSCRFPEE EEGGCELRVK FSRSADAPAY KQGQNQLYNE  420
LNLGRREEYD VLDKRRGRDP EMGGKPRRKN PQEGLYNELQ KDKMAEAYSE IGMKGERRRG  480
KGHDGLYQGL STATKDTYDA LHMQALPPR                                    509

SEQ ID NO: 282          moltype = AA  length = 246
FEATURE                 Location/Qualifiers
REGION                  1..246
                        note = CEA ScFv
source                  1..246
                        mol_type = protein
                        organism = synthetic construct
SEQUENCE: 282
QVQLVQSGSE LKKPGASVKV SCKASGYTFT EFGMNWVRQA PGQGLEWMGW INTKTGEATY  60
VEEFKGRFVF SLDTSVSTAY LQISSLKAED TAVYYCARWD FAYYVEAMDY WGQGTTVTVS  120
SGGGGSGGGG SGGGGSGGDI QMTQSPSSLS ASVGDRVTIT CKASQNVGTN VAWYQQKPGK  180
APKLLIYSAS YRYSGVPSRF SGSGSGTDFT LTISSLQPED FATYYCHQYY TYPLFTFGQG  240
TKLEIK                                                             246

SEQ ID NO: 283          moltype = DNA  length = 1542
FEATURE                 Location/Qualifiers
misc_feature            1..1542
                        note = CEA ScFv
source                  1..1542
                        mol_type = other DNA
                        organism = synthetic construct
SEQUENCE: 283
caggtgcagc tggtgcaatc tgggtctgag ttgaagaagc ctggggcctc agtgaaggtt  60
tcctgcaagg cttctggata caccttcact gagtttggaa tgaactgggt gcgacaggcc  120
cctggacaag ggcttgagtg gatgggatgg ataaacacca aaactggaga ggcaacatat  180
gttgaagagt ttaagggacg gtttgtcttc tccttggaca cctctgtcag cacggcatat  240
ctgcagatca gcagcctaaa ggctgaagac actgccgtgt attactgtgc gagatgggac  300
ttcgcttatt acgtggaggc tatggactac tggggccaag ggaccacggt caccgtctcc  360
tcaggcggag gtggaagcgg agggggagga tctggcggcg gaggaagcgg aggcgatatc  420
cagatgaccc agtctccatc ctccctgtct gcatctgtgg gagacagagt caccatcact  480
tgcaaggcca gtcagaatgt gggtactaat gttgcctggt atcagcagaa accagggaaa  540
gcacctaagc tcctgatcta ttcggcatcc taccgctaca gtggagtccc atcaaggttc  600
agtggcagtg gatctgggac agatttcact ctcaccatca gcagtctgca acctgaagat  660
ttcgcaactt actactgtca ccaatattac acctatcctc tattcacgtt tggccagggc  720
accaagctcg agatcaagat ggacatgagg gtccccgctc agctcctggg gctcctgcta  780
ctctggctcc gaggtgccag atgtcaggtg cagctggtgc aatctgggtc tgagttgaag  840
aagcctgggg cctcagtgaa ggtttcctgc aaggcttctg gatacacctt cactgagttt  900
ggaatgaact gggtgcgaca ggcccctgga caagggcttg agtggatggg atggataaac  960
accaaaactg gagaggcaac atatgttgaa gagtttaagg gacggtttgt cttctccttg  1020
gacacctctg tcagcacggc atatctgcag atcagcagcc taaaggctga agacactgcc  1080
gtgtattact gtgcgagatg ggacttcgct tattacgtgg aggctatgga ctactggggc  1140
caagggacca cggtcaccgt ctcctcaggc ggaggtggaa gcggaggggg aggatctggc  1200
ggcggaggaa gcggaggcga tatccagatg acccagtctc catcctccct gtctgcatct  1260
gtgggagaca gagtcaccat cacttgcaag gccagtcaga atgtgggtac taatgttgcc  1320
tggtatcagc agaaaccagg gaaagcacct aagctcctga tctattcggc atcctaccgc  1380
tacagtggag tcccatcaag gttcagtggc agtggatctg ggacagattt cactctcacc  1440
atcagcagtc tgcaacctga agatttcgca acttactact gtcaccaata ttacacctat  1500
cctctattca cgtttggcca gggcaccaag ctcgagatca ag                     1542

SEQ ID NO: 284          moltype = AA  length = 246
FEATURE                 Location/Qualifiers
REGION                  1..246
                        note = CEA ScFv
source                  1..246
                        mol_type = protein
                        organism = synthetic construct
SEQUENCE: 284
```

-continued

```
QVQLVQSGAE VKKPGASVKV SCKASGYTFT EFGMNWVRQA PGQGLEWMGW INTKTGEATY  60
VEEFKGRVTF TTDTSTSTAY MELRSLRSDD TAVYYCARWD FAYYVEAMDY WGQGTTVTVS  120
SGGGGSGGGG SGGGGSGGDI QMTQSPSSLS ASVGDRVTIT CKASAAVGTY VAWYQQKPGK  180
APKLLIYSAS YRKRGVPSRF SGSGSGTDFT LTISSLQPED FATYYCHQYY TYPLFTFGQG  240
TKLEIK                                                            246

SEQ ID NO: 285         moltype = DNA  length = 738
FEATURE                Location/Qualifiers
misc_feature           1..738
                       note = CEA ScFv
source                 1..738
                       mol_type = other DNA
                       organism = synthetic construct
SEQUENCE: 285
caggtgcagc tggtgcagtc tggcgccgaa gtgaagaaac ctggagctag tgtgaaggtg  60
tcctgcaagg ccagcggcta caccttcacc gagttcggca tgaactgggt ccgacaggct  120
ccaggccagg gcctcgaatg gatgggctgg atcaacacca agaccggcga ggccacctac  180
gtggaagagt tcaagggcag agtgaccttc accacggaca ccagcaccag caccgcctac  240
atggaactgc ggagcctgag aagcgacgac accgccgtgt actactgcgc cagatgggac  300
ttcgcttatt acgtggaagc catggactac tggggccagg gcaccaccgt gaccgtgtct  360
agcggcggag gtggaagcgg agggggagga tctggcggcg gaggaagcgg aggcgatatc  420
cagatgaccc agtctccatc ctccctgtct gcatctgtgg gagacagagt caccatcact  480
tgcaaggcca gtgcggctgt gggtacgtat gttgcgtggt atcagcagaa accagggaaa  540
gcacctaagc tcctgatcta ttcggcatcc taccgcaaaa ggggagtccc atcaaggttc  600
agtggcagtg gatctgggac agatttcact ctcaccatca gcagtctgca acctgaagat  660
ttcgcaactt actactgtca ccaatattac acctatcctc tattcacgtt tggccagggc  720
accaagctcg agatcaag                                               738

SEQ ID NO: 286         moltype = AA  length = 246
FEATURE                Location/Qualifiers
REGION                 1..246
                       note = CEA ScFv
source                 1..246
                       mol_type = protein
                       organism = synthetic construct
SEQUENCE: 286
QVQLVQSGSE LKKPGASVKV SCKASGYTFT EFGMNWVRQA PGQGLEWMGW INTKTGEATY  60
VEEFKGRFVF SLDTSVSTAY LQISSLKAED TAVYYCARWD FAHYFQTMDY WGQGTTVTVS  120
SGGGGSGGGG SGGGGSGGDI QMTQSPSSLS ASVGDRVTIT CKASAAVGTY VAWYQQKPGK  180
APKLLIYSAS YRKRGVPSRF SGSGSGTDFT LTISSLQPED FATYYCHQYY TYPLFTFGQG  240
TKLEIK                                                            246

SEQ ID NO: 287         moltype = DNA  length = 738
FEATURE                Location/Qualifiers
misc_feature           1..738
                       note = CEA ScFv
source                 1..738
                       mol_type = other DNA
                       organism = synthetic construct
SEQUENCE: 287
caggtgcagc tggtgcaatc tgggtctgag ttgaagaagc ctggggcctc agtgaaggtt  60
tcctgcaagg cttctggata caccttcact gagtttggaa tgaactgggt gcgacaggcc  120
cctggacaag ggcttgagtg gatgggatgg ataaacacca aaactggaga ggcaacatat  180
gttgaagagt ttaagggacg gtttgtcttc tccttggaca cctctgtcag cacggcatat  240
ctgcagatca gcagcctaaa ggctgaagac actgccgtgt attactgtgc gagatgggac  300
tttgctcatt actttcagac tatggactac tggggccaag ggaccacggt caccgtctcc  360
tcaggcggag gtggaagcgg agggggagga tctggcggcg gaggaagcgg aggcgatatc  420
cagatgaccc agtctccatc ctccctgtct gcatctgtgg gagacagagt caccatcact  480
tgcaaggcca gtgcggctgt gggtacgtat gttgcgtggt atcagcagaa accagggaaa  540
gcacctaagc tcctgatcta ttcggcatcc taccgcaaaa ggggagtccc atcaaggttc  600
agtggcagtg gatctgggac agatttcact ctcaccatca gcagtctgca acctgaagat  660
ttcgcaactt actactgtca ccaatattac acctatcctc tattcacgtt tggccagggc  720
accaagctcg agatcaag                                               738

SEQ ID NO: 288         moltype = AA  length = 535
FEATURE                Location/Qualifiers
REGION                 1..535
                       note = CEA CAR
source                 1..535
                       mol_type = protein
                       organism = synthetic construct
SEQUENCE: 288
MDMRVPAQLL GLLLLWLRGA RCQVQLVQSG SELKKPGASV KVSCKASGYT FTEFGMNWVR  60
QAPGQGLEWM GWINTKTGEA TYVEEFKGRF VFSLDTSVST AYLQISSLKA EDTAVYYCAR  120
WDFAYYVEAM DYWGQGTTVT VSSGGGGSGG GGSGGGGSGG DIQMTQSPSS LSASVGDRVT  180
ITCKASQNVG TNVAWYQQKP GKAPKLLIYS ASYRYSGVPS RFSGSGSGTD FTLTISSLQP  240
EDFATYYCHQ YYTYPLFTFG QGTKLEIKTT TPAPRPPTPA PTIASQPLSL RPEACRPAAG  300
GAVHTRGLDF ACDFWVLVVV GGVLACYSLL VTVAFIIFWV RSKRSRLLHS DYMNMTPRRP  360
GPTRKHYQPY APPRDFAAYR SKRGRKKLLY IFKQPFMRPV QTTQEEDGCS CRFPEEEEGG  420
```

```
CELRVKFSRS ADAPAYKQGQ NQLYNELNLG RREEYDVLDK RRGRDPEMGG KPRRKNPQEG  480
LYNELQKDKM AEAYSEIGMK GERRRGKGHD GLYQGLSTAT KDTYDALHMQ ALPPR       535

SEQ ID NO: 289          moltype = DNA  length = 1608
FEATURE                 Location/Qualifiers
misc_feature            1..1608
                        note = CEA CAR
source                  1..1608
                        mol_type = other DNA
                        organism = synthetic construct
SEQUENCE: 289
atggacatga gggtccccgc tcagctcctg gggctcctgc tactctggct ccgaggtgcc  60
agatgtcagg tgcagctggt gcaatctggg tctgagttga agaagcctgg ggcctcagtg  120
aaggtttcct gcaaggcttc tggatacacc ttcactgagt ttggaatgaa ctgggtgcga  180
caggcccctg gacaagggct tgagtggatg ggatggataa acaccaaaac tggagaggca  240
acatatgttg aagagtttaa gggacggttt gtcttctcct tggacacctc tgtcagcacg  300
gcatatctgc agatcagcag cctaaaggct gaagacactg ccgtgtatta ctgtgcgaga  360
tgggacttcg cttattacgt ggaggctatg gactactggg gccaagggac cacggtcacc  420
gtctcctcag gcggaggtgg aagcggaggg ggaggatctg gcggcggagg aagcggaggc  480
gatatccaga tgacccagtc tccatcctcc ctgtctgcat ctgtgggaga cagagtcacc  540
atcacttgca aggccagtca gaatgtgggt actaatgttg cctggtatca gcagaaacca  600
gggaaagcac ctaagctcct gatctattcg gcatcctacc gctacagtgg agtcccatca  660
aggttcagtg gcagtggatc tgggacagat ttcactctca ccatcagcag tctgcaacct  720
gaagatttcg caacttacta ctgtcaccaa tattacacct atcctctatt cacgtttggc  780
cagggcacca agctcgagat caagacaacg acgccagctc cccgcccgcc aacccctgca  840
cctacgattg catcacaacc gctgtccctg cggcctgaag cttgtcgccc agccgcaggt  900
ggcgccgtac atacacgggg gctggatttt gcctgtgatt tctgggtgct ggtcgttgtg  960
ggcggcgtgc tggcctgcta cagcctgctg gtgacagtgg ccttcatcat cttttgggtg  1020
aggagcaagc ggagtcgact gctgcacagc gactacatga acatgacccc ccggaggcct  1080
ggccccaccc ggaagcacta ccagccctac gcccctccca gggatttcgc cgcctaccgg  1140
agcaaacggg gcagaaagaa actcctgtat atattcaaac aaccatttat gaggccagta  1200
caaactactc aagaggaaga tggctgtagc tgccgatttc cagaagaaga agaaggagga  1260
tgtgaactga gagtgaagtt cagcaggagc gcagacgccc ccgcgtacaa gcagggccag  1320
aaccagctct ataacgagct caatctagga cgaagagagg agtacgatgt tttggacaag  1380
cgtagaggcc gggaccctga gatgggggga aagccgagaa ggaagaaccc tcaggaaggc  1440
ctgtacaatg aactgcagaa agataagatg gcggaggcct acagtgagat tgggatgaaa  1500
ggcgagcgcc ggaggggcaa ggggcacgat ggcctttacc agggactcag tacagccacc  1560
aaggacacct acgacgccct tcacatgcag gccctgcccc ctcgctag              1608

SEQ ID NO: 290          moltype = AA  length = 537
FEATURE                 Location/Qualifiers
REGION                  1..537
                        note = CEA CAR
source                  1..537
                        mol_type = protein
                        organism = synthetic construct
SEQUENCE: 290
MDMRVPAQLL GLLLLWLRGA RCQVQLVQSG AEVKKPGASV KVSCKASGYT FTEFGMNWVR  60
QAPGQGLEWM GWINTKTGEA TYVEEFKGRV TFTTDTSTST AYMELRSLRS DDTAVYYCAR  120
WDFAYYVEAM DYWGQGTTVT VSSGGGGSGG GGSGGGGSGG DIQMTQSPSS LSASVGDRVT  180
ITCKASAAVG TYVAWYQQKP GKAPKLLIYS ASYRKRGVPS RFSGSGSGTD FTLTISSLQP  240
EDFATYYCHQ YYTYPLFTFG QGTKLEIKRT TTTPAPRPPT PAPTIASQPL SLRPEACRPA  300
AGGAVHTRGL DFACDFWVLV VVGGVLACYS LLVTVAFIIF WVRSKRSRLL HSDYMNMTPR  360
RPGPTRKHYQ PYAPPRDFAA YRSKRGRKKL LYIFKQPFMR PVQTTQEEDG CSCRFPEEEE  420
GGCELRVKFS RSADAPAYKQ GQNQLYNELN LGRREEYDVL DKRRGRDPEM GGKPRRKNPQ  480
EGLYNELQKD KMAEAYSEIG MKGERRRGKG HDGLYQGLST ATKDTYDALH MQALPPR     537

SEQ ID NO: 291          moltype = DNA  length = 1614
FEATURE                 Location/Qualifiers
misc_feature            1..1614
                        note = CEA CAR
source                  1..1614
                        mol_type = other DNA
                        organism = synthetic construct
SEQUENCE: 291
atggacatga gggtccccgc tcagctcctg gggctcctgc tactctggct ccgaggtgcc  60
agatgtcagg tgcagctggt gcagtctggc gccgaagtga agaaacctgg agctagtgtg  120
aaggtgtcct gcaaggccag cggctacacc ttcaccgagt tcggcatgaa ctgggtccga  180
caggctccag gccagggcct cgaatggatg ggctggatca acaccaagac cggcgaggcc  240
acctacgtgg aagagttcaa gggcagagtg accttcacca cggacaccag caccagcacc  300
gcctacatgg aactgcggag cctgagaagc gacgacaccg ccgtgtacta ctgcgccaga  360
tgggacttcg cttattacgt ggaagccatg gactactggg gccagggcac caccgtgacc  420
gtgtctagcg gcggaggtgg aagcggaggg ggaggatctg gcggcggagg aagcggaggc  480
gatatccaga tgacccagtc tccatcctcc ctgtctgcat ctgtgggaga cagagtcacc  540
atcacttgca aggccagtgc ggctgtgggt acgtatgttg cgtggtatca gcagaaacca  600
gggaaagcac ctaagctcct gatctattcg gcatcctacc gcaaaagggg agtcccatca  660
aggttcagtg gcagtggatc tgggacagat ttcactctca ccatcagcag tctgcaacct  720
gaagatttcg caacttacta ctgtcaccaa tattacacct atcctctatt cacgtttggc  780
cagggcacca agctcgagat caagcgtacg acaacgacgc cagctccccg cccgccaacc  840
```

```
cctgcaccta cgattgcatc acaaccgctg tccctgcggc ctgaagcttg tcgcccagcc  900
gcaggtggcg ccgtacatac acgggggctg gattttgcct gtgatttctg ggtgctggtc  960
gttgtgggcg gcgtgctggc ctgctacagc ctgctggtga cagtggcctt catcatcttt  1020
tgggtgagga gcaagcggag tcgactgctg cacagcgact acatgaacat gaccccccgg  1080
aggcctggcc ccacccggaa gcactaccag ccctacgccc ctcccaggga tttcgccgcc  1140
taccggagca aacggggcag aaagaaactc ctgtatatat tcaaacaacc atttatgagg  1200
ccagtacaaa ctactcaaga ggaagatggc tgtagctgcc gatttccaga agaagaagaa  1260
ggaggatgtg aactgagagt gaagttcagc aggagcgcag acgcccccgc gtacaagcag  1320
ggccagaacc agctctataa cgagctcaat ctaggacgaa gagaggagta cgatgttttg  1380
gacaagcgta gaggccggga ccctgagatg gggggaaagc cgagaaggaa gaaccctcag  1440
gaaggcctgt acaatgaact gcagaaagat aagatggcgg aggcctacag tgagattggg  1500
atgaaaggcg agcgccggag gggcaagggg cacgatggcc tttaccaggg actcagtaca  1560
gccaccaagg acacctacga cgcccttcac atgcaggccc tgccccctcg ctag        1614

SEQ ID NO: 292          moltype = AA  length = 536
FEATURE                 Location/Qualifiers
REGION                  1..536
                        note = CEA CAR
source                  1..536
                        mol_type = protein
                        organism = synthetic construct
SEQUENCE: 292
MDMRVPAQLL GLLLLWLRGA RCQVQLVQSG SELKKPGASV KVSCKASGYT FTEFGMNWVR  60
QAPGQGLEWM GWINTKTGEA TYVEEFKGRF VFSLDTSVST AYLQISSLKA EDTAVYYCAR  120
WDFAHYFQTM DYWGQGTTVT VSSGGGGSGG GGSGGGGSGG DIQMTQSPSS LSASVGDRVT  180
ITCKASAAVG TYVAWYQQKP GKAPKLLIYS ASYRKRGVPS RFSGSGSGTD FTLTISSLQP  240
EDFATYYCHQ YYTYPLFTFG QGTKLEIKRT TTPAPRPPTP APTIASQPLS LRPEACRPAA  300
GGAVHTRGLD FACDFWVLVV VGGVLACYSL LVTVAFIIFW VRSKRSRLLH SDYMNMTPRR  360
PGPTRKHYQP YAPPRDFAAY RSKRGRKKLL YIFKQPFMRP VQTTQEEDGC SCRFPEEEEG  420
GCELRVKFSR SADAPAYKQG QNQLYNELNL GRREEYDVLD KRRGRDPEMG GKPRRKNPQE  480
GLYNELQKDK MAEAYSEIGM KGERRRGKGH DGLYQGLSTA TKDTYDALHM QALPPR      536

SEQ ID NO: 293          moltype = DNA  length = 1611
FEATURE                 Location/Qualifiers
misc_feature            1..1611
                        note = CEA CAR
source                  1..1611
                        mol_type = other DNA
                        organism = synthetic construct
SEQUENCE: 293
atggacatga gggtccccgc tcagctcctg gggctcctgc tactctggct ccgaggtgcc  60
agatgtcagg tgcagctggt gcaatctggg tctgagttga agaagcctgg ggcctcagtg  120
aaggtttcct gcaaggcttc tggatacacc ttcactgagt ttggaatgaa ctgggtgcga  180
caggcccctg gacaagggct tgagtggatg ggatggataa acaccaaaac tggagaggca  240
acatatgttg aagagtttaa gggacggttt gtcttctcct tggacacctc tgtcagcacg  300
gcatatctgc agatcagcag cctaaaggct gaagacactg ccgtgtatta ctgtgcgaga  360
tgggactttg ctcattactt tcagactatg gactactggg gccaagggac cacggtcacc  420
gtctcctcag gcggaggtgg aagcggaggg ggaggatctg gcggcggagg aagcggaggc  480
gatatccaga tgacccagtc tccatcctcc ctgtctgcat ctgtgggaga cagagtcacc  540
atcacttgca aggccagtgc ggctgtgggt acgtatgttg cgtggtatca gcagaaacca  600
gggaaagcac ctaagctcct gatctattcg gcatcctacc gcaaaagggg agtcccatca  660
aggttcagtg gcagtggatc tgggacagat ttcactctca ccatcagcag tctgcaacct  720
gaagatttcg caacttacta ctgtcaccaa tattacacct atcctctatt cacgtttggc  780
cagggcacca agctcgagat caagcgtaca acgacgccag ctccccgccc gccaacccct  840
gcacctacga ttgcatcaca accgctgtcc ctgcggcctg aagcttgtcg cccagccgca  900
ggtggcgccg tacatacacg ggggctggat tttgcctgtg atttctgggt gctggtcgtt  960
gtgggcggcg tgctggcctg ctacagcctg ctggtgacag tggccttcat catcttttgg  1020
gtgaggagca agcggagtcg actgctgcac agcgactaca tgaacatgac cccccggagg  1080
cctggcccca cccggaagca ctaccagccc tacgcccctc ccagggattt cgccgcctac  1140
cggagcaaac ggggcagaaa gaaactcctg tatatattca aacaaccatt tatgaggcca  1200
gtacaaacta ctcaagagga agatggctgt agctgccgat ttccagaaga agaagaagga  1260
ggatgtgaac tgagagtgaa gttcagcagg agcgcagacg cccccgcgta caagcagggc  1320
cagaaccagc tctataacga gctcaatcta ggacgaagag aggagtacga tgttttggac  1380
aagcgtagag gccgggaccc tgagatgggg ggaaagccga gaaggaagaa ccctcaggaa  1440
ggcctgtaca atgaactgca gaaagataag atggcggagg cctacagtga gattgggatg  1500
aaaggcgagc gccggagggg caaggggcac gatggccttt accagggact cagtacagcc  1560
accaaggaca cctacgacgc ccttcacatg caggccctgc cccctcgcta g           1611

SEQ ID NO: 294          moltype = AA  length = 5
FEATURE                 Location/Qualifiers
REGION                  1..5
                        note = CEA CDR-H1
source                  1..5
                        mol_type = protein
                        organism = synthetic construct
SEQUENCE: 294
EFGMN                                                              5

SEQ ID NO: 295          moltype = AA  length = 17
```

```
FEATURE                Location/Qualifiers
REGION                 1..17
                       note = CEA CDR-H2
source                 1..17
                       mol_type = protein
                       organism = synthetic construct
SEQUENCE: 295
WINTKTGEAT YVEEFKG                                                   17

SEQ ID NO: 296         moltype = AA  length = 12
FEATURE                Location/Qualifiers
REGION                 1..12
                       note = CEA CDR-H3
source                 1..12
                       mol_type = protein
                       organism = synthetic construct
SEQUENCE: 296
WDFAYYVEAM DY                                                        12

SEQ ID NO: 297         moltype = AA  length = 12
FEATURE                Location/Qualifiers
REGION                 1..12
                       note = CEA CDR-H3
source                 1..12
                       mol_type = protein
                       organism = synthetic construct
SEQUENCE: 297
WDFAHYFQTM DY                                                        12

SEQ ID NO: 298         moltype = AA  length = 11
FEATURE                Location/Qualifiers
REGION                 1..11
                       note = CEA CDR-L1
source                 1..11
                       mol_type = protein
                       organism = synthetic construct
SEQUENCE: 298
KASQNVGTNV A                                                         11

SEQ ID NO: 299         moltype = AA  length = 11
FEATURE                Location/Qualifiers
REGION                 1..11
                       note = CEA CDR-L1
source                 1..11
                       mol_type = protein
                       organism = synthetic construct
SEQUENCE: 299
KASAAVGTYV A                                                         11

SEQ ID NO: 300         moltype = AA  length = 7
FEATURE                Location/Qualifiers
REGION                 1..7
                       note = CEA CDR-L2
source                 1..7
                       mol_type = protein
                       organism = synthetic construct
SEQUENCE: 300
SASYRYS                                                              7

SEQ ID NO: 301         moltype = AA  length = 7
FEATURE                Location/Qualifiers
REGION                 1..7
                       note = CEA CDR-L2
source                 1..7
                       mol_type = protein
                       organism = synthetic construct
SEQUENCE: 301
SASYRKR                                                              7

SEQ ID NO: 302         moltype = AA  length = 10
FEATURE                Location/Qualifiers
REGION                 1..10
                       note = CEA CDR-L3
source                 1..10
                       mol_type = protein
                       organism = synthetic construct
SEQUENCE: 302
HQYYTYPLFT                                                           10
```

```
SEQ ID NO: 303          moltype = AA  length = 10
FEATURE                 Location/Qualifiers
REGION                  1..10
                        note = LB-CYBA-1Y peptide
SITE                    10
                        note = X - X is Y or H
source                  1..10
                        mol_type = protein
                        organism = synthetic construct
SEQUENCE: 303
STMERWGQKX                                                    10

SEQ ID NO: 304          moltype = AA  length = 11
FEATURE                 Location/Qualifiers
REGION                  1..11
                        note = LB-OAS1-1R
SITE                    7
                        note = X - X is R or T
source                  1..11
                        mol_type = protein
                        organism = synthetic construct
SEQUENCE: 304
ETDDPRXYQK Y                                                  11

SEQ ID NO: 305          moltype = AA  length = 9
FEATURE                 Location/Qualifiers
REGION                  1..9
                        note = HA-2 peptide
SITE                    9
                        note = X - X is V or M
source                  1..9
                        mol_type = protein
                        organism = synthetic construct
SEQUENCE: 305
YIGEVLVSX                                                     9

SEQ ID NO: 306          moltype = AA  length = 9
FEATURE                 Location/Qualifiers
REGION                  1..9
                        note = HA-8 peptide
SITE                    1
                        note = X - X is R or P
source                  1..9
                        mol_type = protein
                        organism = synthetic construct
SEQUENCE: 306
XTLDKVLEV                                                     9

SEQ ID NO: 307          moltype = AA  length = 9
FEATURE                 Location/Qualifiers
REGION                  1..9
                        note = HA-3 peptide
SITE                    2
                        note = X - X is T or M
source                  1..9
                        mol_type = protein
                        organism = synthetic construct
SEQUENCE: 307
VXEPGTAQY                                                     9

SEQ ID NO: 308          moltype = AA  length = 11
FEATURE                 Location/Qualifiers
REGION                  1..11
                        note = HwA11-S peptide
SITE                    6
                        note = X - X is S or T
source                  1..11
                        mol_type = protein
                        organism = synthetic construct
SEQUENCE: 308
CIPPDXLLFP A                                                  11

SEQ ID NO: 309          moltype = AA  length = 11
FEATURE                 Location/Qualifiers
REGION                  1..11
                        note = LB-ADIR-1F peptide
SITE                    9
                        note = X - X is F or S
source                  1..11
```

```
                        mol_type = protein
                        organism = synthetic construct
SEQUENCE: 309
SVAPALALXP A                                                    11

SEQ ID NO: 310          moltype = AA  length = 9
FEATURE                 Location/Qualifiers
REGION                  1..9
                        note = LB-HIVEP1-1S peptide
SITE                    6
                        note = X - X is S or N
source                  1..9
                        mol_type = protein
                        organism = synthetic construct
SEQUENCE: 310
SLPKHXVTI                                                       9

SEQ ID NO: 311          moltype = AA  length = 9
FEATURE                 Location/Qualifiers
REGION                  1..9
                        note = LB-NISCH-1A peptide
SITE                    7
                        note = X - X is A or V
source                  1..9
                        mol_type = protein
                        organism = synthetic construct
SEQUENCE: 311
ALAPAPXEV                                                       9

SEQ ID NO: 312          moltype = AA  length = 9
FEATURE                 Location/Qualifiers
REGION                  1..9
                        note = LB-SSR1-1S peptide
SITE                    1
                        note = X - X is S or L
source                  1..9
                        mol_type = protein
                        organism = synthetic construct
SEQUENCE: 312
XLAVAQDLT                                                       9

SEQ ID NO: 313          moltype = AA  length = 10
FEATURE                 Location/Qualifiers
REGION                  1..10
                        note = LB-WNK1-1I peptide
SITE                    7
                        note = X - X is I or M
source                  1..10
                        mol_type = protein
                        organism = synthetic construct
SEQUENCE: 313
RTLSPEXITV                                                      10

SEQ ID NO: 314          moltype = AA  length = 10
FEATURE                 Location/Qualifiers
REGION                  1..10
                        note = T4A peptide
SITE                    10
                        note = X - X is A or E
source                  1..10
                        mol_type = protein
                        organism = synthetic construct
SEQUENCE: 314
GLYTYWSAGX                                                      10

SEQ ID NO: 315          moltype = AA  length = 9
FEATURE                 Location/Qualifiers
REGION                  1..9
                        note = UTA2-1 peptide
SITE                    3
                        note = X - X is L or P
source                  1..9
                        mol_type = protein
                        organism = synthetic construct
SEQUENCE: 315
QLXNSVLTL                                                       9

SEQ ID NO: 316          moltype = AA  length = 9
FEATURE                 Location/Qualifiers
```

```
REGION                1..9
                      note = LB-CLYBL-1Y peptide
SITE                  5
                      note = X - X is Y or D
source                1..9
                      mol_type = protein
                      organism = synthetic construct
SEQUENCE: 316
SLAAXIPRL                                                     9

SEQ ID NO: 317        moltype = AA  length = 10
FEATURE               Location/Qualifiers
REGION                1..10
                      note = TRIM22 peptide
SITE                  7
                      note = X - X is C or R
source                1..10
                      mol_type = protein
                      organism = synthetic construct
SEQUENCE: 317
MAVPPCXIGV                                                    10

SEQ ID NO: 318        moltype = AA  length = 11
FEATURE               Location/Qualifiers
REGION                1..11
                      note = PARP10-1L peptide
SITE                  3
                      note = X - X is L or P
source                1..11
                      mol_type = protein
                      organism = synthetic construct
SEQUENCE: 318
GLXGQEGLVE I                                                  11

SEQ ID NO: 319        moltype = AA  length = 9
FEATURE               Location/Qualifiers
REGION                1..9
                      note = FAM119A-1T peptide
SITE                  8
                      note = X - X is T or I
source                1..9
                      mol_type = protein
                      organism = synthetic construct
SEQUENCE: 319
AMLERQFXV                                                     9

SEQ ID NO: 320        moltype = AA  length = 9
FEATURE               Location/Qualifiers
REGION                1..9
                      note = GLRX3-1S peptide
SITE                  3
                      note = X - X is S or P
source                1..9
                      mol_type = protein
                      organism = synthetic construct
SEQUENCE: 320
FLXSANEHL                                                     9

SEQ ID NO: 321        moltype = AA  length = 9
FEATURE               Location/Qualifiers
REGION                1..9
                      note = HNF4G-1M peptide
SITE                  2
                      note = X - X is M or I
source                1..9
                      mol_type = protein
                      organism = synthetic construct
SEQUENCE: 321
MXYKDILLL                                                     9

SEQ ID NO: 322        moltype = AA  length = 9
FEATURE               Location/Qualifiers
REGION                1..9
                      note = HMMR-1V peptide
SITE                  6
                      note = X - X is V or A
source                1..9
                      mol_type = protein
                      organism = synthetic construct
```

```
SEQUENCE: 322
SLQEKXAKA                                                  9

SEQ ID NO: 323          moltype = AA  length = 9
FEATURE                 Location/Qualifiers
REGION                  1..9
                        note = BCL2A1 peptide
SITE                    4
                        note = X - X is N or K
source                  1..9
                        mol_type = protein
                        organism = synthetic construct
SEQUENCE: 323
VLQXVAFSV                                                  9

SEQ ID NO: 324          moltype = AA  length = 10
FEATURE                 Location/Qualifiers
REGION                  1..10
                        note = CDC26-1F peptide
SITE                    1
                        note = X - X is F or S
source                  1..10
                        mol_type = protein
                        organism = synthetic construct
SEQUENCE: 324
XVAGTQEVFV                                                 10

SEQ ID NO: 325          moltype = AA  length = 10
FEATURE                 Location/Qualifiers
REGION                  1..10
                        note = APOBEC3F-1S/A peptide
SITE                    3
                        note = X - X is S or A
source                  1..10
                        mol_type = protein
                        organism = synthetic construct
SEQUENCE: 325
FLXEHPNVTL                                                 10

SEQ ID NO: 326          moltype = AA  length = 9
FEATURE                 Location/Qualifiers
REGION                  1..9
                        note = LB-PRCP-1D peptide
SITE                    8
                        note = X - X is D or E
source                  1..9
                        mol_type = protein
                        organism = synthetic construct
SEQUENCE: 326
FMWDVAEXL                                                  9

SEQ ID NO: 327          moltype = AA  length = 11
FEATURE                 Location/Qualifiers
REGION                  1..11
                        note = LB-PRCP-1D peptide
SITE                    8
                        note = X - X is D or E
source                  1..11
                        mol_type = protein
                        organism = synthetic construct
SEQUENCE: 327
FMWDVAEXLK A                                               11

SEQ ID NO: 328          moltype = AA  length = 9
FEATURE                 Location/Qualifiers
REGION                  1..9
                        note = LB-CCL4-1T peptide
SITE                    7
                        note = X - X is T or S
source                  1..9
                        mol_type = protein
                        organism = synthetic construct
SEQUENCE: 328
CADPSEXWV                                                  9

SEQ ID NO: 329          moltype = AA  length = 9
FEATURE                 Location/Qualifiers
REGION                  1..9
                        note = LB-NCAPD3-1Q peptide
```

```
SITE                 3
                     note = X - X is Q or R
source               1..9
                     mol_type = protein
                     organism = synthetic construct
SEQUENCE: 329
WLXGVVPVV                                                  9

SEQ ID NO: 330       moltype = AA  length = 9
FEATURE              Location/Qualifiers
REGION               1..9
                     note = LB-NDC80-1P peptide
SITE                 7
                     note = X - X is P or A
source               1..9
                     mol_type = protein
                     organism = synthetic construct
SEQUENCE: 330
HLEEQIXKV                                                  9

SEQ ID NO: 331       moltype = AA  length = 9
FEATURE              Location/Qualifiers
REGION               1..9
                     note = LB-TTK-1D peptide
SITE                 4
                     note = X - X is D or E
source               1..9
                     mol_type = protein
                     organism = synthetic construct
SEQUENCE: 331
RLHXGRVFV                                                  9

SEQ ID NO: 332       moltype = AA  length = 9
FEATURE              Location/Qualifiers
REGION               1..9
                     note = WDR27-1L peptide
SITE                 2
                     note = X - X is L or P
source               1..9
                     mol_type = protein
                     organism = synthetic construct
SEQUENCE: 332
SXDDHVVAV                                                  9

SEQ ID NO: 333       moltype = AA  length = 11
FEATURE              Location/Qualifiers
REGION               1..11
                     note = MIIP peptide
SITE                 8
                     note = X - X is K or E
source               1..11
                     mol_type = protein
                     organism = synthetic construct
SEQUENCE: 333
SEESAVPXRS W                                               11

SEQ ID NO: 334       moltype = AA  length = 10
FEATURE              Location/Qualifiers
REGION               1..10
                     note = MIIP peptide
SITE                 7
                     note = X - X is K or E
source               1..10
                     mol_type = protein
                     organism = synthetic construct
SEQUENCE: 334
EESAVPXRSW                                                 10

SEQ ID NO: 335       moltype = AA  length = 9
FEATURE              Location/Qualifiers
REGION               1..9
                     note = LB-DHX33-1C peptide
SITE                 9
                     note = X - X is C or R
source               1..9
                     mol_type = protein
                     organism = synthetic construct
SEQUENCE: 335
YLYEGGISX                                                  9
```

```
SEQ ID NO: 336          moltype = AA  length = 10
FEATURE                 Location/Qualifiers
REGION                  1..10
                        note = PANE1 peptide
source                  1..10
                        mol_type = protein
                        organism = synthetic construct
SEQUENCE: 336
RVWDLPGVLK                                                          10

SEQ ID NO: 337          moltype = AA  length = 10
FEATURE                 Location/Qualifiers
REGION                  1..10
                        note = SP110 peptide
SITE                    4
                        note = X - X is R or G
source                  1..10
                        mol_type = protein
                        organism = synthetic construct
SEQUENCE: 337
SLPXGTSTPK                                                          10

SEQ ID NO: 338          moltype = AA  length = 9
FEATURE                 Location/Qualifiers
REGION                  1..9
                        note = ACC-1C/Y
SITE                    5
                        note = X - X is Y or C
source                  1..9
                        mol_type = protein
                        organism = synthetic construct
SEQUENCE: 338
DYLQXVLQI                                                           9

SEQ ID NO: 339          moltype = AA  length = 9
FEATURE                 Location/Qualifiers
REGION                  1..9
                        note = P2RX7 peptide
SITE                    6
                        note = X - X is H or R
source                  1..9
                        mol_type = protein
                        organism = synthetic construct
SEQUENCE: 339
WFHHCXPKY                                                           9

SEQ ID NO: 340          moltype = AA  length = 9
FEATURE                 Location/Qualifiers
REGION                  1..9
                        note = ACC-4 peptide
SITE                    9
                        note = X - X is R or G
source                  1..9
                        mol_type = protein
                        organism = synthetic construct
SEQUENCE: 340
ATLPLLCAX                                                           9

SEQ ID NO: 341          moltype = AA  length = 10
FEATURE                 Location/Qualifiers
REGION                  1..10
                        note = ACC-5
SITE                    10
                        note = X - X is R or G
source                  1..10
                        mol_type = protein
                        organism = synthetic construct
SEQUENCE: 341
WATLPLLCAX                                                          10

SEQ ID NO: 342          moltype = AA  length = 9
FEATURE                 Location/Qualifiers
REGION                  1..9
                        note = AKAP13 peptide
SITE                    9
                        note = X - X is M or T
source                  1..9
                        mol_type = protein
```

```
                        organism = synthetic construct
SEQUENCE: 342
APAGVREVX                                                                   9

SEQ ID NO: 343          moltype = AA  length = 10
FEATURE                 Location/Qualifiers
REGION                  1..10
                        note = LB-APOBEC3B-1K peptide
SITE                    1
                        note = X - X is K or E
source                  1..10
                        mol_type = protein
                        organism = synthetic construct
SEQUENCE: 343
XPQYHAEMCF                                                                  10

SEQ ID NO: 344          moltype = AA  length = 9
FEATURE                 Location/Qualifiers
REGION                  1..9
                        note = APOBEC3H peptide
SITE                    5
                        note = X - X is K or E
source                  1..9
                        mol_type = protein
                        organism = synthetic construct
SEQUENCE: 344
KPQQXGLRL                                                                   9

SEQ ID NO: 345          moltype = AA  length = 8
FEATURE                 Location/Qualifiers
REGION                  1..8
                        note = LB-ARHGDIB-1R peptide
SITE                    6
                        note = X - X is R or P
source                  1..8
                        mol_type = protein
                        organism = synthetic construct
SEQUENCE: 345
PRACWXEA                                                                    8

SEQ ID NO: 346          moltype = AA  length = 10
FEATURE                 Location/Qualifiers
REGION                  1..10
                        note = LB-BCAT2-1R peptide
SITE                    3
                        note = X - X is R or T
source                  1..10
                        mol_type = protein
                        organism = synthetic construct
SEQUENCE: 346
QPXRALLFVI                                                                  10

SEQ ID NO: 347          moltype = AA  length = 11
FEATURE                 Location/Qualifiers
REGION                  1..11
                        note = BFAR peptide
SITE                    11
                        note = X - X is M or R
source                  1..11
                        mol_type = protein
                        organism = synthetic construct
SEQUENCE: 347
APNTGRANQQ X                                                                11

SEQ ID NO: 348          moltype = AA  length = 11
FEATURE                 Location/Qualifiers
REGION                  1..11
                        note = C14orf169 peptide
SITE                    4
                        note = X - X is A or V
source                  1..11
                        mol_type = protein
                        organism = synthetic construct
SEQUENCE: 348
RPRXPTEELA L                                                                11

SEQ ID NO: 349          moltype = AA  length = 11
FEATURE                 Location/Qualifiers
REGION                  1..11
```

```
                        note = LB-C16ORF-1R peptide
SITE                    1
                        note = X - X is R or W
source                  1..11
                        mol_type = protein
                        organism = synthetic construct
SEQUENCE: 349
XPCPSVGLSF L                                                                11

SEQ ID NO: 350          moltype = AA  length = 9
FEATURE                 Location/Qualifiers
REGION                  1..9
                        note = C18orf21 peptide
SITE                    6
                        note = X - X is A or T
source                  1..9
                        mol_type = protein
                        organism = synthetic construct
SEQUENCE: 350
NPATPXSKL                                                                   9

SEQ ID NO: 351          moltype = AA  length = 10
FEATURE                 Location/Qualifiers
REGION                  1..10
                        note = LB-EBI3-1I peptide
SITE                    8
                        note = X - X is I or V
source                  1..10
                        mol_type = protein
                        organism = synthetic construct
SEQUENCE: 351
RPRARYYXQV                                                                  10

SEQ ID NO: 352          moltype = AA  length = 9
FEATURE                 Location/Qualifiers
REGION                  1..9
                        note = POP1 peptide
SITE                    7
                        note = X - X is N or K
source                  1..9
                        mol_type = protein
                        organism = synthetic construct
SEQUENCE: 352
LPQKKSXAL                                                                   9

SEQ ID NO: 353          moltype = AA  length = 9
FEATURE                 Location/Qualifiers
REGION                  1..9
                        note = SCRIB peptide
SITE                    7
                        note = X - X is L or P
source                  1..9
                        mol_type = protein
                        organism = synthetic construct
SEQUENCE: 353
LPQQPPXSL                                                                   9

SEQ ID NO: 354          moltype = AA  length = 9
FEATURE                 Location/Qualifiers
REGION                  1..9
                        note = MTRR peptide
SITE                    5
                        note = X - X is S or L
source                  1..9
                        mol_type = protein
                        organism = synthetic construct
SEQUENCE: 354
SPASXRTDL                                                                   9

SEQ ID NO: 355          moltype = AA  length = 9
FEATURE                 Location/Qualifiers
REGION                  1..9
                        note = LLGL2
SITE                    5
                        note = X - X is R or H
source                  1..9
                        mol_type = protein
                        organism = synthetic construct
SEQUENCE: 355
```

```
SPSLXILAI                                                    9

SEQ ID NO: 356         moltype = AA  length = 11
FEATURE                Location/Qualifiers
REGION                 1..11
                       note = LB-ECGF-1H peptide
SITE                   3
                       note = X - X is H or R
source                 1..11
                       mol_type = protein
                       organism = synthetic construct
SEQUENCE: 356
RPXAIRRPLA L                                                 11

SEQ ID NO: 357         moltype = AA  length = 11
FEATURE                Location/Qualifiers
REGION                 1..11
                       note = LB-ERAP1-1R peptide
SITE                   3
                       note = X - X is R or P
source                 1..11
                       mol_type = protein
                       organism = synthetic construct
SEQUENCE: 357
HPXQEQIALL A                                                 11

SEQ ID NO: 358         moltype = AA  length = 9
FEATURE                Location/Qualifiers
REGION                 1..9
                       note = LB-ERAP1-1R peptide
SITE                   3
                       note = X - X is R or P
source                 1..9
                       mol_type = protein
                       organism = synthetic construct
SEQUENCE: 358
HPXQEQIAL                                                    9

SEQ ID NO: 359         moltype = AA  length = 9
FEATURE                Location/Qualifiers
REGION                 1..9
                       note = LB-FUCA2-1V peptide
SITE                   5
                       note = X - X is V or M
source                 1..9
                       mol_type = protein
                       organism = synthetic construct
SEQUENCE: 359
RLRQXGSWL                                                    9

SEQ ID NO: 360         moltype = AA  length = 9
FEATURE                Location/Qualifiers
REGION                 1..9
                       note = LB-GEMIN4-1V peptide
SITE                   9
                       note = X - X is V or E
source                 1..9
                       mol_type = protein
                       organism = synthetic construct
SEQUENCE: 360
FPALRFVEX                                                    9

SEQ ID NO: 361         moltype = AA  length = 11
FEATURE                Location/Qualifiers
REGION                 1..11
                       note = HDGF peptide
SITE                   11
                       note = X - X is L or P
source                 1..11
                       mol_type = protein
                       organism = synthetic construct
SEQUENCE: 361
LPMEVEKNST X                                                 11

SEQ ID NO: 362         moltype = AA  length = 11
FEATURE                Location/Qualifiers
REGION                 1..11
                       note = LB-PDCD11-1F peptide
SITE                   8
```

```
                        note = X - X is F or L
source                  1..11
                        mol_type = protein
                        organism = synthetic construct
SEQUENCE: 362
GPDSSKTXLC L                                                      11

SEQ ID NO: 363          moltype = AA  length = 9
FEATURE                 Location/Qualifiers
REGION                  1..9
                        note = LB-PFAS-1P peptide
SITE                    2
                        note = X - X is P or S
source                  1..9
                        mol_type = protein
                        organism = synthetic construct
SEQUENCE: 363
AXGHTRRKL                                                         9

SEQ ID NO: 364          moltype = AA  length = 10
FEATURE                 Location/Qualifiers
REGION                  1..10
                        note = LB-TEP1-1S peptide
SITE                    9
                        note = X - X is S or P
source                  1..10
                        mol_type = protein
                        organism = synthetic construct
SEQUENCE: 364
APDGAKVAXL                                                        10

SEQ ID NO: 365          moltype = AA  length = 11
FEATURE                 Location/Qualifiers
REGION                  1..11
                        note = LB-TMEM8A-1I peptide
SITE                    7
                        note = X - X is I or V
source                  1..11
                        mol_type = protein
                        organism = synthetic construct
SEQUENCE: 365
RPRSVTXQPL L                                                      11

SEQ ID NO: 366          moltype = AA  length = 10
FEATURE                 Location/Qualifiers
REGION                  1..10
                        note = LB-USP15-1I peptide
SITE                    8
                        note = X - X is I or T
source                  1..10
                        mol_type = protein
                        organism = synthetic construct
SEQUENCE: 366
MPSHLRNXLL                                                        10

SEQ ID NO: 367          moltype = AA  length = 9
FEATURE                 Location/Qualifiers
REGION                  1..9
                        note = LRH-1 peptide
source                  1..9
                        mol_type = protein
                        organism = synthetic construct
SEQUENCE: 367
TPNQRQNVC                                                         9

SEQ ID NO: 368          moltype = AA  length = 9
FEATURE                 Location/Qualifiers
REGION                  1..9
                        note = LB-MOB3A-1C peptide
SITE                    1
                        note = X - X is C or S
source                  1..9
                        mol_type = protein
                        organism = synthetic construct
SEQUENCE: 368
XPRPGTWTC                                                         9

SEQ ID NO: 369          moltype = AA  length = 11
FEATURE                 Location/Qualifiers
```

```
REGION                 1..11
                       note = LB-ZDHHC6-1Y peptide
SITE                   4
                       note = X - X is Y or H
source                 1..11
                       mol_type = protein
                       organism = synthetic construct
SEQUENCE: 369
RPRXWILLVK I                                                       11

SEQ ID NO: 370         moltype = AA  length = 10
FEATURE                Location/Qualifiers
REGION                 1..10
                       note = ZAPHIR peptide
source                 1..10
                       mol_type = protein
                       organism = synthetic construct
SEQUENCE: 370
IPRDSWWVEL                                                         10

SEQ ID NO: 371         moltype = AA  length = 9
FEATURE                Location/Qualifiers
REGION                 1..9
                       note = HEATR1 peptide
SITE                   7
                       note = X - X is E or G
source                 1..9
                       mol_type = protein
                       organism = synthetic construct
SEQUENCE: 371
ISKERAXAL                                                          9

SEQ ID NO: 372         moltype = AA  length = 9
FEATURE                Location/Qualifiers
REGION                 1..9
                       note = LB-GSTP1-1V peptide
SITE                   7
                       note = X - X is V or I
source                 1..9
                       mol_type = protein
                       organism = synthetic construct
SEQUENCE: 372
DLRCKYXSL                                                          9

SEQ ID NO: 373         moltype = AA  length = 9
FEATURE                Location/Qualifiers
REGION                 1..9
                       note = HA-1/B60 peptide
SITE                   6
                       note = X - X is H or R
source                 1..9
                       mol_type = protein
                       organism = synthetic construct
SEQUENCE: 373
KECVLXDDL                                                          9

SEQ ID NO: 374         moltype = AA  length = 9
FEATURE                Location/Qualifiers
REGION                 1..9
                       note = LB-SON-1R peptide
SITE                   6
                       note = X - X is R or C
source                 1..9
                       mol_type = protein
                       organism = synthetic construct
SEQUENCE: 374
SETKQXTVL                                                          9

SEQ ID NO: 375         moltype = AA  length = 9
FEATURE                Location/Qualifiers
REGION                 1..9
                       note = LB-SWAP70-1Q peptide
SITE                   6
                       note = X - X is Q or E
source                 1..9
                       mol_type = protein
                       organism = synthetic construct
SEQUENCE: 375
MEQLEXLEL                                                          9
```

```
SEQ ID NO: 376          moltype = AA  length = 9
FEATURE                 Location/Qualifiers
REGION                  1..9
                        note = LB-TRIP10-1EPC peptide
SITE                    2
                        note = X - X is E or G
SITE                    3
                        note = X - X is P or S
SITE                    7
                        note = X - X is C or G
source                  1..9
                        mol_type = protein
                        organism = synthetic construct
SEQUENCE: 376
GXXQDLXTL                                                      9

SEQ ID NO: 377          moltype = AA  length = 9
FEATURE                 Location/Qualifiers
REGION                  1..9
                        note = LB-NUP133-1R peptide
SITE                    8
                        note = X - X is R or Q
source                  1..9
                        mol_type = protein
                        organism = synthetic construct
SEQUENCE: 377
SEDLILCXL                                                      9

SEQ ID NO: 378          moltype = AA  length = 11
FEATURE                 Location/Qualifiers
REGION                  1..11
                        note = LB-ZNFX1-1Q peptide
SITE                    8
                        note = X - X is Q or H
source                  1..11
                        mol_type = protein
                        organism = synthetic construct
SEQUENCE: 378
NEIEDVWXLD L                                                   11

SEQ ID NO: 379          moltype = AA  length = 11
FEATURE                 Location/Qualifiers
REGION                  1..11
                        note = SLC1A5 peptide
SITE                    3
                        note = X - X is A or P
source                  1..11
                        mol_type = protein
                        organism = synthetic construct
SEQUENCE: 379
AEXTANGGLA L                                                   11

SEQ ID NO: 380          moltype = AA  length = 10
FEATURE                 Location/Qualifiers
REGION                  1..10
                        note = ACC-2 peptide
SITE                    6
                        note = X - X is D or G
source                  1..10
                        mol_type = protein
                        organism = synthetic construct
SEQUENCE: 380
KEFEDXIINW                                                     10

SEQ ID NO: 381          moltype = AA  length = 11
FEATURE                 Location/Qualifiers
REGION                  1..11
                        note = ACC-6 peptide
source                  1..11
                        mol_type = protein
                        organism = synthetic construct
SEQUENCE: 381
MEIFIEVFSH F                                                   11

SEQ ID NO: 382          moltype = AA  length = 10
FEATURE                 Location/Qualifiers
REGION                  1..10
                        note = HB-1H/Y peptide
```

```
SITE                    8
                        note = X - X is H or Y
source                  1..10
                        mol_type = protein
                        organism = synthetic construct
SEQUENCE: 382
EEKRGSLXVW                                                                10

SEQ ID NO: 383          moltype = AA  length = 9
FEATURE                 Location/Qualifiers
REGION                  1..9
                        note = DPH1 peptide
SITE                    2
                        note = X - X is V or L
source                  1..9
                        mol_type = protein
                        organism = synthetic construct
SEQUENCE: 383
SXLPEVDVW                                                                 9

SEQ ID NO: 384          moltype = AA  length = 9
FEATURE                 Location/Qualifiers
REGION                  1..9
                        note = UGT2B17/A02 peptide
source                  1..9
                        mol_type = protein
                        organism = synthetic construct
SEQUENCE: 384
CVATMIFMI                                                                 9

SEQ ID NO: 385          moltype = AA  length = 10
FEATURE                 Location/Qualifiers
REGION                  1..10
                        note = UGT2B17/A29
source                  1..10
                        mol_type = protein
                        organism = synthetic construct
SEQUENCE: 385
AELLNIPFLY                                                                10

SEQ ID NO: 386          moltype = AA  length = 10
FEATURE                 Location/Qualifiers
REGION                  1..10
                        note = UGT2B17/B44 peptide
source                  1..10
                        mol_type = protein
                        organism = synthetic construct
SEQUENCE: 386
AELLNIPFLY                                                                10

SEQ ID NO: 387          moltype = AA  length = 9
FEATURE                 Location/Qualifiers
REGION                  1..9
                        note = DFFRY peptide
SITE                    4
                        note = X - X is C or S
source                  1..9
                        mol_type = protein
                        organism = synthetic construct
SEQUENCE: 387
IVDXLTEMY                                                                 9

SEQ ID NO: 388          moltype = AA  length = 9
FEATURE                 Location/Qualifiers
REGION                  1..9
                        note = SMCY peptide
source                  1..9
                        mol_type = protein
                        organism = synthetic construct
SEQUENCE: 388
FIDSYICQV                                                                 9

SEQ ID NO: 389          moltype = AA  length = 11
FEATURE                 Location/Qualifiers
REGION                  1..11
                        note = TMSB4Y peptide
source                  1..11
                        mol_type = protein
                        organism = synthetic construct
```

```
SEQUENCE: 389
EVLLRPGLHF R                                                     11

SEQ ID NO: 390          moltype = DNA  length = 1533
FEATURE                 Location/Qualifiers
misc_feature            1..1533
                        note = CD19 CAR
source                  1..1533
                        mol_type = other DNA
                        organism = synthetic construct
SEQUENCE: 390
gacatccaga tgacacagac tacatcctcc ctgtctgcct ctctgggaga cagagtcacc  60
atcagttgca gggcaagtca ggacattagt aaatatttaa attggtatca gcagaaacca  120
gatggaactg ttaaactcct gatctaccat acatcaagat tacactcagg agtcccatca  180
aggttcagtg gcagtgggtc tggaacagat tattctctca ccattagcaa cctggagcaa  240
gaagatattg ccacttactt ttgccaacag ggtaatacgc ttccgtacac gttcggaggg  300
gggaccaagc tggagatcac aggcggaggt ggaagcggag gggggaggatc tggcggcgga  360
ggaagcggag gcgaggtgaa actgcaggag tcaggacctg gcctggtggc gccctcacag  420
agcctgtccg tcacatgcac tgtctcaggg gtctcattac ccgactatgg tgtaagctgg  480
attcgccagc ctccacgaaa gggtctggag tggctgggag taatatgggg tagtgaaacc  540
acatactata attcagctct caaatccaga ctgaccatca tcaaggacaa ctccaagagc  600
caagttttct taaaaatgaa cagtctgcaa actgatgaca cagccattta ctactgtgcc  660
aaacattatt actacggtgg tagctatgct atggactact ggggccaagg aacctcagtc  720
accgtgtcct caaccacgac gccagcgccg cgaccaccaa caccggcgcc caccatcgcg  780
tcgcagcccc tgtccctgcg cccagaggcg tgccggccag cggcgggggg cgcagtgcac  840
acgagggggc tggacttcgc ctgtgatttc tgggtgctgg tcgttgtggg cggcgtgctg  900
gcctgctaca gcctgctggt gacagtggcc ttcatcatct tttgggtgag gagcaagcgg  960
agcagactgc tgcacagcga ctacatgaac atgacccccc ggaggcctgg ccccacccgg  1020
aagcactacc agccctacgc ccctcccagg gatttcgccg cctaccggag caaacggggc  1080
agaaagaaac tcctgtatat attcaaacaa ccatttatga ggccagtaca aactactcaa  1140
gaggaagatg gctgtagctg ccgatttcca gaagaagaag aaggaggatg tgaactgaga  1200
gtgaagttca gcaggagcgc agacgccccc gcgtacaagc agggccagaa ccagctctat  1260
aacgagctca atctaggacg aagagaggag tacgatgttt tggacaagcg tagaggccgg  1320
gaccctgaga tggggggaaa gccgagaagg aagaaccctc aggaaggcct gtacaatgaa  1380
ctgcagaaag ataagatggc ggaggcctac agtgagattg ggatgaaagg cgagcgccgg  1440
aggggcaagg ggcacgatgg cctttaccag ggactcagta cagccaccaa ggacacctac  1500
gacgcccttc acatgcaggc cctgcccccct cgc                            1533

SEQ ID NO: 391          moltype = AA  length = 245
FEATURE                 Location/Qualifiers
REGION                  1..245
                        note = EGFR ScFv
source                  1..245
                        mol_type = protein
                        organism = synthetic construct
SEQUENCE: 391
QVQLQESGPG LVKPSQTLSL TCTVSGGSIS SGDYYWSWIR QPPGKGLEWI GYIYYSGSTD  60
YNPSLKSRVT MSVDTSKNQF SLKVNSVTAA DTAVYYCARV SIFGVGTFDY WGQGTLVTVS  120
SGGGGSGGGG SGGGGSGGEI VMTQSPATLS LSPGERATLS CRASQSVSSY LAWYQQKPGQ  180
APRLLIYDAS NRATGIPARF SGSGSGTDFT LTISSLEPED FAVYYCHQYG STPLTFGGGT  240
KAEIK                                                            245
```

The invention claimed is:

1. An engineered immune cell comprising:

an activating receptor that triggers a cytotoxic signal that promotes a cytotoxic response of the engineered immune cell when the activating receptor binds a first ligand of a target cell; and a blocking receptor that sends an interfering signal that inhibits the cytotoxic response of the engineered immune cell when the blocking receptor binds a second ligand of the target cell, said blocking receptor comprising a hinge domain that comprises a peptide comprising at least 24 contiguous amino acids from a leukocyte immunoglobulin-like receptor subfamily B member 1 (LILRB1) protein, wherein cross-talk between the activating receptor and the blocking receptor affects an activation threshold for the cytotoxic response.

2. The immune cell of claim 1, wherein in the absence of the first and second ligands, the effect of the cross-talk on the activation threshold is minimized and/or reduced.

3. The immune cell of claim 1, wherein the effect of the cross-talk on the activation threshold increases with proximity of the activating receptor to the blocking receptor.

4. The immune cell of claim 3, wherein the activating receptor and blocking receptor are covalently linked together, or have physicochemical properties favoring interaction with one another such that the receptors are proximal to one another.

5. The immune cell of claim 1, wherein when the blocking receptor binds to the second ligand, the cross-talk between the blocking and activating receptors causes the immune cell to exhibit reduced surface expression of the activating receptor.

6. The immune cell of claim 1, wherein the immune cell comprises a plurality of the activating and blocking receptors, and when the immune cell contacts a target cell the plurality of the activating and blocking receptors diffuses into a region on the surface of the immune cell proximal to the target cell and forms a micro-cluster in which the effect of the cross-talk on the activation threshold is localized.

7. The immune cell of claim 1, wherein the cross-talk between the activating receptor and the blocking receptor prevents the blocking receptor from binding to the second ligand until the activating receptor binds to the first ligand.

8. A method for treating cancer, the method comprising:

providing an engineered immune cell to a patient, wherein the engineered immune cell comprises an activating receptor and a blocking receptor, each expressed on a surface of the engineered immune cell, wherein:

the activating receptor triggers a cytotoxic signal that promotes a cytotoxic response of the engineered immune cell when the activating receptor binds a first ligand of a target cell; and the blocking receptor sends an interfering signal that inhibits the cytotoxic response of the engineered immune cell when the blocking receptor binds a second ligand of the target cell, said blocking receptor comprising a hinge domain that comprises a peptide comprising at least 24 contiguous amino acids from a leukocyte immunoglobulin-like receptor subfamily B member 1 (LILRB1) protein, wherein cross-talk between the activating receptor and the blocking receptor affects an activation threshold for the cytotoxic response.

9. The method of claim 8, wherein in the absence of the second ligand, the effect of the cross-talk on the activation threshold is minimized and/or reduced.

10. The method of claim 8, wherein the effect of the cross-talk on the activation threshold increases with proximity of the activating receptor to the blocking receptor.

11. The method of claim 10, wherein the activating receptor and blocking receptor are linked together or have physicochemical properties favoring interaction with one another, such that the receptors are proximal to one another.

12. The method of claim 8, wherein when the blocking receptor binds to the second ligand, the cross-talk between the blocking and activating receptors causes the immune cell to exhibit reduced surface expression of the activating receptor.

13. The method of claim 8, wherein the immune cell comprises a plurality of the activating and blocking receptors, and when the immune cell contacts a target cell the plurality of the activating and blocking receptors diffuses into a region on the surface of the immune cell proximal to the target cell and forms a micro-cluster in which the effect of the cross-talk on the activation threshold is localized.

14. The method of claim 8, wherein the cross-talk between the activating receptor and the blocking receptor prevents the blocking receptor from binding to the second ligand until the activating receptor binds to the first ligand.

15. A method of producing an engineered immune cell, the method comprising:

determining an amount of cross-talk between an activating receptor and a blocking receptor for an engineered immune cell, wherein the amount of cross-talk between the activating receptor and the blocking receptor affects an activation threshold for the cytotoxic response; and producing an engineered immune cell that expresses different concentrations of the activating receptor and the blocking receptor based on the determined amount of cross-talk between the activating receptor and the blocking receptor, each said blocking receptor comprising a hinge domain that comprises a peptide comprising at least 24 contiguous amino acids from a leukocyte immunoglobulin-like receptor subfamily B member 1 (LILRB1) protein.

16. The method of claim 15, wherein in the absence of cognate ligands for the activating and blocking receptors, the amount of the cross-talk is minimized and/or reduced.

17. The method of claim 15, wherein producing an engineered immune cell that expresses different concentrations of activating receptors and blocking receptors is further based on a ratio of a quantity of an activating ligand to a quantity of a blocking ligand that are expressed in non-tumor cells of a sample.

18. The method of claim 17, wherein the cross-talk between the activating receptor and the blocking receptor prevents the blocking receptor from binding to the blocking ligand until the activating receptor binds to the activating ligand.

19. The method of claim 15, wherein an amount of the cross-talk between the activating receptor and blocking receptor increases with proximity of the activating receptor to the blocking receptor.

20. The method of claim 19, wherein the activating receptor and blocking receptor are covalently linked, or have physicochemical properties favoring interaction with one another such that the receptors are proximal to one another.

* * * * *